US012564595B2

(12) United States Patent
Yoshinaga et al.

(10) Patent No.: US 12,564,595 B2
(45) Date of Patent: Mar. 3, 2026

(54) PROPHYLACTIC AND THERAPEUTIC PHARMACEUTICAL AGENT FOR HIV INFECTIOUS DISEASES CHARACTERIZED BY COMPRISING COMBINATION OF INTEGRASE INHIBITOR AND ANTI-HIV AGENT

(71) Applicant: Shionogi & Co., Ltd., Osaka (JP)

(72) Inventors: Tomokazu Yoshinaga, Osaka (JP); Yutaka Tomida, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 907 days.

(21) Appl. No.: 17/779,763

(22) PCT Filed: Nov. 27, 2020

(86) PCT No.: PCT/JP2020/044139
§ 371 (c)(1),
(2) Date: May 25, 2022

(87) PCT Pub. No.: WO2021/107066
PCT Pub. Date: Jun. 3, 2021

(65) Prior Publication Data

US 2023/0059640 A1 Feb. 23, 2023

(30) Foreign Application Priority Data

Nov. 28, 2019 (JP) ................................ 2019-214882

(51) Int. Cl.
*A61K 31/5383* (2006.01)
*A61K 31/5386* (2006.01)
(Continued)

(52) U.S. Cl.
CPC ...... *A61K 31/5383* (2013.01); *A61K 31/5386* (2013.01); *A61K 45/00* (2013.01); *A61P 31/18* (2018.01)

(58) Field of Classification Search
CPC .......... A61P 31/18; A61P 31/12; A61P 43/00; A61P 37/00; A61P 3/04; A61P 3/10; A61K 31/4985; A61K 31/53; A61K 31/554; A61K 2300/00; A61K 31/4439; A61K 31/513; A61K 31/5383; A61K 31/5386; A61K 31/56; A61K 31/63; A61K 31/635; A61K 45/00; A61K 45/06; C07D 403/06; C07D 471/04; C07D 209/12; C07D 209/18; C07D 209/20; C07D 209/22; C07D 471/14; C07D 471/22; C07D 498/14; C07D 498/22; C07D 513/14; C07D 333/24; C07D 333/34; C07D 487/06; C07D 513/06; C07D 213/64; C07D 241/18; C07D 401/12; C07D 403/12; C07D 213/69; C07D 231/56; C07D 239/80; C07D 261/20; C07D 263/56; C07D 267/14; C07D 277/20; C07D 277/34; C07D 277/64; C07D 277/68; C07D 401/14; C07D 403/14;
(Continued)

(56) References Cited

U.S. PATENT DOCUMENTS

2009/0143356 A1* 6/2009 Yoshida .............. C07D 498/14 514/230.2
2023/0058677 A1 2/2023 Tomida et al.

FOREIGN PATENT DOCUMENTS

EP 1 950 212 7/2008
EP 3 144 311 3/2017
(Continued)

OTHER PUBLICATIONS

Saishin Soyakukagaku, The Practice of Medicinal Chemistry, Technomics, Inc., 1998, vol. 1, pp. 476, 494-495, with English translation.
(Continued)

*Primary Examiner* — Savitha M Rao
(74) *Attorney, Agent, or Firm* — Wenderoth, Lind & Ponack, L.L.P.

(57) ABSTRACT

A prophylactic or therapeutic pharmaceutical agent for HIV infectious diseases, said pharmaceutical agent being characterized by comprising a combination of: (A) a compound represented by formula (I) (wherein ring A represents a non-aromatic heterocyclic ring; ring B represents a benzene ring or a pyridine ring; Q represents —NHC(O)— or the like: each $R^1$ independently represents a halogen atom or the like: each of $R^{2a}$ and $R^{2b}$ independently represents a hydrogen atom or the like: $R^3$ represents an alkyl group or a haloalky 1 group: $R^4$ represents a hydrogen atom or an alkyl group: and n represents an integer from 1 to 3) or a pharmaceutically acceptable salt thereof, and (B) a compound having an anti-HIV effect or a pharmaceutically acceptable salt thereof.

(I)

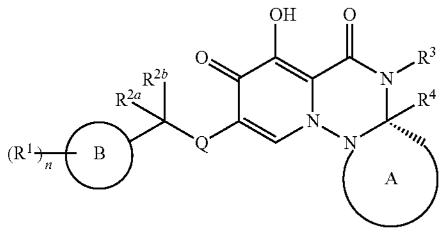

12 Claims, No Drawings

(51) Int. Cl.
*A61K 45/00* (2006.01)
*A61P 31/18* (2006.01)

(58) Field of Classification Search
CPC .. C07D 413/12; C07D 417/12; C07D 213/55; C07D 213/56; C07D 213/57; C07D 213/65; C07D 213/68; C07D 215/233; C07D 235/16; C07D 239/26; C07D 239/52; C07D 241/12; C07D 241/20; C07D 263/32; C07D 277/30; C07D 285/12; C07D 401/06; C07D 405/12; C07D 413/06; C07D 417/06; C07D 471/08; C07D 473/00; C07D 491/147; C07D 491/02
See application file for complete search history.

(56) References Cited

FOREIGN PATENT DOCUMENTS

| | | |
|---|---|---|
| EP | 3 196 201 | 7/2017 |
| EP | 3 305 789 | 4/2018 |
| EP | 3 805 221 | 4/2021 |
| EP | 4 257 137 | 10/2023 |
| JP | 2017-538713 | 12/2017 |
| JP | 2021-91670 | 6/2021 |
| JP | 2021-91671 | 6/2021 |
| WO | 2007/049675 | 5/2007 |
| WO | 2014/200880 | 12/2014 |
| WO | 2015/174511 | 11/2015 |
| WO | 2016/027879 | 2/2016 |
| WO | 2016/106237 | 6/2016 |
| WO | 2016/187788 | 12/2016 |
| WO | 2016/191239 | 12/2016 |
| WO | 2016/194806 | 12/2016 |
| WO | 2019/230857 | 12/2019 |
| WO | 2019/230858 | 12/2019 |

OTHER PUBLICATIONS

Kogakuiseitainobunri, Resolution of Enantiomers, Gakken Syuppan Center, Inc., 1989, pp. 16-17, with English translation.
International Search Report issued Jan. 26, 2021 in International (PCT) Application No. PCT/JP2020/044139.
International Preliminary Report on Patentability issued May 17, 2022 in International (PCT) Application No. PCT/JP2020/044139.
Extended European Search Report issued Nov. 29, 2023 in European Application No. 20894693.9.

* cited by examiner

PROPHYLACTIC AND THERAPEUTIC PHARMACEUTICAL AGENT FOR HIV INFECTIOUS DISEASES CHARACTERIZED BY COMPRISING COMBINATION OF INTEGRASE INHIBITOR AND ANTI-HIV AGENT

TECHNICAL FIELD

The present invention relates to a prophylactic and therapeutic pharmaceutical agent for HIV infectious diseases. More specifically, the present invention relates to a prophylactic and therapeutic pharmaceutical agent for HIV infectious diseases characterized by comprising a combination of a compound with HIV-1 integrase, inhibiting activity, or a pharmaceutically acceptable salt thereof, and at least one compound with anti-HIV activity, or a pharmaceutically acceptable salt thereof.

TECHNICAL BACKGROUND

It is known that the human immunodeficiency virus (hereinafter, abbreviated as HIV), which is a type of retrovirus, is a cause of acquired immunodeficiency syndrome (hereinafter, abbreviated as AIDS). Up to the present time, the chief HIV therapeutic agents are: reverse transcriptase inhibitors (TDF, 3TC etc.), protease inhibiting agents (darunavir etc.) and integrase inhibitors (dolutegravir). However, problems such as side effects and the appearance of drug-resistant viruses have been identified and development of an anti-HIV agent having a different mechanism of action is desired.

With the development of combination antiretroviral therapies (cART) in 1996, which employ a combination of anti-HIV agents, a dramatic improvement was achieved in respect of anti-HIV efficacy and the appearance of drug-resistant viruses, improving the prognosis for HIV-infected patients. cART, in which 2 to 4 types of anti-HIV agent are internally administered in combined fashion for treatment of HIV infectious diseases, has now become the standard treatment for HIV/AIDS. As anti-HIV agents used in cART, three types of agents, namely, polymerase inhibitors, protease inhibitors and integrase inhibitors, are chiefly employed as recommended agents in initial therapy. However, drugs having the same mechanism of action often show cross-resistance, or their effect is merely additive, so that when a mutation occurs that shows common drug resistance, other drugs of the same class can no longer be used. Development of an anti-HIV agent that is effective in regard to existing drug-resistant virus mutations and having a different mechanism of action is therefore desired.

Carbamoyl pyridone derivatives having two or more rings are known as one example of anti-HIV agents having an integrase inhibiting effect (Patent Documents 1 to 29). Of these, Patent Document 3 discloses a carbamoyl pyridotriazine derivative. In addition, pyridone derivatives having a heterocyclic side chain are known as one example of an anti-HIV agent having an integrase inhibiting effect (Patent Documents 5, 8, 9, 12, 13, 19, 23, 24, 27, 30 to 33). Of these, Patent Document 9 discloses a condensed tricyclic pyridopyrazine derivative. Further, Patent Document 5 discloses a condensed tricyclic pyridopyrazine derivative and a condensed tricyclic pyridotriazine derivative.

PRIOR ART DOCUMENTS

Patent Documents

Patent Document 1: International Publication No. 2006/088173 pamphlet

Patent Document 2: International Publication No. 2006/116764 pamphlet

Patent Document 3: International Publication No. 2007/049675 pamphlet

Patent Document 4: international Publication No. 2011/129095 pamphlet

Patent Document 5: International Publication No. 2014/099586 pamphlet

Patent Document 6: International Publication No. 2014/100323 pamphlet

Patent Document 7: International Publication No. 2014/104279 pamphlet

Patent Document 8: International Publication No. 2014/183532 pamphlet

Patent Document 9: International Publication No. 2014/200880 pamphlet

Patent Document 10: International Publication No. 2015/039348 pamphlet

Patent Document 11: International Publication No. 2015/048363 pamphlet

Patent Document 12: International Publication No: 2015/089847 pamphlet

Patent Document 13: International Publication No. 2015/095258 pamphlet

Patent Document 14: International Publication No. 2015/006731 pamphlet

Patent Document 15: international Publication No. 2015/006733 pamphlet

Patent Document 16: International Publication No. 2015/199167 pamphlet

Patent Document 17: International Publication No. 2016/090545 pamphlet

Patent Document 18: International Publication No. 2016/094198 pamphlet

Patent Document 19: International Publication No. 2016/094197 pamphlet

Patent Document 20: International Publication No. 2016/106237 pamphlet

Patent Document 21: International Publication No. 2016/154527 pamphlet

Patent Document 22: International Publication No. 2016/161382 pamphlet

Patent Document 23: International Publication No. 2016/187788 pamphlet

Patent Document 24: International Publication No. 2016/191239 pamphlet

Patent Document 25: International Publication No. 2017/087256 pamphlet

Patent Document 26: International Publication No. 2017/087257 pamphlet

Patent Document 27: International Publication No: 2017/106071 pamphlet

Patent Document 28: International Publication No. 2017/113288 pamphlet

Patent Document 29: International Publication No. 2017/116928 pamphlet

Patent Document 30: International Publication No. 2005/016927 pamphlet

Patent Document 31: international Publication No. 2011/105590 pamphlet

Patent Document 32: International Publication No. 2013/054862 pamphlet

Patent Document 33: International Publication No. 2016/027879 pamphlet

SUMMARY OF THE INVENTION

Problem to be Solved by the Invention

The object of the present invention is to provide a pharmaceutical agent having an efficacious prophylactic or therapeutic effect in regard to HIV infectious diseases, for mutated strains or strains that are resistant to existing drugs.

Means for Solving the Problem

According to the present invention, the following inventions are provided.

[1] A prophylactic or therapeutic pharmaceutical agent for HIV infectious diseases characterized by combining (A) a compound represented by formula (1):

[Chem. 1]

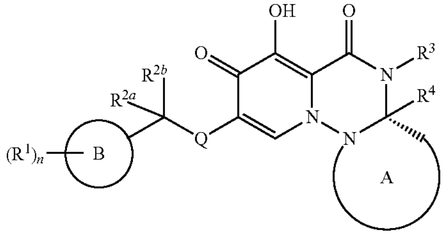

(I)

(where, in this formula, ring A is any of the following rings:

[Chem. 2]

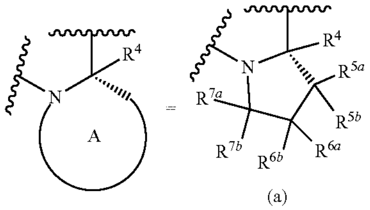

(a)

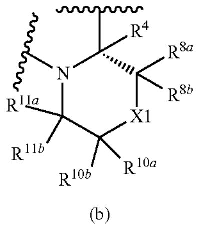

(b)

X1 is $CR^{9a}R^{9b}$ or O;

$R^{5a}$, $R^{5b}$, $R^{6a}$, $R^{6b}$, $R^{7a}$ and $R^{7b}$ are respectively independently hydrogen, halogen, alkyl, haloalkyl, alkyloxy, alkyloxyalkyl or 3-6 member non-aromatic carbon ring groups;

$R^{5a}$ and $R^{6a}$, or $R^{6a}$ and $R^{7a}$ may form, together with an adjacent atom, an aromatic carbon ring, which may be halogen-substituted, a 3-6 member non-aromatic carbon ring, which may be halogen-substituted, or a4-6 member heterocycle, which may be halogen-substituted (in the case where an aromatic carbon ring is formed, $R^{5b}$ and $R^{6b}$, or $R^{6b}$ and $R^{7b}$ may come together to form a bond);

$R^{5b}$ and $R^{6b}$ may come together to form a bond;

$R^{8a}$, $R^{8b}$, $R^{9a}$, $R^{9b}$, $R^{10a}$, $R^{10b}$, $R^{11a}$ and $R^{11b}$ are respectively independently hydrogen, halogen, alkyl, haloalkyl, alkyloxy, alkyloxyalkyl or 3-6 member non-aromatic carbon ring groups;

$R^{8a}$ and $R^{10a}$ may together form a C1-C3 cross-linkage;

$R^{10a}$ and $R^{11a}$, together with an adjacent atom, may form a 5-member non-aromatic carbon ring;

$R^{9a}$ and $R^{9b}$, together with an adjacent atom, may form a 4-member non-aromatic carbon ring or 5-member non-aromatic heterocycle;

$R^{8a}$ and $R^{9a}$ may come together to form a bond;

the B ring is a benzene ring or pyridine ring;

Q is —NHC(O)— or a 5-member aromatic heterocycle;

$R^1$ is respectively independently halogen, alkyl, haloalkyl, alkyloxy, cyano or haloalkyloxy;

$R^{2a}$ and $R^{2b}$ are respectively independently hydrogen, alkyl or haloalkyl;

$R^3$ is alkyl or haloalkyl;

$R^4$ is hydrogen or alkyl; and n is an integer of 1 to 3)

or a pharmaceutically acceptable salt thereof; and a compound (B) having anti-HIV activity, or a pharmaceutically acceptable salt thereof.

[2] The pharmaceutical agent according to [1] wherein $R^3$ is alkyl.

[3] The pharmaceutical agent according to [1] or [2] wherein $R^1$ is respectively independently a halogen.

[4] The pharmaceutical agent according to any of [1] to [3] wherein lea is hydrogen and $R^{2b}$ is hydrogen or alkyl.

[5] The pharmaceutical agent according to any of [1] to [4] wherein Q is —NHC(O)—.

[6] The pharmaceutical agent according to any of [1] to [4] wherein Q is a 5-member aromatic heterocycle.

[7] The pharmaceutical agent according to [1] wherein (A) is selected from the group of compounds I-3, I-7, I-11, I-16, I-23, I-24, I-32, II-1, II-4, II-5, II-13, II-14, II-16, II-19, II-21, II-23, II-26, II-31, II-34, II-36, II-38, II-41, II-43, II-45, II-47, II-49, II-52, II-56, II-58, II-62, II-63, II-64, II-68, II-89, II-92, II-93, II-95, II-96, II-98, II-106, II-109, II-110, II-112, II-113, II-117, II-118, II-125, II-127, II-128, II-129, II-130, II-131, II-132, II-136, II-138, II-139, II-142, II-143, II-144, II-147, II-148, II-149, II-150, II-151, II-155, II-156, II-157 and pharmaceutically acceptable salts thereof.

[8] The pharmaceutical agent according to any of [1] to [7] wherein (B) is at least one selected from: compounds with a polymerase inhibitory activity; compounds with a ribonuclease H inhibitory activity; compounds with an HIV-1 integrase (IN)-lens epithelium-derived growth factor (LEDGF) complex allosteric inhibitory activity; compounds with a protease inhibitory activity; compounds with an adsorption and invasion inhibitory activity; compounds with a budding inhibitory activity; compounds with a maturation inhibitory activity; and compounds with a capsid inhibitory activity; and pharmaceutically acceptable salts thereof.

[8-1] The pharmaceutical agent according to any of [1] to [7] wherein (B) is at least one selected from: compounds with a polymerase inhibitory activity; compounds with a ribonuclease H inhibitory activity; compounds with an HPV-1 integrase (IN)-lens epithelium-derived growth factor (LEDGF) complex allosteric inhibitory activity; compounds with a protease inhibitory activity; compounds with an adsorption and invasion inhibitory activity; compounds with a budding inhibitory activity: a compounds with a maturation inhibitory activity; compounds with a capsid inhibitory activity; pharmaceutically acceptable salts thereof; and an antibody having an anti-HIV action.

[9] The pharmaceutical agent according to [8] wherein the compounds with an HIV-1 integrase (IN)-lens epithelium-derived growth factor (LEDGE) complex allosteric inhibitory activity is a compound represented by formula (1'):

[Chem. 3]

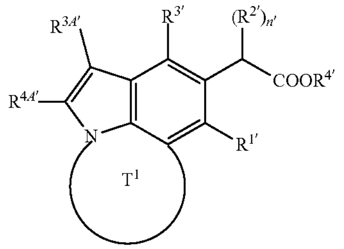

(I')

(where, in this formula, $R^{3A'}$ and $R^{4A'}$ may be respectively independently: hydrogen, halogen, hydroxy, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylcarbonyl, substituted or unsubstituted alkenylcarbonyl, substituted or unsubstituted alkynylcarbonyl, substituted or unsubstituted aromatic carbon ring group, substituted or unsubstituted non-aromatic carbon ring group, substituted or unsubstituted aromatic heterocyclic group, substituted or unsubstituted non-aromatic heterocyclic group, substituted or unsubstituted aromatic carbon ring oxy, substituted or unsubstituted non-aromatic carbon ring oxy, substituted or unsubstituted aromatic heterocyclic oxy, substituted or unsubstituted non-aromatic heterocyclic oxy, substituted or unsubstituted aromatic carbon ring sulfanyl, substituted or unsubstituted non-aromatic carbon ring sulfanyl, substituted or unsubstituted aromatic heterocyclic sulfanyl, substituted or unsubstituted non-aromatic heterocyclic sulfanyl, substituted or unsubstituted aromatic carbon ring carbonyl, substituted or unsubstituted non-aromatic carbon ring carbonyl, substituted or unsubstituted aromatic heterocyclic carbonyl, substituted or unsubstituted non-aromatic heterocyclic carbonyl, substituted or unsubstituted amino, or substituted or unsubstituted carbamoyl;

$R^{3A'}$ and $R^{4A'}$, together with an adjacent atom, may form a substituted or unsubstituted monocyclic carbon ring, or substituted or unsubstituted monocyclic heterocycle, and this carbon ring or heterocycle may be further condensed with a substituted or unsubstituted carbon ring or a substituted or unsubstituted heterocycle.

$R^{4A'}$, together with an atom on an arc of the $T^1$ ring, may form a substituted or unsubstituted heterocycle, and this heterocycle may be further condensed with a substituted or unsubstituted carbon ring or a substituted or unsubstituted heterocycle; the $T^1$ ring is a substituted or unsubstituted monocyclic heterocylic ring, and (1) this heterocycle may be condensed with another substituted or an substituted carbon ring or substituted or unsubstituted heterocycle, and/or (2) two atoms that are not mutually adjacent, constituting this heterocycle, may be crosslinked by a substituted or unsubstituted alkylene, substituted or unsubstituted alkenylene, or substituted or unsubstituted alkynylene;

$R^{1'}$ is a halogen, cyano, nitro or $X^{1'}$—$R^{11'}$, $X^{1'}$ is a single bond, —O—, —S—, —$NR^{12'}$—, —CO—, —SO—, —$SO_2$—, —O—CO—, —CO—O—, —$NR^{12'}$—CO—, —CO—$NR^{12'}$—, —$NR^{12'}$—CO—O—, —$NR^{12'}$—CO—$NR^{13'}$—, —$NR^{12'}$—$SO_2$— or $SO_2$—$NR^{12'}$—, $R^{11'}$ is a hydrogen, substituted or unsubstituted alkyl, substituted or unsubstituted alkenyl, substituted or unsubstituted alkynyl, substituted or unsubstituted aromatic carbon ring group, substituted or unsubstituted non-aromatic carbon ring group, substituted or unsubstituted aromatic heterocyclic group or substituted or unsubstituted non-aromatic heterocyclic group, $R^{12'}$ and $R^{13'}$ are, respectively independently, a hydrogen atom, substituted or unsubstituted alkyl, substituted or unsubstituted alkenyl or substituted or unsubstituted alkynyl, if X1' is —$NR^{12'}$—, —CO—$NR^{12'}$— or $SO_2$—$NR^{12'}$, $R^{11'}$ and $R^{12'}$ may, together with an adjacent nitrogen atom, form a substituted or unsubstituted non-aromatic heterocycle, if $X^{1'}$ is —$NR^{12'}$—CO—$NR^{13'}$—, R11' and $R^{13'}$ may, together with an adjacent nitrogen atom, form a substituted or unsubstituted non-aromatic heterocycle, $R^{1'}$ may, together with a carbon atom or a nitrogen atom on the arc of the $T^1$ ring, form a substituted or unsubstituted monocyclic carbon ring or substituted or unsubstituted monocyclic heterocycle, and this carbon ring or heterocycle may be further condensed with a substituted or unsubstituted carbon ring or substituted or unsubstituted heterocycle;

R2' may be, respectively independently, a substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted cycloalkyloxy, or substituted or unsubstituted cycloalkenyloxy;

n' is 1 or 2;

R3' may be a substituted or unsubstituted aromatic carbon ring group, substituted or unsubstituted non-aromatic carbon ring group, substituted or unsubstituted aromatic heterocyclic group, or substituted or unsubstituted non-aromatic heterocyclic group; and $R^{4'}$ is hydrogen or a carboxy protective group).

[10] The pharmaceutical agent according to [8] wherein (B) is at least one selected from: AZT, 3TC, didanosine, zalcitabine, sanilvudine, abacavir, tenofovir, tenofovir disoproxil, tenofovir alafenamide, emtricitabine, nevirapine, efavirenz, capravirine, etravirine, delavirdine, rilpivirine, VM-1500A, VM-1500, doravirine, MK-8507, MK-8504, MK-8583, a compound I'-001, I'-027, I'-043, I'-189, I'-220, I'-292, I'-304, indinavir, ritonavir, saquinavir, nelfinavir, amprenavir, atazanavir, lopinavir, fosamprenavir, darunavir, maraviroc, Enfuvirtide, Ibalizumab, PRO-140, temsavir, fostemsavir tromethamine, Combinectin, BDM-2, GSK-2838232, GSK-3640254, GS-6207, MK-8527 and MK-8558, and pharmaceutically acceptable salts thereof.

[10-1] The pharmaceutical agent according to [8-1] wherein (B) is at least one selected from: AZT, 3TC, didanosine, zalcitabine, sanilvudine, abacavir, tenofovir, tenofovir disoproxil, tenofovir alafenamide, emtricitabine, nevirapine, efavirenz, capravirine, etravirine, delavirdine, rilpivirine, VM-1500A, VM-1500, doravirine, MK-8507, MK-8504, MK-8583, a compound I'-001, I'-027, I'-043, I'-189, I'-220, I'-292, I'-304, indinavir, ritonavir, saquinavir, nelfinavir, amprenavir, atazanavir, lopinavir, fosamprenavir, darunavir, maraviroc, Enfuvirtide, Ibalizumab, PRO-140, temsavir, fostemsavir tromethamine, Combinectin, BDM-2, GSK-2838232, GSK-3640254, OS-6207, MK-8527 and MK-8558, pharmaceutically acceptable salts thereof, and 3BNC117LS, 10-1074LS, GS-9722, GS-9723, N6LS, ARC07-523LS, and VRC01-LS.

[11] The pharmaceutical agent according to any of [1] to [10], [8-1] and [10-1], wherein (A) and (B) are administered in combination.

[12] The pharmaceutical agent according to any of [1] to [10], [8-1] and [10-1], which is a combined formulation.

[13] anti-HIV action enhancing agent including a compound as specified by (A) of [1] or a pharmaceutically acceptable salt thereof, and a compound as specified by (B) of [1] having an anti-HIV action, or a pharmaceutically acceptable salt thereof.

[14] An anti-HIV action enhancing agent including a compound as specified by (B) of [1] or a pharmaceutically acceptable salt thereof, and a compound as specified by (A) of [1] having an anti-HIV action, or a pharmaceutically acceptable salt thereof.

[15] A pharmaceutical agent containing as an active constituent a compound as specified by (A) of [1] or a pharmaceutically acceptable salt thereof and a compound as specified by (B) of [1] having an anti-HIV action, or a pharmaceutically acceptable salt thereof for use in combination.

[16] A pharmaceutical agent containing as an active constituent a compound as specified by (B) of [1] or a pharmaceutically acceptable salt thereof and a compound as specified by (A) of [1] having an anti-HV action, or a pharmaceutically acceptable salt thereof for use in combination.

Effect of the Invention

The pharmaceutical agent according to the present invention is useful for treatment and/or prophylaxis of HIV infectious diseases.

BEST MODE FOR CARRYING OUT THE INVENTION

Various terms used in this specification will now be described. Unless otherwise specified, these terms shall have same meaning whether they are used alone or in combination with other terms.

The term "consisting of" means only the component requirements. p The term "including" means it is not limited to the component requirements and does not exclude elements not listed.

The present invention is a pharmaceutical agent characterized by combining (A) a compound represented by the formula (I):

[Chem. 4]

(I)

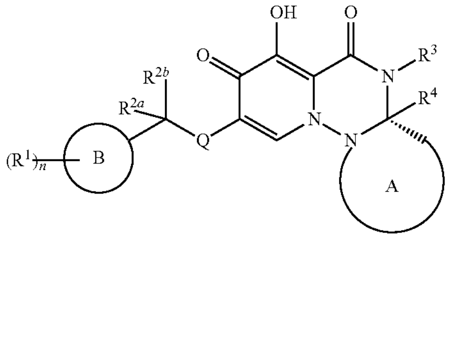

(where, in this formula, ring A is any of the following rings:

[Chem. 5]

(a)

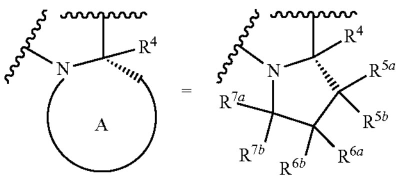

(b)

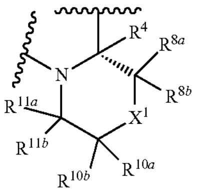

X1 is $CR^{9a}R^{9b}$ or O;

$R^{5a}$, $R^{5b}$, $R^{6a}$, $R^{6b}$, $R^{7a}$ and $R^{7b}$ are respectively independently hydrogen, halogen, alkyl, haloalkyl, alkyloxy, or alkyloxyalkyl or 3-member non-aromatic carbon ring groups;

$R^{5a}$ and $R^{6a}$, or $R^{6a}$ and $R^{7a}$ may form, together with an adjacent atom, an aromatic carbon ring, which may be halogen-substituted, a 3-6 member non-aromatic carbon ring, which may be halogen-substituted, or a 4-6 member non-aromatic heterocycle, which may be halogen-substituted (in the case where an aromatic carbon ring is formed, $R^{5b}$ and $R^{6b}$, or $R^{6b}$ and $R^{7b}$ may come together to form a bond);

$R^{5b}$ and $R^{6b}$ may come together to form a bond;

$R^{8a}$, $R^{8b}$, $R^{9a}$, $R^{9b}$, $R^{10a}$, $R^{10b}$, $R^{11a}$ and $R^{11b}$ are respectively independently hydrogen, halogen, alkyl, haloalkyl, alkyloxy, or alkyloxyalkyl or 3-member non-aromatic carbon ring groups;

$R^{8a}$ and $R^{10a}$ may together form a C1l-C3 cross-linkage;

$R^{10a}$ and $R^{11a}$, together with an adjacent atom, may form a 5-member non-aromatic carbon ring;

$R^{9a}$ and $R^{9b}$, together with an adjacent atom, may form a 4-member non-aromatic carbon ring or 5-member non-aromatic heterocycle;

$R^{8a}$ and $R^{9a}$ may come together to form a bond;

the B ring is a benzene ring or pyridine ring;

Q is —NHC(O)— or a 5-member aromatic heterocycle;

$R^1$ is respectively independently halogen, alkyl, haloalkyl, alkyloxy, cyano or haloalkyloxy;

$R^{2a}$ and $R^{2b}$ are respectively independently hydrogen, alkyl or haloalkyl;

$R^3$ is alkyl or haloalkyl;

$R^4$ is hydrogen or alkyl; and n is an integer of 1 to 3)

or a pharmaceutically acceptable salt thereof; and a compound (B) having anti-HIV activity, or a pharmaceutically acceptable salt thereof.

As the "compounds with anti-HIV activity" of (B) that is combined with (A), a compound ma be employed in respect of which the $EC_{50}$ value when measured in accordance with the method described in the Test Example 1 below is less than 100 μM, preferably less than 1 μM and even more preferably less than 100 mM. However, the "compounds with anti-HIV activity, or pharmaceutically acceptable salt thereof" of (B) is to be a compound different from the compound used as (A) or pharmaceutically acceptable salt thereof.

Given as "compounds with anti-HIV activity" are, for example, a compounds with a polymerase inhibitory activity, a compounds with a ribonuclease H inhibitory activity, a compounds with an HIV-1 integrase (IN)-lens epithelium-derived growth factor (LEDGE) complex allosteric inhibitory activity, compounds with a protease inhibitory activity, compounds with an adsorption and invasion inhibitory activity, compounds with a budding inhibitory activity, compounds with a maturation inhibitory activity, a compounds with a capsid inhibitory activity, or an antibody having an anti-HIV action equivalent to these.

Although "compounds having anti-HIV activity" are not restricted to compounds that are being marketed or are in the course of development, as compounds that are being marketed or are in the course of development, the following may be given as examples: AZT, 3TC, didanosine, zalcitabine, sanilvudine, abacavir, tenofovir, tenofovir disoproxil, tenofovir alafenamide, emtricitabine, nevirapine, efavirenz, capravirine, etravirine, delavirdine, VM-1500A, VM-1500, doravirine, MK-8507, MK-8504, MK-8583, indinavir, ritonavir, saquinavir, nelfinavir, amprenavir, atazanavir, lopinavir, fosamprenavir, darunavir, maraviroc, enfuvirtide, ibalizumab, S-648414, PRO-140, temsavir, fostemsavir tromethamine, combinectin, BDM-2, GSK-2838232, GSK-3640254, GS-6207, MK-8527, MK-8558, 3BNC117LS, 10-1074LS, GS-9722, GS-9723, N6LS, ARC07-523LS, VRC01-LS and the like. 3TC, abacavir, tenofovir, tenofovir alafenamide, emtricitabine, rilpivirine, VM-1500A, VM-1500, doravirine, MK-8504, MK-8583, atazanavir, darunavir, maraviroc, enfuvirtide, ibalizumab, S-648414, PRO-140, fostemsavir tromethamine, combinectin, PDM-2, GSK-2838232, GSK-3640254, GS-6207 and the like are even more preferable. "Compounds with anti-HIV activity" should be those that have a mechanism of action different from that of the compound used as (A) or its pharmaceutically acceptable salt, for example, compounds other than compounds with an HIV integrase inhibitory activity Preferably, these are compounds with a polymerase inhibitory activity, compounds with an HIV-1 integrase (IN)-lens epithelium-derived growth factor (LEDGF) complex allosteric inhibitory activity, or compounds with a protease inhibitory activity. Even more preferably, it should be compounds with a polymerase inhibitory activity.

"Compounds with a polymerase inhibitory activity" can be any compounds that have polymerase inhibitory activity and fall under the above "compounds with anti-HIV activity". Prodrugs of these compounds are also included.

"Compounds having polymerase inhibitory activity" include, hut are not limited to, the following compounds:

3'-azido-3'-deoxythymidine;

(−)-1-[(2R,5S)-2-(hydroxymethyl)-1,3-oxathiolan-5-yl]-cytosine;

2',3'-dideoxyinosine;

2',3'-dideoxycytidine;

(−)-2',3'-didehydro-3'-deoxythymidine;

(1S,4R)-4-[2-amino-6-(cyclopropylamino)-9H-purin-9-yl]-2-cyclopentene-1-methanol;

[[(R)-2-(6-amino-9H-purin-9-yl)-1-methylethoxy]methyl]phosphonic acid;

4-amino-5-fluoro-1-[(2R,5S)-2-(hydroxymethyl)-1,3-oxathiolan-5-yl]pyrimidin-2(H)-one;

11-cyclopropyl-5,11-dihydro-4-methyl-6H-dipyrido[3,2-b:2',3'-e][1,4]diazepin-6-one;

(−)-(S)-6-chloro-4-(cyclopropylethynyl)-1,4-dihydro-4-(trifluoromethyl)-2H-3,1-benzoxazin-2-one;

5-[(3,5-dichlorophenyl)thio]-4-isopropyl-1-(4-pyridylmethyl)imidazole-2-methanol carbamate;

4-[6-amino-5-bromo-2-(4-cyanoanilino)pyrimidin-4-yloxy]-3,5-dimethylbenzonitrile;

N-(2-(4-(3-(isopropylamino)pyridin-2-yl)piperazine-1-carbonyl)-1H-indol-5-yl)methanesulfonamide;

4-[[4-[[4-[(1E)-2-cyanoethenyl]-2,6-dimethylphenyl]amino]pyrimidin-2-yl]amino]benzonitrile;

2-(4-bromo-3-(3-chloro-5-cyanophenoxy)-2-fluorophenyl)-N-(2-chloro-4-sulfamoylphenyl)acetamide;

N-[4-[[2-[4-bromo-3-(3-chloro-5-cyanophenoxy)-2-fluorophenyl]acetyl]amino]-3-chlorophenyl]sulfonylpropanamide;

3-chloro-5-[[1-[(4-methyl-5-oxo-4,5-dihydro-1H-1,2,4-triazol-3-yl)methyl]-2-oxo-4-(trifluoromethyl)-1,2-dihydropyridin-3-yl]oxy]benzonitrile;

MK-8507; and the compounds described in WO2014/058747.

Further, as examples of prodrugs, the following compounds may be given as examples.

(R)-[[2-(6-amino-9H-purin-9-yl)-1-methylethoxy]methyl]phosphonic acid bis(isopropoxycarbonyloxymethyl)ester;

1-methylethyl N-[(S)-[[(1R)-2-(6-amino-9H-purin-9-yl)-1-methylethoxy]methyl]phenoxyphosphinoyl]-L-alaninate;

MK-8504;

MK-8583.

Preferred examples of "compounds with a polymerase inhibitory activity, or pharmaceutically acceptable salt thereof" are: AZT, 3TC, didanosine, zalcitabine, sanilvudine, abacavir, abacavir sulfate, tenofovir, tenofovir disoproxil, tenofovir disoproxil fumarate, tenofovir alafenamide, tenofovir alafenamide fumarate, emtricitabine, nevirapine, efavirenz, capravirine, etravirine, delavirdine, delavirdine mesilate, rilpivirine, rilpivirine hydrochloride, VM-1500A, VM-1500, doravirine, MK-8507, MK-8504, MK-8583 and the like. 3TC, abacavir, abacavir sulfate, tenofovir, tenofovir alafenamide fumarate, emtricitabine, rilpivirine, rilpivirine hydrochloride, VM-1500A, VM-1500, doravirine, MK-8504, MK-8583 and the like are even more preferable.

"Compounds with a ribonuclease H inhibitory activity" can be any inhibitory activity compound that have ribonuclease H inhibitory activity and fall under the category of "compounds with anti-HIV activity" above. Prodrugs of these compounds are also included.

"Compounds with ribonuclease H inhibitory activity" include, but are not limited to, the following compounds:

the compounds described in WO2008/010964; and the compounds described in WO2011/075747.

"Compounds having an HIV-1 integrase (IN)-lens epithelium-derived growth factor (LEDGF) complex allosteric inhibitory activity" means any compound having an HIV-1 integrase (IN)-lens epithelium-derived growth factor (LEDGF) complex allosteric inhibitory activity, and any of the above "compounds having an anti-HIV action" may be used. Their prodrug forms are also included.

As "compounds having an HIV-1 integrase (IN)-lens epithelium-derived growth factor (LEDGF) complex allosteric inhibitory activity", the compounds described in WO2015/174511 and WO2016/194806 and the like may be given as examples. Examples include, but are not but are not limited to these.

[Chem. 6]

(I')

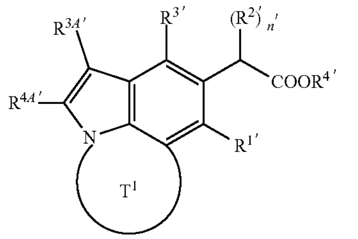

(where, in this formula, $R^{3A'}$ and $R^{4A'}$ are respectively independently, hydrogen, halogen, hydroxy, substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted alkylcarbonyl, substituted or unsubstituted alkenylcarbonyl, substituted or unsubstituted alkynylcarbonyl, substituted or unsubstituted aromatic carbon ring group, substituted or unsubstituted non-aromatic carbon ring group, substituted or unsubstituted aromatic heterocyclic group, substituted or unsubstituted non-aromatic heterocyclic group, substituted or unsubstituted aromatic carbon ring oxy, substituted or unsubstituted non-aromatic carbon ring oxy, substituted or unsubstituted aromatic heterocyclic oxy, substituted or unsubstituted non-aromatic heterocyclic oxy, substituted or unsubstituted aromatic carbon ring sulfanyl, substituted or unsubstituted non-aromatic carbon ring sulfanyl, substituted or unsubstituted aromatic heterocyclic sulfanyl, substituted or unsubstituted non-aromatic heterocyclic sulfanyl, substituted or unsubstituted aromatic carbon ring carbonyl, substituted or unsubstituted non-aromatic carbon ring carbonyl, substituted or unsubstituted aromatic heterocyclic carbonyl, substituted or unsubstituted non-aromatic heterocyclic carbonyl, substituted or unsubstituted amino, or substituted or unsubstituted carbamoyl;

$R^{3A'}$ and $R^{4A'}$, together with an adjacent atom, may form a substituted or unsubstituted monocyclic carbon ring, or substituted or unsubstituted monocyclic heterocycle. This carbon ring or heterocycle may furthermore be condensed with a substituted or unsubstituted carbon ring or substituted or unsubstituted heterocycle;

$R^{4A'}$ may form a substituted or unsubstituted monocyclic heterocycle, together with an atom on the arc of the $T^1$ ring, and this heterocycle may be further condensed with a substituted or unsubstituted carbon ring or a substituted or unsubstituted hetero cyclic ring;

the $T^1$ ring is a substituted or unsubstituted monocyclic heterocycle, (1) this heterocycle may be condensed with another substituted or unsubstituted carbon ring or substituted or unsubstituted heterocycle, and/or two mutually non-adjacent atoms constituting this heterocycle may be crosslinked by a substituted or unsubstituted alkylene, substituted or unsubstituted alkenylene, or substituted or unsubstituted alkynylene;

$R^{1'}$ is a halogen, cyano, nitro or $X^{1'}$—$R^{11'}$, $X^{1'}$ is a single bond, —O—, —S—, $NR^{12'}$—, —CO—, —SO—, —$SO_2$—, —O—CO—, —CO—O—, —$NR^{12'}$—CO—, —CO—$NR^{12'}$—, —$NR^{12'}$—CO—O—, —$NR^{12'}$—CO—$NR^{13'}$—, —$NR^{12'}$—$SO_2$— or $SO_2$—$NR^{12'}$—, $R^{11'}$ is a hydrogen atom, substituted or unsubstituted alkyl, substituted or unsubstituted alkenyl, substituted or unsubstituted alkynyl, substituted or unsubstituted aromatic carbon ring group, substituted or unsubstituted non-aromatic carbon ring group, substituted or unsubstituted aromatic heterocyclic group or substituted or unsubstituted non-aromatic heterocyclic group, $R^{12'}$ and $R^{13'}$ are, respectively independently, a hydrogen atom, substituted or unsubstituted alkyl, substituted or unsubstituted alkenyl or substituted or unsubstituted alkynyl, when X1' is —$NR^{12'}$—, —CO—$NR^{12'}$— or $SO_2$—$NR^{12'}$—, R11' and $R^{12'}$ may form a substituted or unsubstituted aromatic heterocycle together with an adjacent nitrogen atom, when X1' is —$NR^{12'}$—CO—$NR^{13'}$—, R11' and $R^{13'}$ may form a substituted or unsubstituted non-aromatic heterocycle together with an adjacent nitrogen atom, $R^{1'}$, together with a carbon atom or nitrogen atom on the arc of the $T^1$ ring, may form a substituted or unsubstituted monocyclic carbon ring, or substituted or unsubstituted monocyclic heterocycle, and this carbon ring or heterocycle may be further condensed, $R^{2'}$ is, respectively independently, a substituted or unsubstituted alkyl, substituted or unsubstituted alkenyl, substituted or unsubstituted alkynyl, substituted or unsubstituted alkyloxy, substituted or unsubstituted alkenyloxy, substituted or unsubstituted alkynyloxy, substituted or unsubstituted cycloalkyloxy, or substituted or unsubstituted cycloalkenyloxy;

n' is 1 or 2;

$R^{3'}$ is a substituted or unsubstituted aromatic carbon ring group, substituted or unsubstituted non-aromatic carbon ring group, substituted or unsubstituted aromatic heterocyclic group, or substituted or unsubstituted non-aromatic heterocyclic group; and $R^{4'}$ is hydrogen or a carboxy protective group).

As the "compounds with an HIV-1 integrase (IN)-lens epithelium-derived growth factor (LEDGF) complex allosteric inhibitory activity, or pharmaceutically acceptable salt thereof" preferably the following compounds or pharmaceutically acceptable salts thereof may be given as examples.

[Chem. 7]

I'-001

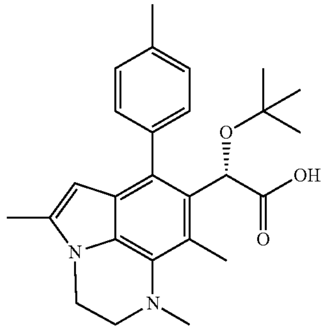

-continued

I'-027

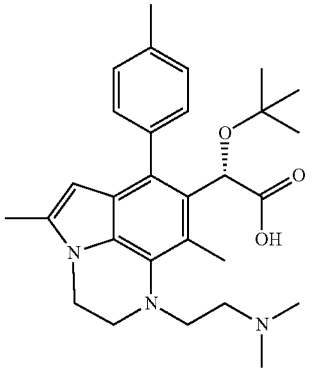

I'-043

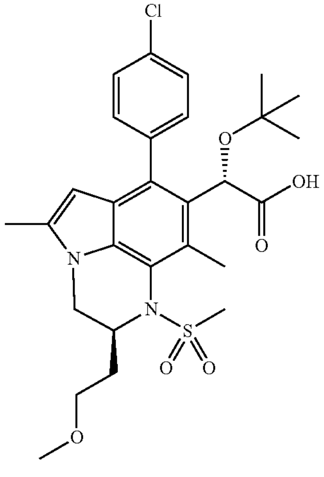

I'-189

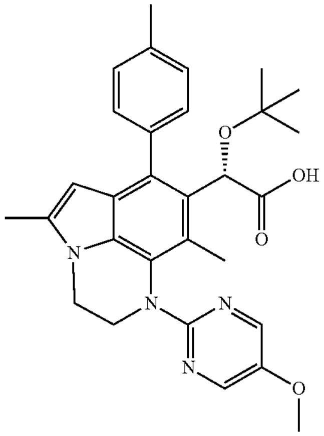

-continued

I'-220

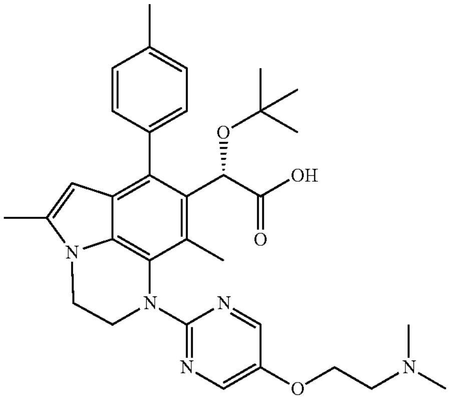

I'-292

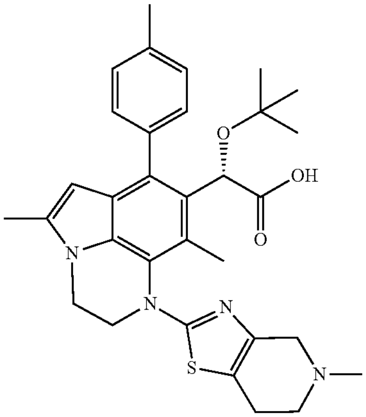

I'-304

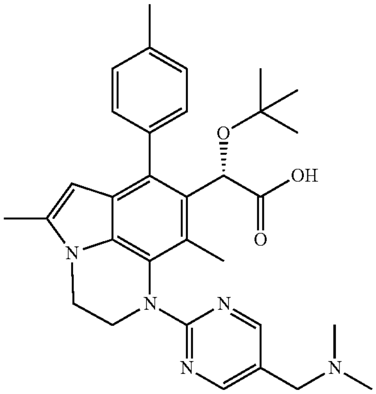

"Compounds with a protease inhibitory activity" means any compounds that have protease inhibitory activity and fall under the category of "compounds with anti-HIV activity" above. Prodrugs of these compounds are also included.

"Compounds having a protease inhibitory activity" include, but are not limited to, the following compounds.

(S)-1-((2S,4R)-4-benzyl-2-hydroxy-5-(((1S,2R)-2-hydroxy-2,3-dihydro-1H-inden-1-yl)amino)-5-oxopentyl)-N-(tert-butyl)-4-(pyridin-3-ylmethyl)piperazine-2-carboxamide;

5-thiazolymethyl [(αS)-α-[(1S,3S)-1-hydroxy-3-[(2S)-2-[3-[(2-isopropyl-4-thiazolyl)methyl]-3-methylureido]-3-methylbutyramido]-4-phenylbutyl]phenetyl]carbamate;

(−)-cis-N-tert-butyldecahydro-2-[(2R,3S)-2-hydroxy-4-phenyl-3-[[N-(2-quinolylcarbonyl)-L-asparaginyl]amino]butyl]-(3S,4aS,8aS)-isoquinoline-3-carboxamide;

(−)-(3S,4aS,8aS)-N-tert-butyl-2-[(2R,3R)-2-hydroxy-3-(3-hydroxy-2-methylbenzoylamino)-4-(phenylthio)butyl]decahydroisoquinoline-3-carboxamide;

(3S)-tetrahydro-3-furyl[N-[(1S,2R)-3-(4-amino-N-isobutylbenzenesulfonamido)-1-benzyl-2-hydroxypropyl]carbamate;

dimethyl (3S,8S,9S,12S)-9-benzyl-3,12-di-tert-butyl-8-hydroxy-4,11-dioxo-6-[4-(pyridin-2-yl)benzyl]-2,5,6,10,13-pentaazatetradecanedioate;

(αS)-tetrahydro-N-[(αS)-α-[(2S,3S)-2-hydroxy-4-phenyl-3-[2-(2,6-xylyloxy)-acetamido]butyl]phenethyl]-α-isopropyl-2-oxo-1(2H)-pyrimidineacetamide;

(S)-tetrahydrofuran-3-yl((2S,3R)-4-((4-amino-N-isobutylphenyl)sulfonamido)-1-phenyl-3-(phosphonooxy)butan-2-yl)carbamate; and (3R,3aS,6aR)-hexahydrofuro[2,3-b]furan-3-yl [(1S,2R)-3-[[(4-aminophenyl)sulfonyl](2-methylpropyl)amino]-1-benzyl-2-hydroxypropyl] carbamate.

As the "compounds with a protease inhibitory activity, or pharmaceutically acceptable salt thereof", indinavir, indinavir sulfate ethanolate, ritonavir, saquinavir, saquinavir mesilate, nelfinavir, nelfinavir mesilate, amprenavir, atazanavir, atazanavir sulfate, lopinavir, fosamprenavir, fosamprenavir calcium hydrate, darunavir, darunavir ethanolate and the like may be given as examples.

Even more preferably, atazanavir, atazanavir sulfate, darunavir, darunavir ethanolate and the like may be given as examples.

"Compounds with an adsorption and invasion inhibitory activity" can be any compounds that have adsorption and penetration inhibitory activity and fall under the above "compounds with anti-HIV activity". Prodrugs of these compounds are also included.

Compounds with adsorption and penetration inhibitory activity" include, but are not limited to, the following compounds.

4,4-difluoro-N-[(1S)-3-[(1R,3S,5S)-3-[3-methyl-5-(propan-2-yl)-4H-1,2,4-triazol-4-yl]-8-azabicyclo[3.2.1]octan-8-yl]-1-phenylpropyl]cyclohexanecarboxamide;

N-acetyl-L-tyrosyl-L-threonyl-L-seryl-L-leucyl-L-isoleucyl-L-histadyl-L-seryl-L-leucyl-L-isoleucyl-L-α-glutamyl-L-α-glutamyl-L-seryl-L-glutaminyl-L-asparaginyl-L-glutaminyl-L-glutaminyl-L-α-glutamyl-L-lysyl-L- asparaginyl-L-α-glutamyl-L-glutaminyl-L-α-glutamyl-L-leucyl-L-leucyl-L-α-glutamyl-L-leucyl-L-α-aspartyl-L-lysyl-L-tryptophyl-L-alanyl-L-seryl-L-leucyl-L-tryptophyl-L-asparaginyl-L-tryptophyl-L-phenylalaninamide;

anti-CD4 antibody;

anti-CCR5 antibody;

1-(4-benzoylpiperazin-1-yl)-2-[4-methoxy-7-(3-methyl-1H-1,2,4-triazol-1-yl)-1H-pyrrolo[2,3-c]pyridin-3-yl]ethane-1,2-dione;

combinectin.

Further, as a prodrug, for example, the following compound may be given as examples: fostemsavir tromethamine.

Preferably, "compounds with an adsorption and invasion inhibitory activity, or pharmaceutically acceptable salt thereof", include maraviroc, enfuvirtide, ibalizumab, PRO-140, temsavir, fostemsavir tromethamine, or combinectin.

"Compounds with a budding inhibitory activity" can be any compounds that have budding inhibitory activity and fall under the above "compounds with anti-HIV activity". Prodrug forms thereof are also included.

"Compounds with a maturation inhibitory activity" means any compounds that have maturation inhibitory action and fall under the above "compounds having anti-HIV activity". Their prodrug forms are also included.

"Compounds having a maturation inhibitory activity" include but are not limited to, the compounds listed below.

GSK-2838232;

GSK-3640254.

Preferably, GSK-2838232, GSK-3640254, and the like are listed as "compounds having maturation inhibitory activity or pharmaceutically acceptable salts thereof.

"Compounds with a capsid inhibitory activity" means any compounds that have Capsid inhibitory activity and fall under "compounds with anti-HIV activity" above. Their prodrug forms are also included.

"Compounds having a capsid inhibitory activity include, but are not limited to, the compounds listed below.

The compounds described in WO2012/065062;
The compounds described in WO2013/006738;
The compounds described in WO2014/110296;
The compounds described in WO2014/110297;
The compounds described in WO2014/110298;
The compounds described in WO2014/134566;
The compounds described in WO2015/130966;
The compounds described in WO2016/033243;
The compounds described in WO2018/035359;
The compounds described in WO2018/203235;
The compounds described in WO2019/161017;
The compounds described in WO2019/198024;
The compounds described in WO2020/031112;
The compounds described in WO2020/053811;
The compounds described in WO2020/058844;
The compounds described in WO2020/084480;
The compounds described in WO2020/084491;
The compounds described in WO2020/084492;
The compounds described in WO2020/089778;
The compounds described in WO2020/095176;
The compounds described in WO2020/095177;
The compounds described in WO2020/157697.

Preferably, "compounds with a capsid inhibitory activity, or pharmaceutically acceptable salts thereof" include GS-6207 (Lenacapavir).

[Chem. 8]

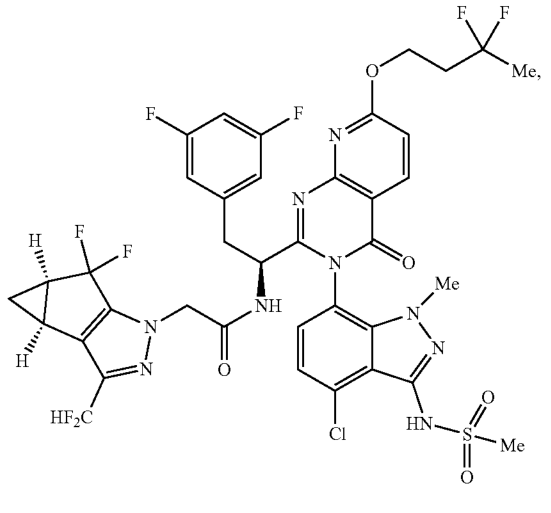

-continued

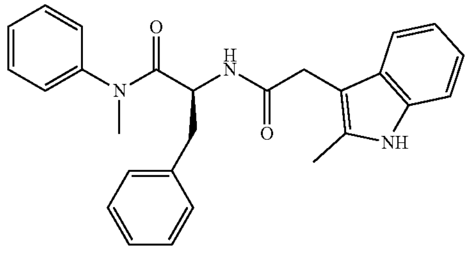

C

The term “antibodies with equivalent anti-HIV activity” means any compounds that have anti-HIV activity and fall under the category of “compounds with anti-HIV activity” mentioned above.

“Antibodies having an anti-HIV action equivalent to these” include, but are not limited to, the antibodies listed below.

3BNC117LS;

10-1074LS;

GS-9722;

GS-9723;

N6LS;

ARC07-523LS;

VRC01-LS.

“Antibody having an anti-HIV action, or pharmaceutically acceptable salt thereof” means one or more than one agent, and is not limited to one agent.

The compound of Formula (I) of (A), or a pharmaceutically acceptable salt thereof, or a solvate thereof, may be described as follows.

“Halogen” includes a fluorine atom, chlorine atom, bromine atom and iodine atom. Fluorine atoms and chlorine atoms are particularly preferred.

“Alkyl” includes straight-chain or branched hydrocarbon groups with 1 to 15 carbons, preferably 1 to 10 carbons, more preferably 1 to 6 carbons, and even more preferably 1 to 4 carbons. Examples include: methyl, ethyl, n-propyl, isopropyl, n-butyl, isobutyl, sec-butyl, tert-butyl, n-pentyl, isopentyl, neopentyl, n-hexyl, isohexyl, n-heptyl, isoheptyl, n-octyl, isooctyl, n-nonyl, n-decyl and the like.

Preferred examples of “alkyl” are: methyl, ethyl, n-propyl, isopropyl, n-butyl, isobutyl, sec-butyl, tert-butyl, and n-pentyl. More preferred examples are: methyl, ethyl, n-propyl, isopropyl, or tert-butyl.

“Alkenyl” includes straight-chain or branched hydrocarbon groups having one or more double bonds in an arbitrary position, with 2 to 15 carbons, preferably 2 to 10 carbons, more preferably 2 to 6 carbons, and even more preferably 2 to 4 carbons. Given as examples are: vinyl, allyl, propenyl, isopropenyl, butenyl, isobutenyl, prenyl, butadienyl, pentenyl, isopentenyl, pentadienyl, hexenyl, isohexenyl, hexadienyl, heptenyl, octenyl, nonenyl, decenyl, undecenyl, dodecenyl, tridecenyl, tetradecenyl, pentadecenyl and the like.

Preferred examples of “alkenyl” are: vinyl, allyl, propenyl, isopropenyl, or butenyl. Even more preferred examples are ethenyl, n-propenyl and the like.

“Alkynyl” includes straight-chain or branched hydrocarbon groups having one or more triple bonds in an arbitrary position, with 2 to 15 carbons, preferably 2 to 8 carbons, more preferably 2 to 6 carbons, and even more preferably 2 to 4 carbons. Furthermore, a double bond may be present at an arbitrary position. Examples include: ethynyl, propynyl, butynyl, pentynyl, hexynyl, heptynyl, octynyl, nonynyl, decynyl and the like.

Preferred examples of “alkynyl” are: ethynyl, propynyl, butynyl, and pentynyl. Even more preferred examples are ethynyl, propynyl and the like.

“Alkylene” includes straight-chain or branched divalent hydrocarbon groups with 1 to 15, preferably 1 to 10, more preferably 1 to 6 carbons, and even more preferably 1 to 4 carbons. Examples include: methylene, ethylene, trimethylene, propylene, tetramethylene, pentamethylene, and hexamethylene.

“Alkenylene” includes straight-chain or branched divalent hydrocarbon groups having one or more double bonds at an arbitrary position, with 2 to 15 carbons, preferably 2 to 10 carbons, more preferably 2 to 6 carbons, and even more preferably 2 to 4 carbons.

Examples are vinylene, propenylene, butenylene, pentenylene and the like.

“Alkynylene” includes straight-chain or branched divalent hydrocarbon groups having one or more triple bonds at an arbitrary position, with 2 to 15 carbons, preferably 2 to 10 carbons, more preferably 2 to 6 carbons, and even more preferably 2 to 4 carbons. Furthermore, a double bond may be present at an arbitrary position. Examples include: ethynylene, propynylene, butynylene, pentynylene and hexynylene.

An “aromatic carbon ring group” means a monocyclic or bicyclic cyclic aromatic hydrocarbon group. Examples include: phenyl, naphthyl, anthryl, or phenanthryl and the like.

Phenyl is a preferred example of an “aromatic carbon ring group”.

A “non-aromatic carbon ring group” means a monocyclic or bicyclic cyclic saturated hydrocarbon group or cyclic non-aromatic unsaturated hydrocarbon group. A bicyclic or more “non-aromatic carbon ring group” includes the result of condensing the ring in the above “aromatic carbon ring group” with a monocyclic, bicyclic or more non-aromatic carbon ring group.

Furthermore, a “non-aromatic carbon ring group” includes groups that are cross-linked as shown below or a group forming a spiro ring.

[Chem. 9]

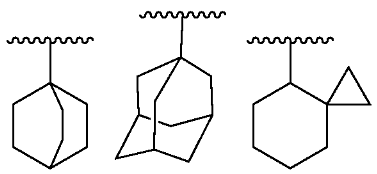

For the monocyclic non-aromatic carbon ring group, 3 to 16 carbons is preferable, 3 to 12 carbons is more preferable, and 4 to 8 carbons is even more preferable. Examples include: cyclopropyl, cyclobutyl, cyclopentyl, cyclohexyl, cycloheptyl, cyclooctyl, cyclononyl, cyclodecyl, cyclopropenyl, cyclobutenyl, cyclopentenyl, cyclohexenyl, cycloheptenyl, and cyclohexadienyl.

For the bicyclic or more non-aromatic carbon ring group, 8 to 20 carbons is preferable, and 8 to 16 carbons is more preferable. Examples include: indanyl, indenyl, acenaphthyl, tetrahydronaphthyl, or fluorenyl.

For the “cycloalkyl” 3 to 10 carbons is preferable and 3 to 7 carbons is more preferable; examples include: cyclopropyl, cyclobutyl, cyclopentyl, cyclohexyl, cycloheptyl, cyclooctyl, cyclononyl, or cyclodecyl.

For the "cycloalkenyl", examples include: cyclopropenyl, cyclobutenyl, cyclopenenyl, cyclohexenyl, cycloheptenyl, or cyclohexadienyl.

An "aromatic heterocyclic group means a monocyclic or bicyclic or more aromatic group having in the ring one or more heteroatoms, which may be the same or different, arbitrarily selected from O, S and N.

A bicyclic or more aromatic heterocyclic group includes a group produced by condensing the ring in the above "aromatic carbon ring group" with a monocyclic or bicyclic aromatic heterocyclic group; the bond may be in either ring.

As the monocyclic aromatic heterocyclic group, a 5 to 8 member group is preferred, more preferably a 5 or 6 member ring. Examples of 5-member aromatic heterocyclic groups are: pyrrolyl, imidazolyl, pyrazolyl, triazolyl, tetrazolyl, furyl, thienyl, isoxazolyl, oxazolyl, oxadiazolyl, isothiazolyl, thiazolyl, thiadiazolyl, and the like. Examples of 6-member aromatic heterocyclic groups are: pyridyl, pyridazinyl, pyrimidinyl, pyrazinyl, triazinyl and the like.

As the bicyclic aromatic heterocyclic group, an 8 to 10 member ring is preferred, and more preferably a 9 or 10 member ring.

Examples are; indolyl, isoindolyl, indolizinyl, quinolinyl, isoquinolinyl, cinnolinyl, phthalazinyl, quinazolinyl, naphthyridinyl, quinoxalinyl, plinyl, pteridinyl, benzimidazolyl, benzisoxazolyl, benzoxazolyl, benzoxadiazolyl, benzisothiazolyl, benzothiazolyl, benzothiadiazolyl, benzofuryl, isobenrofuryl, benzothienyl, benzotriarolyl, imidazopyridyl, triazolopyridyl, imidazothiarolyl, pyrazinopyridazinyl, oxazolopyridyl, or thiazolopyridyl.

As the tricyclic or more aromatic heterocyclic group, a 13 to 15 member ring is preferred. Examples include: carbazolyl, acridinyl, xanthenyl, phenothiazinyl, phenoxathiinyl, phenoxazinyl, or dibenzofuryl and the like.

A "non-aromatic heterocyclic group" means a monocyclic or bicyclic or more non-aromatic cyclic group having in the ring one or more hetero atoms, which may be the same or different, arbitrarily selected from O, S and N. A bicyclic or more non-aromatic heterocyclic group includes the case where, a respective ring in the above "aromatic carbon ring group", "non-aromatic carbon ring group" and/or "aromatic heterocyclic group" is condensed with a monocyclic or bicyclic or more aromatic heterocyclic group, and, furthermore, includes the case where a ring in the above "aromatic heterocyclic group" is condensed with a monocyclic or bicyclic or more non-aromatic carbon ring group; the bond may be in either ring.

Furthermore, a "non-aromatic heterocyclic group" includes the case where groups are cross-linked or form a spiro ring, as shown below.

[Chem. 10]

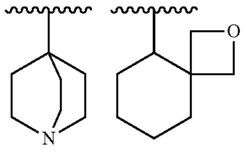

For the monocyclic non-aromatic heterocyclic group, a 3 to 8 member ring is preferable and a 5 or 6 member ring is more preferable.

3-member non-aromatic heterocyclic groups include for example thiiranyl, oxiranyl, or aziridinyl. 4-member non-aromatic heterocyclic groups include, for example, oxetanyl or azethidinyl. 5-member non-aromatic hetero groups include for example oxathiolanyl, thiazolidinyl, pyrrolidinyl, pyrrolinyl, imidazolinyl, imidazolinyl, pyrazolidinyl, pyrazolinyl, tetrahydrofuryl, dihydrothiazolyl, tetrahydroisothiazolyl, dioxolanyl, dioxolyl, or thiolanyl and the like. 6-member non-aromatic hetero groups include, for example, dioxanyl, thianyl, piperidyl, piperazinyl, morpholinyl, morpholine, thiomorpholinyl, thiomorpholino, dihydropyridyl, tetrahydropyridyl, tetrahydropyranyl, dihydrooxazinyl, tetrahydropyridazinyl, hexahydropyrimidinyl, dioxazinyl, thinlyl, thiazinyl and the like. 7-member non-aromatic hetero groups include, for example, hexahydroazepinyl, tetrahydrodiazepinyl, and oxepanyl.

Bicyclic aromatic heterocyclic groups are preferably of 8 to 20 members, more preferably 8 to 10 members. Examples include indolinyl, isoindolinyl, chromanyl, isochromanyl and the like.

"Aromatic carbon ring", "nonaromatic carbon ring", "aromatic heterocycle" and "non-aromatic heterocycle" respectively denote rings derived from the above "aromatic carbon ring group", "nonaromatic carbon ring group", "aromatic heterocyclic group" and "non-aromatic heterocyclic group".

A "carbon ring" denotes the above "aromatic carbon ring" or a "non-aromatic carbon ring".

A "heterocycle" denotes the above "aromatic heterocycle" or a "non-aromatic heterocycle".

A "carboxy protective group" may be for example an alkyl (example: methyl, ethyl, t-butyl) or aralkyl (example: benzyl), more preferably an alkyl with 1 to 4 carbons.

In this specification, "which may be substituted by a substituent α" signifies "which may be substituted by one or more groups selected from the set α of substituent groups".

The same applies to substituent groups β, γ, γ' and E.

"Which may be substituted by a halogen" signifies "which may be substituted by one or more groups selected from halogens". Substitution may be performed with one to three halogens.

As the substituent groups denoted by "substituent alkyl", "substituent alkenyl", "substituent alkylene", "substituent alkenylene", "substituent alkynylene", "substituent alkyloxy", "substituent alkenyloxy", "substituent alkynyloxy", "substituent alkylcarbonyl, "substituent alkenylcarbonyl" and "substituent alkynylcarbonyl", the following set A of substituent groups may be given as examples. A carbon atom in an arbitrary position may be bonded with one or more groups selected from the following set of substituent groups A.

The set of constituent groups A is: halogen, hydroxy, carboxy, formyl, formyloxy, sulfanyl, sulfino, sulfo, thioformyl, thiocarboxy, dithyocarboxy, thiocarbamoyl, cyano, nitro, nitroso, azide, hydrazino, ureide, amidino, guanidine, pentafluorothio, or trialkylsilyl;

alkyloxy, which may be substituted by the set a of substituent groups, alkenyloxy, which may be substituted by the set α of substituent groups, alkynyloxy, which may be substituted by the set α of substituent groups, alkylcarbonyloxy, which may be substituted by the set α of substituent groups, alkenylcarbonyloxy, which may be substituted by the set α of substituent groups, alkynylcarbonyloxy, which may be substituted by the set α of substituent groups, alkylcarbonyl, which may be substituted by the set α of substituent groups, alkenylcarbonyl, which nay be substituted by the set α of substituent groups, alkynylcarbonyl, which may be substituted by the set α of substituent groups, alkyloxycarbonyl, which may be substituted by the set α of substituent groups, alkenyloxycarbonyl, which may be substituted by the set α of substituent groups, alkynyloxycarbonyl, which may be substituted by the set α of substituent groups, alkylsulfanyl, which may be substituted by the set α of substituent groups, alkenylsulfanyl, which may be substituted by the set α of substituent groups, alkynylsulfanyl, which may be substituted by the set α of substituent groups, alkylsulfynyl, which may be substituted by the set α of substituent groups, alkenylsulfynyl, which may be substituted by the set α of substituent groups, alkynylsulfynyl, which may be substituted by the set α of substituent groups, alkylsulfonyl, which may be substituted by the set α of substituent groups, alkenylsulfonyl, which may be substituted by the set α of substituent groups, alkynylsulfonyl, which may be substituted by the set α of substituent groups, amino, which may be substituted by the set β of substituent groups, imino, which may be substituted by the set β of substituent groups, carbamoyl, which may be substituted by the set β of substituent groups, sulfamoyl, which may be substituted by the set β of substituent groups, aromatic carbon ring group, which may be substituted by the set γ of substituent groups, non-aromatic carbon ring group which may be substituted by the set γ' of substituent groups, aromatic heterocyclic group which may be substituted by the set γ of substituent groups, non-aromatic heterocyclic group which may be substituted by the set γ' of substituent groups, aromatic carbon ring oxy which may be substituted by the set γ of substituent groups, non-aromatic carbon ring oxy which may be substituted by the set γ' of substituent groups, aromatic heterocyclic oxy which may be substituted by the set γ of substituent groups, non-aromatic heterocyclic oxy which may be substituted by the set γ' of substituent groups, aromatic carbon ring carbonyloxy which may be substituted by the set γ of substituent groups, non-aromatic carbon ring carbonyloxy which may be substituted by the set γ' of substituent groups, aromatic heterocyclic carbonyloxy which may be substituted by the set γ of substituent groups, non-aromatic heterocyclic carbonyloxy which may be substituted by the set γ' of substituent groups, aromatic carbon ring carbonyl which may be substituted by the set γ of substituent groups, non-aromatic carbon ring carbonyl which may be substituted by the set γ' of substituent groups, aromatic heterocyclic carbonyl which may be substituted by the set γ of substituent groups, non-aromatic heterocyclic carbonyl which may be substituted by the set γ' of substituent groups, aromatic carbon ring oxycarbonyl which may be substituted by the set γ of substituent groups, non-aromatic carbon ring oxycarbonyl which may be substituted by the set γ' of substituent groups, aromatic heterocyclic oxycarbonyl which may be substituted by the set γ of substituent groups, non-aromatic heterocyclic oxycarbonyl which may be substituted by the set γ' of substituent groups, aromatic carbon ring alkyloxy which may be substituted by the set γ of substituent groups, non-aromatic carbon ring alkyloxy which may be substituted by the set γ" of substituent groups, aromatic heterocyclic alkyloxy which may be substituted by the set γ of substituent groups, non-aromatic heterocyclic alkyloxy which may be substituted by the set γ' of substituent groups, aromatic carbon ring alkyloxycarbonyl which may be substituted by the set γ of substituent groups, non-aromatic carbon ring alkyloxycarbonyl which may be substituted by the set γ' of substituent groups, aromatic heterocyclic alkyloxycarbonyl which may be substituted by the set γ of substituent groups, non-aromatic heterocyclic alkyloxycarbonyl which may be substituted by the set γ' of substituent groups, aromatic carbon ring sulfonyl which may be substituted by the set γ of substituent groups, non-aromatic carbon ring sulfanyl which may be substituted by the set γ' of substituent groups, aromatic heterocyclic sulfanyl which may be substituted by the set γ of substituent groups, non-aromatic heterocyclic sulfanyl which may be substituted by the set γ" of substituent groups, aromatic carbon ring sulfynyl which may be substituted by the set γ of substituent groups, non-aromatic carbon ring sulfynyl which may be substituted by the set γ' of substituent groups, aromatic heterocyclic sulfynyl which may be substituted by the set γ of substituent groups, non-aromatic heterocyclic sulfynyl which may be substituted by the set γ' of substituent groups, aromatic carbon ring sulfonyl which may be substituted by the set γ of substituent groups, non-aromatic carbon ring sulfonyl which may be substituted by the set γ' of substituent groups, aromatic heterocyclic sulfonyl which may be substituted by the set γ of substituent groups and non-aromatic heterocyclic sulfonyl which may be substituted by the set γ' of substituent groups.

The set α of substituent groups halogen, hydroxy, carboxy, alkyloxy, haloalkyloxy, alkenyloxy, alkynyloxy, alkylamino, dialkylamino, alkylaminoalkyloxy, dialkylaminoalkyloxy, sulfanyl, cyano, nitro, guanidino and pentafluorothio.

The set β of substituent groups: halogen, hydroxy, carboxy, cyano, alkyl which may be substituted by the set α of substituent groups, alkenyl which may be substituted by the set α of substituent groups, alkynyl which may be substituted by the set α of substituent groups, alkylcarbonyl which may be substituted by the set α of substituent groups, alkenylcarbonyl which may be substituted by the set α of substituent groups, alkynylcarbonyl which may be substituted by the set α of substituent groups, alkylsulfanyl which may be substituted by the set α of substituent groups, alkenylsulfanyl which may be substituted by the set α of substituent groups, alkynylsulfanyl which may be substituted by the set α of substituent groups, alkylsulfynyl which may be substituted by the set α of substituent groups, alkenylsulfynyl which may be substituted by the set α of substituent groups, alkynylsulfynyl which may be substituted by the set α of substituent groups, alkylsulfonyl which may be substituted by the set α of substituent groups, alkenylsulfonyl which may be substituted by the set α of substituent groups, alkynylsulfonyl which may be substituted by the set α of substituent groups, aromatic carbon ring group which may be substituted by the set γ of substituent groups, non-aromatic carbon ring group which may be substituted by the set γ' of substituent groups, aromatic heterocyclic group which may be substituted by the set γ of substituent groups, non-aromatic heterocyclic group which may be substituted by the set γ' of substituent groups, aromatic carbon ring alkyl which may be substituted by the set γ of substituent groups, non-aromatic carbon ring alkyl which may be substituted by the set γ' of substituent groups, aromatic heterocyclic alkyl which may be substituted by the set γ of substituent groups, non-aromatic heterocyclic alkyl which may be substituted by the set γ' of substituent groups, aromatic carbon ring carbonyl which may be substituted by the set γ of substituent groups, non-aromatic carbon ring carbonyl which may be substituted by the set γ' of substituent groups, aromatic heterocyclic carbonyl which may be substituted by the set γ of substituent groups, aromatic heterocyclic carbonyl, non-aromatic heterocyclic carbonyl which may be substituted by the set γ' of substituent groups, aromatic carbon ring oxycarbonyl which may be substituted by the set γ of substituent groups, non-aromatic carbon ring oxycarbonyl which may be substituted by the set γ' of substituent groups, aromatic heterocyclic oxycarbonyl which may be substituted by the set γ of substituent groups, aromatic carbon ring sulfanyl which may be substituted by the set γ of substituent groups, non-aromatic carbon ring sulfanyl which may be substituted by the set γ' of substituent groups, aromatic heterocyclic sulfanyl which may be substituted by the set γ of substituent groups, non-aromatic heterocyclic sulfanyl which may be substituted by the set γ' of substituent groups, aromatic carbon ring sulfynyl which may be substituted by the set γ of substituent groups, non-aromatic carbon ring sulfynyl which may be substituted by the set γ' of substituent groups, aromatic heterocyclic sulfynyl which may be substituted by the set γ of substituent groups, non-aromatic heterocyclic sulfynyl which may be substituted by the set γ' of substituent groups, aromatic carbon ring sulfonyl which may be substituted by the set γ of substituent groups, non-aromatic carbon ring sulfonyl which may be substituted by the set γ' of substituent groups, aromatic heterocyclic sulfonyl which may be substituted by the set γ' of substituent groups, and non-aromatic heterocyclic sulfonyl which may be substituted by the set γ' of substituent groups.

The set γ of substituent groups: the set α of substituent groups, alkyl, haloalkyl, hydroxy alkyl, alkenyl, alkynyl, alkylcarbonyl, haloalkylcarbonyl, alkenylcarbonyl, and alkynylcarbonyl.

The set γ' of substituent groups: the set γ of substituent groups and oxo.

As the substituent groups on the rings of the "aromatic carbon rings" and "aromatic heterocycles", such as "substituted aromatic carbon ring group", "substituted aromatic heterocyclic group", "substituted aromatic carbon ring", "substituted aromatic heterocycle", "substituted aromatic carbon ring oxy", "substituted aromatic heterocyclic oxy, "substituted aromatic carbon ring carbonyl", "substituted aromatic heterocyclic carbonyl", "substituted aromatic carbon ring sulfanyl", and "substituted aromatic heterocyclic sulfanyl", the following set of substituent groups B may be given as examples. An atom at an arbitrary position on the ring may be bonded with one or more groups selected from the following set of substituent groups B.

Set of substituent groups B: halogen, hydroxy, carboxy, formyl, formyloxy, sulfanyl, sulfino, sulfo, thioformyl, thiocarboxy, dithiocarboxy, thiocarbamoyl, cyano, nitro, nitroso, azide, hydrazino, ureide, amidino, guanidino, pentafluorothio, trialkylsilyl, alkyl, which may be substituted by the set of substituent groups α, alkenyl, which may be substituted by the set of substituent groups α, alkynyl, which may be substituted by the set of substituent groups α, alkyloxy, which may be substituted by the set of substituent groups α, alkenyloxy, which may be substituted by the set of substituent groups α, alkynyloxy, which may be substituted by the set of substituent groups α, alkylcarbonyloxy, which may be substituted by the set of substituent groups α, alkenylcarbonyloxy, which may be substituted by the set of substituent groups α, alkynylcarbonyloxy, which may be substituted by the set of substituent groups α, alkylcarbonyl, which may be substituted by the set of substituent groups α, alkenylcarbonyl, which may be substituted by the set of substituent groups α, alkynylcarbonyl, which may be substituted by the set of substituent groups α, alkyloxycarbonyl, which may be substituted by the set of substituent groups α, alkenyloxycarbonyl, which may be substituted by the set of substituent groups α, alkynyloxycarbonyl, which may be substituted by the set of substituent groups α, alkylsulfanyl, which may be substituted by the set of substituent groups α, alkenylsulfanyl, which may be substituted by the set of substituent groups α, alkynylsulfanyl, which may be substituted by the set of substituent groups α, alkylsulfynyl, which may be substituted by the set of substituent groups α, alkenylsulfynyl, which may be substituted by the set of substituent groups α, alkynylsulfynyl, which may be substituted by the set of substituent groups α, alkylsulfonyl, which may be substituted by the set of substituent groups α, alkenylsulfonyl, which may be substituted by the set of substituent groups α, alkynylsulfonyl, which may be substituted by the set of substituent groups α, amino, which may be substituted by the set of substituent groups β, imino, which may be substituted by the set of substituent groups β, carbamoyl, which may be substituted by the set of substituent groups β, sulfamoyl, which may be substituted by the set of substituent groups β, aromatic carbon ring group which may be substituted by the set γ of substituent groups, non-aromatic carbon ring group which may be substituted by the set γ' of substituent groups, aromatic heterocyclic group which may be substituted by the set γ of substituent groups, non-aromatic heterocyclic group which may be substituted by the set γ' of substituent groups, aromatic carbon ring oxy which may be substituted by the set γ of substituent groups, non-aromatic carbon ring oxy which may be substituted by the set γ' of substituent groups, aromatic heterocyclic oxy which may be substituted by the set γ of substituent groups, non-aromatic heterocyclic oxy which may be substituted by the set γ' of substituent groups, "aromatic carbon ring carbonyloxy which may be substituted by the set γ of substituent groups", "non-aromatic carbon ring carbonyloxy which may be substituted by the set γ' of substituent groups", "aromatic heterocyclic carbonyloxy which may be substituted by the set γ of substituent groups", and "non-aromatic heterocyclic carbonyloxy which may be substituted by the set γ' of substituent groups", aromatic carbon ring carbonyl which may be substituted by the set γ of substituent groups, non-aromatic carbon ring carbonyl which may be substituted by the set γ' of substituent groups, aromatic heterocyclic carbonyl which may be substituted by the set γ of substituent groups, non-aromatic heterocyclic carbonyl which may be substituted by the set γ' of substituent groups, aromatic carbon ring oxycarbonyl which may be substituted by the set γ of substituent groups, non-aromatic carbon ring oxycarbonyl which may be substituted by the set γ' of substituent groups, aromatic heterocyclic oxycarbonyl which may be substituted by the set γ of substituent groups, non-aromatic heterocyclic oxycarbonyl which may be substituted by the set γ' of substituent groups, aromatic carbon ring alkyl which may be substituted by the set γ of substituent groups, non-aromatic carbon ring alkyl which may be substituted by the set γ' of substituent groups, aromatic heterocyclic alkyl which may be substituted by the set γ of substituent groups, non-aromatic heterocyclic alkyl which may be substituted by the set γ' of substituent groups, aromatic carbon ring alkyloxy which may be substituted by the set γ of substituent groups, non-aromatic carbon ring alkyloxy which may be substituted by the set γ' of substituent groups, aromatic heterocyclic alkyloxy which may be substituted by the set γ of substituent groups, non-aromatic heterocyclic alkyloxy which may be substituted by the set γ' of substituent groups, aromatic carbon ring alkyloxycarbonyl which may be substituted by the set γ of substituent groups, non-aromatic carbon ring alkyloxycarbonyl which may be substituted by the set γ'' of substituent groups, aromatic heterocyclic alkyloxycarbonyl which may be substituted by the set γ of substituent groups, non-aromatic heterocyclic alkyloxycarbonyl which may be substituted by the set γ' of substituent groups, aromatic carbon ring alkyloxyalkyl which may be substituted by the set γ of substituent groups, non-aromatic carbon ring alkyloxyalkyl which may be substituted by the set γ' of substituent groups, aromatic heterocyclic alkyloxyalkyl which may be substituted by the set γ of substituent groups, non-aromatic heterocyclic alkyloxyalkyl which may be substituted by the set γ' substituent groups, aromatic carbon ring sulfanyl which may be substituted by the set γ of substituent groups, non-aromatic carbon ring sulfanyl which may be substituted by the set γ' of substituent groups, aromatic heterocyclic sulfanyl which may be substituted by the set γ of substituent groups, non-aromatic heterocyclic sulfanyl which may be substituted by the set γ' of substituent groups, aromatic carbon ring sulfynyl which may be substituted by the set γ of substituent groups, non-aromatic carbon ring sulfynyl which may be substituted by the set γ' of substituent groups, aromatic heterocyclic sulfynyl which may be substituted by the set γ of substituent groups, non-aromatic heterocyclic sulfynyl which may be substituted by the set γ' of substituent groups, aromatic carbon ring sulfonyl which may be substituted by the set γ of substituent groups, non-aromatic carbon ring sulfonyl which may be substituted by the set γ' of substituent groups, aromatic heterocyclic sulfonyl which may be substituted by the set γ of substituent groups and non-aromatic heterocyclic sulfonyl which may be substituted by the set γ' of substituent groups.

As the substituent groups on the rings of the "non-aromatic carbon rings" and "non-aromatic heterocycles", such as "substituted non-aromatic carbon ring group", "substituted non-aromatic heterocyclic group", "substituted non-aromatic carbon ring", "substituted non-aromatic heterocycle", "substituted non-aromatic carbon ring oxy", "substituted cycloalkyloxy", "substituted cycloalkenyloxy", "substituted non-aromatic heterocyclic oxy", "substituted non-aromatic carbon ring carbonyl", "substituted non-aromatic heterocyclic carbonyl", "substituted non-aromatic carbon ring sulfanyl", and "substituted non-aromatic heterocyclic sulfanyl" the following set of substituent groups C may be given as examples. An atom at an arbitrary position on the ring may be bonded with one or more groups selected from the following set of substituent groups C.

Substituent Group C: Substituent Group B and Oxo.

When a "non-aromatic carbon ring" or "non-aromatic heterocyclic" is substituted with "oxo", this means that a ring is produced wherein the two hydrogen atoms on a carbon atom are substituted as shown below.

[Chem. 11]

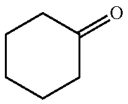
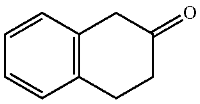
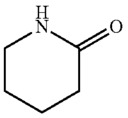

-continued

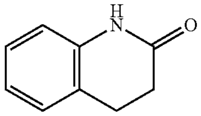

The following set D of substituent groups may be given as examples as substituent groups of "substituted amino" and "substituted carbamoyl". Substitution may be effected using one or two groups selected from the set D of substituent groups.

Set D of substituent groups: halogen, hydroxy, carboxy, cyano, alkyl, which may be substituted by the set of substituent groups α, alkenyl, which may be substituted by the set of substituent groups α, alkynyl, which may be substituted by the set of substituent groups α, alkylcarbonyl, which may be substituted by the set of substituent groups α, alkenylcarbonyl, which may be substituted by the set of substituent groups α, alkynylcarbonyl, which may be substituted by the set of substituent groups α, alkylsulfanyl, which may be substituted by the set of substituent groups α, alkenylsulfanyl, which may be substituted by the set of substituent groups α, alkynylsulfanyl, which may be substituted by the set of substituent groups α, alkylsulfynyl, which may be substituted by the set of substituent groups α, alkenylsulfynyl, which may be substituted by the set of substituent groups α, alkynylsulfynyl, which may be substituted by the set of substituent groups α, alkylsulfonyl, which may be substituted by the set of substituent groups α, alkenylsulfonyl, which may be substituted by the set of substituent groups α, alkynylsulfonyl, which may be substituted by the set of substituent groups α, amino, which may be substituted by the set β of substituent groups, imino, which may be substituted by the set β of substituent groups, carbamoyl, which may be substituted by the set β of substituent groups, sulfamoyl, which may be substituted by the set β of substituent groups, aromatic carbon ring group, which may be substituted by the set γ of substituent groups, non-aromatic carbon ring group, which may be substituted by the set γ' of substituent groups, aromatic heterocyclic group which may be substituted by the set γ of substituent groups, non-aromatic heterocyclic group which may be substituted by the set γ' of substituent groups, aromatic carbon ring alkyl which may be substituted by the set γ of substituent groups, non-aromatic carbon ring alkyl which may be substituted by the set γ' of substituent groups, aromatic heterocyclic alkyl which may be substituted by the set γ of substituent groups, non-aromatic heterocyclic alkyl which may be substituted by the set γ' of substituent groups, aromatic carbon ring carbonyl which may be substituted by the set γ of substituent groups, non-aromatic carbon ring carbonyl which may be substituted by the set γ' of substituent groups, aromatic heterocyclic carbonyl which may be substituted by the set γ of substituent groups, non-aromatic heterocyclic carbonyl which may be substituted by the set γ' of substituent groups, aromatic carbon ring oxycarbonyl which may be substituted by the set γ of substituent groups, non-aromatic carbon ring oxycarbonyl which may be substituted by the set γ' of substituent groups, aromatic heterocyclic oxycarbonyl which may be substituted by the set γ of substituent groups, non-aromatic heterocyclic oxycarbonyl which may be substituted by the set γ' of substituent groups, aromatic carbon ring sulfanyl which may be substituted by the set γ of substituent groups, non-aromatic carbon ring sulfanyl which may be substituted by the set γ' of substituent groups, aromatic heterocyclic sulfonyl which may be substituted by the set γ of substituent groups, non-aromatic heterocyclic sulfonyl which may be substituted by the set γ' of substituent groups, aromatic carbon ring sulfynyl which may be substituted by the set γ of substituent groups, non-aromatic carbon ring sulfynyl which may be substituted by the set γ' of substituent groups, aromatic heterocyclic sulfynyl which may be substituted by the set γ of substituent groups, non-aromatic heterocyclic sulfynyl which may be substituted by the set γ' of substituent groups, aromatic carbon ring sulfonyl which may be substituted by the set γ of substituent groups, non-aromatic carbon ring sulfonyl which may be substituted by the set γ' of substituent groups, aromatic heterocyclic sulfonyl which may be substituted by the set γ of substituent groups and non-aromatic heterocyclic sulfonyl which may be substituted by the set γ' of substituent groups.

In the compounds indicated by formula (I) of (A), preferred modes of the respective symbols are indicated below. As the compounds indicated by formula (I), all modes of combination of the specific examples shown below are given.

The ring A may be any of the following rings:

[Chem. 12]

(a)

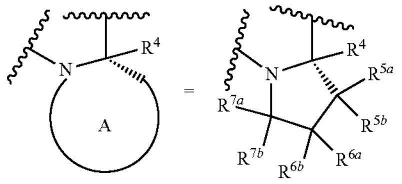

(b)

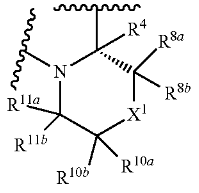

A preferred mode of ring A may be as follows.

[Chem. 13]

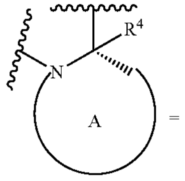

(a)

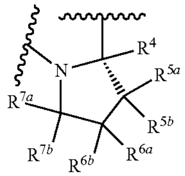

-continued (b-1)

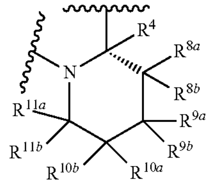

(b-2)

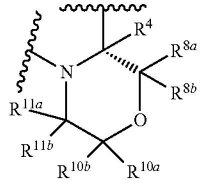

Even more preferred modes of ring A are the above (a) or (1)-1).

Ring B may be a benzene ring or pyridine ring.

A preferred mode of the ring B is a benzene ring.

$R^1$ may be, respectively independently, halogen, alkyl, haloalkyl, alkyloxy, cyano or haloalkyloxy.

A preferred mode of $R^1$ is halogen, alkyl or haloalkyl.

An even more preferred mode of $R^1$ is halogen.

$R^{2a}$ and $R^{2b}$ may be, respectively independently, hydrogen, alkyl, or haloalkyl.

A preferred mode of $R^{2a}$ and $R^{2b}$ is hydrogen.

A preferred mode of $R^{2a}$ is hydrogen.

A preferred mode of $R^{2b}$ is hydrogen or methyl; an even more preferred mode is hydrogen.

A preferred mode of $R^3$ is alkyl, or haloalkyl.

A preferred mode of $R^3$is $R^4$ may be hydrogen or alkyl.

A preferred mode of $R^4$ is hydrogen or methyl; an even more preferred mode is hydrogen.

$R^{5a}$, $R^{5b}$, $R^{6a}$, $R^{6b}$, $R^{7a}$ and $R^{7b}$ may be respectively independently, hydrogen, halogen, alkyl, haloalkyl, alkyloxy, alkyloxyalkyl or a 3-6 member non-aromatic carbon ring group (for example, cyclopropyl or the like).

A preferred mode of $R^{5a}$, $R^{5b}$, $R^{6a}$, $R^{6b}$, $R^{7a}$ and $R^{7b}$ is, respectively independently, hydrogen, halogen, C1-3 alkyl, C1-3 haloalkyl, C1-3 alkyloxy, C1-3 alkyloxy C1-3 alkyl.

A preferred mode of $R^{5a}$ is hydrogen or alkyl, even more preferably hydrogen.

Another preferred mode of $R^{5a}$ is hydrogen C1-3 alkyl.

A preferred mode of $R^{5b}$ is hydrogen or alkyl; an even more preferred mode is hydrogen.

Another preferred mode of $R^{5b}$ is hydrogen C1-3 alkyl.

A preferred mode of $R^{6a}$ is hydrogen, alkyl or alkyloxyalkyl; an even more preferred mode is hydrogen.

Another preferred mode of $R^{6a}$ is hydrogen, C1-3 alkyl C1-3 alkyloxy C1-3 alkyl.

Another preferred mode of $R^{6a}$ is hydrogen, halogen, alkyl, haloalkyl, alkyloxyalkyl or 3-6 member non-aromatic carbon ring group (for example, cyclopropyl and the like); an even more preferred mode is hydrogen.

Another preferred mode of $R^{6a}$ is hydrogen, halogen, C1-3 alkyl, C1-3 haloalkyl, C1-3 alkyloxy C1-3 alkyl.

A preferred mode of $R^{6b}$ is hydrogen.

A preferred mode of $R^{7a}$ is hydrogen, alkyl or alkyloxyalkyl; an even more preferred mode is alkyloxyalkyl.

Another preferred mode of $R^{7a}$ is hydrogen, C1-3 alkyl C1-3 alkyloxy C1-3 alkyl.

Another preferred mode of $R^{7a}$ is hydrogen, halogen, alkyl, haloalkyl, alkyloxyalkyl or a 3-6 member non-aromatic carbon ring group (for example, cyclopropyl and the like); an even more preferred mode is alkyloxyalkyl.

A preferred mode of $R^{7b}$ is hydrogen.

Together with an adjacent atom, $R^{5a}$ and $R^{6a}$, or $R^{6a}$ and $R^{7}$ may form an aromatic carbon ring (for example, benzene and the like), which may be substituted by a halogen, a 3-6 member non-aromatic carbon ring (for example, cyclopropane or cyclopentane and the like), which may be substituted by a halogen, or a 4-6 member non-aromatic heterocycle (for example, tetrahydrofurane and the like), which may be substituted by a halogen. (When an aromatic carbon ring is formed, the ring may be formed by coupling $R^{5b}$ and $R^{6b}$, or $R^{6b}$ and $R^{7b}$).

$R^{5b}$ and $R^{6b}$ may also form a bond together.

$R^{8a}$, $R^{8b}$, $R^{9a}$, $R^{9b}$, $R^{10a}$, $R^{10b}$, $R^{11a}$ and $R^{11b}$ may be, respectively independently, hydrogen, halogen, alkyl, haloalkyl, alkyloxy, alkyloxyalkyl or a 3-member non-aromatic carbon ring group (for example, cyclopropyl and the like).

A preferred mode of $R^{8a}$, $R^{8b}$, $R^{9a}$, $R^{9b}$, $R^{10a}$, $R^{10b}$, $R^{11a}$ and $R^{11b}$ is, respectively independently, hydrogen, halogen, C1-3 alkyl, C1-3 haloalkyl, C1-3 alkyloxy, C1-3 alkyloxy C1-3 alkyl.

A preferred mode of $R^{8a}$ is hydrogen or alkyl; an even more preferred mode is hydrogen.

Another preferred mode of $R^{8a}$ is hydrogen C1-3 alkyl.

A preferred mode of $R^{8b}$ is hydrogen or alkyl; an even more preferred mode is hydrogen.

Another preferred mode of $R^{8b}$ is hydrogen C1-3 alkyl.

A preferred mode of $R^{9a}$ is hydrogen, alkyl or alkyloxyalkyl.

Another preferred mode of $R^{9a}$ is hydrogen, C1-3 alkyl or C1-3 alkyloxy C1-3 alkyl.

Another preferred mode of $R^{9a}$ is hydrogen, halogen, alkyl, haloalkyl, alkyloxyalkyl or a 3-6 member non-aromatic carbon ring group (for example, cyclopropyl and the like).

A preferred mode of $R^{9b}$ is hydrogen or alkyl; an even more preferred mode is hydrogen.

Another preferred mode of $R^{9b}$ is hydrogen or C1-3 alkyl.

A preferred mode of $R^{10a}$ is hydrogen, alkyl or alkyloxy; an even more preferred mode is hydrogen.

Another preferred mode of $R^{10a}$ is hydrogen, C1-3 alkyl or C1-3 alkyloxy.

Another preferred mode of $R^{10a}$ is hydrogen, halogen, alkyl, haloalkyl, alkyloxyalkyl or a 3-6 member non-aromatic carbon ring group (for example, cyclopropyl and the like).

A preferred mode of $R^{10b}$ is hydrogen.

A preferred mode of $R^{11a}$ is hydrogen or alkyl; an even more preferred mode is hydrogen.

Another preferred mode of $R^{11a}$ is hydrogen or C1-3 alkyl.

Another preferred mode of $R^{11a}$ is hydrogen, halogen, alkyl, haloalkyl, alkyloxyalkyl or a 3-6 member non-aromatic carbon ring group (for example, cyclopropyl and the like).

A preferred mode of $R^{11b}$ is hydrogen.

$R^{8a}$ and $R^{10a}$ may together form a C1-C3 cross-linkage, preferably a C1-C2 cross-linkage.

Together with an adjacent atom, $R^{10a}$ and $R^{11a}$ may form a 5-member non-aromatic carbon ring (for example, cyclopropane and the like).

Together with an adjacent atom, $R^{9a}$ and $R^{9b}$ may form a 4-member non-aromatic carbon ring (for example, cyclopropane and the like) or 5-member non-aromatic heterocycle (for example, 1, 3-dioxolane and the like).

$R^{8a}$ and $R^{9a}$ may form a bond together.

n may be an integer of 1 to 3.

A preferred mode of n is an integer of 2 to 3.

An even more preferred mode of n is an integer of 1 to 2.

Q may be —NHC(O)— or a 5-member aromatic heterocycle.

A preferred mode of Q is —NHC(O)— (the left-side bond is coupled with $CR^{2a}R^{2b}$).

Another preferred mode of Q is a 5-member aromatic heterocycle.

Another preferred mode of Q is any of the following rings (the left--side bond is coupled with $CR^{2a}R^{2b}$).

[Chem. 14]

(1)

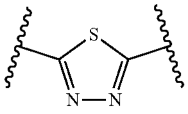

(2)

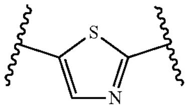

(3)

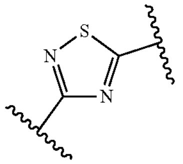

(4)

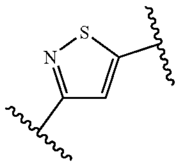

(5)

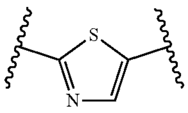

(6)

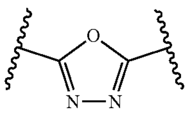

(7)

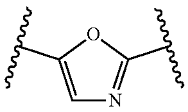

(8)

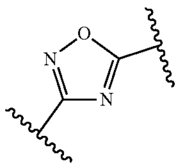

-continued (9)

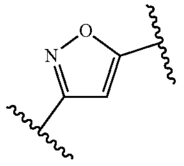

(10)

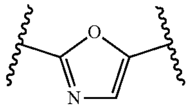

(11)

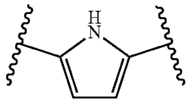

(12)

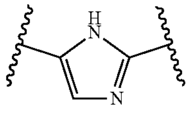

(13)

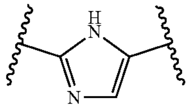

(14)

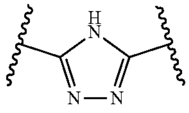

(15)

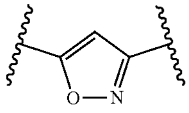

(16)

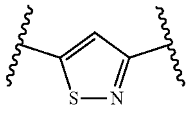

(17)

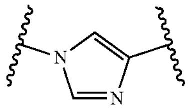

(18)

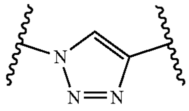

(19)

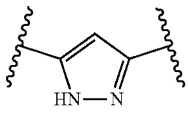

Another preferred mode of Q is any of the following rings (the left-side bond is coupled with $CR^{2a}R^{2b}$).

[Chem. 15]

(1)

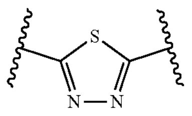

(2)

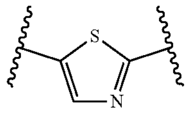

(20)

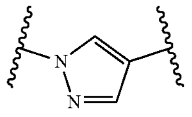

An even more preferred mode of Q is a ring as indicated by the above (1).

Preferred compounds, in the compounds indicated by formula (I) of (A), may be mode compounds: I-3, I-7, I-11, I-16, I-23, I-24, I-32, II-1, II-4, II-5, II-13, II-14, II-16, II-19, II-21, II-23, II-26, II-31, II-34, II-36, II-38, II-41, II-43, II-45, II-47, II-49, II-52, II-56, II-58, II-62, II-63, II-64, II-68, II-89, II-92, II-93, II-95, II-96, II-98, II-106, II-109, II-110, II-112, II-113, II-117, II-118, II-125, II-127, II-128, II-129, II-130, II-131, II-132, II-136, II-138, II-139, II-142, II-143, II-144, II-147, II-148, II-149, II-150, II-151, II-155, II-156 and II-157 and the like.

Even more preferred compounds, in the compounds indicated by formula (I) of (A), may be mode compounds: I-7, I-11, II-26, II-36, II-52, II-92, II-96, II-109, II-110, and II-158 and the like.

In the compounds indicated by formula (I') of (B), preferred modes are indicated below.

EXAMPLE 1

Formula (1') is as follows:

[Chem. 16]

(I'-1-1B)

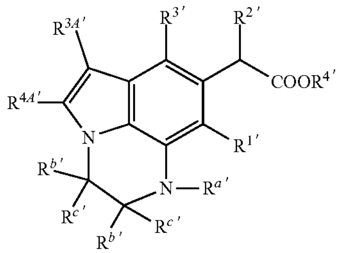

(where, in this formula, $R^{1'}$ is alkyl or halogen;

$R^{2'}$ is alkyloxy;

$R^{3'}$ is an aromatic carbon ring group, which may be substituted by halogen, alkyl and/or alkyloxy, a non-aromatic carbon ring group, which may be substituted by halogen, alkyl and/or alkyloxy, an aromatic heterocyclic group, which may be substituted by halogen, alkyl and/or alkyloxy, or a non-aromatic heterocyclic group which may be substituted by halogen, alkyl and/or alkyloxy;

$R^{4\prime}$ is hydrogen;

$R^{3A\prime}$ is hydrogen or halogen;

$R^{4A\prime}$ is alkyl which may be substituted by cyano, halogen, hydroxy or alkyloxy, or a non-aromatic carbon ring group which may be substituted by halogen, or alkynyl;

$R^{a\prime}$ is hydrogen, alkyl, haloalkyl, amino alkyl, alkyl amino alkyl, dialkyl amino alkyl, alkyloxyalkyl, alkylsulfonyl, or haloalkylsulfonyl;

$R^{b\prime}$ is, respectively independently, hydrogen, alkyl, haloalkyl, or alkyloxyalkyl;

$R^{c\prime}$ is, respectively independently, hydrogen, alkyl, haloalkyl, or alkyloxyalkyl).

EXAMPLE 2

Formula (I') is as follows:

[Chem. 17]

(I'-1-1B)

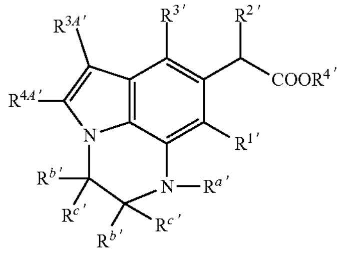

(where, in this formula, $R^{1\prime}$ is alkyl or halogen;

$R^{2\prime}$ is alkyloxy;

$R^{3\prime}$ is an aromatic carbon ring group which may be substituted by halogen, alkyl and/or alkyloxy, a non-aromatic carbon ring group which may be substituted by halogen, alkyl and/or alkyloxy, an aromatic heterocyclic group which may be substituted by halogen, alkyl and/or alkyloxy, or a non-aromatic heterocyclic group which may he substituted by halogen, alkyl and/or alkyloxy;

$R^{4\prime}$ is hydrogen;

$R^{3A\prime}$ is hydrogen or halogen;

$R^{4A\prime}$ is alkyl which may be substituted by cyano, halogen, hydroxy or alkyloxy, or a non-aromatic carbon ring group which may be substituted by halogen or alkynyl;

$R^{a\prime}$ is an aromatic heterocyclic group which may be substituted by one or more group selected from the set E of substituent groups or a non-aromatic heterocyclic group which may be substituted by one or more group selected from the set E of substituent groups; where the set F of substituent groups is alkyl, halogen, alkyloxy, dialkylaminoalkyloxy, alkylaminoalkyloxy, aminoalkyloxy, non-aromatic heterocyclic alkyloxy, non-aromatic heterocyclic oxy which may be substituted by alkyl and/or oxo, non-aromatic heterocyclic group which may be substituted by alkyl and/or oxo, dialkylaminoalkyl, alkylaminoalkyl, aminoalkyl, non-aromatic heterocyclic alkyl, and aromatic heterocyclic group which may be substituted by alkyl;

$R^{b\prime}$ is, respectively independently, hydrogen, alkyl, haloalkyl, or alkyloxyalkyl;

$R^{c\prime}$ is, respectively independently, hydrogen, alkyl, haloalkyl, or alkyloxyalkyl).

Unless otherwise specified, the compounds according to the present invention are not limited to specific isomers and all possible isomers (for example, keto-enol isomers, imine-enamine isomers, diastereomers, optical isomers, or rotary isomers or the like), racemic forms or mixtures thereof are included.

Radioactively labelled compounds according to the present invention may be prepared by the methods that are well known in this technical field. For example, tritium-labeled compounds according to the present invention may be prepared by introducing tritium into a specified compound according to the present invention by a catalytic dehydrogenation reaction using tritium. This reaction includes reacting tritium gas with a suitably halogen-substituted precursor of a compound according to the present invention in the presence of a suitable catalyst such as for example Pd/C, in the presence or absence of a base.

For suitable methods of preparing lithium-labelled compounds, "Isotopes in the Physical and Biomedical Sciences, Vol. 1, Labeled Compounds (Part A), Chapter 6 (1987)" may be referred to. $^{14}C$-labeled compounds may be prepared by employing a raw material having, $^{14}C$ carbon.

As pharmaceutically acceptable salts of compounds according to the present invention there may be employed for example salts of a compound according to the present invention with: an alkali metal (for example lithium, sodium, potassium and the like), an alkaline earth metal (calcium, barium and the like), magnesium, a transition metal (for example zinc, iron or the like), ammonia, an organic base (such as for example trimethylamine, triethylamine, tricyclohexylamine, ethanolamine, diethanolamine, triethanolamine, meglumine, ethylenediamine, pyridine, picoline, or quinoline and the like), and salts of amino acids or inorganic acids (such as for example hydrochloric acid, sulfuric acid, nitric acid, carbonic acid, hydrobromic acid, phosphoric acid, or hydroiodic acid and the like), and organic acids (such as for example formic acid, acetic acid, propionic acid, trifluoroacetic acid, citric acid, lactic acid, tartaric acid, oxalic acid, maleic acid, fumaric acid, mandelic acid, glutaric acid, malic acid, benzoic acid, phthalic acid, ascorbic acid, benzene sulfonic acid, p-toluene sulfonic acid, methane sulfonic acid, ethane sulfonic acid and the like). These salts may be prepared by the ordinary methods.

The compounds according to the present invention and pharmaceutically acceptable salts thereof may form solvates (for example hydrates and the like), co-crystals and/or polymorphic forms; the present invention includes such solvates, co-crystals and polymorphic forms. In a "solvate", an arbitrary number of solvent molecules (for example, water molecules and the like) may be coordinated with a compound according to the present invention. By exposure to the atmosphere a compound according to the present invention or pharmaceutically acceptable salt thereof may absorb moisture or adsorbed water may adhere thereto, or a hydrate may be formed. Also, a compound according to the present invention or pharmaceutically acceptable salt thereof may form a polymorphic form by recrystallisation.

A "co-crystal" means that counter molecules are present in the same crystal lattice as the compound or salt according to the present invention; an arbitrary number of counter molecules may be included.

The compounds according to the present invention or pharmaceutically acceptable salts thereof may form prodrugs; the present invention includes various types of such prodrugs. A prodrug is a derivative of a compound according to the present invention having a group that can he chemically or metabolically decomposed, and is thus a compound that produces a pharmaceutically active compound according to the present invention by solvolysis or under physiological conditions. Prodrugs include compounds that are enzymatically converted into an active compound by for example oxidation, reduction, or hydrolysis under physiological conditions in vivo, and compounds that are converted to an active compound by hydrolysis by gastric acids and the like. Methods of selecting and manufacturing suitable prodrug derivatives are described in for example "Design of Prodrugs, Elsevier, Amsterdam, 1985". Some prodrugs do themselves have activity.

Methods of Manufacturing Compounds According to the Present Invention

The following are examples of general production methods for compounds used in the present invention. in addition, for extraction and purification and the like, can be performed by ordinary organic chemistry experiments.

Synthesis of the compounds used in the present invention can be performed with reference to methods known in the field.

The raw material compounds can be commercially available compounds, those described herein, those described in the literature cited herein, and other known compounds.

When it is desired to obtain a salt of a compound according to the present invention, if the compound employed in the present invention is obtained in the form of a salt, it may be directly purified, or if they obtained in a free form, it may be dissolved. or suspended in a suitable organic solvent and the salt may be formed by the usual methods by addition of acid or a base.

The compound shown in formula (I) of (A) used in the present invention can be adjusted, for example, by the method described below.

X(Preparation Method 1) when Q is —NHC(O)—

[Chem. 18]

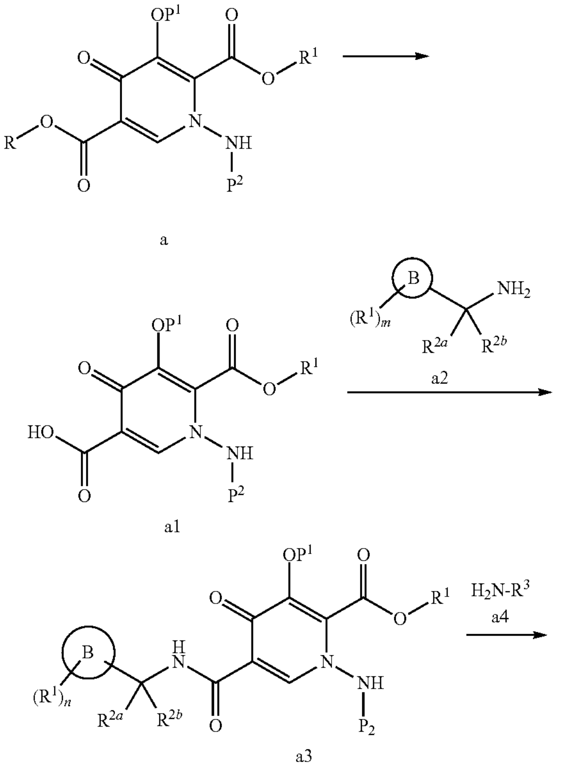

a, a1, a3

-continued

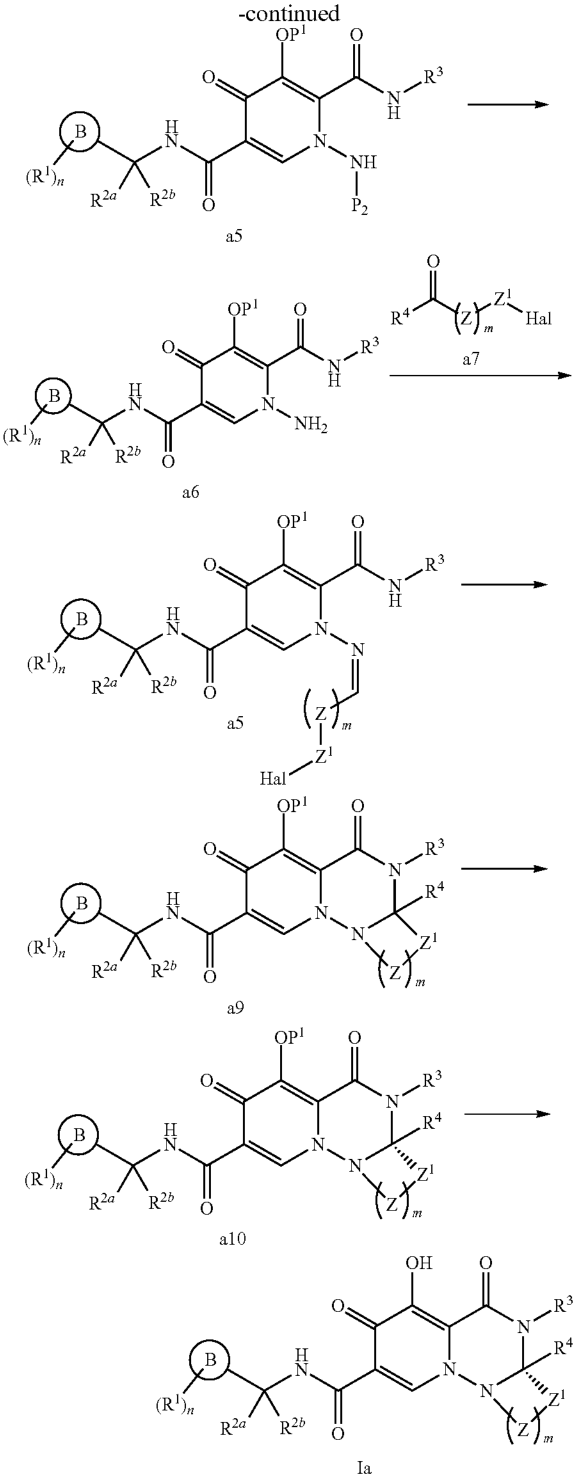

a5, a6, a5, a9, a10, Ia (where, in these formulas, $P^1$ is a hydroxy protective group; $P^2$ is an amino protective group; R and R' are carboxy protective groups; $Z^1$ is $CR^{5a}R^{5b}$ or $CR^{8a}R^{8b}$; m is an integer of 2 to 3, when m is 2, —$(Z)_2$— is —$(CR^{7a}R^{7b}$—$CR^{6a}R^{6b})$—, when m is 3, —$(Z)_3$— is —$(CR^{11a}R^{11b}$—$CR^{10a}R^{10b}$—$CR^{9a}R^{9b})$—, or $(CR^{11a}R^{11b}$—$CR^{10a}R^{10b}$—O)—; Hal is halogen; $P^1$, $P^2$, R and R' may be groups that can be protected or unprotected by the methods described in Protective Groups in Organic Synthesis, Theodora W Greene (John Wiley & Sons), for example. For example, $P^1$ may be an aromatic carbon ring alkyl and the like, $P^2$ may be alkyloxycarbonyl and the like, R and R' may be alkyl and the like; other symbols have the same meaning as above.)

Step 1

Compound a1 can be obtained by subjecting compound a obtained commercially or prepared by a known method to an ordinary deprotecting reaction for carboxy protective groups.

Step 2

Compound a1 is reacted with a condensation agent such as HATU, HCl, PyBOP, in the presence of a solvent such as DMF, DMA, NMP, THF, chloroform or dichloromethane. Compound a2, can be commercially obtained or prepared by known methods, and a ternary amine such as triethylamine, N-methylmorpholine, pyridine, or DIEA are added; compound a3 can be obtained by adding tertiary amines such as triethylamine, N-methylmorpholine, pyridine, and DIEA, and reacting for 0.1 h to 24 h, preferably 1 h to 12 h, at 10° C. to 60° C., preferably 20° C. to 40° C.

Step 3

Compound a5 is obtained by adding compound a4 to compound a3 in the presence of a solvent such as THF, methanol, ethanol, chloroform, dichloromethane or THF; reaction is then performed for 0.5 h to 24 h, preferably 1 h to 12 h, at 60° C. to 120° C., preferably 80° C. to 100° C.

Step 4

Compound a6 may then be obtained by subjecting compound a5 to an ordinary deprotecting reaction of the amino protective group.

Step 5

Compound a6 is reacted with compound a7, which is commercially available or can be prepared by a known method, and an acid such as acetic acid, p-toluene sulfonic acid, methanesulfonic acid, or the like, in the presence of a solvent such as dichloromethane, dichloroethane, chloroform, methanol, ethanol, toluene, DMF, DMA, THF, or the like, and the reaction is carried out for 0.1 h to 24 h, preferably 1 h to 12 h, at 20° C. to 130° C., preferably 20° C. to 100° C.

Step 6

Compound a8 is reacted with a base such as cesium carbonate or potassium carbonate and a salt such as sodium or potassium potassium oxalate in the presence of a solvent such as DMF, DMA, NMP or THF, to obtain compound a9 by reacting for 0.1 h to 24 h, preferably 1 h to 12 h, at 0° C. to 60° C., preferably 0° C. to 40° C.

Step 7

Compound a9 can be separated to a10 by chiral SFC.

Step 8

Compound Ia can be obtained by subjecting compound a10 to an ordinary deprotecting reaction of the hydroxy protective group.

(Preparation Method 2)

[Chem.19]

a5

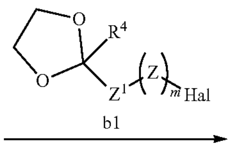

b1

-continued

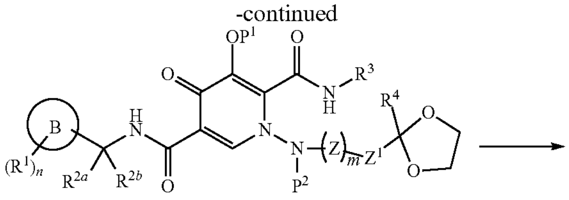

b2

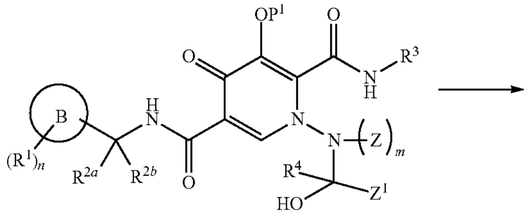

b3

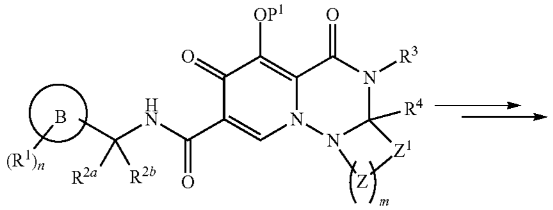

a9

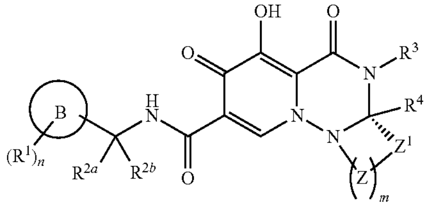

Ia (where, in these for the various symbols have the same meaning as above.)

Step 1

Compound a5 is reacted with a base such as cesium or potassium carbonate or triethylamine in the presence of a solvent such as DMF, DMA, NMP, THF, or the like and a salt such as sodium iodide or potassium iodide, where Hal is chloro, and compound b1, which can be prepared commercially or by known methods, is added, to obtain compound b2 by reacting for 0.1 h to 24 h, preferably 1 h to 12 h, at 0° C. to 60° C., preferably 20° C. to 40° C.

Step 2

Compound b3 may be obtained by subjecting compound b2 to an ordinary deprotecting reaction of the acetal.

Step 3

Compound b3 is reacted with acetic acid, p-toluenesulfonic acid, methanesulfonic acid, trifluoroacetic acid, or other acids in the presence of solvents such as dichloromethane, dichloroethane, chloroform, acetonitrile, methanol, ethanol, toluene, DMF, DMA, and THF: compound a9 can then be obtained by reacting for 0.1 h to 24 h, preferably 1 h to 12 h, at 20° C. to 130° C., preferably 80° C. to 120° C.

Step 4

Compound Ia can be synthesized in accordance with Steps 7 and 8 of Preparation method 1.

(Preparation Method 3)

[Chem. 20]

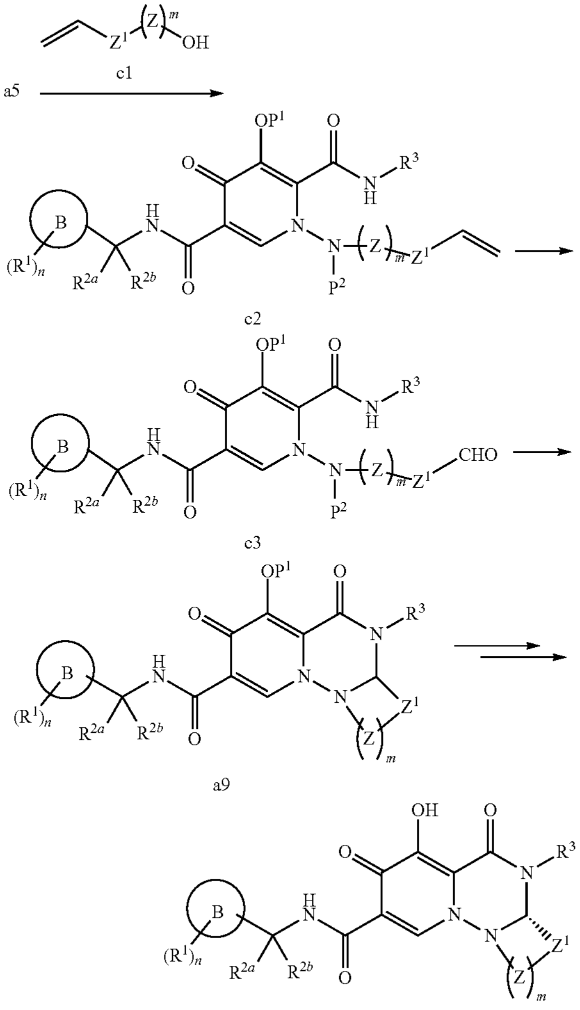

c2 c3 a9

I9

(where, in these formulas, the various symbols have the same meaning as above.)

Step 1

Compound c2 can be obtained by adding compound c1 to compound a5, which may be obtained commercially or prepared by known methods, and adding a Mitsunobu reagent such as DEAD/$PPh_3$, DIAD/$PPh_3$, DMEAD/$PPh_3$, or ADDP/n-$Bu_3P$, in the presence of a solvent such as THF or toluene and reacting for 0.1 h to 24 h, preferably 1 h to 12 h, at 0° C. to 100° C., preferably 20° C. to 80° C.

Step 2

Compound c3 can be obtained by subjecting compound c2 to an ordinary cleavage reaction of an alkene. For example, ozone decomposition or $K_2OsO_4$/$NaIO_4$ may be employed.

Step 3

Compound a9 may be obtained by reacting compound c3 under the same conditions as Step 3 of preparation method 2.

Step 4

Compound Ia may be synthesized in accordance with Steps 7 and 8 of preparation method 1.

(Preparation Method 4)

[Chem. 21]

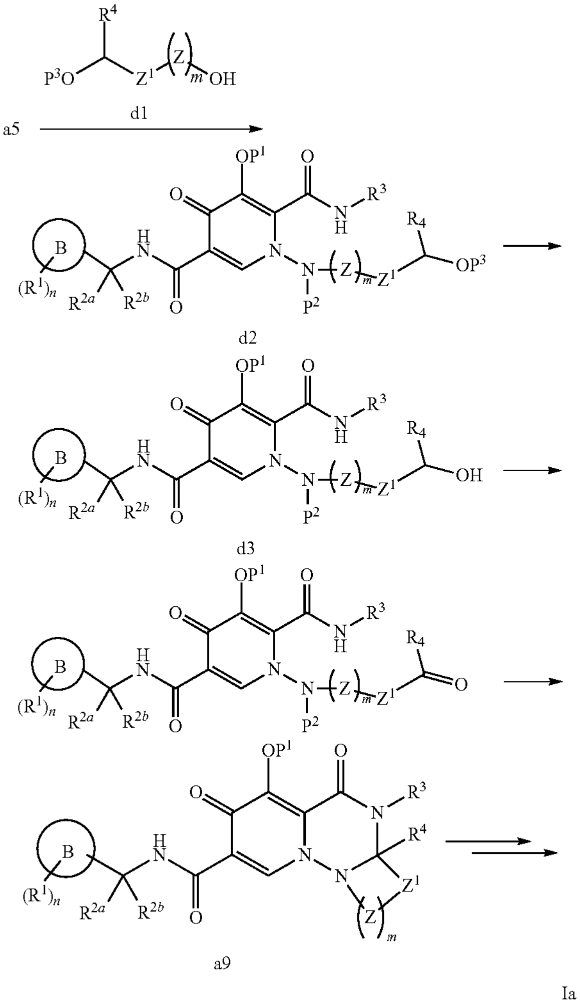

d2 d3 a9

Ia (where, in these for the various symbols have the same meaning as above.)

Step 1

Compound d2 can be obtained by reacting compound a5 and compound d1 under the same conditions as Step 1 of preparation method 3.

Step 2

Compound d3 can be obtained by subjecting compound d1 to an ordinary deprotecting reaction of the hydroxy protective group Step 3

Compound d4 can be obtained by subjecting compound d3 to an ordinary oxidation reaction of the hydroxyl group.

Step 4

Compound a9 can be obtained by reacting compound d4 under the same conditions as Step 3 of preparation method 2.

Compound Ia can be synthesized in accordance with Steps 7 and 8 of preparation method I.

(Preparation Method 5)

[Chem. 22]

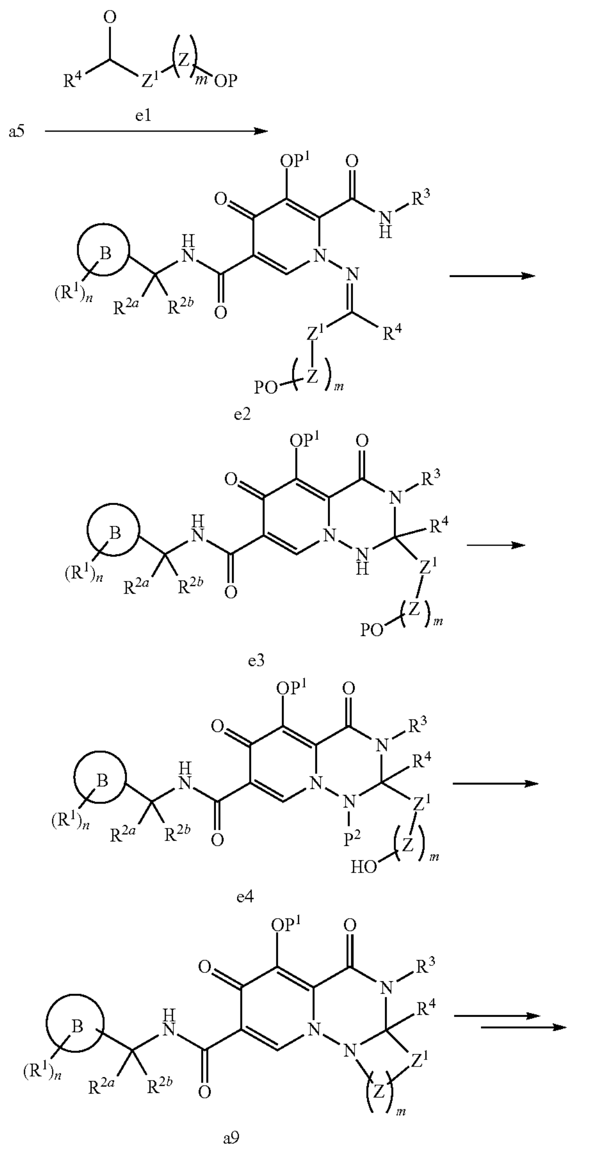

(where, in the formulas, the various symbols have the same meaning as above.)

Step 1

Compound e2 can be obtained by reacting compound a5 and compound e1 under the same conditions as Step 5 of preparation example 1.

Step 2

Compound e3 can be obtained by reacting adding a base such as cesium carbonate or potassium carbonate to compound e2 the presence of a solvent such as DMF, DMA, NMP, or THF, and, at 0° C. to 60° C., preferably 0° C. to 40° C.

Step 3

Compound e4 can be Obtained by subjecting this to an ordinary deprotecting reaction of the hydroxy protective group.

Step 4

Compound a9 can be obtained by adding, to compound e4, a Mitsunobu reagent such as DEAD/$PPh_3$, DIAD/$PPh_3$, DMEAD/$PPh_3$, ADDP/n-$Bu_3P$, in the presence of a solvent such as THF or toluene, and reacting at 0° C. to 100° C., preferably 20° C. to 80° C., for 0.1 h to 24 h, preferably 1 h to 12 h.

Step 5

Compound Ia can be synthesized in accordance with Steps 7 and 8 of preparation method 1.

(Preparation method 6) When Q is a 5-member aromatic heterocycle.

[Chemical. 23]

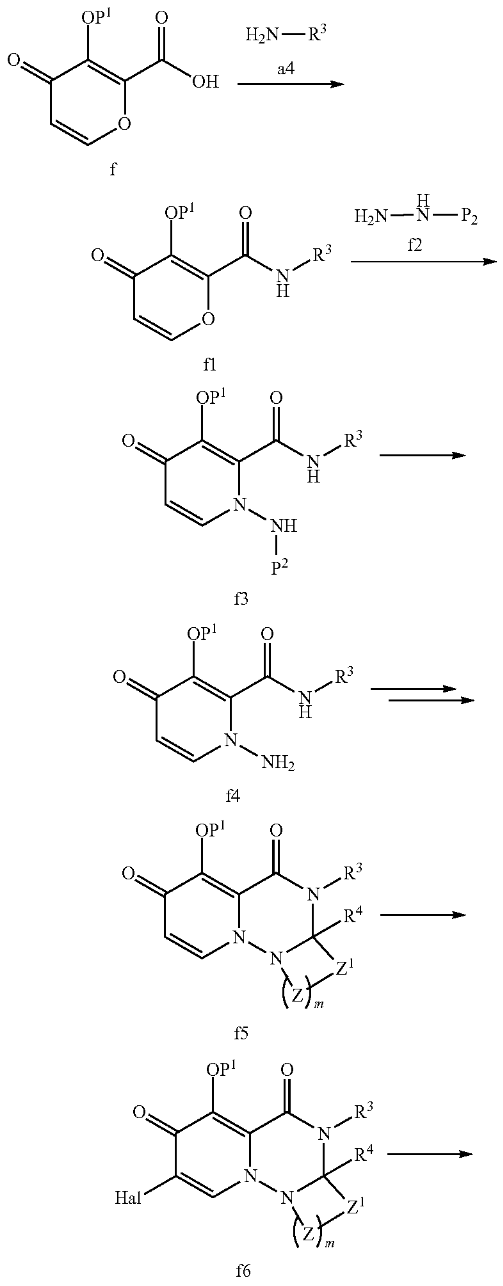

-continued

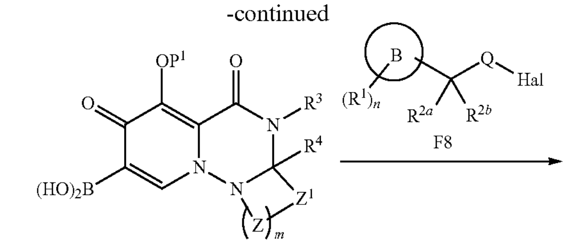

F8 f7

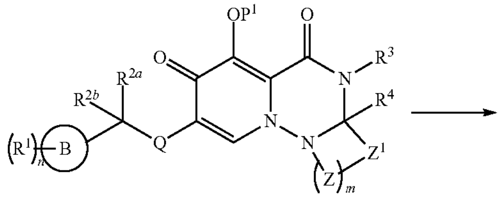

f9

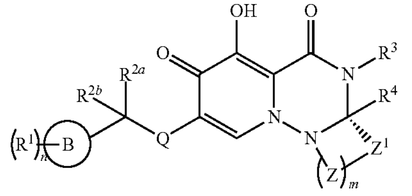

Ib (where, in the formulas, Q is a 5-member aromatic heterocycle; other symbols have the same meaning as above.)

Step 1

To a compound f prepared by known methods or obtained commercially, in the presence of a solvent such as DMF, DMA, NMP, THF, chloroform, or dichloromethane, there is added a condensation agent such as HATU, WSC.HCl, or PyBOP, and there is added a compound a4 prepared by known methods or obtained commercially and a ternary amine such as triethylamine, N-methymorpholine, pyridine, or diisopropyl ethylamine, and the compound f1 may be obtained by reacting at 10° C. to 60° C., preferably 20° C. to 40° C., for 0.1 h to 24 h, preferably 1 h to 12 h.

Step 2

Compound f3 may be obtained by adding, to the compound f1, in the presence of a solvent such as DMF, DMA or NMP, compound f2 prepared by known methods or Obtained commercially and an acid such as acetic acid, p-toluenesulfonic acid pyridium, p-toluenesulfonic acid, or methanesulfonic acid, and reacting at 20° C. to 120° C., preferably 60° C. to 100° C., for 0.1 h to 24 h, preferably 1 h to 12 h.

Step 3

Compound f4 can be obtained by subjecting compound f3 to a known ordinary deprotecting reaction of an amino group.

Step 4

Compound f5 can be obtained by reacting compound f4 under the same conditions as in the method described in preparation methods 1 to 5.

Step 5

In a solvent such as dichloromethane, dichloroethane, acetonitrile or DMF, by adding a halogenating reagent such as bromine or NBS, NCS or NIS to compound f5, in the case where Hal is bromo, compound f6 can be obtained by reacting at −30° C. to 50° C., preferably −10° C. to 20° C., for 0.1 h to 10 h, preferably 0.5 h to 2 h. If Hal is chloro or iodo, compound f6 can be obtained by reacting at 10° C. to 150° C., preferably 60° C. to 120° C., for 0.5 h to 24 h, preferably 1 h to 6 h.

Step 7

Compound f7 can be obtained by adding to compound f6, in a solvent or mixed solvent such as dioxane, DMF, DME, THF, DMSO, a palladium catalyst such as $Pd(PPh_3)_4$, $Pd(OAc)_2$, $Pd(PPh_3)_2Cl_2$, $Pd(dppf)_2Cl_2$ or Pd(dtbpf), a base such as potassium acetate, sodium acetate, potassium carbonate or potassium phosphate, and bis(pinacolato)diboron, and reacting, under a nitrogen atmosphere, at 0° C. to 150° C., preferably 60° C. to 120° C., for 0.5 h to 24 h, preferably 1 h to 12 h.

Step 8

Compound f9 can be obtained by adding to compound f7, in a solvent or mixed solvent of dioxane, DMF, DME, THF or water and the like, a palladium catalyst such as $Pd(PPh_3)_4$, $Pd(OAc)_2$, $Pd(PPh_3)_2Cl_2$, $Pd(dppf)_2Cl$ or Pd(dtbpf), a base such as potassium carbonate, sodium carbonate, cesium carbonate or potassium phosphate and a compound f8 prepared by known methods or obtained commercially, and reacting at 0° C. to 150° C., preferably 60° C. to 120° C., for 0.5 h to 24 h, preferably 1 h to 12 h, under a nitrogen atmosphere.

Step 9

Compound Ib may be synthesized by Steps 7 and 8 of preparation method 1.

(Preparation Method 7)

[Chem. 24]

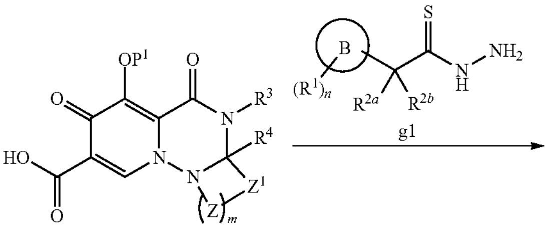

g1 g

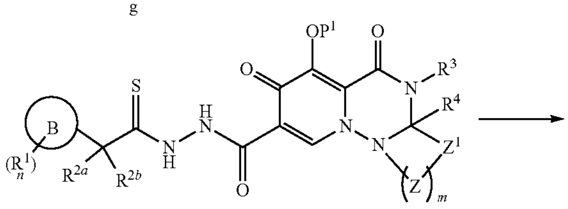

g2

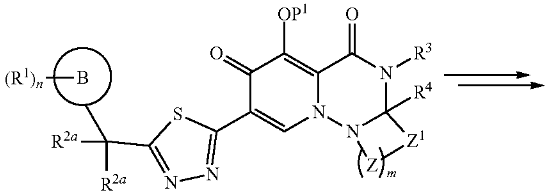

g3

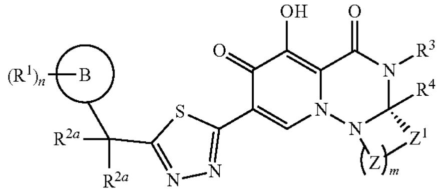

IC (where, in the formulas, the other symbols have the same meaning as above.)

Step 1

Compound g2 can be obtained by converting compound g to the acid chloride by adding thereto a base such as triethylamine or diisopropyl ethylamine, in the presence of a solvent such as dichloromethane, dichloroethane, chloroform, DMF, DMA, NMP or THF and ethyl chloroformate, then adding compound g1, which may be prepared by known methods or obtained commercially, and reacting at 0° C. to 60° C., preferably 0° C. to 20° C., for 0.1 h to 24 h, preferably 1 h to 12 h.

Step 2

Compound g3 can be obtained by subjecting compound g2 to the action of an acid such as T3P, trifluoroacetic acid, phosphoric acid, hydrochloric acid, sulfuric acid or hydrobromic acid, in the presence of a solvent such as ethyl acetate, dichloromethane, dichloroethane, chloroform, dioxane, DMF, DMA or THF, and reacting at 20° C. to 130° C., preferably 60° C. to 100° C., for 0.1 h to 24 h, preferably 1 h to 12 h.

Step 3

Compound Ic can be synthesized in accordance with Steps 7 and 8 of preparation method 1.

Other compounds can be synthesized by further chemical modification of the compounds obtained above. Also, in the above reactions, when reactive functional groups (e.g. OH, COOH, $NH_2$) are present in for example sidechain portions, in accordance with requirements, these may be protected prior to reaction and deprotected after reaction.

As protective groups (such as amino protective groups, hydroxy protective groups and the like), the protective groups described in for example Protective Groups in Organic Synthesis, by T. W. Greene, John Wiley & Sons Inc. (1991), such as ethoxy carbonyl, tert-butoxy carbonyl, acetyl or benzyl may be given as examples. As methods for introduction or removal of protective groups, the methods commonly used in organic synthetic chemistry [see for example Protective Groups in Organic Synthesis, by T. W. Greene, John Wiley & Sons Inc. (1991)], or methods based thereon may be employed. Further, apart from the production methods described above, conversion of the functional groups contained in the various substituent groups may be performed by known methods [for example, Comprehensive Organic Transformations, by R. C. Larock (1989)], and further novel derivatives may be produced by employing these as synthesis intermediates in the compounds according to the present invention. The intermediates and target compounds in the above production methods may be isolated and purified by employing the methods of purification that are commonly used in organic synthetic chemistry, such as for example neutralization, filtration, extraction, washing, drying, concentration, recrystallization and various types of chromatography. In regard to intermediates, it is sometimes also possible to supply these to the next reaction without especial purification.

As the compounds indicated by (B) employed in the present invention, a commercially obtainable compound may be employed, or they may be prepared by the methods described in, for example, U.S. Pat. No. 6,838,464B, WO2018/035359, WO2015/174511, WO2016/194806 and the like.

As one aspect, a pharmaceutical agent according to the present invention is characterized by combining (A) a compound represented by formula (I):

[Chem. 25]

(I)

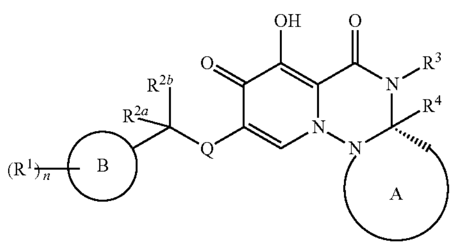

(where, in this formula, ring A is any of the following rings:

[Chem. 26]

(a)

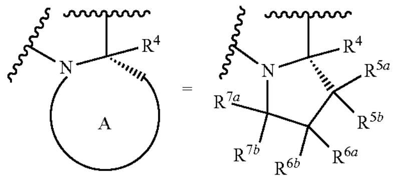

(b)

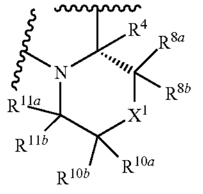

X1 is $CR^{9a}R^{9b}$ or O;

$R^{5a}$, $R^{5b}$, $R^{6a}$, $R^{6b}$, $R^{7a}$ and $R^{7b}$ are respectively independently hydrogen, alkyl, alkyloxy, or alkyloxyalkyl groups;

$R^{5a}$ and $R^{6a}$, or $R^{6a}$ and $R^{7a}$ may form, together with an adjacent atom, an aromatic carbon ring, which may be halogen-substituted, a 3-6 member non-aromatic carbon ring, which may be halogen-substituted, or a 4-6 member heterocycle, which may be halogen-substituted (in the case where an aromatic carbon ring is formed, $R^{5b}$ and $R^{6b}$, or $R^{6b}$ and $R^{7b}$ may come together to form a bond);

$R^{5b}$ and $R^{6b}$ may come together to form a bond;

$R^{8a}$, $R^{8b}$, $R^{9a}$, $R^{9b}$, $R^{10a}$, $R^{10b}$, $R^{11a}$ and $R^{11b}$ are respectively independently hydrogen, alkyl, alkyloxy, or alkyloxyalkyl groups;

$R^{8a}$ and $R^{10a}$ may together form a C1-C3 cross-linkage;

$R^{10a}$ and $R^{11a}$, together with an adjacent atom, may form a 5-member non-aromatic carbon ring;

$R^{9a}$ and $R^{9b}$, together with an adjacent atom, may form a 4-member non-aromatic carbon ring or 5-member non-aromatic heterocycle;

$R^{8a}$ and $R^{9a}$ may come together to form a bond;

the B ring is a benzene ring or pyridine ring;

Q is —NHC(O)— or a 5-member aromatic heterocycle;

$R^1$ is respectively independently halogen, alkyl, haloalkyl, alkyloxy, cyano or haloalkyloxy;

$R^{2a}$ and $R^{2b}$ are respectively independently hydrogen, alkyl or haloalkyl;

$R^3$ is alkyl or haloalkyl;

$R^4$ is hydrogen or alkyl; and n is an integer of 1 to 3)

or a pharmaceutically acceptable salt thereof; and a compound (B) having anti-HIV activity, or a pharmaceutically acceptable salt thereof.

The pharmaceutical agent according to the present invention is used for prophylaxis and/or treatment of HIV infectious diseases. As one mode, the present invention provides a pharmaceutical agent for prophylaxis and/or treatment of HIV infectious diseases which is a combination of (A) and (B). In another mode, according to the present invention, there is provided a pharmaceutical agent for prophylaxis and/or treatment of HIV infectious diseases which contains (A) and (B).

In a further aspect, the present invention provides an anti-HIV action enhancing agent combining (A) and (B).

Herein, "pharmaceutical agent characterized by a combination" includes: a pharmaceutical agent including each compound; a mode of use of these compounds as a combination drug; a mode of use as a kit; a mode in which these are administered concurrently; a mode in which these are administered with a time interval; or a mode in which one pharmaceutical agent is used together with another pharmaceutical agent: the abbreviation "combination (combined)" may be used, with the same meaning. Preferably, they are used in the form of a mixture.

The compound indicated by (A), or pharmaceutically acceptable salt thereof may be employed together with the compound (B) having anti-HIV activity, or pharmaceutically acceptable salt thereof, or may be used to enhance the anti-HIV action of compound (B) having anti-HIV activity, or pharmaceutically acceptable salt thereof. Further, the compound (B) having anti-HIV activity, or pharmaceutically acceptable salt thereof may be employed together with the compound indicated by (A), or pharmaceutically acceptable salt thereof, or may be used to enhance the anti-HIV action of the compound indicated by (A), or pharmaceutically acceptable salt thereof.

As another aspect, a pharmaceutical agent according to the present invention is characterized by combining (A) a compound represented by formula (I)

[Chem. 27]

(I)

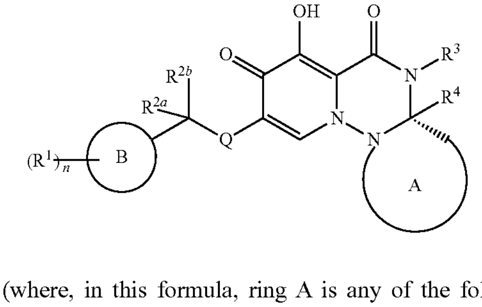

(where, in this formula, ring A is any of the following rings:

[Chem. 28]

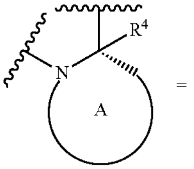

-continued

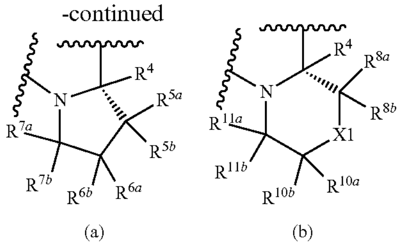

X1 is $CR^{9a}R^{9b}$ or O;

$R^{5a}$, $R^{5b}$, $R^{6a}$, $R^{6b}$, $R^{7a}$ and $R^{7b}$ are respectively independently hydrogen, alkyl, alkyloxy, or alkyloxyalkyl groups;

$R^{5a}$ and $R^{6a}$, or $R^{6a}$ and $R^{7a}$ may form, together with an adjacent atom, an aromatic carbon ring, which may be halogen-substituted, a 3-6 member non-aromatic carbon ring, which may be halogen-substituted, or a 4-6 member heterocycle, which may be halogen-substituted (in the case where an aromatic carbon ring is formed, $R^{5a}$ and $R^{6b}$, or $R^{6b}$ and $R^{7b}$ may come together to form a bond);

$R^{5b}$ and $R^{6b}$ may come together to form a bond;

$R^{8a}$, $R^{8b}$, $R^{9a}$, $R^{9b}$, $R^{10a}$, $R^{10b}$, $R^{11a}$ and $R^{11b}$ are respectively independently hydrogen, alkyloxy, or alkyloxyalkyl groups;

$R^{8a}$ and $R^{10a}$ may together form a C1-C3 cross-linkage;

$R^{10a}$ and $R^{11a}$, together with an adjacent atom, may form a 5-member non-aromatic carbon ring;

$R^{9a}$ and $R^{9b}$, together with an adjacent atom, may form a 4-member non-aromatic carbon ring or 5-member non-aromatic heterocycle;

$R^{8a}$ and $R^{9a}$ may come together to form a bond;

the B ring is a benzene ring or pyridine ring;

Q is —NHC(O)— or a 5-member aromatic heterocycle;

$R^1$ is respectively independently halogen, alkyl, haloalkyl, alkyloxy, cyano or haloalkyloxy;

$R^{2a}$ and $R^{2b}$ are respectively independently hydrogen, alkyl or haloalkyl;

$R^3$ is alkyl or haloalkyl;

$R^4$ is hydrogen or alkyl; and n is an integer of 1 to 3)

or a pharmaceutically acceptable salt thereof; and (B) at least one selected from: compounds with a polymerase inhibitory activity, compounds with a ribonuclease H inhibitory activity, compounds with an HIV-1 integrase (IN)-lens epithelium-derived growth factor (LEDGF) complex allosteric inhibitory activity, compounds with a protease inhibitory activity, compounds with an adsorption and invasion inhibitory activity, compounds with a budding inhibitory activity, compounds with a maturation inhibitory activity, compounds with a capsid inhibitory activity, and pharmaceutically acceptable salts thereof.

As another aspect, a pharmaceutical agent according to the present invention is characterized by combining (A) a compound represented by formula (I):

[Chem. 29]

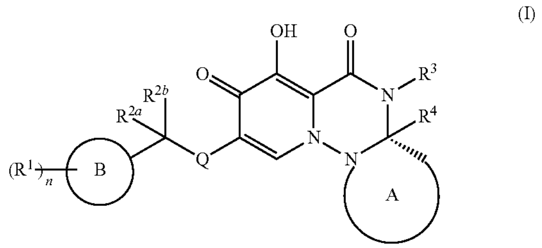

(where, in this formula, ring A is any of the following rings:

[Chem. 30]

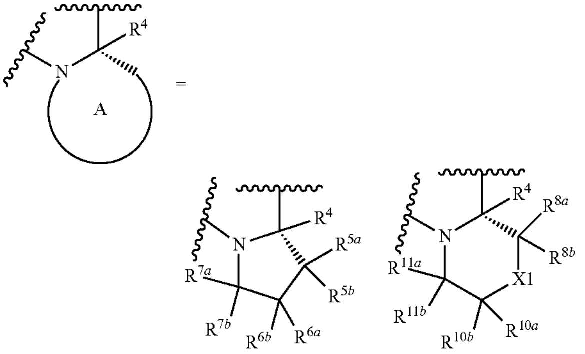

(a) (b)

X1 is $CR^{9a}R^{9b}$ or O;

$R^{5a}$, $R^{5b}$, $R^{6a}$, $R^{6b}$, $R^{7a}$ and $R^{7b}$ are respectively independently hydrogen, alkyl, alkyloxy, or alkyloxyalkyl groups;

$R^{5a}$ and $R^{6a}$, or $R^{6a}$ and $R^{7a}$ may form, together with an adjacent atom, an aromatic carbon ring, which may be halogen-substituted, a 3-6 member non-aromatic carbon ring, which may be halogen-substituted, or a 4-6 member heterocycle, which may be halogen-substituted (in the case where an aromatic carbon ring is formed, $R^{5b}$ and $R^{6b}$, or $R^{6b}$ and $R^{7b}$ may come together to form a bond);

$R^{5b}$ and $R^{6b}$ may come together to form a bond;

$R^{8a}$, $R^{8b}$, $R^{9a}$, $R^{9b}$, $R^{10a}$, $R^{10b}$, $R^{11a}$ and $R^{11b}$ are respectively independently hydrogen, alkyl, alkyloxy, or alkyloxyalkyl groups;

$R^{8a}$ and $R^{10a}$ may together form a C1-C3 cross-linkage;

$R^{10a}$ and $R^{11a}$, together with an adjacent atom, may form a 5-member non-aromatic carbon ring;

$R^{9a}$ and $R^{9b}$, together with an adjacent atom, may form a 4-member non-aromatic carbon ring or 5-member non-aromatic heterocycle;

$R^{8a}$ and $R^{9a}$ may come together to form a bond;

the B ring is a benzene ring or pyridine ring;

Q is —NHC(O)— or a 5-member aromatic heterocycle;

$R^1$ is respectively independently halogen, alkyl, haloalkyl, alkyloxy, cyano or haloalkyloxy;

$R^{2a}$ and $R^{2b}$ are respectively independently hydrogen, alkyl or haloalkyl;

$R^3$ is alkyl or haloalkyl;

$R^4$ is hydrogen or alkyl; and n is an integer of 1 to 3)

or a pharmaceutically acceptable salt thereof; and (B) at least one selected from AZT, 3TC, didanosine, zalcitabine, sanilvudine, abacavir, tenofovir, tenofovir disoproxil, tenofovir alafenamide, emtricitabine, nevirapine, efavirenz, capravirine, etravirine, delavirdine, rilpivirine, VM-1500A, VM-1500, doravirine, MK-8507, MK-8504, MK-8583, compound I'-001, I'-027, I'-043, I'-189, I'-220, I'-292, I'-304, indinavir, ritonavir, saquinavir, nelfinavir, amprenavir, atazanavir, lopinavir, fosamprenavir, darunavir, maraviroc, enfuvirtide, ibalizumab, PRO-140, temsavir, fostemsavir tromethamine, combinectin, BDM-2, GSK-2838232, GSK-3640254, GS-6207, MK-8527, MK-8558, and pharmaceutically acceptable salts thereof.

As another aspect, a pharmaceutical agent according to the present invention is characterized by combining (A) a compound represented by formula (I):

[Chem. 31]

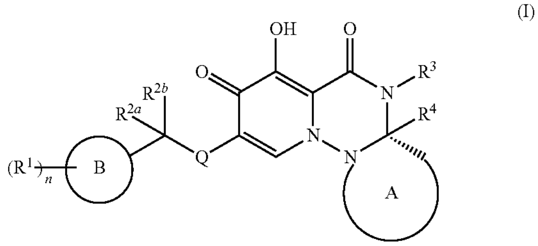

(where, in this formula, ring A is any of the following rings:

[Chem. 32]

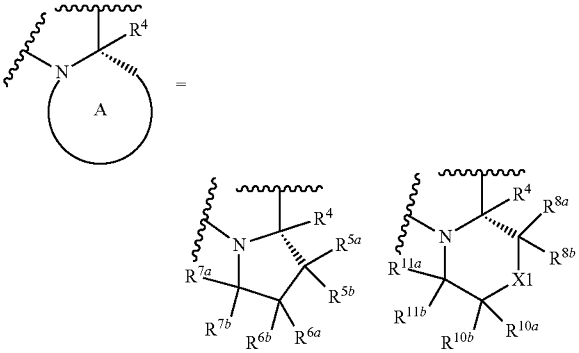

(a) (b)

X1 is $CR^{9a}R^{9b}$ or O;

$R^{5a}$, $R^{5b}$, $R^{6a}$, $R^{6b}$, $R^{7a}$ and $R^{7b}$ are respectively independently hydrogen, alkyl, alkyloxy, or alkyloxyalkyl groups;

$R^{5a}$ and $R^{6a}$, or $R^{6a}$ and $R^{7a}$ may form, together with an adjacent atom, an aromatic carbon ring, which may be halogen-substituted, a 3-6 member non-aromatic carbon ring, which may be halogen-substituted, or a 4-6 member heterocycle, which may be halogen-substituted (in the case where an aromatic carbon ring is formed, $R^{5b}$ and $R^{6b}$, or $R^{6b}$ and $R^{7b}$ may come together to form a bond);

$R^{5b}$ and $R^{6b}$ may come together to form a bond;

$R^{8a}$, $R^{8b}$, $R^{9a}$, $r^{9b}$, $R^{10a}$, $R^{10b}$, $R^{11a}$ and $R^{11b}$ are respectively independently hydrogen, alkyl, alkyloxy, or alkyloxyalkyl groups;

$R^{8a}$ and $R^{10a}$ may together form a C1-C3 cross-linkage;

$R^{10a}$ and $R^{11a}$, together with an adjacent atom, may form a 5-member non-aromatic carbon ring;

$R^{9a}$ and $R^{9b}$, together with an adjacent atom, may form a 4-member non-aromatic carbon ring or 5-member non-aromatic heterocycle;

$R^{8a}$ and $R^{9a}$ may come together to form a bond;

the B ring is a benzene ring or pyridine ring;

Q is —NHC(O)— or a 5-member aromatic heterocycle;

$R^1$ is respectively independently halogen, alkyl, haloalkyl, alkyloxy, cyano or haloalkyloxy;

$R^{2a}$ and $R^{2b}$ are respectively independently hydrogen, alkyl or haloalkyl;

$R^3$ is alkyl or haloalkyl;

$R^4$ is hydrogen or alkyl; and n is an integer of 1 to 3)

or a pharmaceutically acceptable salt thereof; and (B) the following compound.

[Chem. 33]

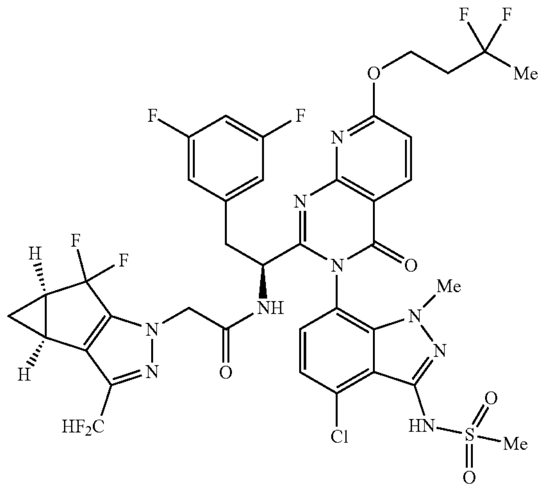

or pharmaceutically acceptable salt thereof.

As another aspect, a pharmaceutical agent according to the present invention is characterized by combining (A) a compound represented by formula (I):

[Chem. 34]

(I)

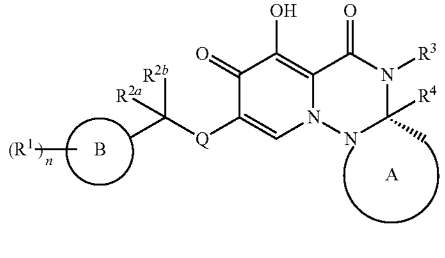

(where, in this formula, ring A is any of the following rings:

[Chem. 35]

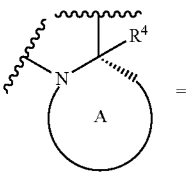

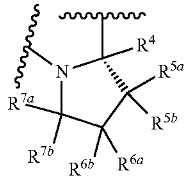

(a)

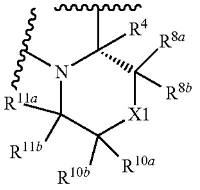

(b)

X1 is $CR^{9a}R^{9b}$ or O;

$R^{5a}$, $R^{5b}$, $R^{6a}$, $R^{6b}$, $R^{7a}$ and $R^{7b}$ are respectively independently hydrogen, alkyl, alkyloxy, or alkyloxyalkyl groups;

$R^{5a}$ and $R^{6a}$, or $R^{6a}$ and $R^{7a}$ may form, together with an adjacent atom, an aromatic carbon ring, which may be halogen-substituted, a 3-6 member non-aromatic carbon ring, which may be halogen-substituted, or a 4-6 member heterocycle, which may be halogen-substituted (in the case where an aromatic carbon ring is formed, $R^{5b}$ and $R^{6b}$, or $R^{6b}$ and $R^{7b}$ may come together to form a bond);

$R^{5b}$ and $R^{6b}$ may come together to form a bond;

$R^{8a}$, $R^{8b}$, $R^{9a}$, $R^{9b}$, $R^{10a}$, $R^{10b}$, $R^{11a}$ and $R^{11b}$ are respectively independently hydrogen, alkyl, alkyloxy, or alkyloxyalkyl groups;

$R^{8a}$ and $R^{10a}$ may together form a C1-C3 cross-linkage;

$R^{10a}$ and $R^{11a}$, together with an adjacent atom, may form a 5-member non-aromatic carbon ring;

$R^{9a}$ and $R^{9b}$, together with an adjacent atom, may form a 4-member non-aromatic carbon ring or 5-member non-aromatic heterocycle;

$R^{8a}$ and $R^{9a}$ may come together to form a bond;

the B ring is a benzene ring or pyridine ring;

Q is —NHC(O)— or a 5-member aromatic heterocycle;

$R^1$ is respectively independently halogen, alkyl, haloalkyl, alkyloxy, cyano or haloalkyloxy;

$R^{2a}$ and $R^{2b}$ are respectively independently hydrogen, alkyl or haloalkyl;

$R^3$ is alkyl or haloalkyl;

$R^4$ is hydrogen or alkyl; and n is an integer of 1 to 3)

or a pharmaceutically acceptable salt thereof; and (B) at least one selected from 3BNC117LS, 10-1074LS, GS-9722, GS-9723, N6LS, ARC07-523LS, and VRC01-LS.

As another aspect, a pharmaceutical agent according to the present invention is characterized by combining (A) a compound I-7, I-11, II-26, II-36, II-52, II-92, II-96, II-109, II-110, II-158, or a pharmaceutically acceptable salt thereof; and (B) at least one selected from: 3TC, abacavir, tenofovir, tenofovir alafenamide, emtricitabine, rilpivirine, VM-1500A, VM-1500, doravirine, MK-8504, MK-8583, compound I'-001, I'-027, I'-043, I'-189, I'-220, I'-292, I'-304, atazanavir, darunavir, maraviroc, enfuvirtide, ibalizumab, PRO-140, fostemsavir tromethamine, combinectin, BDM-2, GSK-2838232, GSK-3640254, GS-6207, and pharmaceutically acceptable salts thereof.

As another aspect, a pharmaceutical agent according to the present invention is characterized by combining (A) a compound I-7, I-11, II-26, II-36, II-52, II-92, II-96, II-109, II-110, II-158, or a pharmaceutically acceptable salt thereof; and (B) at least one selected from: 3TC, abacavir, tenofovir, tenofovir alafenamide, emtricitabine, compound I'-001, I'-027, I'-043, I'-189, I'-220, I'-292, I'-304, and pharmaceutically acceptable salts thereof.

As another aspect, a pharmaceutical agent according to the present invention is characterized by combining (A) a compound I-7, I-11, II-26, II-36, II-52, II-92, II-96, II-109, II-110, II-158, or a pharmaceutically acceptable salt thereof; and (B) the compound below:

[Chem. 36]

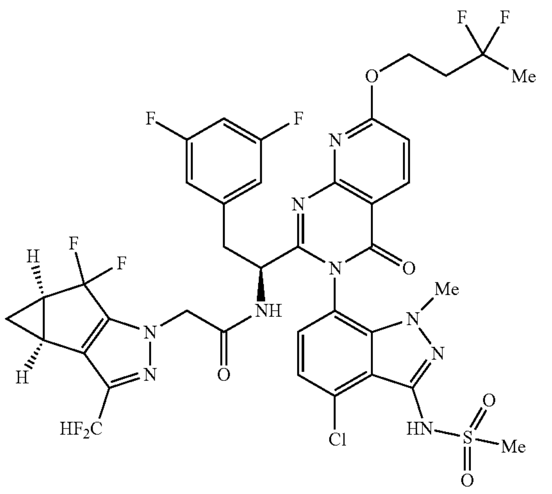

or a pharmaceutically acceptable salt thereof.

As another aspect, a pharmaceutical agent according to the present invention is characterized by combining (A) a compound I-7, I-11, II-26, II-36, II-52, II-92, II-96, II-109, II-110, II-158, or a pharmaceutically acceptable salt thereof; and (B) at least one selected from: 3BNC117LS, 10-1074LS, GS-9722, GS-9723, N6LS, ARC07-523LS, and VRC01-LS and pharmaceutically acceptable salts thereof.

As another aspect, a pharmaceutical agent according to the present invention is characterized by combining (A) a compound I-7, I-11, II-26, II-36, II-52, II-92, II-96, II-109, II-110, II-158, or a pharmaceutically acceptable salt thereof; and (B) at least one selected from: 3TC, abacavir, tenofovir, tenofovir alafenamide, emtricitabine, rilpivirine, VM-1500A, VM-1500, doravirine, MK-8504, MK-8583, compound I'-001, I'-027, I'-043, I'-189, I'-220, I'-292, I'-304, atazanavir, darunavir, maraviroc, enfuvirtide, ibalizumab, PRO-140, fostemsavir tromethamine, combinectin, BDM-2, GSK-2838232, GSK-3640254, GS-6207, the following compound:

[Chem. 37]

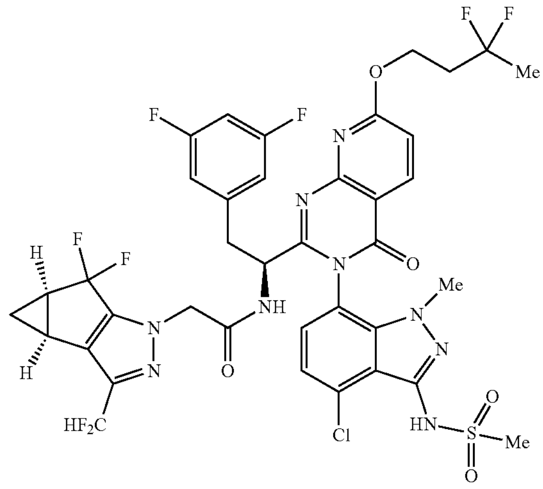

a pharmaceutically acceptable salt thereof or 3BNC117LS, 10-1074LS, GS-9722, GS-9723, N6LS, ARC07-523LS, and VRC01-LS.

As another aspect, a pharmaceutical agent according to the present invention is characterized by combining (A) a compound I-7, I-11, II-26, II-36, II-52, II-92, II-96, II-109, II-110, II-158, or a pharmaceutically acceptable salt there of; and (B) at least one selected from; 3TC, rilpivirine, VM-1500A, VM-1500, I'-189, darunavir, GSK-2838232, GS-6207, and pharmaceutically acceptable salts thereof.

A pharmaceutical agent according to the present invention may be administered by oral or non-oral methods. Given as methods for non-oral administration are, for example, percutaneous, subcutaneous, intravenous, intra-arterial, intramuscular, intraperitoneal, transmucosal, inhalation, nasally, eyedrops, eardrops, or intravaginal administration.

Oral administration may be effected by preparing and administering any of the formulations usually employed, by the ordinary methods, such as solid formulations for internal use (for example, tablets, powders, granules, capsules, pills or films and the like) or liquid formulations for internal use (for example, suspensions, emulsions, elixirs, syrups, lemonades, liquors, spirits, aromatic waters, extracts, decoctions, or tinctures. The tablets may be sugar-coated tablets, film-coated tablets, enteric-coated tablets, slow-release tablets, troches, sublingual tablets, buccal tablets, chewable tablets or tablets that decompose in the oral cavity; powders and granules or may also be dry syrups; capsules may be soft capsules, microcapsules or slow-release capsules.

Preparations for non-oral administration may be injections, drips, external agents (for example, eye drops, nose drops, ear drops, aerosols, inhalants, lotions, injections, coating agents, mouthwash, enemas, ointments, plasters, jellies, creams, patches, poultices, external powders, suppositories and the like) or similar commonly used preparations. Injections may be emulsions such as O/W, W/O, O/W/O, or W/O/W.

A pharmaceutical composition can be obtained, depending on the type of agent, by mixing an effective dose of the compound according to the present invention with various types of pharmaceutical additives such as excipients, binders, disintegrants, or detergents, in accordance with requirements. Furthermore, these pharmaceutical compositions may be employed as pharmaceutical compositions for children, elderly persons, seriously ill patients or for operations by suitably altering the effective dose of the compound of the present invention used in the pharmaceutical agent according to the present invention, the type thereof and/or the various pharmacological additives. For example, the pharmaceutical agent composition for children may be administered to neonates (up to four weeks after birth), nursing infants (from four weeks after birth to one year), infants (age 1 to 7 years), children (7 to 15) or patients of 15 to 18 years of age. The pharmaceutical agent composition for elderly persons, for example, may be administered to patients of 65 years of age or older.

The dosage of the pharmaceutical agent according to the present invention may be suitably selected, employing the dosage that is clinically used as standard. Also, the combination ratio of the compound used in (A) and the pharmaceutical agent (B) used in combination therewith may be suitably selected depending on the combination of the administration subject, administration route, the target disease and symptoms. For example, when the subject of administration is a person, 0.01 to 400 weight parts of the combination pharmaceutical agent (B) may be used for one weight part of the compound indicated by (A).

EXAMPLES

The present invention is described below in further detail with reference to modes and test examples of the present invention, but is not limited to these. Further, modifications may be made without departing from the scope of the present invention. It should be noted that the chemical names given in the modes and comparative. examples below are not necessarily in accordance with the IUPAC naming system. The NMR analysis employed in the modes was conducted at 300 MHz, and measurements were made using DMSO-$d_6$, and $CDCl_3$.

In addition, when the NMR data are shown, in some cases not all of the measured peaks are noted.

In the examples, "No." is the compound number, "structure" is the chemical structure, and "MS" indicates the atomic weight by LC/MS (liquid chromatography/mass analysis).

(Measurement Conditions)

(A) Column: ACQUITY UPLC (registered trademark) BEH C18 (1.7 μm i.d. 2.1×50 mm) (Waters)

Flow rate: 0.8 mL/min; UV detection wavelength: 254 nm;

Mobile phase: [A] was an aqueous solution containing 0.1% formic acid, [B] was an acetonitrile solution containing 0.1% formic acid;

a rear gradient of 5% to 100% of solvent [B] was applied for 3.5 min; solvent [B] was then maintained at 100% for 0.5 min.

(B) Column: Shim-pack XR-ODS (2.2 μm i.d. 50×3.0 mm) (Shimadzu)

Flow rate: 1.6 mL/min; UV detection wavelength 254 nm;

Mobile phase: [A] was an aqueous solution containing 0.1% formic acid, [B] was an acetonitrile solution containing 0.1% formic acid;

Gradient: a rear gradient of 10% to 100% of solvent [B] was applied for 3 min; solvent [B] was then maintained at 100% for 0.5 min.

(C) Column: Shim-pack XR-ODS (2.2 μm, i.d. 50×3.0 mm) (Shimadzu)

Flow rate:1.6 mL/min.; U detection wavelength:254 nm;

Mobile phase: [A] was an aqueous solution containing 0.1% formic acid, [B] was an acetonitrile solution containing 0.1% formic acid;

Gradient: a rear gradient of 10% to 100% of solvent [B] was applied for 8 min; solvent [B] was then maintained at 100% for 0.5 min.

Examples relating to formula (I) of (A) are described below.

Example 1

[Chem.38]

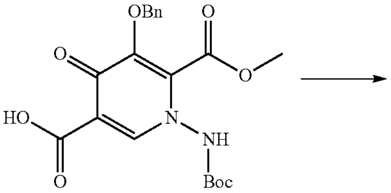

1

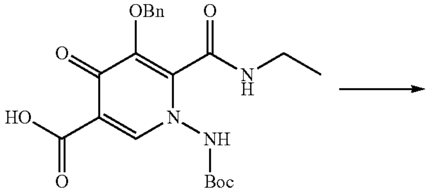

2

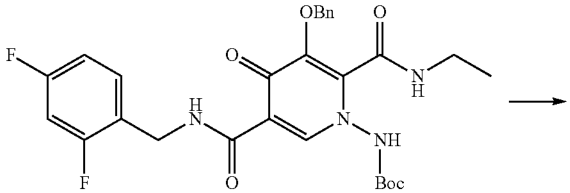

3

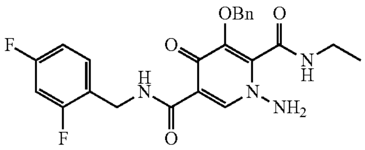

4

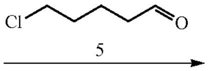

5

-continued

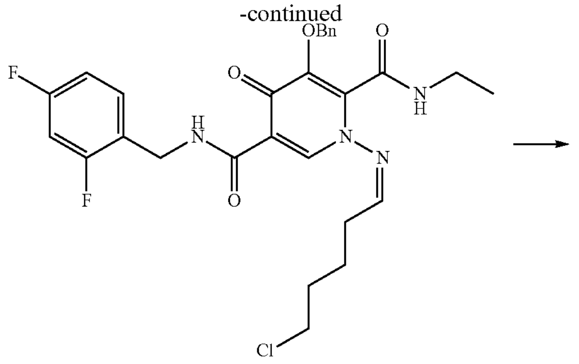

6

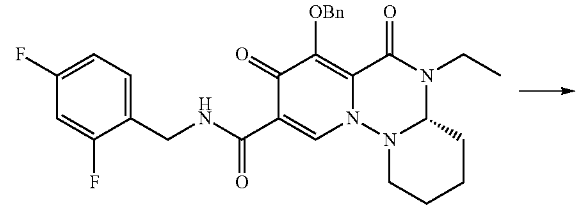

7

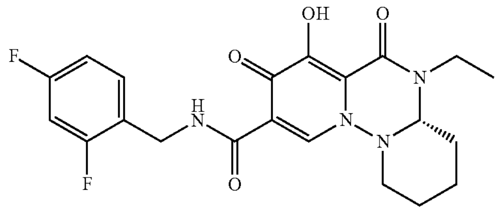

I-23

Step 1

A methanol solution (17.9 ml, 35.9 mmol) of 2 mol/L of ethylamine was added to compound 1 (1.50 g, 3.59 mmol) and stirred for 1 h at 100° C. under microwave irradiation. After removing the solvent from the reaction liquid by distilling under reduced pressure, acidification was effected by adding dilute hydrochloric acid, and extraction was performed with ethyl acetate. The solvent was distilled off after drying the organic layer with sodium sulfate. The residue obtained was purified using silica gel column chromatography (chloroform-methanol), to obtain compound 2 (1.15 g, yield 74%).

$^1$H-NMR ($CDCl_3$) δ: 14.53 (s, 1H), 8.64 (brs, 1H), 8.46 (s, 1H), 7.37 (m, 5H), 6.57 (brs, 1H), 5.38 (s, 2H), 3.24 (dt, J=14.0, 6.6 Hz, 2H), 1.45 (s, 9H), 1.02 (t, J=7.3 Hz, 4H).

Step 2

Compound 2 (9.59 g, 22.2 mmol) was dissolved in dichloromethane (180 ml); (2,4-difluorophenyl) methaneamine (4.77 g, 33.3 mmol), PyBOP (13.9 g, 26.7 mmol) and DIEA (11.7 ml, 66.7 mmol) were added, and the mixture was stirred for 18 h at room temperature. The reaction liquid was washed with water and a saturated aqueous solution of common salt, the organic layer dried with sodium sulfate, and the solvent then distilled off. The residue obtained was purified using silica gel chromatography (chloroform-methanol), to obtain compound 3 (11.5 g, yield 93%).

$^1$H-NMR ($CDCl_3$) δ: 10.20 (t, J=5.8 Hz, 1H), 8.54 (brs, 1H), 8.49 (s, 1H), 7.38 (m, 5H), 6.87-6.79 (m, 2H), 6.61 (t, J=5.5 Hz, 1H), 5.28 (s, 2H), 4.64 (d, J=5.9 Hz, 2H), 3.18 (ddt, J=18.8, 10.2, 3.8 Hz, 3H), 1.83-1.80 (m, 1H), 1.43 (s, 9H), 0.99 (t, J=7.3 Hz, 3H).

Step 3

Compound 3 (11.5 g, 9.54 mmol) was dissolved in dioxane (57.5 mL), and 4 mol/L of hydrochloric acid/dioxane solution (300 mL) were added and stirred for 4 h. The reaction liquid was distilled under reduced pressure to remove the solvent, and a saturated aqueous solution of sodium carbonate was added and extraction performed using chloroform-methanol. The organic layer was dried using sodium sulfate and the crude product obtained by distilling off the solvent was solidified from diisopropyl ether, to obtain compound 4 (7.80 g, yield 83%).

$^1$H-NMR ($CDCl_3$) δ: 10.33 (s, 1H), 8.60 (s, 1H), 7.39 (m, 5H), 6.83 (m, 3H), 5.82 (s, 2H), 5.26 (s, 2H), 4.64 (d, J=5.8 Hz, 2H), 3.28-3.21 (m, 2H), 1.02 (t, J=7.3 Hz, 3H).

Step 4

Compound 4 (200 mg, 0.438 mmol) was dissolved in dichloromethane (4 ml), and compound 5 (111 mg, 0.920 mmol) and acetic acid (catalytic amount) were added and stirred for 19 h at room temperature. After concentrating the reaction liquid under reduced pressure, purification was conducted using silica gel chromatography (chloroform-methanol), to obtain compound 6 (265 mg, yield 100%).

MS: m/z=559 [M+H]+

Step 5

Compound 6 (245 mg, 0.438 mmol) was dissolved in DMF (5 mL), and cesium carbonate (428 mg, 1.31 mmol) was added at 0° C. and stirred at room temperature for 18 h. Dilute hydrochloric acid was added to the reaction liquid, and extraction was conducted with ethyl acetate. The organic layer was washed with water and dried with sodium sulfate, and the solvent distilled off. The residue obtained was purified using silica gel chromatography (chloroform-methanol), to obtain a racemic mixture (1.39 mg, yield 60%).

The racemic mixture obtained was optically resolved using SFC, to obtain compound 7.

Column: CHIRALPACK IA/SFC (5 μm, i.d. 250×20 mm)

Flow rate: 30 mL/min

UV detection wavelength: 250 nm

Resolution conditions: maintaining a composition of ratio $MeOH/CO_2$=45/55, liquid feed for 21 min.

$^1$H-NMR ($CDCl_3$) δ: 10.46 (s, 1H), 8.51 (s, 1H), 7.58 (m, 2H), 7.34 (m, 4H), 6.81 (m, 2H), 5.41 (d, J=10.4 Hz, 1H), 5.26 (d, J=10.4 Hz, 1H), 4.91 (s, 1H), 4.64 (m, 2H), 4.39 (dd, J=14.3, 7.2 Hz, 1H), 3.18-2.88 (m, 3H), 2.24 (d, J=14.7 Hz, 1H), 2.00 (m, 1H), 1.85 (m, 2H), 1.72 (d, J=13.6 Hz, 1H), 1.38 (m, 1H), 1.16 (t, J=7.1 Hz, 3H).

Step 6

Compound 7 (44.0 mg, 0.0840 mmol) was dissolved in DMF (0.88 ml), lithium chloride (35.7 mg, 0.842 mmol) was added and stirred for 1.5 h at 90° C. Water was added to the reaction liquid, and the mixture was acidified with 10% aqueous citric acid solution, then extracted with ethyl acetate. The organic layer was washed with water, dried with sodium sulfate and the solvent then distilled off. The crude product obtained was solidified from diethyl ether, to obtain compound I-23 (19 mg, yield 52%). $^1$H-NMR ($CDCl_3$) δ: 11.98 (s, 1H), 10.42 (s, 1H), 8.46 (s, 1H), 7.36 (dd, J=15.2, 8.6 Hz, 1H), 6.83-6.77 (m, 2H), 5.06 (s, 1H), 4.64 (m, 2H), 4.35 (td, J=14.2, 6.9 Hz, 1H), 3.20-3.09 (m, 2H), 3.00 (d, J=10.8 Hz, 1H), 2.31(d, J=15.4 Hz, 1H), 2.06 (m, 1H), 1.89 (m, 2H), 1.76 (m, 1H), 1.42-1.36 (m, 1H), 1.24 (t, J=7.1 Hz, 4H).

Example 2

[Chem 39]

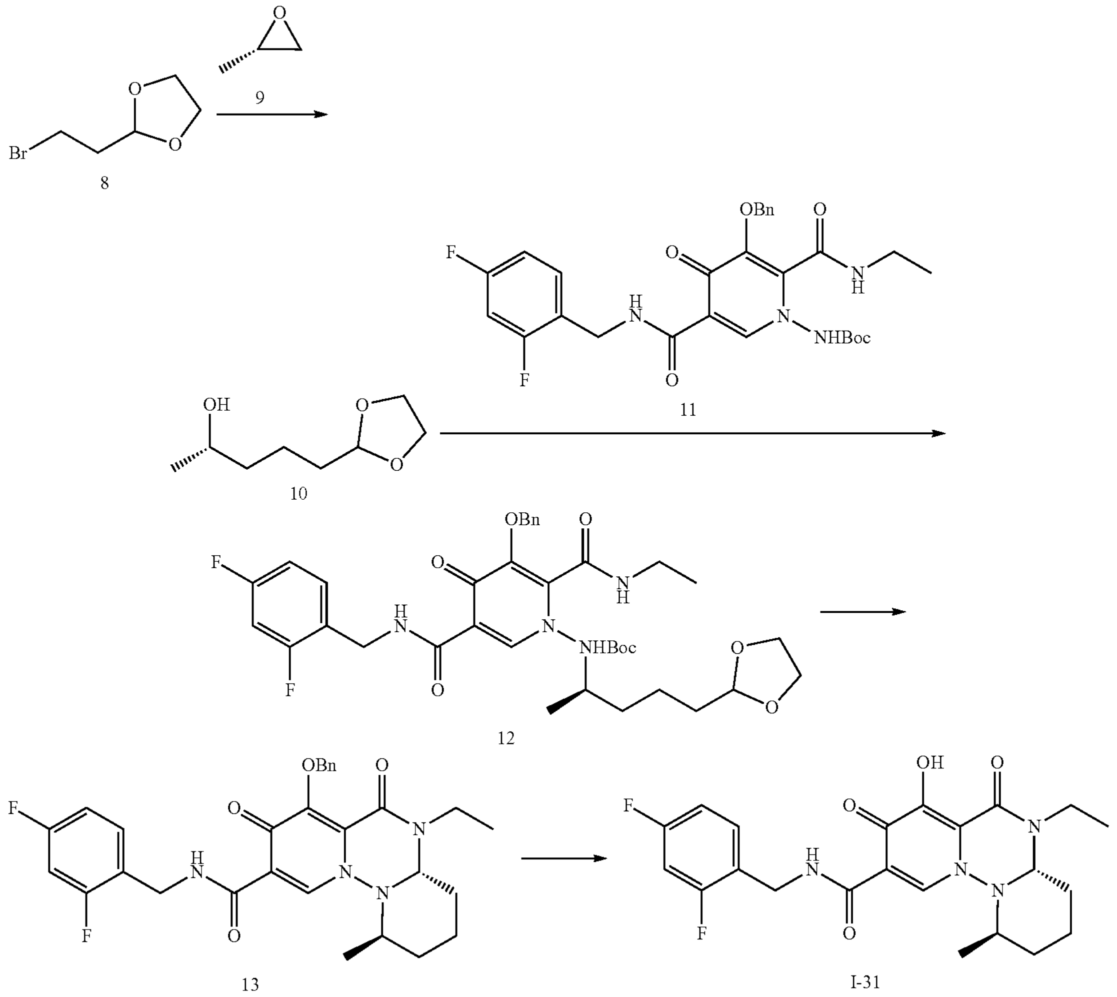

Step 1

Under a nitrogen atmosphere, a THF (7.0 ml) solution of compound 8 (1.3 ml, 11.1 mmol) was added dropwise to a THF (3.0 mL) solution of magnesium (322 mg, 13.3 mmol), and stirred for 30 min at room temperature. The reaction liquid was cooled to 0° C., copper iodide (210 mg, 1.1 mmol) was added, and a THF (6.0 mL) solution of compound 9 (1.2 mL, 16.6 mmol) was added dropwise and stirred for 2 h while warming to room temperature. An aqueous solution of saturated ammonium chloride was added to the reaction solution and extraction performed with ethyl acetate. The organic layer was washed with a saturated aqueous common salt solution, dried with anhydrous sodium sulfate, and the solvent was then distilled off. The residue obtained was purified using silica gel column chromatography (hexane-ethyl acetate), to obtain compound 10 (192 mg, yield 11%).

1H-NMR($CDCl_3$)δ: 4.86(t, J=4.8 Hz, 1H), 3.99-3.96(m, 2H), 3.90-3.79(m, 3H), 1.72-1.67(m, 2H), 1.55-1.48(m, 4H), 1.36(d, J=4.5 Hz, 1H), 1.20(d, J=6.3 Hz, 3H).

Step 2

Compound 10 (192.2 mg, 1.2 mmol), triphenylphosphine (315 mg, 1.2 mmol) and azodicarboxylate bis(2-methoxyethyl) (281 mg, 1.0 mmol) were added to a THF(2.0 mL) solution of compound 11 (334 mg, 0.60 mmol), and stirred for 1 h at room temperature. Water was added to the reaction liquid and extraction performed using ethyl acetate. The organic layer was washed with a saturated aqueous solution of common salt, dried with anhydrous sodium sulfate, and the solvent distilled off. Rough purification of the residue obtained was carried out using silica gel column chromatography (hexane-ethyl acetate).

MS: m/z=699 [M+H]+

Step 3

Para-toluene sulfonic acid hydrate (45.1 mg, 0.242 mmol) was added to an acetonitrile (1.0 mL) solution of the roughly purified product (100 mg) obtained in Step 2, and heating under reflux was carried out for 210 min. The reaction liquid was allowed to cool to room temperature, a saturated aqueous solution of sodium hydrogen carbonate was added, and extraction was performed using ethyl acetate. The organic layer was washed with a saturated aqueous solution of common salt, dried with anhydrous sodium sulfate, and the solvent distilled off. The residue obtained was dissolved in DMF (1.0 ml), cesium carbonate (140 mg, 0.43 mmol) and benzyl bromide (34.1 μL, 0.29 mmol) were added, and stirred for 3 h at room temperature. Water was added to the reaction liquid and extraction performed using ethyl acetate. The organic layer was washed with a saturated aqueous solution of common salt, dried with anhydrous sodium sulfate, and the solvent then distilled off. The residue obtained was purified using silica gel column chromatography (chloroform-methanol), to obtain compound 13 (65.1 mg).

MS: m/z=537 [M+H]+

Step 4

Compound I-31 (31 mg, yield 57%) was obtained by carrying out the same reaction as in Step 6 of Example 1.

1H-NMR($CDCl_3$)δ: 11.93(s, 1H), 10.40(s, 1H), 8.39(s, 1H), 7.40-7.34(m, 1H), 6.84-6.77(m, 2H), 5.11-5.09(m, 1H), 4.64(d, J=5.8 Hz, 2H), 4.40-4.31(m, 1H), 3.27-3.21(m, 1H), 3.13-3.06(m, 1H), 2.32-2.28(m, 1H), 2.12-2.04(m, 1H), 1.86-1.83(m, 1H), 1.79-1.75(m, 1H), 1.63-1.48(m, 2H), 1.21 (t, J=7.2 Hz, 3H), 0.89(d, H=6.3 Hz, 3H).

Example 3

[Chem. 40]

11

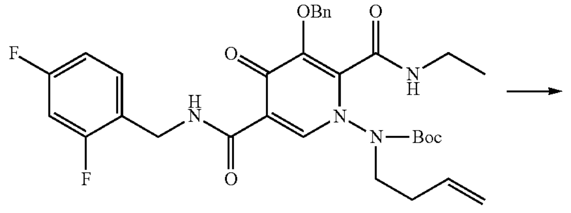

14

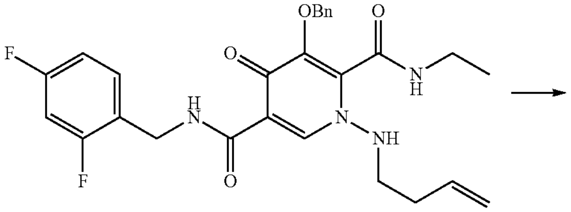

15

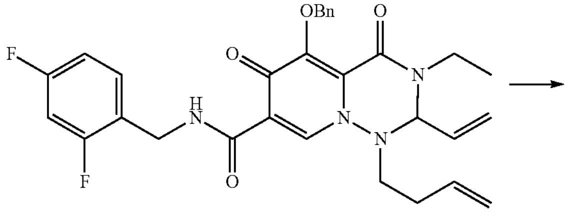

16

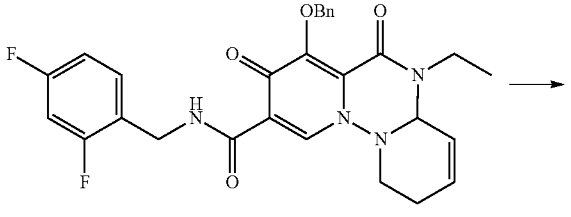

17

-continued

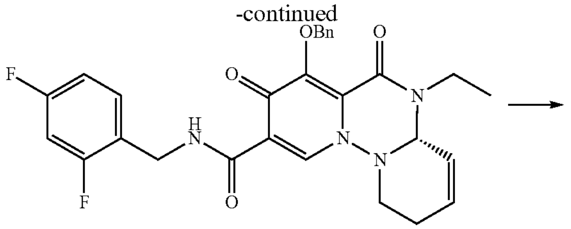

18

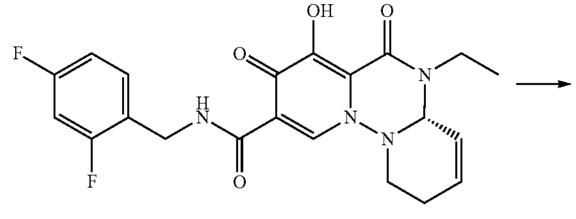

II-65

Step 1

Potassium carbonate (261 mg, 1.89 mmol) and 4-bromobutene (147 mg, 0.943 mmol) were added to a DMF (3.5 ml) solution of compound 11 (352 mg, 0.629 mmol) and reacted overnight at room temperature. Water was added to the reaction liquid, and extraction carried out using ethyl acetate. The organic layer was washed with a saturated aqueous solution of common salt, dried with anhydrous sodium sulfate, and the solvent then distilled off.

MS: m/z=611 [M+H]+

Step 2

A 4 mol/L hydrochloric acid/dioxane solution (3.15 ml) was added to the crude product obtained in Step 1, and stirred for 2 h at room temperature. A saturated aqueous solution of sodium carbonate was added to the reaction liquid and extraction performed using ethyl acetate. The organic layer was washed with a saturated aqueous solution of common salt, and dried with anhydrous sodium sulfate, and the solvent then distilled off.

MS: m/z=511 [M+H]+

Step 3

The crude product obtained in Step 2, acrolein (102 mg, 1.83 mmol), and para-toluene sulfonic acid hydrate (11.6 mg, 0.061 mmol) were dissolved in dichloroethane (9.6 mL), and stirred for 6 h at 100° C. The reaction liquid was left to cool to room temperature, water and a saturated aqueous solution of sodium carbonate were added, and extraction was performed using ethyl acetate. The organic layer was washed with a saturated aqueous solution of common salt, dried with anhydrous sodium sulfate, and the solvent then distilled off. The residue obtained was purified using silica gel column chromatography (hexane-ethyl acetate) to obtain compound 16 (115 mg).

MS: m/z=549 [M+H]+

Step 4

Compound 16 (66.4 mg, 0.121 mmol) and Hoveyda-Grubbs second generation catalyst (60 mg, 0.139 mmol) were dissolved in dichloromethane (10 mL) and heated under reflux for 6 h. The solvent of the reaction liquid was distilled off, and the residue obtained was roughly purified using silica gel column chromatography (ethyl acetate-methanol).

MS: m/z=521 [M+H]+

Step 5

Compound 17 obtained in Step 4 was optically resolved using SFC to obtain compound 18.

Column: CHIRALPAK IC/SFC (5 μm, i.d. 250×20 mm)

Flow rate: 20 mL/min.

UV detection wavelength: 220 nm

Resolution conditions: liquid feed for 21 min, maintaining a composition ratio of $MeOH/CO_2$=70/30.

Step 6

Compound II-65 (11 mg, yield 74%) was obtained by performing the same reaction as in Step 6 of Example 1.

1H-NMR($CDCl_3$)δ: 11.93(s, 1H), 10.42(t, J=5.6 Hz, 1H), 8.50(s, 1H), 7.40-7.33(m, 1H), 6.84-6.77(m, 2H), 6.28-6.24 (m, 1H), 5.96-5.91(m, 1H), 5.32(d, J=5.2 Hz, 1H), 4.68(dd, J=15.2, 6.0 Hz, 1H), 4.61(dd, J=15.6, 6.0 Hz, 1H), 3.83(dt, J=21.2, 7.2 Hz, 1H), 3.53(dt, J=20.8, 6.8 Hz, 1H), 3.39(td, J=11.2, 4.4 Hz, 1H), 3.04(dd, J=10.8, 6.8 Hz, 1H), 2.77-2.68(m, 1H), 2.35(dt, J=18.8, 4.8 Hz, 1H), 1.23(t, J=7.2 Hz, 3H).

Example 4

[Chem.41]

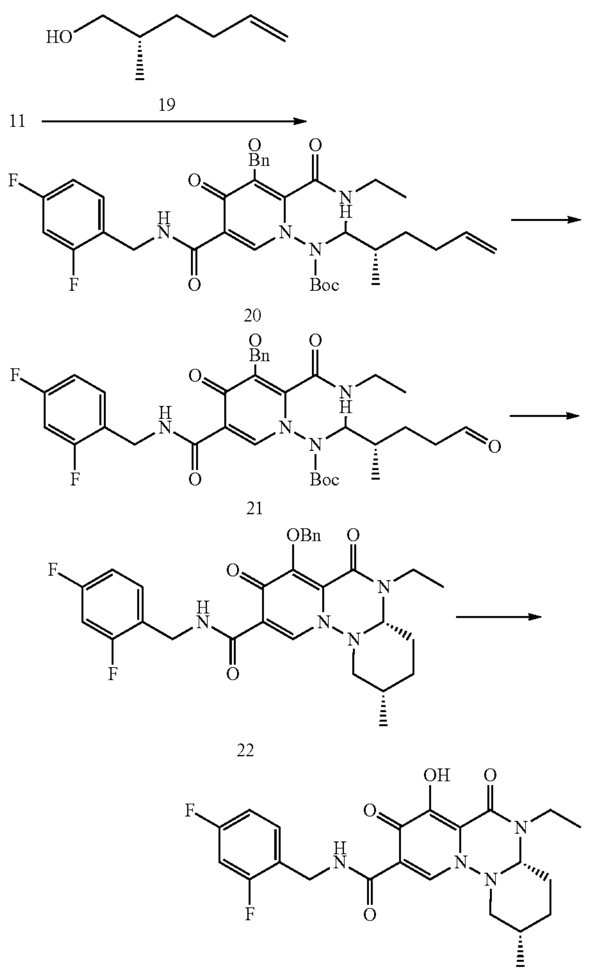

19

11

20

21

22

II-34

Step 1

Azodicarboxylic acid di-2-methoxylethyl (274 mg, 1.18 mmol) was added at 0° C. to a THE (3.5 mL) solution of compound 11 (326 mg, 0.59 mmol), compound 19 (87 mg, 0.77 mmol) and biphenyl phosphine (307 mg, 1.18 mmol), and left to stand for 12 h at room temperature. Water was added to the reaction liquid, and extraction carried out using ethyl acetate. The organic layer was washed with water and a saturated aqueous solution of common salt, then dried with anhydrous sodium sulphate, and the solvent distilled off. The residue obtained was purified using silica gel column chromatography (hexane-ethyl acetate), to obtain compound 20 (293 mg, yield 77%).

MS: m/z=653 [M+H]+

Step 2

Compound 20 (287 mg, 0.44 mmol) was suspended dissolved in dioxane (3.4 mL) and water (2.3 and, at 0° C., 2, 6-lutidine (0.10 sodium periodate (282 mg, 1.32 mmol), and potassium osmate (VI) dihydrate (8.0 mg, 0.02 mmol) were added and the reaction liquid warmed from 0° C. to room temperature over 5 h. The reaction liquid was filtered with Celite (registered trademark), and a 10% aqueous solution of sodium thiosulfate was added and extraction performed with ethyl acetate. The organic layer was washed with water and a saturated aqueous solution of common salt, dried with anhydrous sodium sulfate, and the solvent distilled off. The residue obtained was purified using silica gel column chromatography (hexane-ethyl acetate), to obtain compound 21 (223 mg, yield 78%).

MS: m/z=655 [M+H]+

Step 3

Compound 21 (192 mg, 0.29 mmol) was dissolved in 4 mol/L hydrochloric acid/dioxane solution (1.47 ml) and stirred for 2 h at room temperature. The solvent was distilled off, and the crude product obtained was dissolved in toluene (2.0 ml), a catalytic amount of acetic acid added, and stirred for 2 h at 90° C. A saturated aqueous solution of sodium carbonate was added to the reaction solution and extraction was performed using ethyl acetate. The organic layer was washed with water and a saturated aqueous solution of common salt, dried with sodium sulfate and the solvent distilled off. The residue obtained was purified using silica gel column chromatography, to obtain a mixture of diastereomers. The mixture of diastereomers obtained was optically resolved using SFC, to obtain compound 22 (69 mg, yield 44%).

Column: CHIRALPAK IC/SFC (5 μm, i.d.250×20 mm), two columns arranged in series.

Flow rate:20 mL/min.

UV detection wavelength: 220 nm

Resolution conditions: liquid feed was conducted for 35 min, maintaining a composition ratio of $MeOH/CO_2$=65/35.

MS: m/z=537 [M+H]+

Step 4

Compound II-34 was obtained by performing the same reaction as in Step 6 of Example 1.

MS: m/z=447 [M+H]+

Example 5

[Chem. 42]

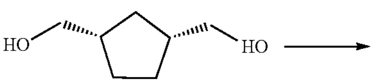

23

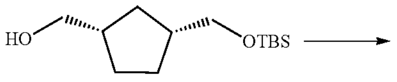

24

-continued

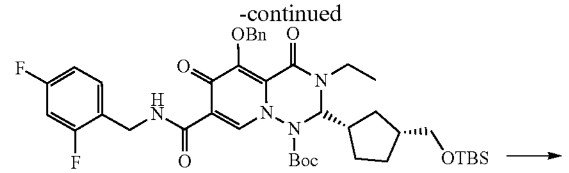

25

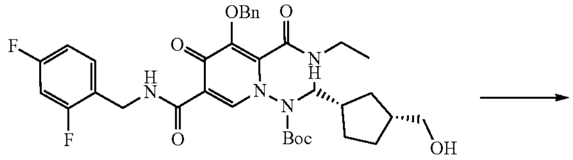

26

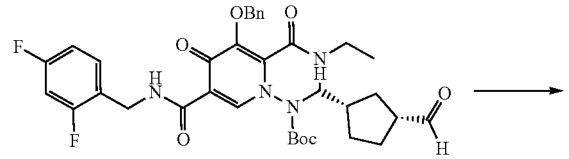

27

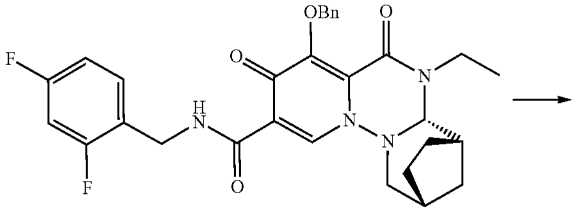

28

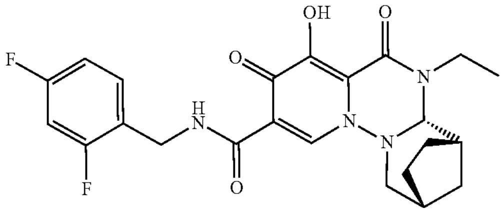

II-1

Step 1

Imidazole (0.998 g, 14.66 mmol) and t-butyldimethylsilyl chloride (1.84 g, 12.21 mmol) were added at 0° C. to a DMF (16.0 mL) solution of compound 23 (1.59 g, 12.2 mmol), and stirred for 3 h at room temperature. A saturated aqueous solution of ammonium chloride was added to the reaction liquid, and extraction performed using ethyl acetate. The organic layer was washed with water and a saturated aqueous solution of common salt, dried with anhydrous sodium sulphate, and the solvent distilled off. The residue Obtained was purified using silica gel column chromatography (hexane-ethyl acetate), to obtain compound 24 (1.39 g, yield 47%).

1H-NMR($CDCl_3$)δ: 3.47-3.55(m, 4H), 2.09-2.15(m, 2H), 1.88-1.95(s, 1H), 1.65-1.79(m, 2H), 1.32-1.42(m, 2H), 0.88-0.89(m, 1H), 0.85(s, 9H), 0.039(s, 6H).

Step 2

Azodicarboxylic acid di-2-methoxyethyl (589 mg, 2.52 mmol) was added at 0° C. to a THE (7 mL) solution of compound 24 (400 mg, 0.164 mmol), compound 11 (700 mg, 1.26 mmol) and triphenyl phosphine (660 mg, 2.52. mmol), and left to stand for 12 h at room temperature. Water was added to the reaction liquid, and extraction was conducted using ethyl acetate. The organic layer was washed with water, dried with anhydrous sodium sulphate, and the solvent distilled off.

The residue obtained was roughly purified using silica gel column chromatography (hexane-ethyl acetate).

Step 3

A 1 mol/L TBAF/THF solution (1.63 ml, 1.63 mmol) was added to a THF(10.0 mL) solution of compound 25 (1.06 g, 1.35 mmol), and stirred for 12 h at room temperature. A saturated aqueous solution of ammonium chloride was added to the reaction liquid and extraction performed using ethyl acetate. The organic layer was washed with water and a saturated aqueous solution of common salt, dried with anhydrous sodium sulphate, and the solvent distilled off. The residue obtained was purified using silica gel column chromatography (hexane-ethyl acetate), to obtain compound 26 (720 mg, yield 80%).

MS: m/z=669 [M+H]+

Step 4

Dess-Martin periodinane was added at 0° C. to a dichloromethane (8.0 mL) solution of compound 26 (720 mg, 1.08 mmol), and stirred for 1 h at room temperature. A 10% aqueous solution of sodium thiosulfate and a saturated aqueous solution of sodium hydrogen carbonate were added to the reaction liquid, and extraction was performed with chloroform. The organic layer was washed with water and an aqueous solution of common salt, dried with anhydrous sodium sulphate, and the solvent distilled off. The residue obtained was purified using silica gel column chromatography (hexane-ethyl acetate), to obtain compound 27 (393 mg, yield 55%).

MS: m/z=667 [M+H]+

Step 5

An acetonitrile (8.0 mL) solution of compound 27 (393 mg, 0.59 mmol) was heated to 60° C. and stirred for 80 min. A saturated aqueous solution of sodium hydrogen carbonate was added to the reaction liquid, which was then extracted with ethyl acetate. The organic layer was washed with water and a saturated aqueous solution of common salt, dried with anhydrous sodium sulphate, and the solvent distilled off. The crude product obtained was dissolved in DMF (4.0 mL), and, cesium carbonate (576 mg, 1.77 mmol) and benzyl bromide (0.21 mL, 1.77 mmol) were added at 0° C. and stirred at room temperature overnight. Water was added to the reaction liquid and extraction was performed using ethyl acetate. The organic layer was washed with water and a saturated aqueous solution of common salt, dried with anhydrous sodium sulphate, and the solvent distilled off. The residue obtained was purified using silica gel column chromatography (hexane-ethyl acetate), and optically resolved with SFC, to obtain compound 28 (89 mg, yield 28%). Column: CHIRALPAK IC/SFC (5 μm, i.d. 250×20 mm); two columns arranged in series.

Flow rate:20 mL/min

UV detection wavelength: 220 nm

Resolution conditions: liquid feed for 45 min, maintaining a composition ratio of MeOH/$CO_2$=75/25.

MS: m/z=549 [M+H]+

Step 6

Compound II-1 (11 mg, yield 74%) was obtained by performing the same reaction as in Step 6 of Example 1.

MS: m/z=459 [M+H]+

Example 6

[Chem. 43]

2

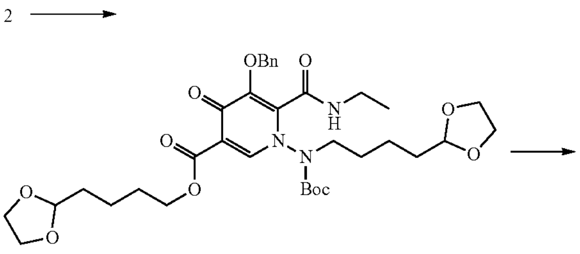

29

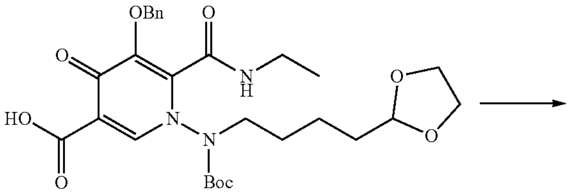

30

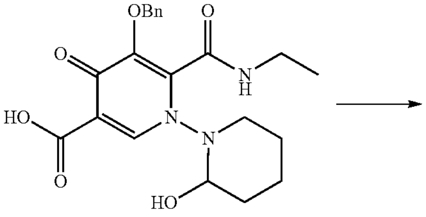

31

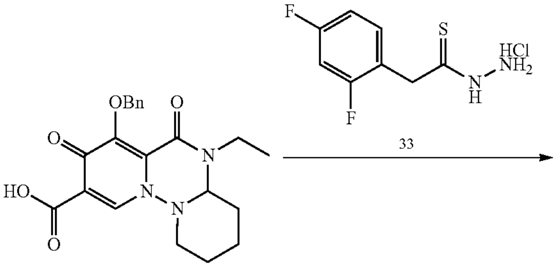

33

32

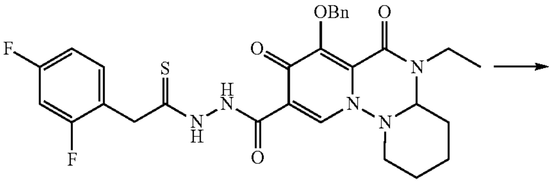

34

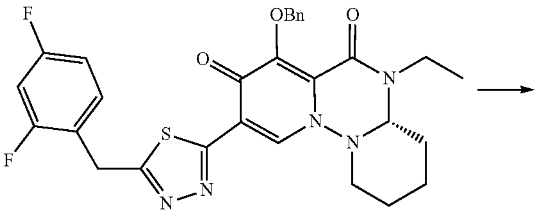

35

-continued

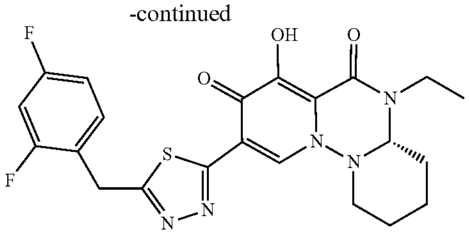

I-11

Step 1

Potassium carbonate (2.02 g, 14.6 mmol) and 2-(4-bromobutyl)-1,3-dioxolane (2.53 ml, 16.7 mmol) were added to a DMF (60 ml) solution of compound 2 (3 g, 6.95 mmol) and the solution was allowed to react overnight at room temperature. The reaction liquid was neutralised with 1 mol/L hydrochloric acid then extracted with ethyl acetate. The organic layer was washed with water and a saturated aqueous solution of common salt, dried with sodium sulphate, and the solvent distilled off, to obtain compound 29.

MS: m/z=688 [M+H]+

Step 2

A2 mol/L aqueous solution of sodium hydroxide (17.38 ml, 139 mmol) was added to a THF (47.8 mL) solution of compound 29, and stirred for 2 h at room temperature. The reaction liquid was neutralised by adding 2 mol/L hydrochloric acid little by little and extracted with ethyl acetate. The organic layer was washed with a saturated aqueous solution of common salt, dried with sodium sulphate, and the solvent distilled off under reduced pressure, to obtain compound 30.

MS: m/z=560 [M+H]+

Step 3

4 mol/L hydrogen chloride (1, 4-dioxane solution, 34.8 ml, 139 mmol) was added to a 1,4-dioxane solution (5 mL) of compound 30, and stirred for 1 h at room temperature. The solvent of the reaction liquid was distilled off and, by adding toluene and re-distilling, compound 31 was obtained.

MS: m/z=416 [M+H]+

Step 4

A few drops of acetic acid were added to a toluene solution of compound 31 (50 mL), and stirred for 30 min at 110° C. The solvent of the reaction liquid was distilled off and the residue obtained was solidified using ethanol/isopropyl ether, to obtain compound 32 (2.44 g, yield of the four steps: 88%).

$^1$H-NMR($CDCl_3$)δ: 15.1(s, 1H), 8.48(s, 1H), 7.57-7.55 (m, 2H), 7.36-7.29(m, 3H), 5.53(d, J=10.4 Hz, 1H), 5.36(d, J=10.4 Hz 1H), 4.93-4.91(m, 1H), 4.20(td, J=21.6, 7.2 Hz, 1H), 3.24-3.02(m, 3H), 2.28-1.73(m, 5H), 1.41-1.31(m, 1H), 1.18(t, J=7.2 Hz, 3H).

Step 5 triethylamine (0.419 ml, 3.02 mmol) and ethyl chloraformate (90.0 mg, 0.830 mmol), were added at 0° C. to a dichloromethane (3 ml) solution of compound 32 (300 mg, 0.755 mmol), and stirred for 30 min at room temperature. Compound 33 (216 mg, 0.906 mmol) was added to the reaction liquid and stirred for 1 h at room temperature. The reaction liquid was concentrated and the residue obtained was purified using silica gel column chromatography (chloroform-methanol), to obtain compound 34 (466 mg, yield 100%).

MS: m/z=582 [M+H]+

Step 6

A 50% T3P/ethyl acetate solution (2.25 ml, 7.55 mmol) was added to an ethyl acetate (6 ml) solution of compound 34 (439 mg: 0.755 ml) and stirred for 1 h at 100° C. A saturated aqueous solution of sodium hydrogen carbonate was added to the reaction liquid, and extraction performed using ethyl acetate. The organic layer was washed with water, dried with sodium sulphate, and the solvent distilled off. The residue obtained was purified using silica gel column chromatography (chloroform-methanol), to obtain a racemate. The racemate was optically resolved using SFC to obtain compound 35.

Column: CHIRALPAK IA/SFC (5 μm, i.d. 250×20 mm)

Flow rate: 20 mL/min.

UV detection wavelength: 220 nm

Resolution conditions: liquid feed was conducted for 25 min, maintaining the composition ratio: MeOH/$CO_2$=65/35.

1H-NMR($CDCl_3$)δ: 8.80(s, 1H), 7.60(m, 2H), 7.34-7.27 (m, 4H), 6.85(t, J=8.9 Hz, 2H), 5.55(d, J=10.3 Hz, 1H), 5.33(d, J=10.4 Hz, 1H), 4.97(m, 1H), 4.46(s, 2H), 4.40(m, 1H), 3.23(m, 1H), 3.10-3.03(m, 2H), 2.24(m, 1H), 2.02(m, 1H), 1.89(m, 2H), 1.72(m, 1H), 1.42(m, 1H), 1.17(t, J=7.2 Hz, 3H).

Step 7

Compound I-11 (63 mg, yield 68%) was attained by the same method as in step six of Example 1.

1H-NMR($CDCl_3$)δ: 12.04(s, 1H), 8.73(s, 1H), 7.31(m, 1H), 6.84(t, J=8.6 Hz, 2H), 5.14(s, 1H), 4.45(s, 2H), 4.36(m, 1H), 3.26-3.04(m, 3H), 2.33(d, J=14.9 Hz, 1H), 2.08(t, J=14.7 Hz, 1H), 1.91(m, 3H), 1.42(m, 1H), 1.24(t, J=7.2 Hz, 3H).

Example 7

[Chem.44]

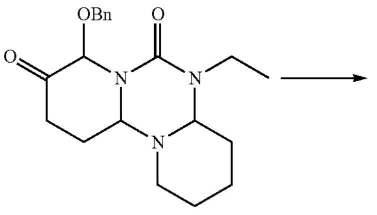

36

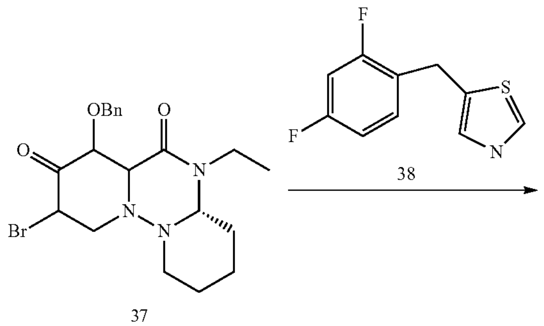

38

37

-continued

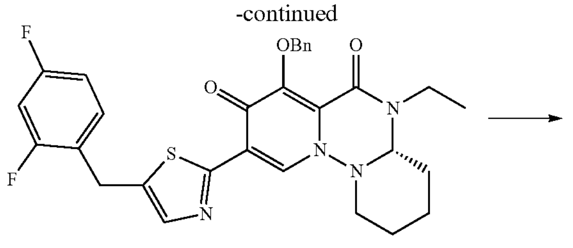

39

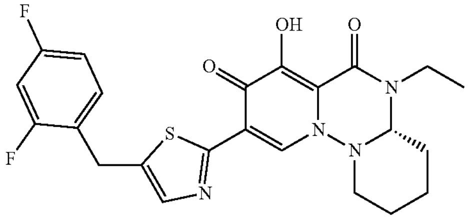

I-2

Step 1

A dichloromethane (10 mL) solution of compound 36 (1.0 g, 2.8 mmol) synthesized in the same way as in Example 1 was cooled to 0° C. and NBS (0.56 g, 3.1 mmol) was added thereto and stirred overnight at room temperature. The solvent of the reaction liquid was distilled off, and the residue obtained was purified using silica gel column chromatography (chloroform-methanol), to obtain a racemate. The racemate was optically resolved using SFC to obtain compound 37.

Column: CHIRALPAK IB/SFC (5 μm, i.d. 250×20 mm)

Flow rate:30 mL/min.

UV detection wavelength: 220 nm

Resolution conditions: liquid feed was conducted for 21 min, maintaining a composition ratio of MeOH/CO2=35/65.

1H-NMR($CDCl_3$)δ: 7.83(s, 1H), 7.64(d, J=7.0 Hz, 2H), 7.34-7.27(m, 3H), 5.48(d, J=10.3 Hz, 1H), 5.26(d, J=10.3 Hz, 1H), 4.92-4.90(m, 1H), 4.43-4.39(m, 1H), 3.20-3.14(m, 1H), 3.05-2.98(m, 2H), 2.26-2.22(m, 1H), 1.97-1.94(m, 1H), 1.84-1.82(m, 2H), 1.73-1.69(m, 1H), 1.41-1.39(m, 1H), 1.16 (t, J=7.2 Hz, 3H).

Step 2

Compound 37 (250 mg, 0.58 mmol) was dissolved in toluene, and compound 38 (183 mg, 0.87 mmol), Pd(OAc)$_2$(13.0 mg, 0.06 mmol), 2-dicyclohexyl phosphino-2'-(N, N-diamino) biphenyl (46 mg, 0.12 mmol) and cesium carbonate (565 mg, 1.7 mmol) were added thereto and sealed, and stirred at 140° C. for 2 h. The reaction liquid was then left to cool to room temperature, insoluble substances were removed by Celite filtration, and the solvent was distilled off. The residue obtained was roughly purified using silica gel column chromatography (hexane-ethyl acetate), to obtain compound 39 by reverse-phase purification (40 mg, yield 12%).

1H-NMR($CDCl_3$)δ: 8.63(s, 1H), 7.64-7.61(m, 3H), 7.34-7.19(m, 4H), 6.83-6.79(m, 2H), 5.58(d, J=10.3 Hz, 1H), 5.33(d, J=10.3 Hz, 1H), 4.96-4.94(m, 1H), 4.44-4.40(m, 1H), 4.19(s, 2H), 3.22-3.18(m, 1H), 3.09-3.02(m, 2H), 2.27-2.23(m, 1H), 2.01-1.97(m, 1H), 1.86-1.84(m, 2H), 1.74-1.70 (m, 1H), 1.43-1.40(m, 1H), 1.17(t, J=7.0 Hz, 3H).

Step 8

Compound I-2 (22 mg, yield 67%) was obtained by the same method as in Step 6 of Example 1.

1H-NMR($CDCl_3$)δ: 11.81(brs, 1H), 8.59(s, 1H), 7.54(s, 1H), 7.20-7.18(m, 1H), 6.83-6.78(m, 2H), 5.11-5.09(m, 1H), 4.40-4.31(m, 1H), 4.18(s, 2H), 3.24-3.02(m, 3H), 2.34-2.29 (m, 1H), 2.09-2.01(m, 1H), 1.90-1.85(m, 2H), 1.78-1.74(m, 1H), 1.46-1.36(m, 1H), 1.23(t, J=7.0 Hz, 3H).

Example 8

[Chem.45]

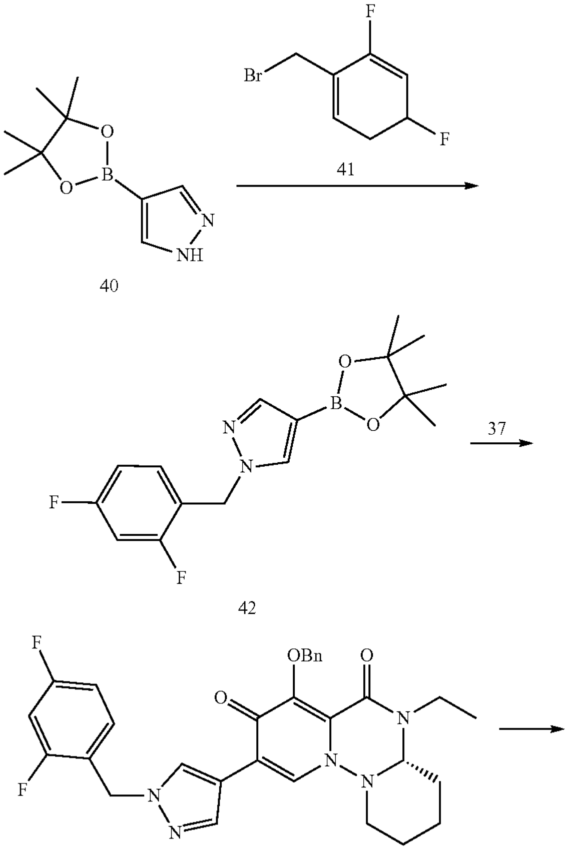

40

42

43

-continued

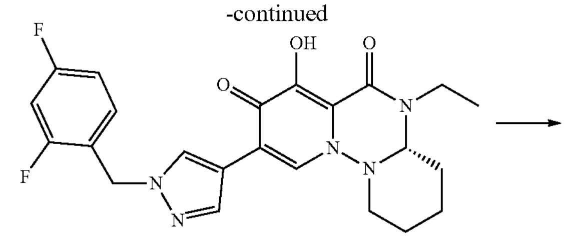

II-100

Step 1

Sodium hydroxide (60 wt %, 135 mg, 3.38 mmol) was added to a THF (5.0 mL) solution of compound 40 (528 mg, 2.10 mmol), and stirred for 10 min at 0° C. Compound 41 (500 mg, 2.415 mmol) was added to the reaction liquid and the temperature raised to room temperature, after which reaction was performed overnight. Water was added to the reaction liquid and extracted with ethyl acetate. The reaction liquid was washed with a saturated aqueous solution of common salt, dried with anhydrous sodium sulphate, and the solvent distilled off. The residue obtained was purified using silica gel column chromatography (hexane-ethyl acetate), to obtain compound 42 (517 mg, yield 67%).

MS: m/z=321 [M+H]+

Step 2

Compound 42 (89 mg, 0.278 mmol), compound 37 (60 mg, 0.139 mmol), cesium carbonate (68 mg, 0.208 mmol), and tetrakistriphenyl phosphine palladium (16 mg, 0.014 mmol) were dissolved in dioxane (1.8 mL), and reacted for 7 h at 90° C. Water was added to the reaction liquid and extraction performed using ethyl acetate. The organic layer was washed with a saturated aqueous solution of common salt, dried with anhydrous sodium sulphate, and the solvent distilled off. The residue obtained was roughly purified using silica gel column chromatography (ethyl acetate-methanol).

MS: m/z=546 [M+H]+

Step 3

Compound II-100 was obtained by the same method as in Step 6 of Example 1.

1H-NMR(CDCl3)δ: 8.66(s, 1H), 7.77(s, 1H), 7.72(s, 1H), 7.20-7.15(m, 1H), 6.86-6.80(m, 2H), 5.35(s, 2H), 5.08(s, 1H), 4.40-4.30(m, 1H), 3.20-2.95(m, 3H), 2.35-2.25(m, 1H), 2.01-1.40(m, 6H), 1.22(t, J=7.2 Hz, 3H).

The following compounds were synthesized in the same way, using the methods of synthesis described in Examples 1 to 8 or ordinary methods of synthesis as described above.

TABLE 1

| No. | Structure |
|---|---|
| I-001 | 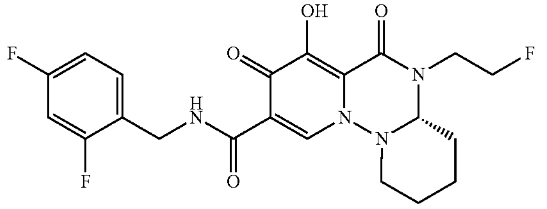 [SMILES: O=C(NCc1ccc(F)cc1F)c1cn2c(c(O)c1=O)C(=O)N(CCF)[C@@H]1CCCCN12] |

TABLE 1-continued
| No. | Structure |
| --- | --- |
| I-003 | 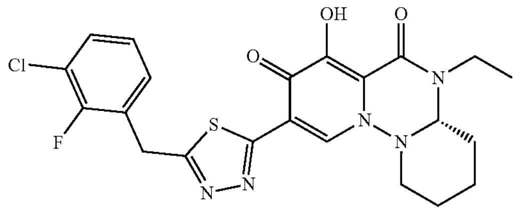 [SMILES: CCN1C(=O)c2c(O)c(=O)c(-c3nnc(Cc4cccc(Cl)c4F)s3)cn2N2CCCC[C@@H]12] |
| I-004 | 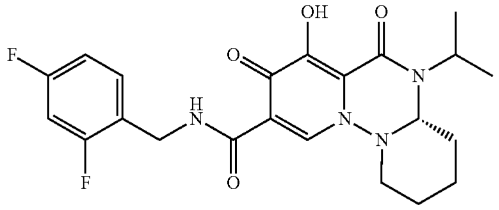 [SMILES: CC(C)N1C(=O)c2c(O)c(=O)c(C(=O)NCc3ccc(F)cc3F)cn2N2CCCC[C@@H]12] |
| I-005 | 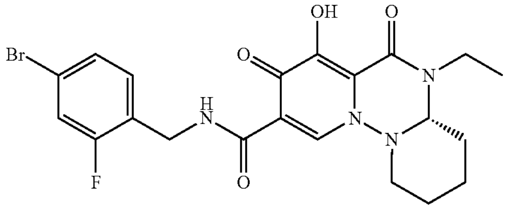 [SMILES: CCN1C(=O)c2c(O)c(=O)c(C(=O)NCc3ccc(Br)cc3F)cn2N2CCCC[C@@H]12] |
| I-006 | 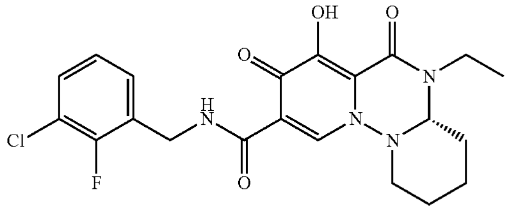 [SMILES: CCN1C(=O)c2c(O)c(=O)c(C(=O)NCc3cccc(Cl)c3F)cn2N2CCCC[C@@H]12] |
| I-007 | 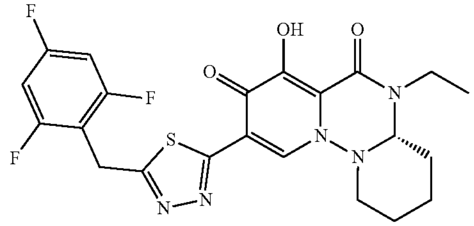 [SMILES: CCN1C(=O)c2c(O)c(=O)c(-c3nnc(Cc4c(F)cc(F)cc4F)s3)cn2N2CCCC[C@@H]12] |
| I-008 | 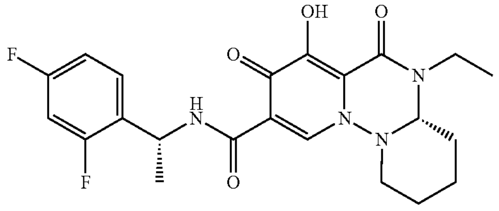 [SMILES: CCN1C(=O)c2c(O)c(=O)c(C(=O)N[C@H](C)c3ccc(F)cc3F)cn2N2CCCC[C@@H]12] |
| I-009 | 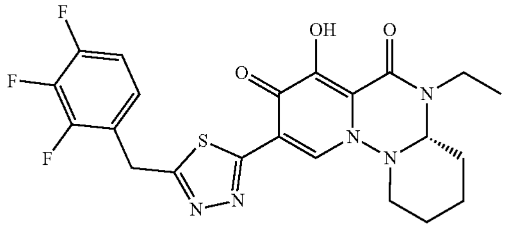 [SMILES: CCN1C(=O)c2c(O)c(=O)c(-c3nnc(Cc4ccc(F)c(F)c4F)s3)cn2N2CCCC[C@@H]12] |

TABLE 1-continued
| No. | Structure |
| --- | --- |
| I-010 | 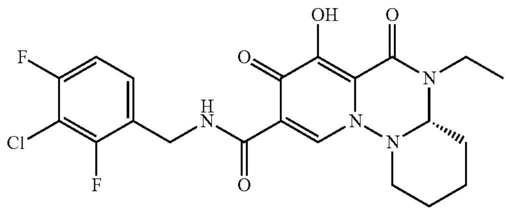 [SMILES: CCN1C(=O)c2c(O)c(=O)c(C(=O)NCc3ccc(F)c(Cl)c3F)cn2N2CCCC[C@@H]12] |
| I-012 | 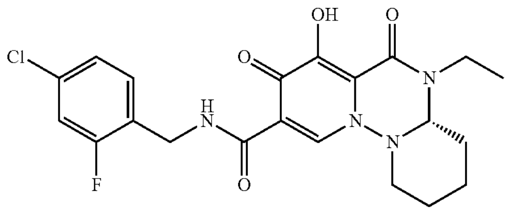 [SMILES: CCN1C(=O)c2c(O)c(=O)c(C(=O)NCc3ccc(Cl)cc3F)cn2N2CCCC[C@@H]12] |
| I-013 | 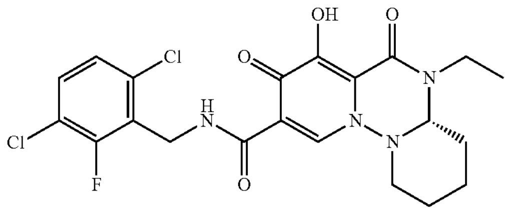 [SMILES: CCN1C(=O)c2c(O)c(=O)c(C(=O)NCc3c(Cl)ccc(Cl)c3F)cn2N2CCCC[C@@H]12] |
| I-014 | 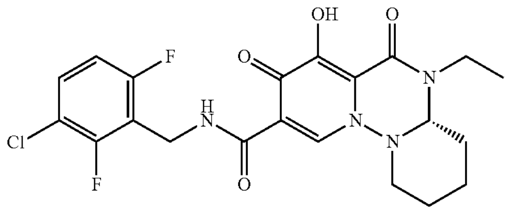 [SMILES: CCN1C(=O)c2c(O)c(=O)c(C(=O)NCc3c(F)ccc(Cl)c3F)cn2N2CCCC[C@@H]12] |
| I-015 | 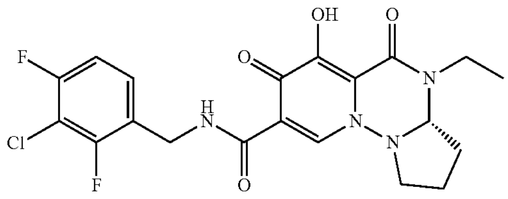 [SMILES: CCN1C(=O)c2c(O)c(=O)c(C(=O)NCc3ccc(F)c(Cl)c3F)cn2N2CCC[C@@H]12] |
| I-016 | 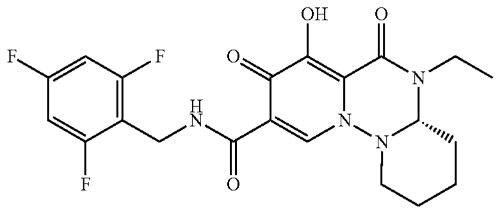 [SMILES: CCN1C(=O)c2c(O)c(=O)c(C(=O)NCc3c(F)cc(F)cc3F)cn2N2CCCC[C@@H]12] |
| I-017 | 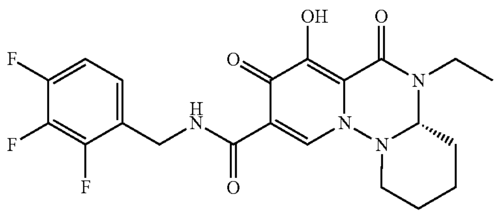 [SMILES: CCN1C(=O)c2c(O)c(=O)c(C(=O)NCc3ccc(F)c(F)c3F)cn2N2CCCC[C@@H]12] |

TABLE 1-continued
| No. | Structure |
| --- | --- |
| I-018 | 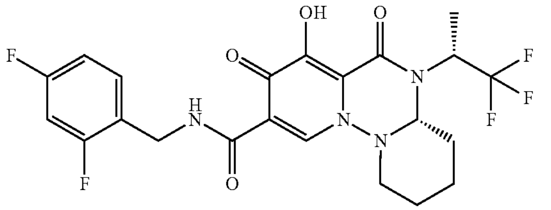 [SMILES: C[C@@H](N1C(=O)c2c(O)c(=O)c(C(=O)NCc3ccc(F)cc3F)cn2N2CCCC[C@@H]12)C(F)(F)F] |
| I-019 | 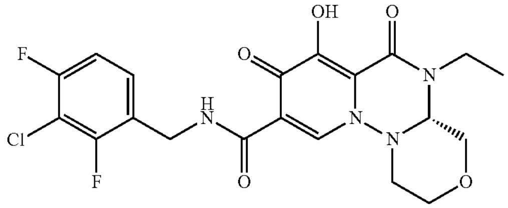 [SMILES: CCN1C(=O)c2c(O)c(=O)c(C(=O)NCc3ccc(F)c(Cl)c3F)cn2N2CCOC[C@@H]12] |
| I-020 | 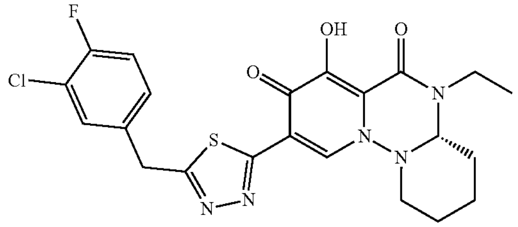 [SMILES: CCN1C(=O)c2c(O)c(=O)c(-c3nnc(Cc4ccc(F)c(Cl)c4)s3)cn2N2CCCC[C@@H]12] |
TABLE 2
| No. | Structure |
| --- | --- |
| I-021 | 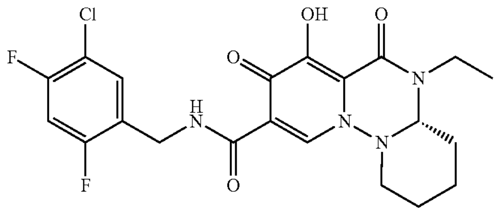 [SMILES: CCN1C(=O)c2c(O)c(=O)c(C(=O)NCc3cc(Cl)c(F)cc3F)cn2N2CCCC[C@@H]12] |
| I-022 | 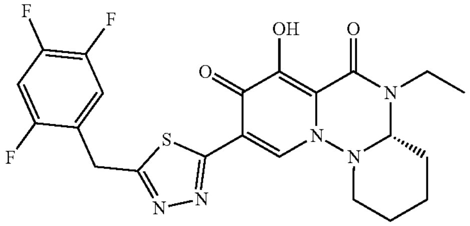 [SMILES: CCN1C(=O)c2c(O)c(=O)c(-c3nnc(Cc4cc(F)c(F)cc4F)s3)cn2N2CCCC[C@@H]12] |
| I-024 | 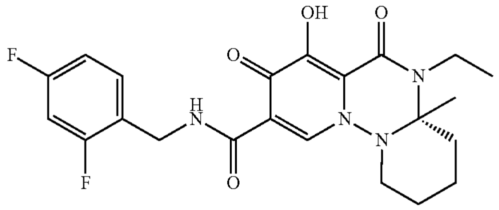 [SMILES: CCN1C(=O)c2c(O)c(=O)c(C(=O)NCc3ccc(F)cc3F)cn2N2CCCC[C@@]12C] |

TABLE 2-continued
| No. | Structure |
| --- | --- |
| I-025 | 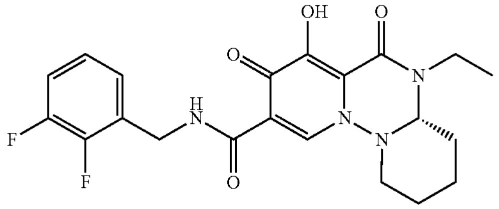 [SMILES: CCN1C(=O)c2c(O)c(=O)c(C(=O)NCc3cccc(F)c3F)cn2N2CCCC[C@@H]12] |
| I-026 | 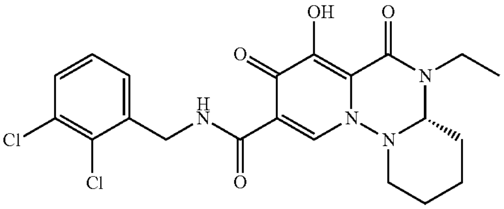 [SMILES: CCN1C(=O)c2c(O)c(=O)c(C(=O)NCc3cccc(Cl)c3Cl)cn2N2CCCC[C@@H]12] |
| I-027 | 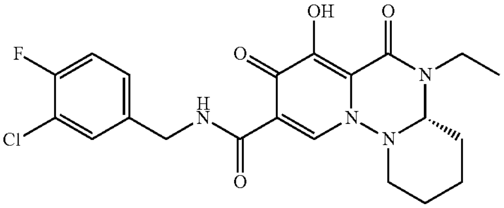 [SMILES: CCN1C(=O)c2c(O)c(=O)c(C(=O)NCc3ccc(F)c(Cl)c3)cn2N2CCCC[C@@H]12] |
| I-028 | 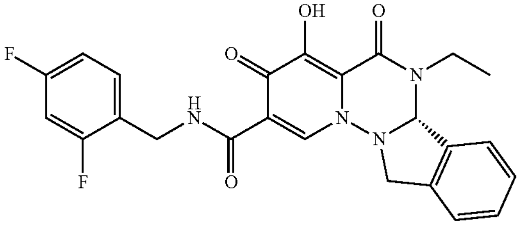 [SMILES: CCN1C(=O)c2c(O)c(=O)c(C(=O)NCc3ccc(F)cc3F)cn2N2Cc3ccccc3[C@@H]12] |
| I-029 | 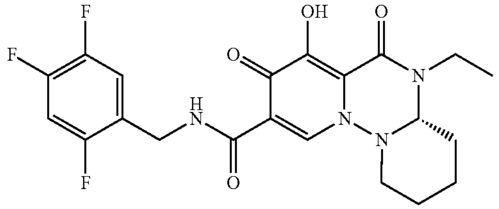 [SMILES: CCN1C(=O)c2c(O)c(=O)c(C(=O)NCc3cc(F)c(F)cc3F)cn2N2CCCC[C@@H]12] |
| I-030 | 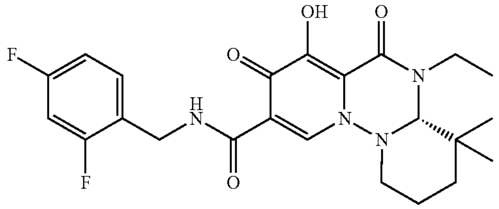 [SMILES: CCN1C(=O)c2c(O)c(=O)c(C(=O)NCc3ccc(F)cc3F)cn2N2CCCC(C)(C)[C@@H]12] |
| I-032 | 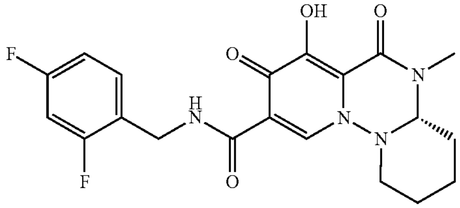 [SMILES: CN1C(=O)c2c(O)c(=O)c(C(=O)NCc3ccc(F)cc3F)cn2N2CCCC[C@@H]12] |

TABLE 2-continued
| No. | Structure |
| --- | --- |
| II-002 | 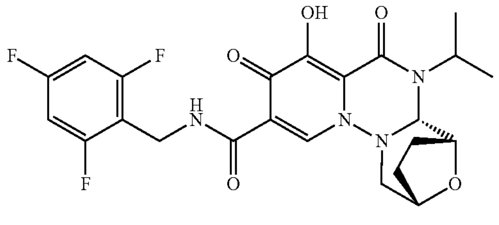 [SMILES: CC(C)N1C(=O)c2c(O)c(=O)c(C(=O)NCc3c(F)cc(F)cc3F)cn2N2C[C@@H]3CC[C@@H](O3)[C@@H]12] |
| II-003 | 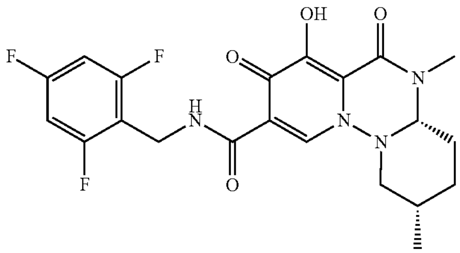 [SMILES: C[C@H]1CC[C@H]2N(C)C(=O)c3c(O)c(=O)c(C(=O)NCc4c(F)cc(F)cc4F)cn3N2C1] |
| II-004 | 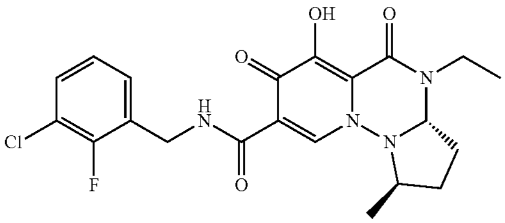 [SMILES: CCN1C(=O)c2c(O)c(=O)c(C(=O)NCc3cccc(Cl)c3F)cn2N2[C@H](C)CC[C@@H]12] |
| II-005 | 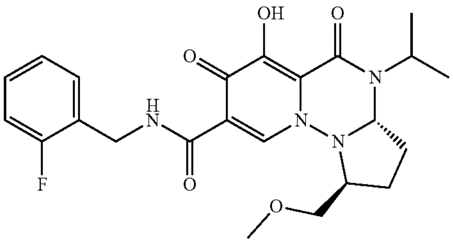 [SMILES: COC[C@@H]1CC[C@H]2N(C(C)C)C(=O)c3c(O)c(=O)c(C(=O)NCc4ccccc4F)cn3N12] |
| II-006 | 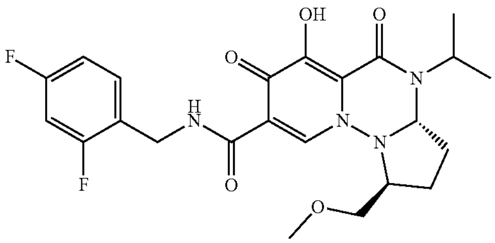 [SMILES: COC[C@@H]1CC[C@H]2N(C(C)C)C(=O)c3c(O)c(=O)c(C(=O)NCc4ccc(F)cc4F)cn3N12] |
| II-007 | 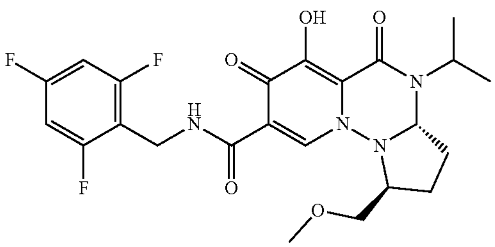 [SMILES: COC[C@@H]1CC[C@H]2N(C(C)C)C(=O)c3c(O)c(=O)c(C(=O)NCc4c(F)cc(F)cc4F)cn3N12] |

TABLE 2-continued
| No. | Structure |
|---|---|
| II-008 | 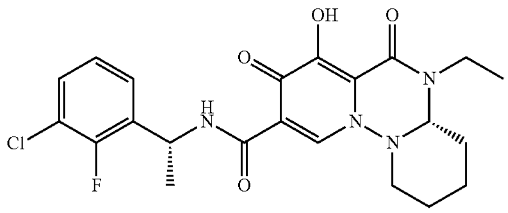 [SMILES: CCN1C(=O)c2c(O)c(=O)c(C(=O)N[C@H](C)c3cccc(Cl)c3F)cn2N2CCCC[C@@H]12] |
| II-009 | 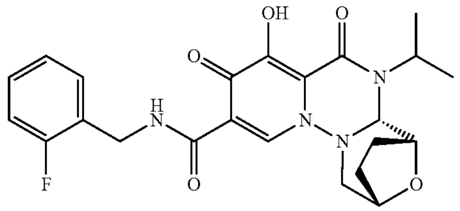 [SMILES: CC(C)N1C(=O)c2c(O)c(=O)c(C(=O)NCc3ccccc3F)cn2N2C[C@@H]3CC[C@@H](O3)[C@@H]12] |
TABLE 3
| No. | Structure |
|---|---|
| II-010 | 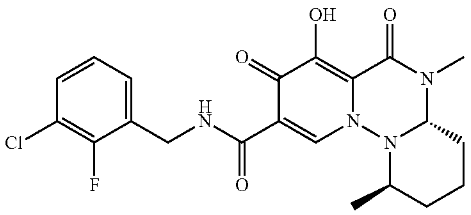 [SMILES: C[C@@H]1CCC[C@H]2N(C)C(=O)c3c(O)c(=O)c(C(=O)NCc4cccc(Cl)c4F)cn3N12] |
| II-011 | 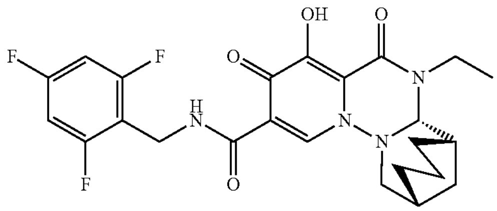 [SMILES: CCN1C(=O)c2c(O)c(=O)c(C(=O)NCc3c(F)cc(F)cc3F)cn2N2C[C@@H]3CCC[C@@H](C3)[C@@H]12] |
| II-012 | 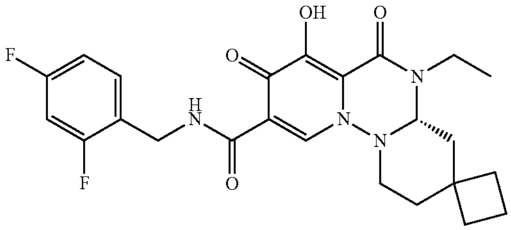 [SMILES: CCN1C(=O)c2c(O)c(=O)c(C(=O)NCc3ccc(F)cc3F)cn2N2CCC3(CCC3)C[C@@H]12] |
| II-013 | 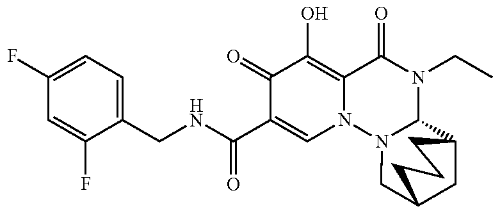 [SMILES: CCN1C(=O)c2c(O)c(=O)c(C(=O)NCc3ccc(F)cc3F)cn2N2C[C@@H]3CCC[C@@H](C3)[C@@H]12] |

TABLE 3-continued
| No. | Structure |
|---|---|
| II-014 | 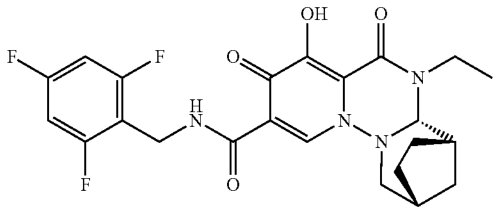 [SMILES: CCN1C(=O)c2c(O)c(=O)c(C(=O)NCc3c(F)cc(F)cc3F)cn2N2C[C@@H]3CC[C@@H](C3)[C@@H]12] |
| II-015 | 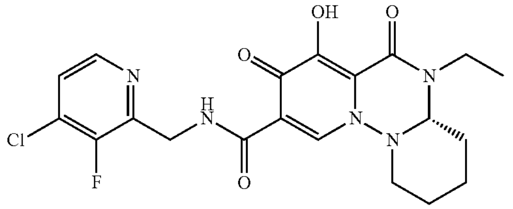 [SMILES: CCN1C(=O)c2c(O)c(=O)c(C(=O)NCc3nccc(Cl)c3F)cn2N2CCCC[C@@H]12] |
| II-016 | 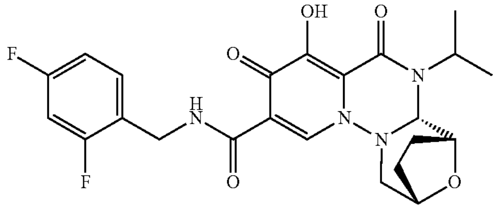 [SMILES: CC(C)N1C(=O)c2c(O)c(=O)c(C(=O)NCc3ccc(F)cc3F)cn2N2C[C@@H]3CC[C@@H](O3)[C@@H]12] |
| II-017 | 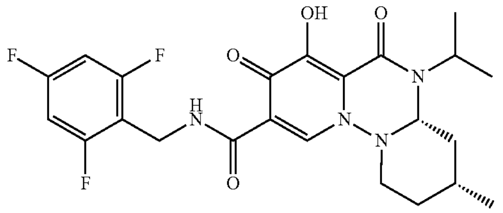 [SMILES: CC(C)N1C(=O)c2c(O)c(=O)c(C(=O)NCc3c(F)cc(F)cc3F)cn2N2CC[C@@H](C)C[C@@H]12] |
| II-018 | 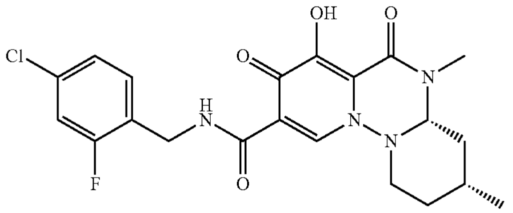 [SMILES: C[C@@H]1CCN2[C@@H](C1)N(C)C(=O)c1c(O)c(=O)c(C(=O)NCc3ccc(Cl)cc3F)cn12] |
| II-019 | 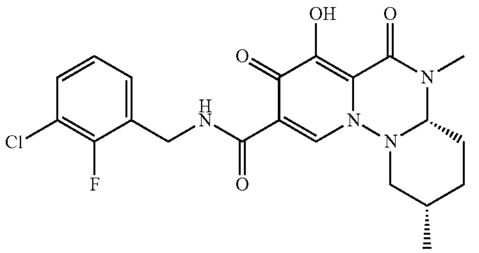 [SMILES: C[C@H]1CC[C@H]2N(C)C(=O)c3c(O)c(=O)c(C(=O)NCc4cccc(Cl)c4F)cn3N2C1] |

TABLE 3-continued
| No. | Structure |
|---|---|
| II-020 | 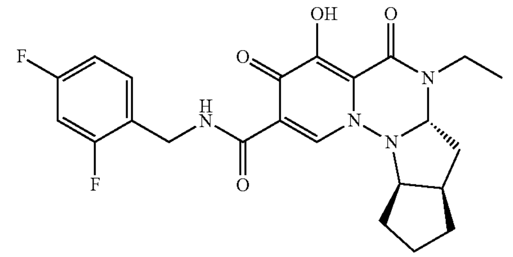 [SMILES: CCN1C(=O)c2c(O)c(=O)c(C(=O)NCc3ccc(F)cc3F)cn2N2[C@@H]3CCC[C@@H]3C[C@@H]12] |
| II-021 | 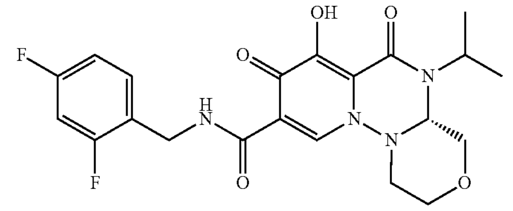 |
| II-022 | 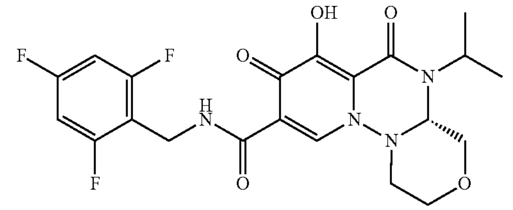 [SMILES: CC(C)N1C(=O)c2c(O)c(=O)c(C(=O)NCc3c(F)cc(F)cc3F)cn2N2CCOC[C@@H]12] |
| II-023 | 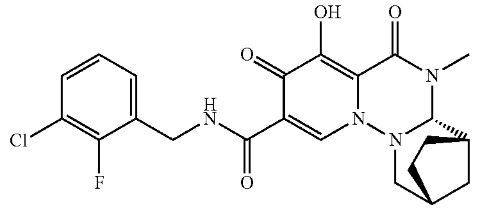 [SMILES: CN1C(=O)c2c(O)c(=O)c(C(=O)NCc3cccc(Cl)c3F)cn2N2C[C@@H]3CC[C@@H](C3)[C@@H]12] |
| II-024 | 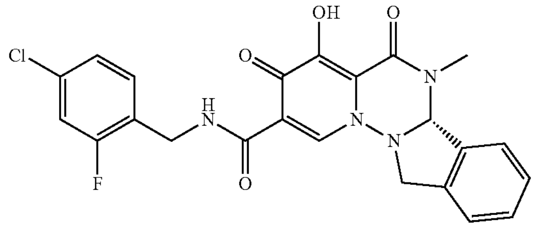 [SMILES: CN1C(=O)c2c(O)c(=O)c(C(=O)NCc3ccc(Cl)cc3F)cn2N2Cc3ccccc3[C@@H]12] |
| II-025 | 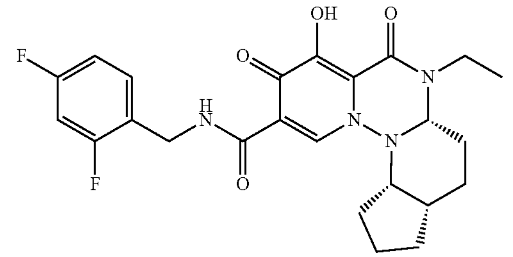 [SMILES: CCN1C(=O)c2c(O)c(=O)c(C(=O)NCc3ccc(F)cc3F)cn2N2[C@H]3CCC[C@H]3CC[C@@H]12] |

TABLE 3-continued
| No. | Structure |
| --- | --- |
| II-026 | 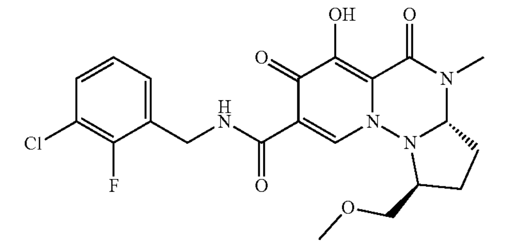 [SMILES: COC[C@@H]1CC[C@H]2N(C)C(=O)c3c(O)c(=O)c(C(=O)NCc4cccc(Cl)c4F)cn3N12] |
| II-027 | 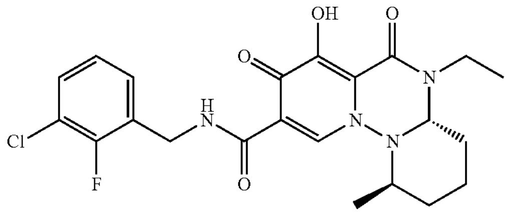 [SMILES: CCN1C(=O)c2c(O)c(=O)c(C(=O)NCc3cccc(Cl)c3F)cn2N2[C@H](C)CCC[C@@H]12] |
TABLE 4
| No. | Structure |
| --- | --- |
| II-028 | 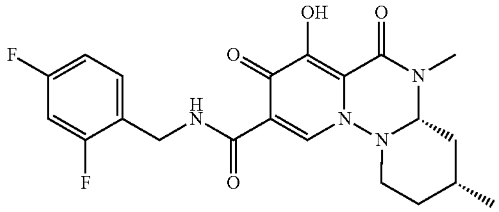 [SMILES: C[C@@H]1CCN2[C@@H](C1)N(C)C(=O)c1c(O)c(=O)c(C(=O)NCc3ccc(F)cc3F)cn12] |
| II-029 | 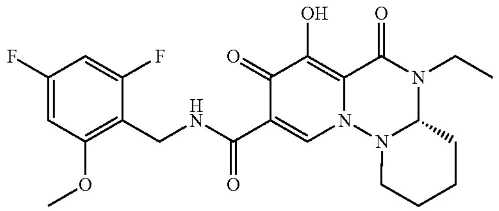 [SMILES: CCN1C(=O)c2c(O)c(=O)c(C(=O)NCc3c(F)cc(F)cc3OC)cn2N2CCCC[C@@H]12] |
| II-030 | 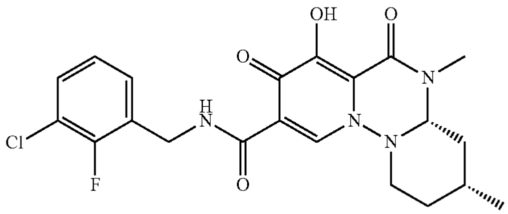 [SMILES: C[C@@H]1CCN2[C@@H](C1)N(C)C(=O)c1c(O)c(=O)c(C(=O)NCc3cccc(Cl)c3F)cn12] |
| II-031 | 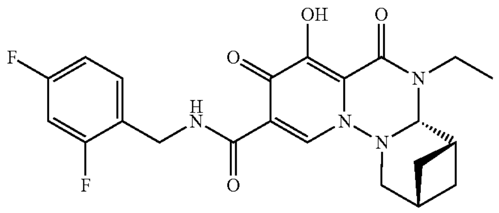 [SMILES: CCN1C(=O)c2c(O)c(=O)c(C(=O)NCc3ccc(F)cc3F)cn2N2C[C@H]3C[C@H](C3)[C@@H]12] |

TABLE 4-continued
| No. | Structure |
| --- | --- |
| II-032 | 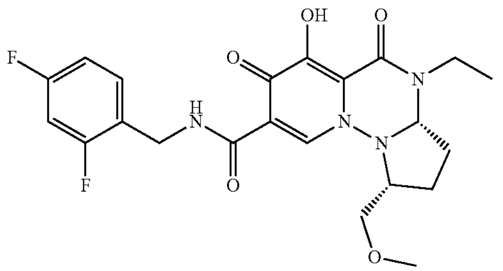 [SMILES: CCN1C(=O)c2c(O)c(=O)c(C(=O)NCc3ccc(F)cc3F)cn2N2[C@@H](COC)CC[C@@H]12] |
| II-033 | 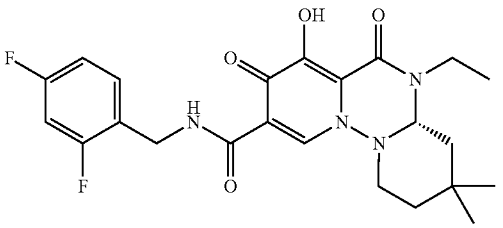 [SMILES: CCN1C(=O)c2c(O)c(=O)c(C(=O)NCc3ccc(F)cc3F)cn2N2CCC(C)(C)C[C@@H]12] |
| II-035 | 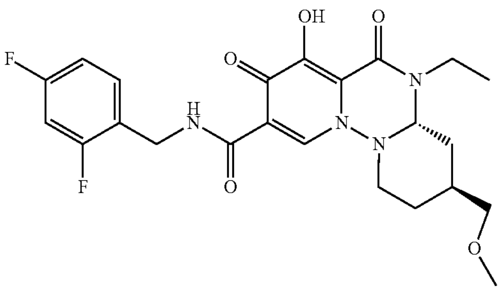 [SMILES: CCN1C(=O)c2c(O)c(=O)c(C(=O)NCc3ccc(F)cc3F)cn2N2CC[C@H](COC)C[C@@H]12] |
| II-036 | 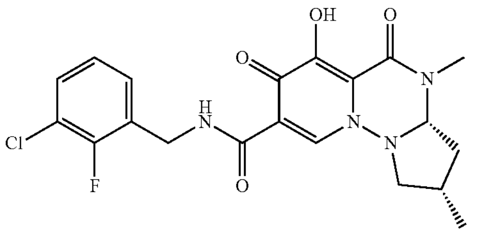 [SMILES: C[C@H]1C[C@H]2N(C)C(=O)c3c(O)c(=O)c(C(=O)NCc4cccc(Cl)c4F)cn3N2C1] |
| II-037 | 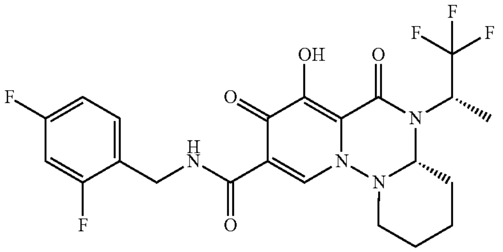 [SMILES: C[C@H](N1C(=O)c2c(O)c(=O)c(C(=O)NCc3ccc(F)cc3F)cn2N2CCCC[C@@H]12)C(F)(F)F] |
| II-038 | 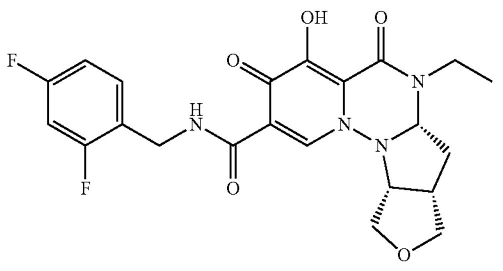 [SMILES: CCN1C(=O)c2c(O)c(=O)c(C(=O)NCc3ccc(F)cc3F)cn2N2[C@H]3COC[C@H]3C[C@@H]12] |

TABLE 4-continued
| No. | Structure |
| --- | --- |
| II-039 | 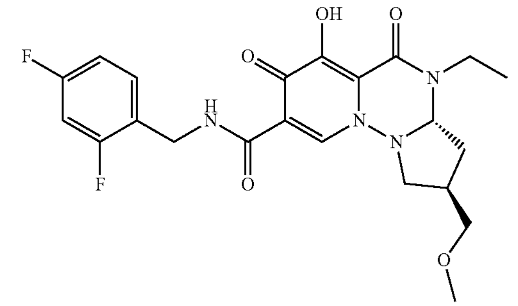 [SMILES: CCN1C(=O)c2c(O)c(=O)c(C(=O)NCc3ccc(F)cc3F)cn2N2C[C@H](COC)C[C@@H]12] |
| II-040 | 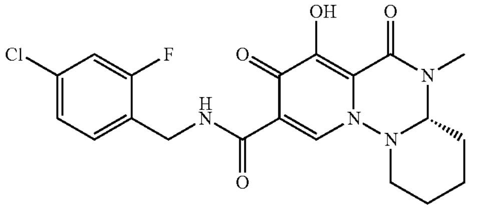 [SMILES: CN1C(=O)c2c(O)c(=O)c(C(=O)NCc3ccc(Cl)cc3F)cn2N2CCCC[C@@H]12] |
| II-041 | 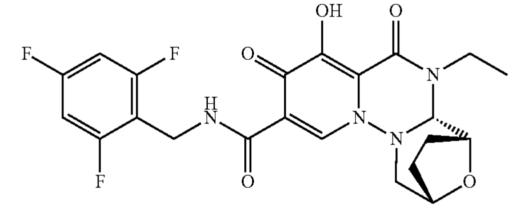 [SMILES: CCN1C(=O)c2c(O)c(=O)c(C(=O)NCc3c(F)cc(F)cc3F)cn2N2C[C@@H]3CC[C@@H](O3)[C@@H]12] |
| II-042 | 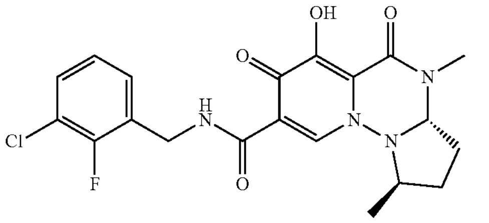 [SMILES: C[C@@H]1CC[C@H]2N(C)C(=O)c3c(O)c(=O)c(C(=O)NCc4cccc(Cl)c4F)cn3N12] |
| II-043 | 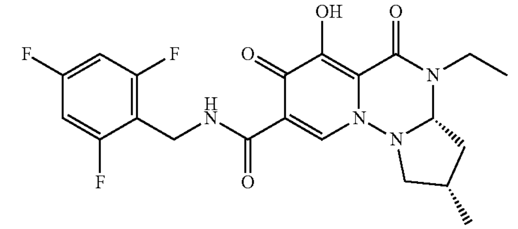 [SMILES: CCN1C(=O)c2c(O)c(=O)c(C(=O)NCc3c(F)cc(F)cc3F)cn2N2C[C@@H](C)C[C@@H]12] |
| II-044 | 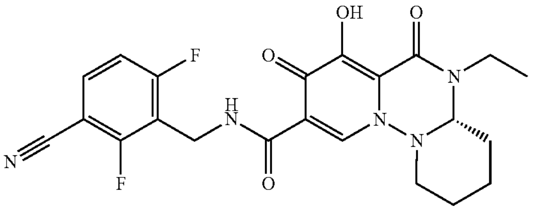 [SMILES: CCN1C(=O)c2c(O)c(=O)c(C(=O)NCc3c(F)ccc(C#N)c3F)cn2N2CCCC[C@@H]12] |

TABLE 5
| No. | Structure |
| --- | --- |
| II-045 | 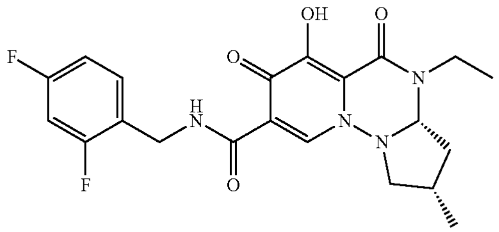 [SMILES: CCN1C(=O)c2c(O)c(=O)c(C(=O)NCc3ccc(F)cc3F)cn2N2C[C@@H](C)C[C@@H]12] |
| II-046 | 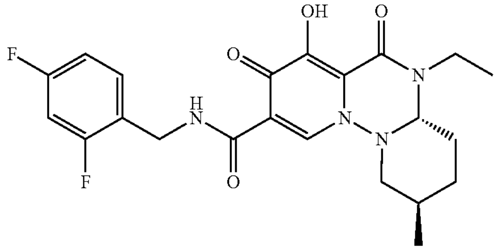 [SMILES: CCN1C(=O)c2c(O)c(=O)c(C(=O)NCc3ccc(F)cc3F)cn2N2C[C@H](C)CC[C@@H]12] |
| II-047 | 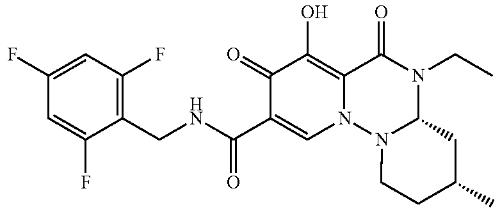 [SMILES: CCN1C(=O)c2c(O)c(=O)c(C(=O)NCc3c(F)cc(F)cc3F)cn2N2CC[C@@H](C)C[C@@H]12] |
| II-048 | 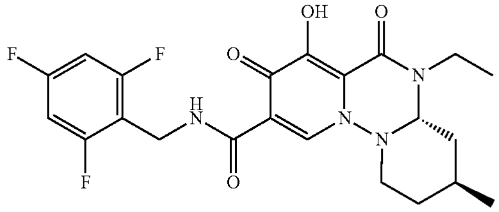 [SMILES: CCN1C(=O)c2c(O)c(=O)c(C(=O)NCc3c(F)cc(F)cc3F)cn2N2CC[C@H](C)C[C@@H]12] |
| II-049 | 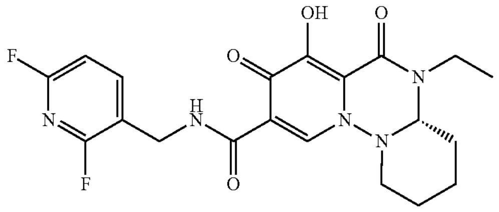 [SMILES: CCN1C(=O)c2c(O)c(=O)c(C(=O)NCc3ccc(F)nc3F)cn2N2CCCC[C@@H]12] |
| II-050 | 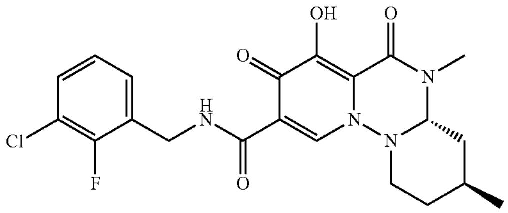 [SMILES: C[C@H]1CCN2[C@@H](C1)N(C)C(=O)c1c(O)c(=O)c(C(=O)NCc3cccc(Cl)c3F)cn12] |

TABLE 5-continued
| No. | Structure |
| --- | --- |
| II-051 | 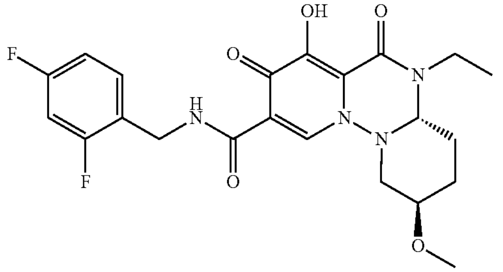 [SMILES: CCN1C(=O)c2c(O)c(=O)c(C(=O)NCc3ccc(F)cc3F)cn2N2C[C@H](OC)CC[C@@H]12] |
| II-052 | 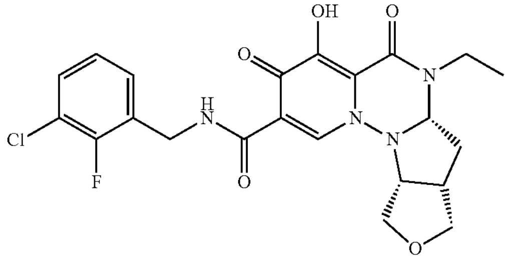 |
| II-053 | 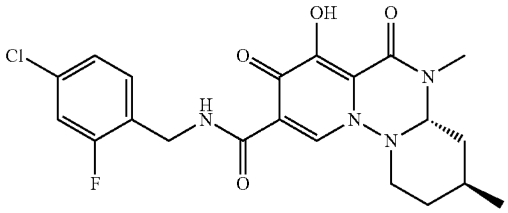 [SMILES: C[C@H]1CCN2[C@@H](C1)N(C)C(=O)c1c(O)c(=O)c(C(=O)NCc3ccc(Cl)cc3F)cn12] |
| II-054 | 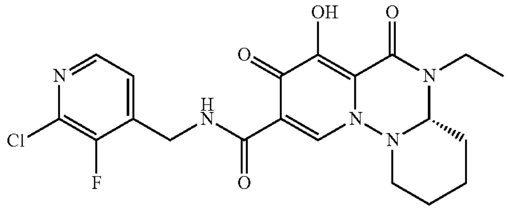 |
| II-055 | 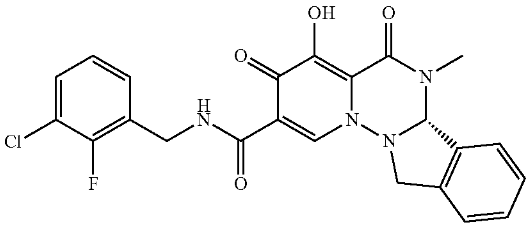 [SMILES: CN1C(=O)c2c(O)c(=O)c(C(=O)NCc3cccc(Cl)c3F)cn2N2Cc3ccccc3[C@@H]12] |
| II-056 | 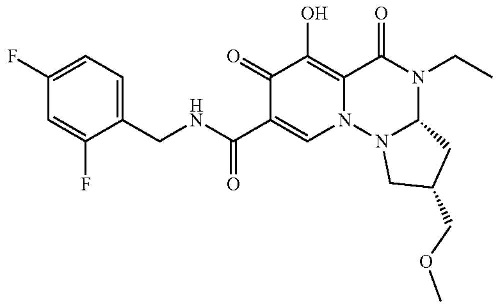 [SMILES: CCN1C(=O)c2c(O)c(=O)c(C(=O)NCc3ccc(F)cc3F)cn2N2C[C@@H](COC)C[C@@H]12] |

TABLE 5-continued
| No. | Structure |
| --- | --- |
| II-057 | 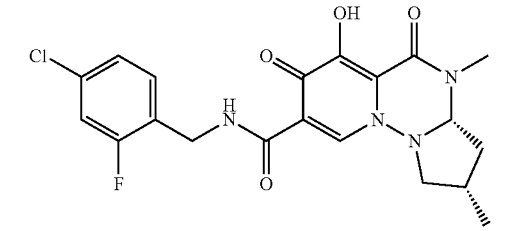 [SMILES: C[C@H]1C[C@H]2N(C)C(=O)c3c(O)c(=O)c(C(=O)NCc4ccc(Cl)cc4F)cn3N2C1] |
| II-058 | 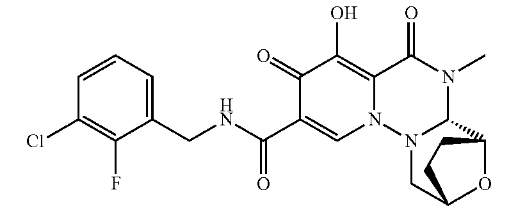 [SMILES: CN1C(=O)c2c(O)c(=O)c(C(=O)NCc3cccc(Cl)c3F)cn2N2C[C@@H]3CC[C@@H](O3)[C@@H]12] |
| II-059 | 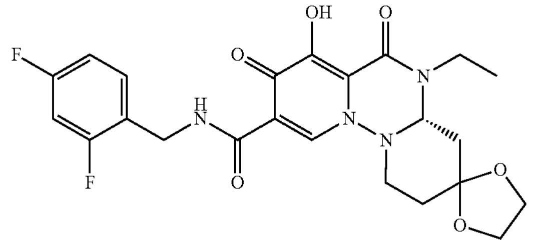 [SMILES: CCN1C(=O)c2c(O)c(=O)c(C(=O)NCc3ccc(F)cc3F)cn2N2CCC3(C[C@@H]12)OCCO3] |
| II-060 | 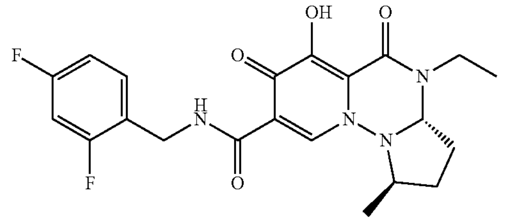 [SMILES: CCN1C(=O)c2c(O)c(=O)c(C(=O)NCc3ccc(F)cc3F)cn2N2[C@H](C)CC[C@@H]12] |
TABLE 6
| No. | Structure |
| --- | --- |
| II-061 | 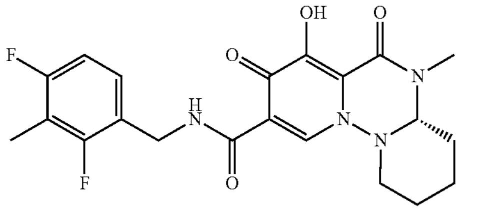 [SMILES: Cc1c(F)ccc(CNC(=O)c2cn3c(c(O)c2=O)C(=O)N(C)[C@@H]2CCCCN23)c1F] |
| II-062 | 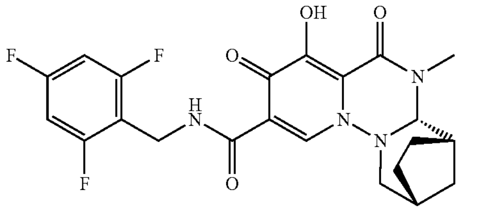 [SMILES: CN1C(=O)c2c(O)c(=O)c(C(=O)NCc3c(F)cc(F)cc3F)cn2N2C[C@@H]3CC[C@@H](C3)[C@@H]12] |

TABLE 6-continued
| No. | Structure |
|---|---|
| II-063 | 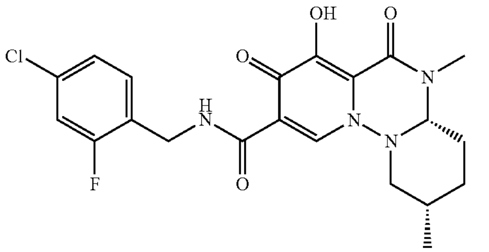 [SMILES: C[C@H]1CC[C@H]2N(C)C(=O)c3c(O)c(=O)c(C(=O)NCc4ccc(Cl)cc4F)cn3N2C1] |
| II-064 | 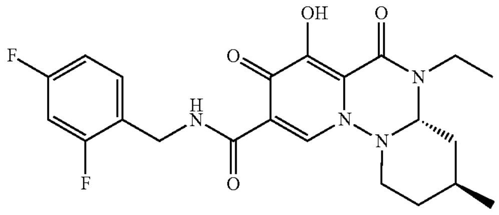 [SMILES: CCN1C(=O)c2c(O)c(=O)c(C(=O)NCc3ccc(F)cc3F)cn2N2CC[C@H](C)C[C@@H]12] |
| II-066 | 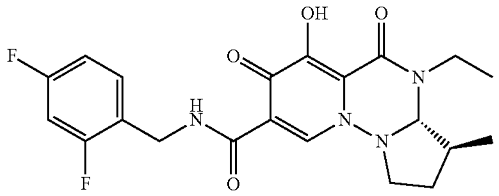 [SMILES: CCN1C(=O)c2c(O)c(=O)c(C(=O)NCc3ccc(F)cc3F)cn2N2CC[C@H](C)[C@@H]12] |
| II-067 | 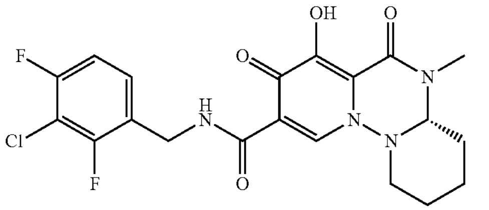 [SMILES: CN1C(=O)c2c(O)c(=O)c(C(=O)NCc3ccc(F)c(Cl)c3F)cn2N2CCCC[C@@H]12] |
| II-068 | 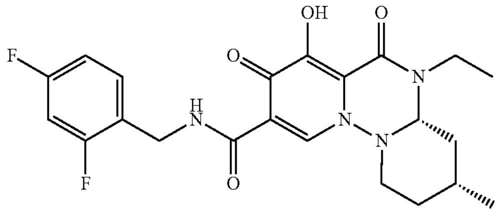 [SMILES: CCN1C(=O)c2c(O)c(=O)c(C(=O)NCc3ccc(F)cc3F)cn2N2CC[C@@H](C)C[C@@H]12] |
| II-069 | 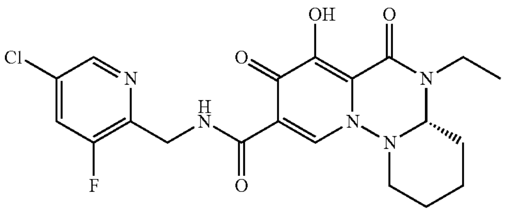 [SMILES: CCN1C(=O)c2c(O)c(=O)c(C(=O)NCc3ncc(Cl)cc3F)cn2N2CCCC[C@@H]12] |
| II-070 | 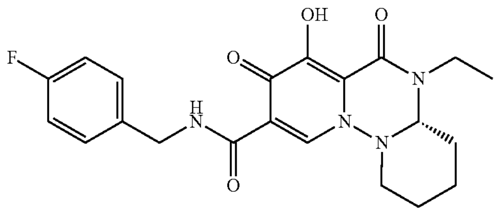 [SMILES: CCN1C(=O)c2c(O)c(=O)c(C(=O)NCc3ccc(F)cc3)cn2N2CCCC[C@@H]12] |

TABLE 6-continued
| No. | Structure |
|---|---|
| II-071 | 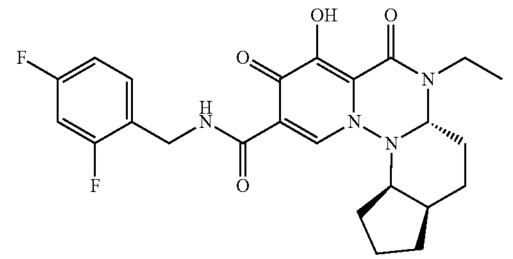 [SMILES: CCN1C(=O)c2c(O)c(=O)c(C(=O)NCc3ccc(F)cc3F)cn2N2[C@@H]3CCC[C@@H]3CC[C@@H]12] |
| II-072 | 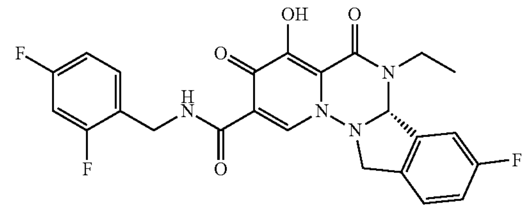 [SMILES: CCN1C(=O)c2c(O)c(=O)c(C(=O)NCc3ccc(F)cc3F)cn2N2Cc3ccc(F)cc3[C@@H]12] |
| II-073 | 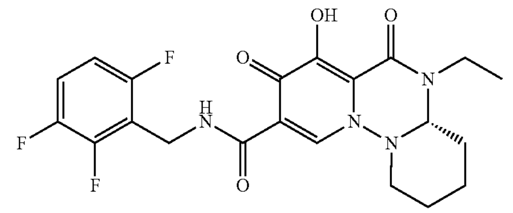 [SMILES: CCN1C(=O)c2c(O)c(=O)c(C(=O)NCc3c(F)ccc(F)c3F)cn2N2CCCC[C@@H]12] |
| II-074 | 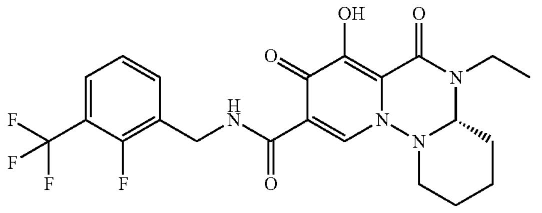 [SMILES: CCN1C(=O)c2c(O)c(=O)c(C(=O)NCc3cccc(C(F)(F)F)c3F)cn2N2CCCC[C@@H]12] |
| II-075 | 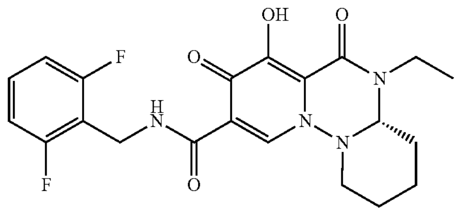 [SMILES: CCN1C(=O)c2c(O)c(=O)c(C(=O)NCc3c(F)cccc3F)cn2N2CCCC[C@@H]12] |
| II-076 | 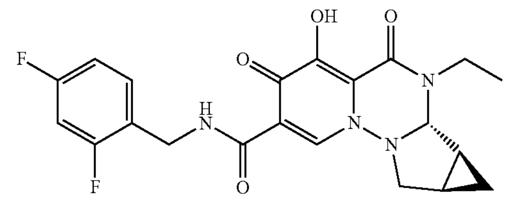 [SMILES: CCN1C(=O)c2c(O)c(=O)c(C(=O)NCc3ccc(F)cc3F)cn2N2C[C@@H]3C[C@@H]3[C@@H]12] |
| II-077 | 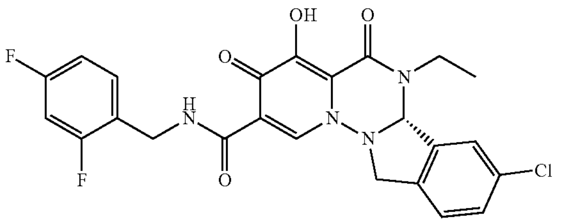 [SMILES: CCN1C(=O)c2c(O)c(=O)c(C(=O)NCc3ccc(F)cc3F)cn2N2Cc3ccc(Cl)cc3[C@@H]12] |

TABLE 6-continued
| No. | Structure |
| --- | --- |
| II-078 | 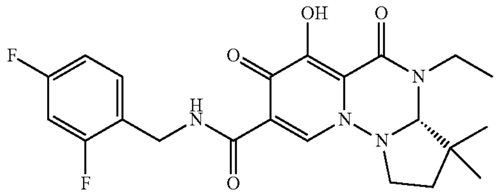 [SMILES: CCN1C(=O)c2c(O)c(=O)c(C(=O)NCc3ccc(F)cc3F)cn2N2CCC(C)(C)[C@@H]12] |
| II-079 | 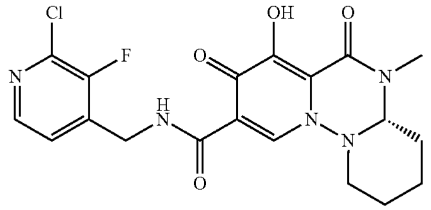 [SMILES: CN1C(=O)c2c(O)c(=O)c(C(=O)NCc3ccnc(Cl)c3F)cn2N2CCCC[C@@H]12] |
TABLE 7
| No. | Structure |
| --- | --- |
| II-080 | 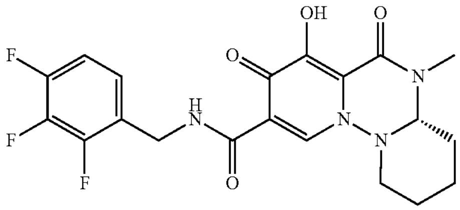 [SMILES: CN1C(=O)c2c(O)c(=O)c(C(=O)NCc3ccc(F)c(F)c3F)cn2N2CCCC[C@@H]12] |
| II-081 | 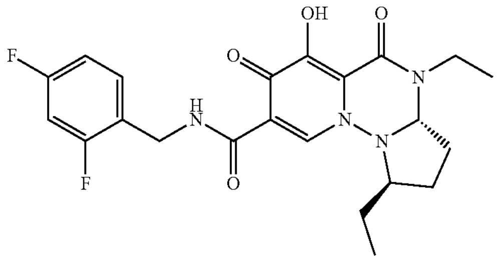 [SMILES: CC[C@@H]1CC[C@H]2N(CC)C(=O)c3c(O)c(=O)c(C(=O)NCc4ccc(F)cc4F)cn3N12] |
| II-082 | 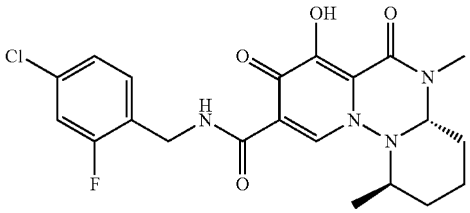 [SMILES: C[C@@H]1CCC[C@H]2N(C)C(=O)c3c(O)c(=O)c(C(=O)NCc4ccc(Cl)cc4F)cn3N12] |
| II-083 | 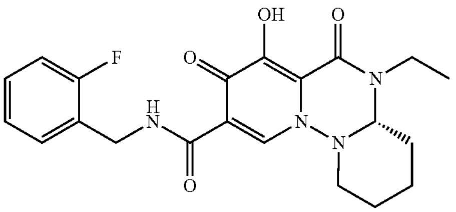 [SMILES: CCN1C(=O)c2c(O)c(=O)c(C(=O)NCc3ccccc3F)cn2N2CCCC[C@@H]12] |

TABLE 7-continued
| No. | Structure |
| --- | --- |
| II-084 | 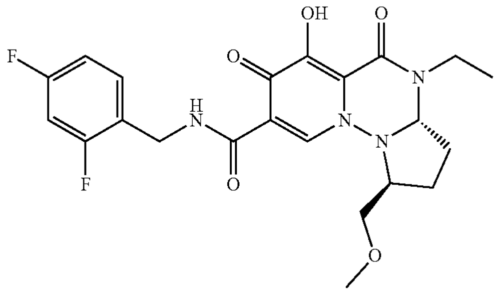 [SMILES: CCN1C(=O)c2c(O)c(=O)c(C(=O)NCc3ccc(F)cc3F)cn2N2[C@H](COC)CC[C@@H]12] |
| II-085 | 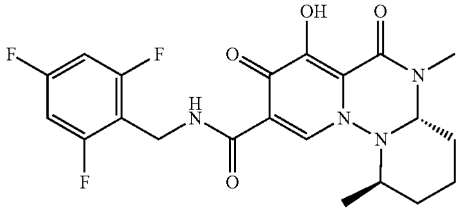 [SMILES: C[C@@H]1CCC[C@H]2N(C)C(=O)c3c(O)c(=O)c(C(=O)NCc4c(F)cc(F)cc4F)cn3N12] |
| II-086 | 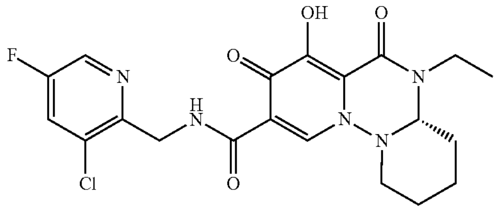 [SMILES: CCN1C(=O)c2c(O)c(=O)c(C(=O)NCc3ncc(F)cc3Cl)cn2N2CCCC[C@@H]12] |
| II-087 | 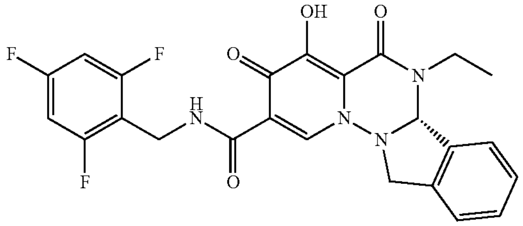 [SMILES: CCN1C(=O)c2c(O)c(=O)c(C(=O)NCc3c(F)cc(F)cc3F)cn2N2Cc3ccccc3[C@@H]12] |
| II-088 | 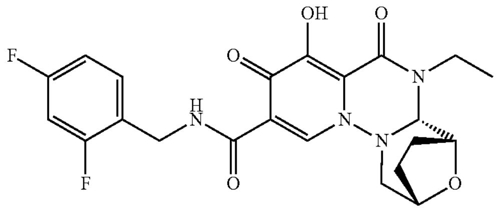 [SMILES: CCN1C(=O)c2c(O)c(=O)c(C(=O)NCc3ccc(F)cc3F)cn2N2C[C@@H]3CC[C@@H](O3)[C@@H]12] |
| II-089 | 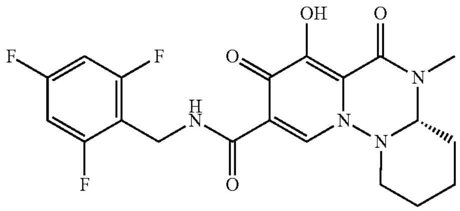 [SMILES: CN1C(=O)c2c(O)c(=O)c(C(=O)NCc3c(F)cc(F)cc3F)cn2N2CCCC[C@@H]12] |

TABLE 7-continued
| No. | Structure |
|---|---|
| II-090 | 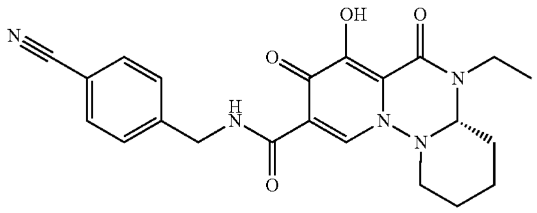 [SMILES: CCN1C(=O)c2c(O)c(=O)c(C(=O)NCc3ccc(C#N)cc3)cn2N2CCCC[C@@H]12] |
| II-091 | 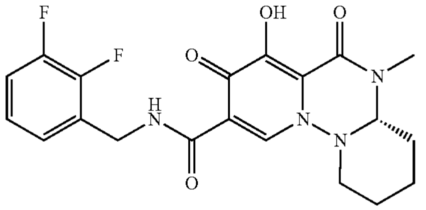 [SMILES: CN1C(=O)c2c(O)c(=O)c(C(=O)NCc3cccc(F)c3F)cn2N2CCCC[C@@H]12] |
| II-092 | 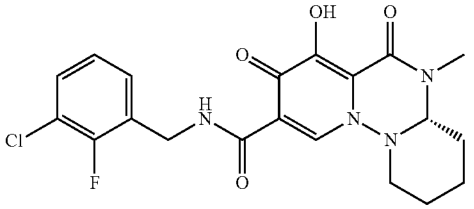 [SMILES: CN1C(=O)c2c(O)c(=O)c(C(=O)NCc3cccc(Cl)c3F)cn2N2CCCC[C@@H]12] |
| II-093 | 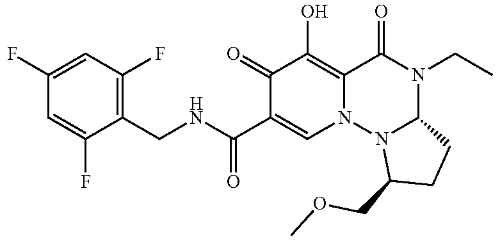 [SMILES: CCN1C(=O)c2c(O)c(=O)c(C(=O)NCc3c(F)cc(F)cc3F)cn2N2[C@H](COC)CC[C@@H]12] |
| II-094 | 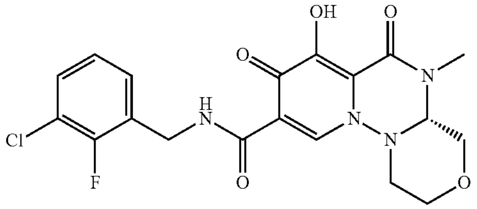 [SMILES: CN1C(=O)c2c(O)c(=O)c(C(=O)NCc3cccc(Cl)c3F)cn2N2CCOC[C@@H]12] |
| II-095 | 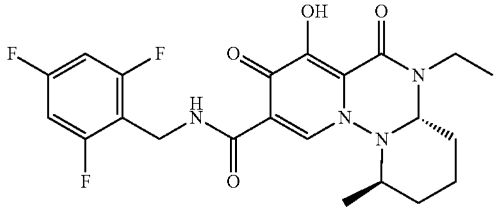 [SMILES: CCN1C(=O)c2c(O)c(=O)c(C(=O)NCc3c(F)cc(F)cc3F)cn2N2[C@H](C)CCC[C@@H]12] |
| II-096 | 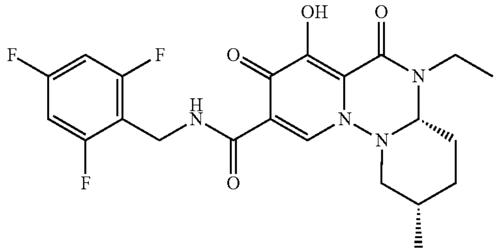 |

TABLE 7-continued
| No. | Structure |
|---|---|
| II-097 | 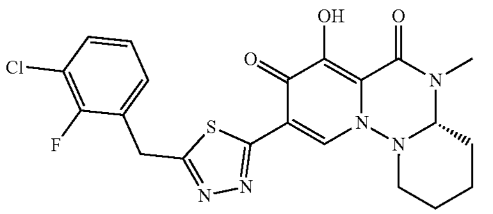 [SMILES: CN1C(=O)c2c(O)c(=O)c(-c3nnc(Cc4cccc(Cl)c4F)s3)cn2N2CCCC[C@@H]12] |
TABLE 8
| No. | Structure |
|---|---|
| II-098 | 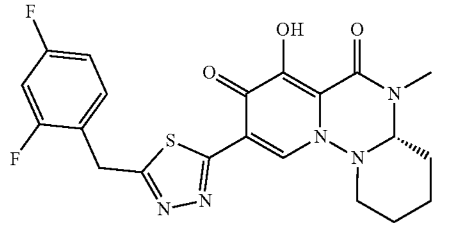 [SMILES: CN1C(=O)c2c(O)c(=O)c(-c3nnc(Cc4ccc(F)cc4F)s3)cn2N2CCCC[C@@H]12] |
| II-099 | 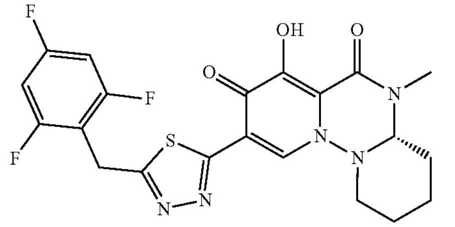 [SMILES: CN1C(=O)c2c(O)c(=O)c(-c3nnc(Cc4c(F)cc(F)cc4F)s3)cn2N2CCCC[C@@H]12] |
| II-101 | 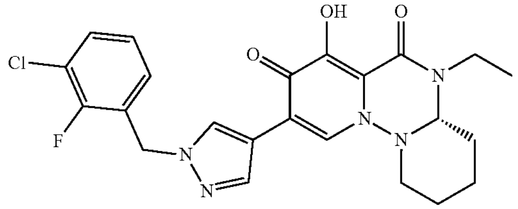 [SMILES: CCN1C(=O)c2c(O)c(=O)c(-c3cnn(Cc4cccc(Cl)c4F)c3)cn2N2CCCC[C@@H]12] |
| II-102 | 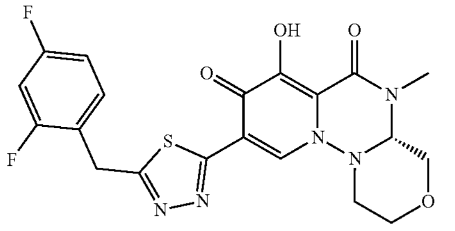 [SMILES: CN1C(=O)c2c(O)c(=O)c(-c3nnc(Cc4ccc(F)cc4F)s3)cn2N2CCOC[C@@H]12] |
| II-103 | 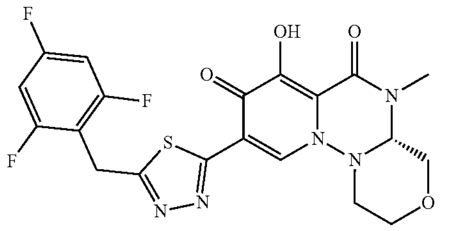 [SMILES: CN1C(=O)c2c(O)c(=O)c(-c3nnc(Cc4c(F)cc(F)cc4F)s3)cn2N2CCOC[C@@H]12] |

TABLE 8-continued
| No. | Structure |
| --- | --- |
| II-104 | 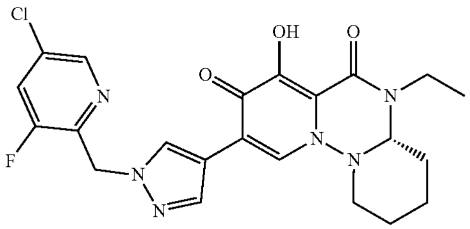 [SMILES: CCN1C(=O)c2c(O)c(=O)c(-c3cnn(Cc4ncc(Cl)cc4F)c3)cn2N2CCCC[C@@H]12] |
| II-105 | 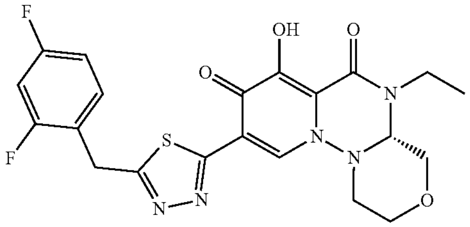 [SMILES: CCN1C(=O)c2c(O)c(=O)c(-c3nnc(Cc4ccc(F)cc4F)s3)cn2N2CCOC[C@@H]12] |
| II-106 | 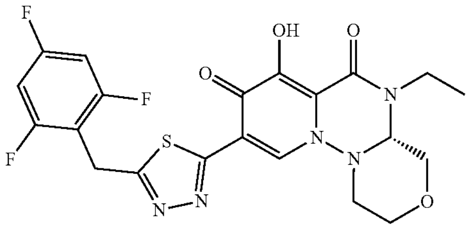 [SMILES: CCN1C(=O)c2c(O)c(=O)c(-c3nnc(Cc4c(F)cc(F)cc4F)s3)cn2N2CCOC[C@@H]12] |
| II-107 | 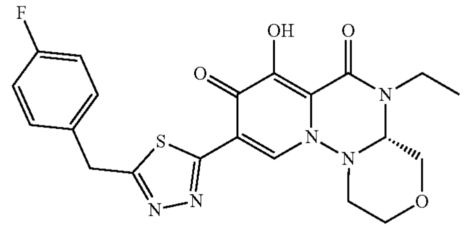 [SMILES: CCN1C(=O)c2c(O)c(=O)c(-c3nnc(Cc4ccc(F)cc4)s3)cn2N2CCOC[C@@H]12] |
| II-108 | 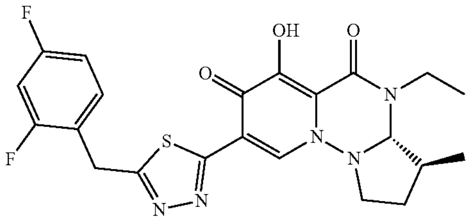 [SMILES: CCN1C(=O)c2c(O)c(=O)c(-c3nnc(Cc4ccc(F)cc4F)s3)cn2N2CC[C@H](C)[C@@H]12] |
| II-109 | 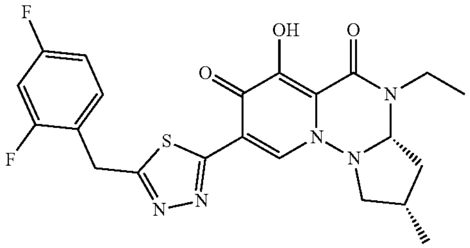 [SMILES: CCN1C(=O)c2c(O)c(=O)c(-c3nnc(Cc4ccc(F)cc4F)s3)cn2N2C[C@@H](C)C[C@@H]12] |

TABLE 8-continued
| No. | Structure |
| --- | --- |
| II-110 | 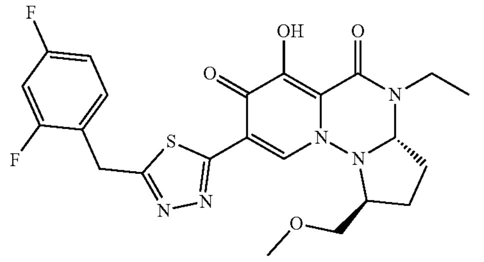 [SMILES: CCN1C(=O)c2c(O)c(=O)c(-c3nnc(Cc4ccc(F)cc4F)s3)cn2N2[C@H](COC)CC[C@@H]12] |
| II-111 | 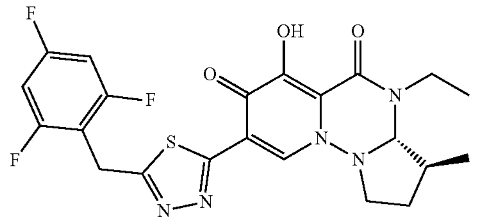 [SMILES: CCN1C(=O)c2c(O)c(=O)c(-c3nnc(Cc4c(F)cc(F)cc4F)s3)cn2N2CC[C@H](C)[C@@H]12] |
| II-112 | 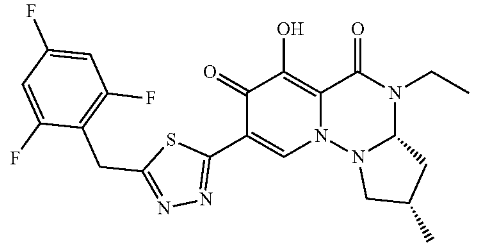 [SMILES: CCN1C(=O)c2c(O)c(=O)c(-c3nnc(Cc4c(F)cc(F)cc4F)s3)cn2N2C[C@@H](C)C[C@@H]12] |
| II-113 | 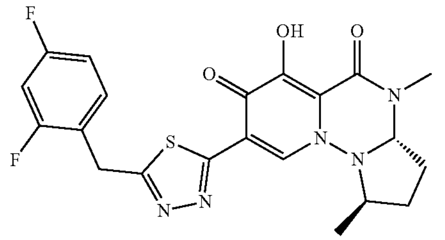 [SMILES: C[C@@H]1CC[C@H]2N(C)C(=O)c3c(O)c(=O)c(-c4nnc(Cc5ccc(F)cc5F)s4)cn3N12] |
| II-114 | 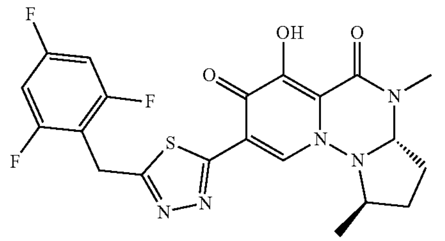 [SMILES: C[C@@H]1CC[C@H]2N(C)C(=O)c3c(O)c(=O)c(-c4nnc(Cc5c(F)cc(F)cc5F)s4)cn3N12] |
| II-115 | 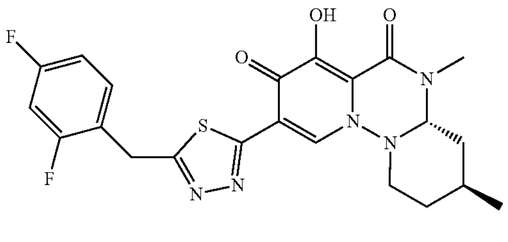 [SMILES: C[C@H]1CCN2[C@@H](C1)N(C)C(=O)c1c(O)c(=O)c(-c3nnc(Cc4ccc(F)cc4F)s3)cn12] |

TABLE 8-continued
| No. | Structure |
|---|---|
| II-116 | 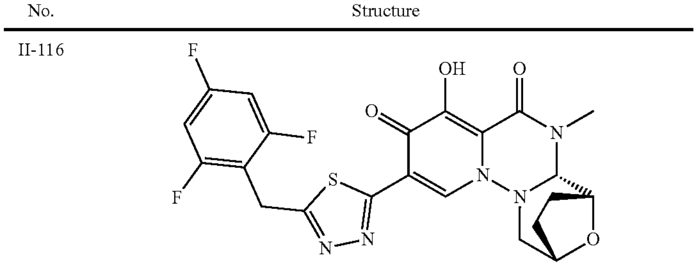 |
TABLE 9
| No. | Structure |
|---|---|
| II-117 | 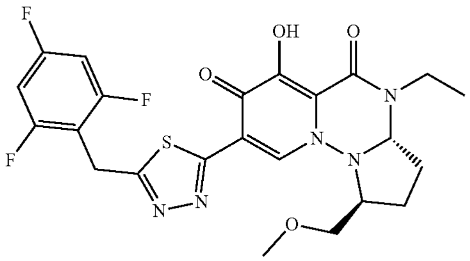 [SMILES: CCN1C(=O)c2c(O)c(=O)c(-c3nnc(Cc4c(F)cc(F)cc4F)s3)cn2N2[C@H](COC)CC[C@@H]12] |
| II-118 | 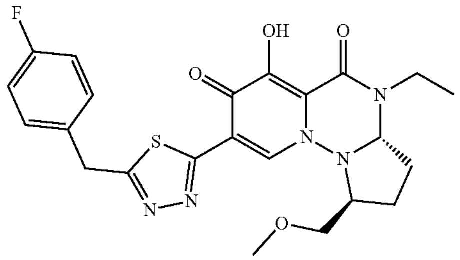 [SMILES: CCN1C(=O)c2c(O)c(=O)c(-c3nnc(Cc4ccc(F)cc4)s3)cn2N2[C@H](COC)CC[C@@H]12] |
| II-119 | 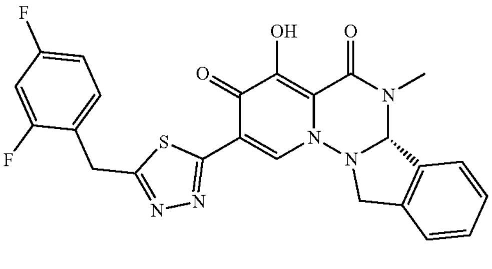 [SMILES: CN1C(=O)c2c(O)c(=O)c(-c3nnc(Cc4ccc(F)cc4F)s3)cn2N2Cc3ccccc3[C@@H]12] |
| II-120 | 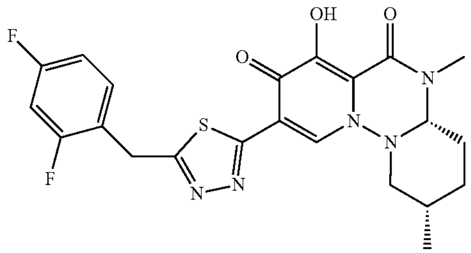 [SMILES: C[C@H]1CC[C@H]2N(C)C(=O)c3c(O)c(=O)c(-c4nnc(Cc5ccc(F)cc5F)s4)cn3N2C1] |

TABLE 9-continued
| No. | Structure |
| --- | --- |
| II-121 | 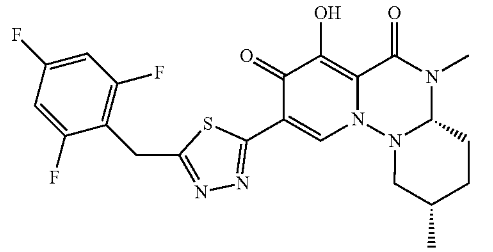 [SMILES: C[C@H]1CC[C@H]2N(C)C(=O)c3c(O)c(=O)c(-c4nnc(Cc5c(F)cc(F)cc5F)s4)cn3N2C1] |
| II-122 | 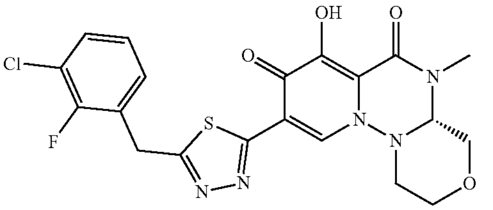 [SMILES: CN1C(=O)c2c(O)c(=O)c(-c3nnc(Cc4cccc(Cl)c4F)s3)cn2N2CCOC[C@@H]12] |
| II-123 | 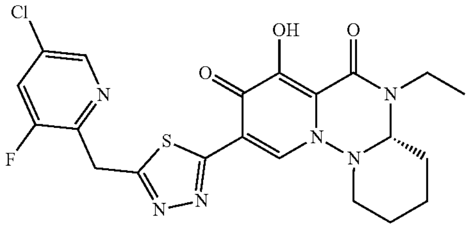 [SMILES: CCN1C(=O)c2c(O)c(=O)c(-c3nnc(Cc4ncc(Cl)cc4F)s3)cn2N2CCCC[C@@H]12] |
| II-124 | 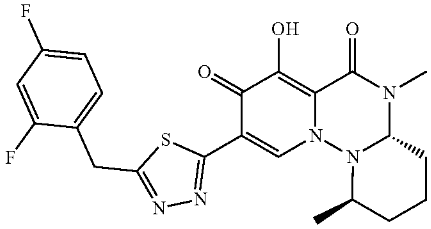 [SMILES: C[C@@H]1CCC[C@H]2N(C)C(=O)c3c(O)c(=O)c(-c4nnc(Cc5ccc(F)cc5F)s4)cn3N12] |
| II-125 | 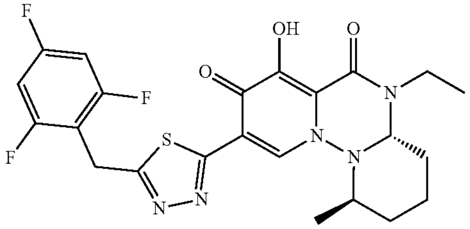 [SMILES: CCN1C(=O)c2c(O)c(=O)c(-c3nnc(Cc4c(F)cc(F)cc4F)s3)cn2N2[C@H](C)CCC[C@@H]12] |
| II-126 | 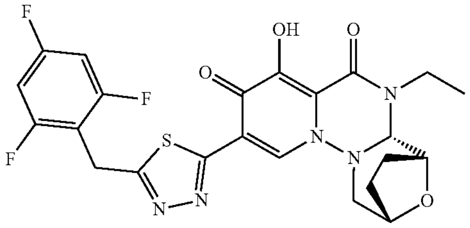 [SMILES: CCN1C(=O)c2c(O)c(=O)c(-c3nnc(Cc4c(F)cc(F)cc4F)s3)cn2N2C[C@@H]3CC[C@@H](O3)[C@@H]12] |

TABLE 9-continued
| No. | Structure |
|---|---|
| II-127 | 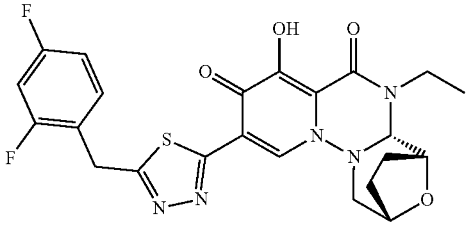 [SMILES: CCN1C(=O)c2c(O)c(=O)c(-c3nnc(Cc4ccc(F)cc4F)s3)cn2N2C[C@@H]3CC[C@@H](O3)[C@@H]12] |
| II-128 | 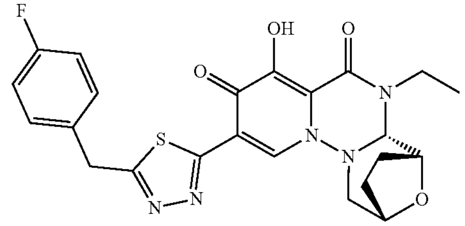 [SMILES: CCN1C(=O)c2c(O)c(=O)c(-c3nnc(Cc4ccc(F)cc4)s3)cn2N2C[C@@H]3CC[C@@H](O3)[C@@H]12] |
| II-129 | 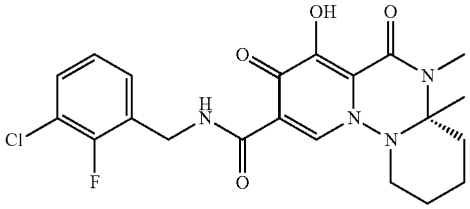 [SMILES: CN1C(=O)c2c(O)c(=O)c(C(=O)NCc3cccc(Cl)c3F)cn2N2CCCC[C@@]12C] |
| II-130 | 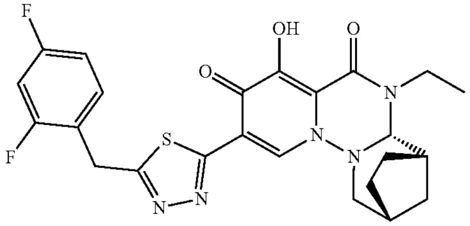 [SMILES: CCN1C(=O)c2c(O)c(=O)c(-c3nnc(Cc4ccc(F)cc4F)s3)cn2N2C[C@@H]3CC[C@@H](C3)[C@@H]12] |
| II-131 | 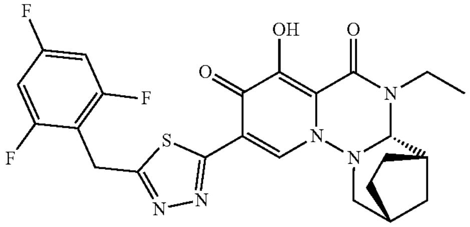 [SMILES: CCN1C(=O)c2c(O)c(=O)c(-c3nnc(Cc4c(F)cc(F)cc4F)s3)cn2N2C[C@@H]3CC[C@@H](C3)[C@@H]12] |
| II-132 | 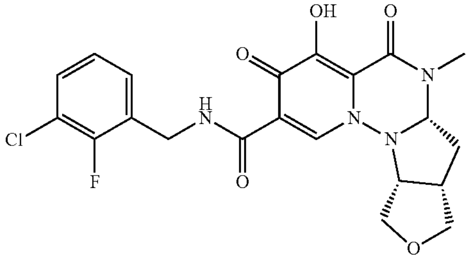 [SMILES: CN1C(=O)c2c(O)c(=O)c(C(=O)NCc3cccc(Cl)c3F)cn2N2[C@H]3COC[C@H]3C[C@@H]12] |

TABLE 10
| No. | Structure |
| --- | --- |
| II-133 | 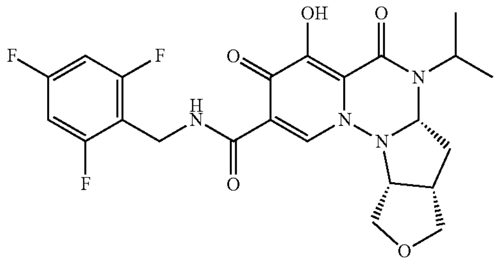 [SMILES: CC(C)N1C(=O)c2c(O)c(=O)c(C(=O)NCc3c(F)cc(F)cc3F)cn2N2[C@H]3COC[C@H]3C[C@@H]12] |
| II-134 | 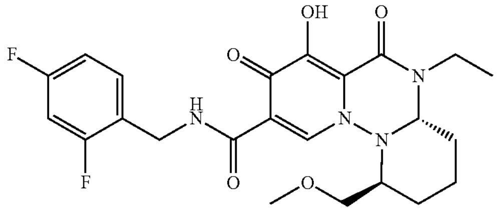 [SMILES: CCN1C(=O)c2c(O)c(=O)c(C(=O)NCc3ccc(F)cc3F)cn2N2[C@H](COC)CCC[C@@H]12] |
| II-135 | 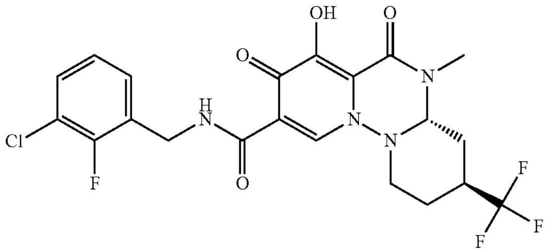 [SMILES: CN1C(=O)c2c(O)c(=O)c(C(=O)NCc3cccc(Cl)c3F)cn2N2CC[C@H](C(F)(F)F)C[C@@H]12] |
| II-136 | 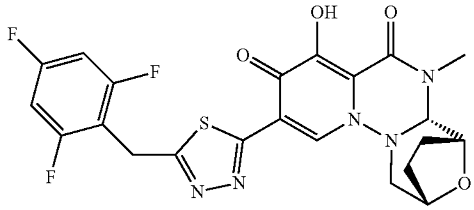 [SMILES: CN1C(=O)c2c(O)c(=O)c(-c3nnc(Cc4c(F)cc(F)cc4F)s3)cn2N2C[C@@H]3CC[C@@H](O3)[C@@H]12] |
| II-137 | 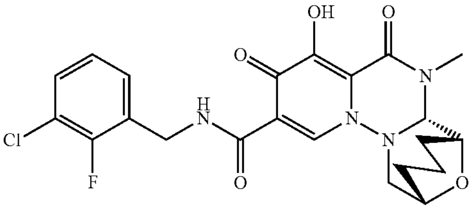 [SMILES: CN1C(=O)c2c(O)c(=O)c(C(=O)NCc3cccc(Cl)c3F)cn2N2C[C@@H]3CCC[C@@H](O3)[C@@H]12] |
| II-138 | 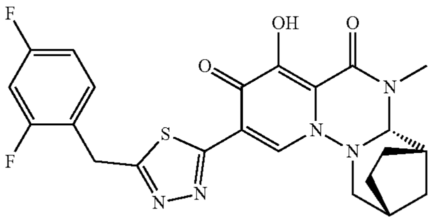 [SMILES: CN1C(=O)c2c(O)c(=O)c(-c3nnc(Cc4ccc(F)cc4F)s3)cn2N2C[C@@H]3CC[C@@H](C3)[C@@H]12] |

TABLE 10-continued
| No. | Structure |
| --- | --- |
| II-139 | 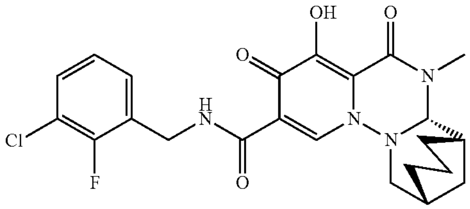 [SMILES: CN1C(=O)c2c(O)c(=O)c(C(=O)NCc3cccc(Cl)c3F)cn2N2C[C@@H]3CCC[C@@H](C3)[C@@H]12] |
| II-140 | 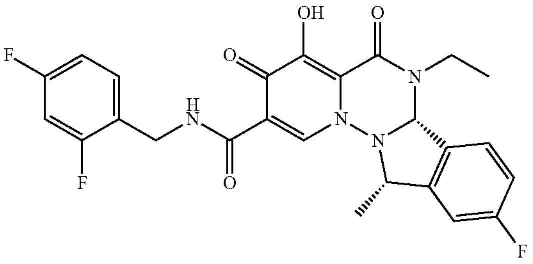 [SMILES: CCN1C(=O)c2c(O)c(=O)c(C(=O)NCc3ccc(F)cc3F)cn2N2[C@@H](C)c3cc(F)ccc3[C@@H]12] |
| II-141 | 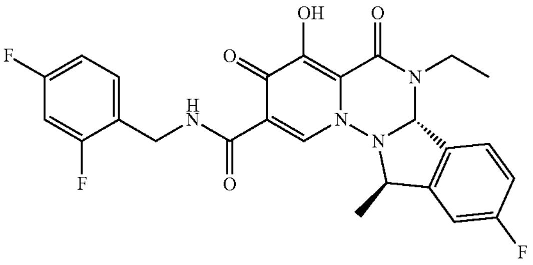 [SMILES: CCN1C(=O)c2c(O)c(=O)c(C(=O)NCc3ccc(F)cc3F)cn2N2[C@H](C)c3cc(F)ccc3[C@@H]12] |
| II-142 | 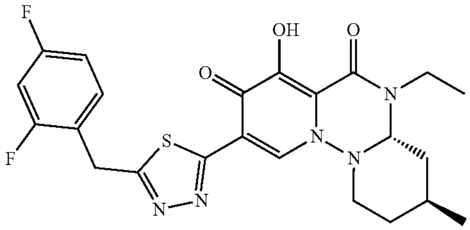 [SMILES: CCN1C(=O)c2c(O)c(=O)c(-c3nnc(Cc4ccc(F)cc4F)s3)cn2N2CC[C@H](C)C[C@@H]12] |
| II-143 | 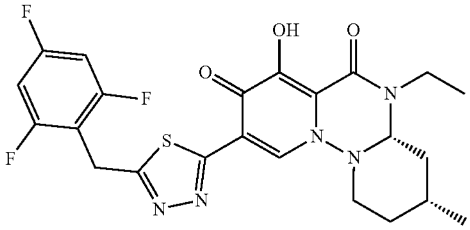 [SMILES: CCN1C(=O)c2c(O)c(=O)c(-c3nnc(Cc4c(F)cc(F)cc4F)s3)cn2N2CC[C@@H](C)C[C@@H]12] |
| II-144 | 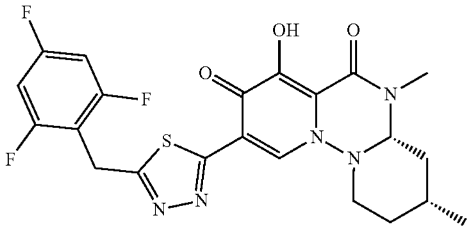 [SMILES: C[C@@H]1CCN2[C@@H](C1)N(C)C(=O)c1c(O)c(=O)c(-c3nnc(Cc4c(F)cc(F)cc4F)s3)cn12] |

TABLE 10-continued
| No. | Structure |
| --- | --- |
| II-145 | 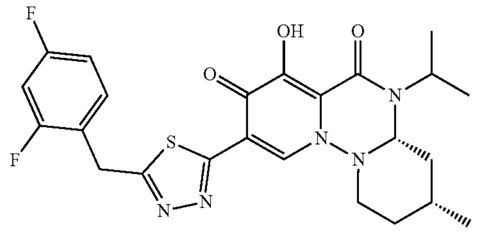 |
| II-146 | 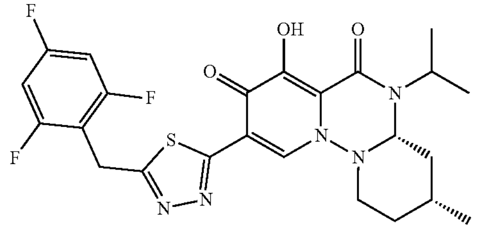 [SMILES: CC(C)N1C(=O)c2c(O)c(=O)c(-c3nnc(Cc4c(F)cc(F)cc4F)s3)cn2N2CC[C@@H](C)C[C@@H]12] |
| II-147 | 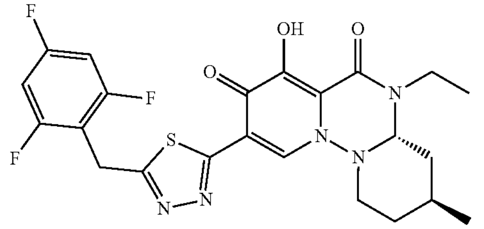 [SMILES: CCN1C(=O)c2c(O)c(=O)c(-c3nnc(Cc4c(F)cc(F)cc4F)s3)cn2N2CC[C@H](C)C[C@@H]12] |
| II-148 | 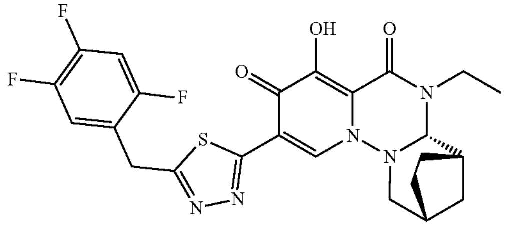 [SMILES: CCN1C(=O)c2c(O)c(=O)c(-c3nnc(Cc4cc(F)c(F)cc4F)s3)cn2N2C[C@@H]3CC[C@@H](C3)[C@@H]12] |
TABLE 11
| No. | Structure |
| --- | --- |
| II-149 | 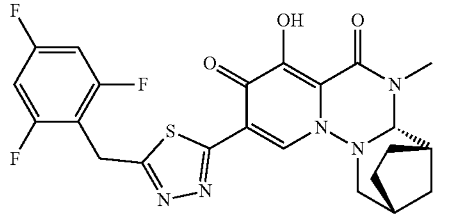 |
| II-150 | 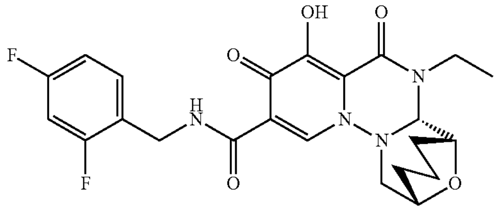 [SMILES: CCN1C(=O)c2c(O)c(=O)c(C(=O)NCc3ccc(F)cc3F)cn2N2C[C@@H]3CCC[C@@H](O3)[C@@H]12] |

TABLE 11-continued
| No. | Structure |
| --- | --- |
| II-151 | 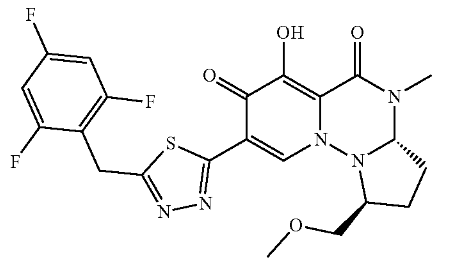 [SMILES: COC[C@@H]1CC[C@H]2N(C)C(=O)c3c(O)c(=O)c(-c4nnc(Cc5c(F)cc(F)cc5F)s4)cn3N12] |
| II-152 | 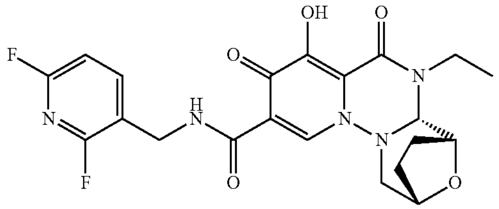 [SMILES: CCN1C(=O)c2c(O)c(=O)c(C(=O)NCc3ccc(F)nc3F)cn2N2C[C@@H]3CC[C@@H](O3)[C@@H]12] |
| II-153 | 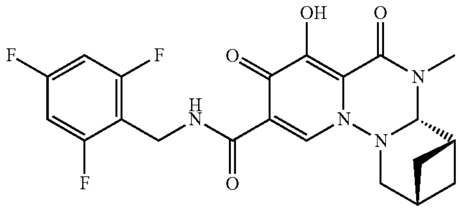 [SMILES: CN1C(=O)c2c(O)c(=O)c(C(=O)NCc3c(F)cc(F)cc3F)cn2N2C[C@H]3C[C@H](C3)[C@@H]12] |
| II-154 | 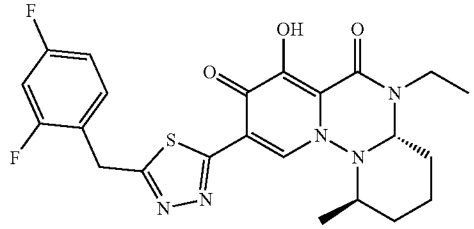 [SMILES: CCN1C(=O)c2c(O)c(=O)c(-c3nnc(Cc4ccc(F)cc4F)s3)cn2N2[C@H](C)CCC[C@@H]12] |
| II-155 | 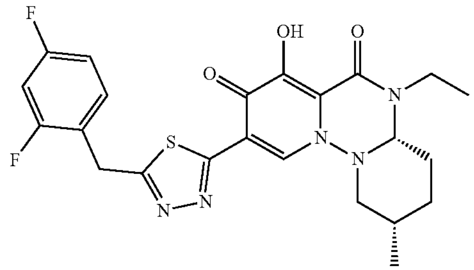 [SMILES: CCN1C(=O)c2c(O)c(=O)c(-c3nnc(Cc4ccc(F)cc4F)s3)cn2N2C[C@@H](C)CC[C@@H]12] |
| II-156 | 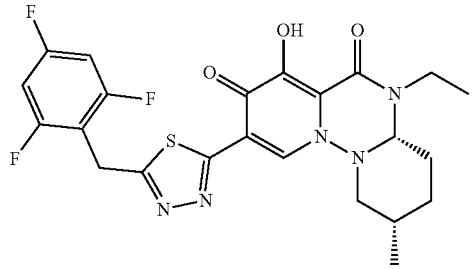 [SMILES: CCN1C(=O)c2c(O)c(=O)c(-c3nnc(Cc4c(F)cc(F)cc4F)s3)cn2N2C[C@@H](C)CC[C@@H]12] |

TABLE 11-continued

| No. | Structure |
|---|---|
| II-157 | 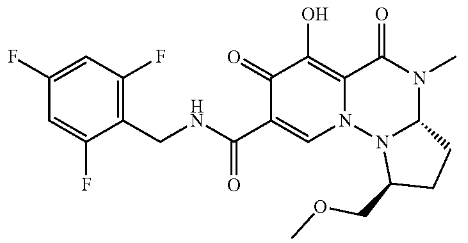 [SMILES: COC[C@@H]1CC[C@H]2N(C)C(=O)c3c(O)c(=O)c(C(=O)NCc4c(F)cc(F)cc4F)cn3N12] |
| II-158 | 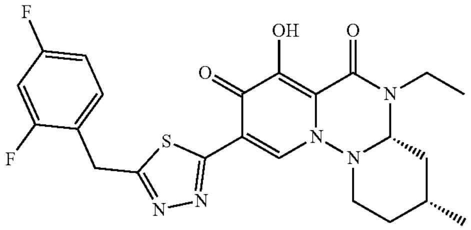 [SMILES: CCN1C(=O)c2c(O)c(=O)c(-c3nnc(Cc4ccc(F)cc4F)s3)cn2N2CC[C@@H](C)C[C@@H]12] |
| II-159 | 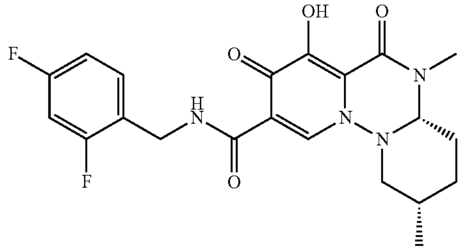 [SMILES: C[C@H]1CC[C@H]2N(C)C(=O)c3c(O)c(=O)c(C(=O)NCc4ccc(F)cc4F)cn3N2C1] |

The physical data of the respective compounds are given below.

TABLE 12

| No. | MS | Charge |
|---|---|---|
| I-001 | 451 | M + H |
| I-002 | 473 | M + H |
| I-003 | 490 | M + H |
| I-004 | 447 | M + H |
| I-005 | 493 | M + H |
| I-006 | 449 | M + H |
| I-007 | 492 | M + H |
| I-008 | 447 | M + H |
| I-009 | 492 | M + H |
| I-010 | 467 | M + H |
| I-011 | 474 | M + H |
| I-012 | 449 | M + H |
| I-013 | 483 | M + H |
| I-014 | 467 | M + H |
| I-015 | 453 | M + H |
| I-016 | 451 | M + H |
| I-017 | 451 | M + H |
| I-018 | 501 | M + H |
| I-019 | 469 | M + H |
| I-020 | 490 | M + H |
| I-021 | 467 | M + H |
| I-022 | 492 | M + H |
| I-023 | 433 | M + H |
| I-024 | 447 | M + H |
| I-025 | 433 | M + H |
| I-026 | 466 | M + H |
| I-027 | 449 | M + H |
| I-028 | 467 | M + H |
| I-029 | 451 | M + H |
| I-030 | 461 | M + H |
| I-031 | 447 | M + H |

TABLE 12-continued

| No. | MS | Charge |
|---|---|---|
| I-032 | 419 | M + H |
| II-001 | 459 | M + H |
| II-002 | 493 | M + H |
| II-003 | 451 | M + H |
| II-004 | 449 | M + H |
| II-005 | 459 | M + H |
| II-006 | 477 | M + H |
| II-007 | 495 | M + H |
| II-008 | 463 | M + H |
| II-009 | 457 | M + H |
| II-010 | 449 | M + H |
| II-011 | 491 | M + H |
| II-012 | 473 | M + H |
| II-013 | 473 | M + H |
| II-014 | 477 | M + H |
| II-015 | 450 | M + H |
| II-016 | 475 | M + H |
| II-017 | 479 | M + H |
| II-018 | 449 | M + H |
| II-019 | 449 | M + H |
| II-020 | 459 | M + H |
| II-021 | 449 | M + H |
| II-022 | 467 | M + H |
| II-023 | 461 | M + H |
| II-024 | 469 | M + H |
| II-025 | 473 | M + H |
| II-026 | 465 | M + H |
| II-027 | 463 | M + H |
| II-028 | 431 | M + H |
| II-029 | 463 | M + H |
| II-030 | 449 | M + H |
| II-031 | 445 | M + H |
| II-032 | 463 | M + H |
| II-033 | 461 | M + H |
| II-034 | 447 | M + H |

TABLE 12-continued

| No. | MS | Charge |
|---|---|---|
| II-035 | 478 | M + H |
| II-036 | 435 | M + H |
| II-037 | 501 | M + H |
| II-038 | 461 | M + H |
| II-039 | 463 | M + H |
| II-040 | 435 | M + H |
| II-041 | 479 | M + H |
| II-042 | 435 | M + H |
| II-043 | 451 | M + H |
| II-044 | 458 | M + H |
| II-045 | 433 | M + H |
| II-046 | 447 | M + H |
| II-047 | 465 | M + H |
| II-048 | 464 | M + H |
| II-049 | 434 | M + H |
| II-050 | 449 | M + H |
| II-051 | 463 | M + H |
| II-052 | 477 | M + H |
| II-053 | 449 | M + H |
| II-054 | 450 | M + H |
| II-055 | 469 | M + H |
| II-056 | 463 | M + H |
| II-057 | 435 | M + H |
| II-058 | 463 | M + H |
| II-059 | 491 | M + H |
| II-060 | 433 | M + H |
| II-061 | 433 | M + H |
| II-062 | 467 | M + H |
| II-063 | 449 | M + H |
| II-064 | 447 | M + H |
| II-065 | 431 | M + H |
| II-066 | 433 | M + H |
| II-067 | 453 | M + H |
| II-068 | 447 | M + H |
| II-069 | 450 | M + H |
| II-070 | 415 | M + H |
| II-071 | 473 | M + H |
| II-072 | 485 | M + H |
| II-073 | 451 | M + H |
| II-074 | 483 | M + H |
| II-075 | 433 | M + H |
| II-076 | 431 | M + H |
| II-077 | 501 | M + H |
| II-078 | 447 | M + H |
| II-079 | 436 | M + H |
| II-080 | 437 | M + H |
| II-081 | 447 | M + H |
| II-082 | 449 | M + H |
| II-083 | 415 | M + H |
| II-084 | 463 | M + H |
| II-085 | 451 | M + H |
| II-086 | 450 | M + H |
| II-087 | 485 | M + H |
| II-088 | 461 | M + H |
| II-089 | 437 | M + H |
| II-090 | 422 | M + H |
| II-091 | 419 | M + H |
| II-092 | 435 | M + H |
| II-093 | 481 | M + H |
| II-094 | 437 | M + H |
| II-095 | 465 | M + H |
| II-096 | 465 | M + H |
| II-097 | 476 | M + H |
| II-098 | 460 | M + H |
| II-099 | 478 | M + H |
| II-100 | 456 | M + H |
| II-101 | 472 | M + H |
| II-102 | 462 | M + H |
| II-103 | 480 | M + H |
| II-104 | 473 | M + H |
| II-105 | 476 | M + H |
| II-106 | 494 | M + H |
| II-107 | 458 | M + H |
| II-108 | 474 | M + H |
| II-109 | 474 | M + H |
| II-110 | 504 | M + H |
| II-111 | 492 | M + H |
| II-112 | 492 | M + H |

TABLE 12-continued

| No. | MS | Charge |
|---|---|---|
| II-113 | 460 | M + H |
| II-114 | 478 | M + H |
| II-115 | 474 | M + H |
| II-116 | 506 | M + H |
| II-117 | 522 | M + H |
| II-118 | 486 | M + H |
| II-119 | 494 | M + H |
| II-120 | 474 | M + H |
| II-121 | 492 | M + H |
| II-122 | 478 | M + H |
| II-123 | 491 | M + H |
| II-124 | 474 | M + H |
| II-125 | 506 | M + H |
| II-126 | 520 | M + H |
| II-127 | 502 | M + H |
| II-128 | 484 | M + H |
| II-129 | 449 | M + H |
| II-130 | 500 | M + H |
| II-131 | 518 | M + H |
| II-132 | 463 | M + H |
| II-133 | 493 | M + H |
| II-134 | 477 | M + H |
| II-135 | 503 | M + H |
| II-136 | 534 | M + H |
| II-137 | 477 | M + H |
| II-138 | 486 | M + H |
| II-139 | 475 | M + H |
| II-140 | 499 | M + H |
| II-141 | 499 | M + H |
| II-142 | 489 | M + H |
| II-143 | 506 | M + H |
| II-144 | 492 | M + H |
| II-145 | 502 | M + H |
| II-146 | 520 | M + H |
| II-147 | 506 | M + H |
| II-148 | 518 | M + H |
| II-149 | 504 | M + H |
| II-150 | 475 | M + H |
| II-151 | 508 | M + H |
| II-152 | 462 | M + H |
| II-153 | 449 | M + H |
| II-154 | 488 | M + H |
| II-155 | 488 | M + H |
| II-156 | 506 | M + H |
| II-157 | 467 | M + H |
| II-158 | 531 | M + H |
| II-159 | 433 | M + H |

Examples relating to (B), formula F) will now be described.

Examples 9

The following compounds were likewise synthesized in the same way using the methods of synthesis described in, for example, WO2015/174511 or WO2016/194806.

[Chem. 46]

I'-001

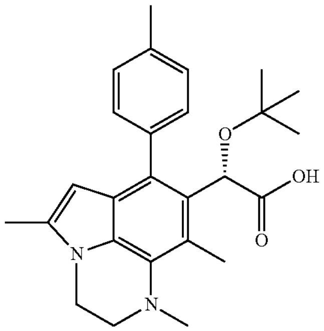

I'-027

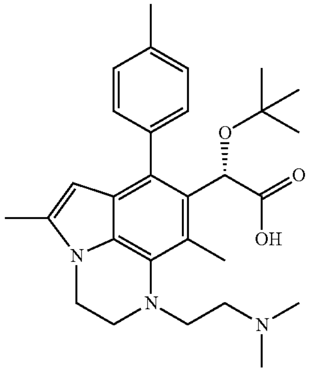

I'-043

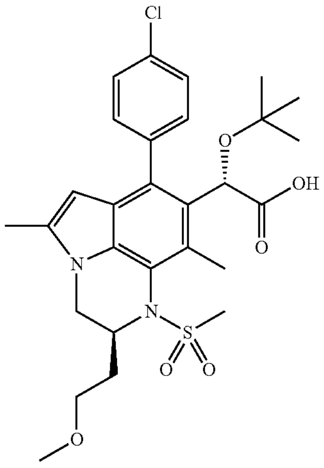

I'-189

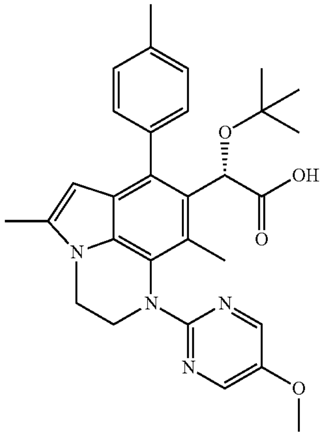

-continued

I'-220

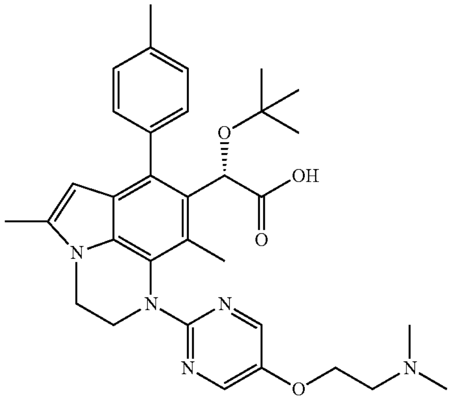

I'-292

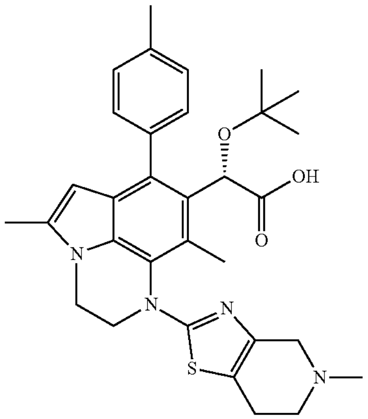

I'-304

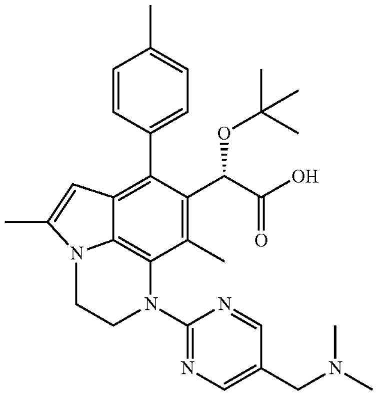

The other compounds of (B) were synthesized by known methods or commercially obtained compounds were employed.

Examples of biological tests of compounds according to the present invention are given below.

Test Example 1

Anti-HIV Activity

A serial dilution series of test samples was prepared in 96-well microplates (50 μL/well).

100 μL/well in each case were dispensed onto plates having test samples of 2.5×105/mL MT-4 cell suspension, and HIV virus solution was then dispensed thereto in the amount of 50 μL/well. Mixing was performed using a plate mixer and culturing was performed for four days in a CO2 incubator. MTT (3-(4,5-dimethylthiazol-2-yl)-2,5-diphenyltetrazolium bromide) liquid was dispensed into each well in the amount of 30 μL in each case. The reaction was conducted for 1 h in a CO2 incubator. 150 μL of supernatant were removed from each well, taking care not to aspirate any cells. 150 μL of cell solution were added, and thorough mixing was performed with a plate mixer until all the cells had been dissolved. The optical absorbance of the mixed plates was measured at two wavelengths: 560 nm/690 nm, with a microplate reader. The 50% HIV inhibition concentration (EC50) was determined from the concentration dependence curve, using a 4-parameter logistic curve fitting model as indicated below.

$$y=A+((B-A)/(1+((C/x)D)))$$

A=minimum value of inhibition rate (negative control, 0%)

B=maximum Value of inhibition rate (positive control, 100%)

C=concentration of the compound at the point of inflection

D=slope coefficient x=concentration of compound y=inhibition rate (%)

(Results)

The results of the compounds of the example compounds relating to formula (I) of (A) are indicated below.

TABLE 13

| No. | EC50_nM |
|---|---|
| I-001 | 0.73 |
| I-002 | 3.20 |
| I-003 | 2.70 |
| I-004 | 2.50 |
| I-005 | 10.00 |
| I-006 | 1.80 |
| I-007 | 1.60 |
| I-008 | 12.00 |
| I-009 | 1.30 |
| I-010 | 1.40 |
| I-011 | 3.20 |
| I-012 | 3.20 |
| I-013 | 2.30 |
| I-014 | 1.20 |
| I-015 | 1.30 |
| I-016 | 2.20 |
| I-017 | 1.90 |
| I-018 | 0.66 |
| I-019 | 0.56 |
| I-020 | 3.80 |
| I-021 | 4.00 |
| I-022 | 4.80 |
| I-023 | 1.40 |
| I-024 | 0.76 |
| I-025 | 0.72 |
| I-026 | 2.50 |
| I-027 | 1.30 |
| I-028 | 2.10 |
| I-029 | 1.40 |
| I-030 | 1.30 |
| I-031 | 0.62 |
| I-032 | 3.60 |
| II-001 | 0.92 |
| II-002 | 0.62 |
| II-003 | 0.62 |
| II-004 | 1.50 |
| II-005 | 2.60 |
| II-006 | 1.00 |
| II-007 | 0.49 |
| II-008 | 3.60 |
| II-009 | 0.40 |
| II-010 | 0.55 |

TABLE 13-continued

| No. | EC50_nM |
|---|---|
| II-011 | 0.65 |
| II-012 | 1.60 |
| II-013 | 2.90 |
| II-014 | 0.95 |
| II-015 | 0.23 |
| II-016 | 0.72 |
| II-017 | 1.20 |
| II-018 | 6.30 |
| II-019 | 1.40 |
| II-020 | 1.10 |
| II-021 | 0.18 |
| II-022 | 0.39 |
| II-023 | 1.40 |
| II-024 | 3.80 |
| II-025 | 0.86 |
| II-026 | 0.34 |
| II-027 | 1.50 |
| II-028 | 1.00 |
| II-029 | 1.30 |
| II-030 | 3.80 |
| II-031 | 0.64 |
| II-032 | 2.00 |
| II-033 | 2.90 |
| II-034 | 2.60 |
| II-035 | 0.58 |
| II-036 | 3.20 |
| II-037 | 1.40 |
| II-038 | 0.65 |
| II-039 | 0.58 |
| II-040 | 2.00 |
| II-041 | 0.19 |
| II-042 | 0.57 |
| II-043 | 0.77 |
| II-044 | 2.80 |
| II-045 | 0.74 |
| II-046 | 0.62 |
| II-047 | 0.84 |
| II-048 | 0.90 |
| II-049 | 1.70 |
| II-050 | 0.79 |
| II-051 | 0.66 |
| II-052 | 0.27 |
| II-053 | 3.40 |
| II-054 | 3.20 |
| II-055 | 3.60 |
| II-056 | 0.66 |
| II-057 | 4.90 |
| II-058 | 0.17 |
| II-059 | 0.62 |
| II-060 | 0.61 |
| II-061 | 0.34 |
| II-082 | 0.58 |
| II-063 | 3.20 |
| II-064 | 0.74 |
| II-065 | 0.83 |
| II-068 | 0.25 |
| II-087 | 0.22 |
| II-068 | 0.46 |
| II-069 | 3.30 |
| II-070 | 1.10 |
| II-071 | 1.10 |
| II-072 | 0.66 |
| II-073 | 0.58 |
| II-074 | 18.00 |
| II-075 | 0.74 |
| II-076 | 0.95 |
| II-077 | 1.80 |
| II-078 | 1.30 |
| II-079 | 3.70 |
| II-080 | 0.71 |
| II-081 | 0.94 |
| II-082 | 4.10 |
| II-083 | 0.33 |
| II-084 | 0.32 |
| II-085 | 0.57 |
| II-086 | 1.90 |
| II-087 | 1.00 |
| II-088 | 0.61 |

TABLE 13-continued

| No. | EC50__nM |
|---|---|
| II-089 | 1.40 |
| II-090 | 18.00 |
| II-091 | 0.69 |
| II-092 | 0.74 |
| II-093 | 0.22 |
| II-094 | 0.61 |
| II-095 | 1.40 |
| II-096 | 1.50 |
| II-097 | 1.60 |
| II-098 | 0.62 |
| II-099 | 0.70 |
| II-100 | 3.70 |
| II-101 | 4.50 |
| II-102 | 1.30 |
| II-103 | 0.25 |
| II-104 | 32.00 |
| II-105 | 0.19 |
| II-106 | 0.52 |
| II-107 | 0.70 |
| II-108 | 0.67 |
| II-109 | 1.20 |
| II-110 | 0.13 |
| II-111 | 0.39 |
| II-112 | 1.90 |
| II-113 | 0.66 |
| II-114 | 0.13 |
| II-115 | 0.13 |
| II-116 | 0.28 |
| II-117 | 0.62 |
| II-118 | 0.96 |
| II-119 | 1.30 |
| II-120 | 0.25 |
| II-121 | 0.20 |
| II-122 | 0.24 |
| II-123 | 4.00 |
| II-124 | 3.50 |
| II-125 | 1.40 |
| II-126 | 0.60 |
| II-127 | 0.74 |
| II-128 | 0.66 |
| II-129 | 0.33 |
| II-130 | 0.66 |
| II-131 | 0.66 |
| II-132 | 0.43 |
| II-133 | 0.55 |
| II-134 | 0.55 |
| II-135 | 1.60 |
| II-136 | 1.00 |
| II-137 | 0.70 |
| II-138 | 0.14 |
| II-139 | 0.74 |
| II-140 | 0.67 |
| II-141 | 1.20 |
| II-142 | 0.76 |
| II-143 | 1.70 |
| II-144 | 0.69 |
| II-145 | 1.00 |
| II-146 | 2.70 |
| II-147 | 1.80 |
| II-148 | 5.20 |
| II-149 | 0.60 |
| II-150 | 0.33 |
| II-151 | 0.37 |
| II-152 | 2.20 |
| II-153 | 0.27 |
| II-154 | 1.10 |
| II-155 | 0.30 |
| II-156 | 1.20 |
| II-157 | 0.70 |
| II-158 | 1.70 |
| II-159 | 2.00 |

The results of the example compounds relating to formula (I') of (B) are indicated below.

Compound I'-001: 0.69 nm

Compound I'-027: 9.9 nm

Compound I'-043: 1.4 nm

Compound I'-189: 1.6 nm

Compound I'-220: 5.9 nm

Compound I'-292: 2.5 nm

Compound I'-304: 4.1 nm

From the above test results, it can be seen that the compounds according to the present invention show high anti-HIV activity, so their utility as HIV pharmaceutical agents is clear.

Test Example 2

Resistance Evaluation Test

A serial dilution series of test samples in 96-well microplates was prepared (50 ∞L/well).

$2.5\times10^4$/mL of HeLa-CD4 cell suspension was dispensed into each of the microplates containing test sample, in the amount of 100 µL/well, and HIV virus liquid (wild strain and mutant strain) was then dispensed in an amount of 50 µL/well. Mixing was performed using a plate mixer and culturing was performed for three days in a $CO_2$ incubator. After removing the cultured supernatant of each well by suction, 100 µL of the cell solution buffer in the reporter measurement kit was dispensed thereto, and freezing was conducted in a refrigerator (−80° C.). The plates frozen in the refrigerator were defrosted at room temperature, then mixed using a plate mixer and centrifuged for 5 min at 1,200 rpm. The supernatant of each well was divided to 96-well microplates (BLACK) in the amount of 20 µL in each case. The chemiluminescence reagent in the reporter assay kit was dispensed in the amount of 100 µL in each case, and, after reacting for about 1 h at room temperature, the amount of luminescence was measured using a MicroBeta TRILUX. The 50% HIV inhibition concentration (EC50) was determined from the concentration dependence curve, using a 4-parameter logistic curve fitting model as indicated below.

$$y=A+((B-A)/(1+((C/x)^D)))$$

A=minimum value of inhibition rate (negative control, 0%)

B=maximum value of inhibition rate (positive control, 100%)

C=concentration of the compound at the point of inflection

D=slope coefficient x=concentration of compound y=inhibition rate (%)

The degree of resistance (fold change (FC)) of each mutant strain was also calculated using the following formula.

$$FC=EC50 \text{ of mutant strain}/EC50 \text{ of wild strain}$$

(Results)

The results of the example compounds relating to formula (I) of (A) are shown below. The PC in respect of mutant strain 1 (E138K/G140S/Q148H/N155H) and the FC in respect of mutant strain 2 (E92Q/E138T/G140S/Q148H) are shown in the Table.

TABLE 14

| No. | Mutant Strain 1 | Mutant Strain 2 |
|---|---|---|
| I-007 | 3.8 | 6.9 |
| I-011 | 5.6 | 7.5 |
| I-016 | 13 | 10 |
| I-022 | 23 | 46 |

TABLE 14-continued

| No. | Mutant Strain 1 | Mutant Strain 2 |
|---|---|---|
| I-023 | 24 | 22 |
| I-024 | 24 | 16 |
| I-032 | 51 | 18 |
| II-001 | 3.1 | 4.2 |
| II-002 | 3.1 | 7.4 |
| II-005 | 4.6 | 7.7 |
| II-009 | 5.6 | 6.4 |
| II-013 | 6.1 | 8.7 |
| II-014 | 5.7 | 7.3 |
| II-016 | 6.6 | 9 |
| II-019 | 7.3 | 7 |
| II-021 | 8.1 | 14 |
| II-023 | 9.9 | 15 |
| II-026 | 10 | 6.9 |
| II-034 | 15 | 16 |
| II-036 | 15 | 7.9 |
| II-038 | 78 | 110 |
| II-039 | 48 | 62 |
| II-041 | 17 | 28 |
| II-043 | 18 | 17 |
| II-045 | 19 | 21 |
| II-052 | 22 | 16 |
| II-056 | 15 | 28 |
| II-058 | 25 | 15 |
| II-063 | 38 | 25 |
| II-064 | 27 | 22 |
| II-068 | 7 | 4.2 |
| II-070 | 32 | 36 |
| II-084 | 39 | 38 |
| II-088 | 47 | 45 |
| II-089 | 38 | 14 |
| II-091 | 48 | 17 |
| II-092 | 6.8 | 7.7 |
| II-093 | 49 | 25 |
| II-094 | 50 | 27 |
| II-096 | 6.4 | 8.9 |
| II-098 | 8.8 | 12 |
| II-102 | 25 | 22 |
| II-106 | 15 | 20 |
| II-109 | 4.1 | 2.5 |
| II-110 | 8.2 | 11 |
| II-112 | 4.7 | 7 |
| II-113 | 7.2 | 6.5 |
| II-117 | 10 | 11 |
| II-118 | 20 | 31 |
| II-120 | 5.8 | 8 |
| II-122 | 30 | 25 |
| II-124 | 6.8 | 11 |
| II-125 | 11 | 26 |
| II-126 | 17 | 20 |
| II-127 | 7.9 | 19 |
| II-128 | 20 | 29 |
| II-129 | 44 | 26 |
| II-130 | 2.5 | 3.9 |
| II-131 | 2.3 | 3.5 |
| II-132 | 76 | 17 |
| II-133 | 17 | 34 |
| II-136 | 3.5 | 8.2 |
| II-138 | 15 | 11 |
| II-139 | 18 | 10 |
| II-142 | 5.9 | 8.8 |
| II-143 | 3 | 3.6 |
| II-144 | 6.1 | 6.1 |
| II-147 | 5.1 | 7.3 |
| II-148 | 8.3 | 6.6 |
| II-149 | 14 | 12 |
| II-150 | 26 | 16 |
| II-151 | 27 | 17 |

TABLE 14-continued

| No. | Mutant Strain 1 | Mutant Strain 2 |
|---|---|---|
| II-152 | 36 | 25 |
| II-155 | 5.2 | 5.1 |
| II-156 | 3.5 | 4.6 |
| II-157 | 53 | 24 |
| II-158 | 2 | 4.8 |

FC in respect of mutant strain 3 (E92Q/E138K/G140S/Q148H)
Compound I-032: 7.7
Compound I-011: 7.7
FC in respect of mutant strain 4 (T97A/E138T/G140S/Q148H)
compound I-032: 10
compound I-011: 3.2

The above results show that the resistance barrier of the compounds according to the present invention is high, so generation of an HIV-resistant virus is unlikely. Therefore, since the compounds relating to formula (I) of (A) show high anti-HIV activity, they can provide pharmaceutical agents that are useful as therapeutic and/or prophylactic pharmaceutical agents for HIV infectious diseases.

Test Example 3

Test for Confirmation of Combined Use Effect

The two compounds in respect of which the effect of combined use was desired to be examined were mixed in various ratios, and the anti-HIV activity (50% HIV inhibiting concentration) for each combination was found by the method of test example 1. The combined use effect was evaluated by using these results to calculate the dosewise additivity value (D value) by the method of calculation of reference document 1. A brief description of the method of calculating the D value is given below.

If the 50% HIV inhibition concentration of compound I on its own is taken as $X_I$, and the concentration of compound I that exhibits 50% inhibition in a particular combination of compound I and compound J is taken as $x_1$, then $FIC_1$ is defined as follows.

$$FIC_I=x_1/X_I$$

The D value that is found by evaluating the anti-HIV activity of respective combinations of M concentrations of compound X1 and N concentrations of compound X2 is calculated by the following mathematical expression 1.

$$D=\left(\sum_{I=1}^{M}\sum_{J=1}^{N}FIC_{I,J}-M\right)/M \qquad \text{[Math 1]}$$

(Results)

The D values for the combination of the compound relating to formula (I) of (A) (compound (A)) and the compound (B) having anti-HIV activity (compound (B)) are shown in the following Table.

TABLE 15

| Compound (A) | INLAI Compound I'-189 | Polymerase inhibitor Ramipzin (3TC) | Lilpiperine | VM-1500 | PI Darunavin | Maturation inhibitor GSK2838232 | CAI GS-6207 | Compound C |
|---|---|---|---|---|---|---|---|---|
| Compound II-026 | 0.056 | −0.232 | −0.077 | −0.155 | −0.137 | −0.061 | −0.043 | 0.043 |
| Compound II-036 | | −0.184 | −0.044 | | −0.115 | 0.021 | −0.117 | 0.032 |
| Compound II-052 | | −0.156 | −0.020 | | −0.076 | −0.009 | −0.003 | 0.038 |
| Compound II-096 | 0.070 | −0.177 | −0.035 | −0.115 | −0.130 | 0.001 | −0.125 | 0.065 |
| Compound II-092 | | −0.118 | −0.022 | | −0.117 | 0.000 | −0.093 | 0.056 |
| Compound I-007 | 0.053 | −0.231 | −0.054 | −0.097 | −0.096 | 0.017 | −0.040 | 0.059 |
| Compound I-011 | | −0.195 | −0.137 | | −0.057 | 0.029 | −0.024 | 0.064 |
| Compound II-110 | | −0.145 | −0.073 | | −0.058 | −0.048 | 0.025 | 0.075 |
| Compound II-109 | 0.056 | −0.145 | −0.096 | −0.094 | −0.143 | −0.054 | −0.059 | 0.071 |
| Compound II-158 | | −0.199 | −0.180 | | −0.199 | −0.040 | −0.019 | −0.041 |

INLAI: HIV-1 Integrase (IN)-Lens epithelium-derived growth factor (LEDGF) complex allosteric inhibitor
PI: Protease inhibitor
CAI: Capsid inhibitor The effect of combined use was evaluated in terms of the D value in accordance with the following criteria −0.5 to −0.2: strong synergetic effect
−0.2 to −0.1: weak synergetic effect
−0.1 to −0.1: additive synergetic effect
0.1 to 0.2: weak antagonism
0.2 to 0.5: strong antagonism The effect of combined use is shown in the following Table.

TABLE 16

| Compound (A) | INLAI Compound I'-189 | Polymerase inhibitor Ramipzin (3TC) | Lilpiperine | VM-1500 | PI Darunavir | Maturation inhibitor GSK2838232 | CAI GS-6207 | Compound C |
|---|---|---|---|---|---|---|---|---|
| Compound II-026 | Additive | Strong synergy | Additive | Weak synergy | Weak synergy | Additive | Additive | Additive |
| Compound II-036 | | Weak synergy | Additive | | Weak synergy | Additive | Weak synergy | Additive |
| Compound II-052 | | Weak synergy | Additive | | Additive | Additive | Additive | Additive |
| Compound II-096 | Additive | Weak synergy | Additive | Weak synergy | Weak synergy | Additive | Weak synergy | Additive |
| Compound II-092 | | Weak synergy | Additive | | Weak synergy | Additive | Additive | Additive |
| Compound I-007 | Additive | Strong synergy | Additive | Additive | Additive | Additive | Additive | Additive |
| Compound I-011 | | Weak synergy | Weak synergy | | Additive | Additive | Additive | Additive |
| Compound II-110 | | Weak synergy | Additive | | Additive | Additive | Additive | Additive |
| Compound II-109 | Additive | Weak synergy | Additive | Additive | Weak synergy | Additive | Additive | Additive |
| Compound II-158 | | Weak synergy | Weak synergy | | Weak synergy | Additive | Additive | Additive |

INLAI: HIV-1 Integrase (IN)-Lens epithelium-derived growth factor (LEDGF) complex allosteric inhibitor
PI: Protease inhibitor
CAI: Capsid inhibitor The compounds relating to formula (I) of (A) show a synergetic effect with ramipzin, but show an additive effect with maturation inhibitors and compounds C.

Reference document: X. Interactions of 1263W94 with other antiviral agents in inhibition of human cytomegalovirus replication. Selleseth D W, Talarico C L, Mille R T, Lutz M W, Biron K K, Harvey R J.

Antimicrob Agents Chemother. 2003 April; 47(4):1468-71.

PMID: 1:2654696

Test Example 4

CYP Inhibition Test

Using commercially available pooled human liver microsomes, taking as an index the typical substrate metabolic reactions of the chief types of human CYP5 molecular types (CYP1A2, 2C9, 2C19, 2D6, 3A4), specifically, O-deethylation of 7-ethoxyresorufin (CYP1A2), methyl-hydroxylation of tolbutamide (CYP2C9), 4'-hydroxylation of mephenytoin (CYP2C19), O-demethylation of dextromethorphan (CYP2D6), and hydroxylation of terfenadine (CYP3A4), the degree to which the amounts of the respective metabolic products was inhibited was evaluated.

The reaction conditions were as follows: substrates: 0.5 μmol/L ethoxyresorufin (CYP1A2), 100 μmol/L tolbutamide (CYP2C9) 50 μmol/L S-mephenytoin (CYP2C19), 5 μmol/L dextromethorphan (CYP2D6), 1 μmol/L terfenadine (CYP3A4); reaction time, 15 min; reaction temperature, 37° C.; enzyme, pooled human liver microsomes 0.2 mg protein/mL; concentration of compound according to the invention, 1, 5, 10, 20 μmol/L (4 points).

Each of five substrates in 50 mmol/L Hepes buffer solution were added to 96-well plates, and human liver microsomes and compounds according to the present invention were added with the above compositions; NADPH coenzyme was added, and the metabolic reactions serving as indexes were initiated. After reacting at 37° C. for 15 min, the reaction was stopped by adding methanol/acetonitrile=1/1 (V/V) solution. After centrifuging for 15 min at 3000 rpm, the resorufin in the centrifuge supernatant (CYP1A2 metabolic product) was assayed using a fluorescent multi-label counter or LC/MS/MS, and the tolbutamide hydroxide (CYP2C9 metabolic product), mephenytoin 4' hydroxide (CYP2C19 metabolic product), dextromethorphan (CYP2D6 metabolic product), and terfenadine (CYP3A4 metabolic product) were assayed using LC/MS/MS.

Using as control (100%) a mixture obtained by adding to the reaction liquid a solution consisting only of the solvent DMSO, in which some compound instead of the compound according to the present invention was dissolved, the residual activities (%) were calculated and, using the concentration and suppression ratio, the $IC_{50}$ was calculated by inverse prediction using a logistic model.

Test Example 5

CYP3A4(MDZ) MBI Test

This is a test in which, for the CYP3A4 inhibition of the compound according to the present invention, the mechanism-based inhibition (MBI) action is evaluated from the enhancement of the innovation action caused by the metabolic reaction of the compound according to the present invention. The CYP3A4 inhibition was evaluated, using as an index the 1-hydroxylation reaction of midazolam (MDZ), using pooled human liver microsomes.

The reaction conditions were as follows: substrates: 10 μmol/L MDZ; pre-reaction time, 0 to 30 min; substrate metabolic reaction time, 2 min; reaction temperature, 37° C.; pooled human liver microsomes, pre-reaction time 0.5 mg/mL, reaction time 0.05 mg/mL (when diluted 10 times); concentrations of compound according to the present invention for pre-reaction, 1, 5, 10, 20 μmol/L (4 points) or 0.83, 5, 10, 20 μmol/L (4 points).

As a pre-reaction liquid, pooled human liver microsomes in K-Pi buffer (pH 7.4) As a pre-reaction solution, pooled human liver microsomes in K-Pi buffer (pH 7.4j and a solution of the compound according to the present invention are added to a 96-well plate in the composition of the above pre-reaction; part of this pre-reaction composition was transferred to another 96-well plate, where it was diluted to 1/10 with K-Pi buffer containing the substrate; the coenzyme NADPH was then added and the reaction serving as the index was initiated (no pre-reaction: pre-incubation 0 min); after a prescribed reaction time, the reaction was stopped by addition of a solution of methanol/acetonitrile=1/1 (V/V). NADPH was also added to the remaining pre-reaction liquid and the pre-reaction commenced (in this case, there was a pre-reaction: pre-incubation 30 min). After reacting for a prescribed time, part thereof was transferred to another plate, where it was diluted to 1/10 with K-Pi buffer containing the substrate, and the reaction serving as the index was initiated. After a prescribed reaction time, the reaction was stopped by addition of a solution of methanol/acetonitrile=1/1 (V/V). After the index reactions had been performed, the plates were centrifuged for 15 minutes at 3000 rpm, and the 1-midazolam hydroxide in the centrifuge supernatant was assayed with LLC/MS/MS.

Using as control (100%) a mixture obtained by adding to the reaction liquid a solution consisting only of the solvent DMSO, in which some compound instead of the compound according to the present invention was dissolved, the residual activities (%) when respective concentrations of the compound according to the present invention were added were calculated and, using the concentration and inhibition ratio, the IC was calculated by inverse prediction using a logistic model. Taking the ratio of the preincubation 0 min IC/preincubation 30 min IC as the shifted IC value, if the shifted IC is 1.5 or more, this is deemed to be positive (+); if the shifted IC is 1.0 or less, this is deemed to be negative (−).

(Results)

The results for the example compounds relating to formula (I) of (A) are shown below.

Compound I-032: (−)
Compound II-058: (−)
Compound II-117: (−)
Compound II-130: (−)

Test Example 6

BA Test

Observation Materials and Methods for Test of Oral Absorption (1) Animal used: rats were employed.

(2) Breeding conditions: the rats were allowed to freely ingest solid food and sterilised mains water.

(3) Settings for dosage and definition of groups: oral administration and intravenous administration were performed with prescribed dosages. The groups were set up as described below. (In some cases, the dosage is different for different compounds.)

Oral administration: 2 to 60 μmol/kg or 1 to 30 mg/kg (n=2 to 3)

Intravenous administration: 1 to 30 μmol/kg or 0.5 to 10 mg/kg (n=2 to 3)

(4) Preparation of administered liquids: for oral administration, administration was effected using a solution or suspension. For intravenous administration, administration was effected in solubilized form.

(5) Method of administration: in the case of oral administration, intragastric gavage was performed using an oral probe. In the case of intravenous administration, administration was performed from the tail vein, using a syringe fitted with an injection needle.

(6) Items evaluated: blood samples were collected over time, and the serum concentration of the compound according to the present invention was measured using LC/MS/MS.

(7) Statistical analysis: for the serum concentration of the compound according to the present invention, the area under the curve (AUC) of the serum concentration-time curve was calculated by the moment analysis method, and the bioavailability (BA) of the compound according to the present invention was calculated from the dosage ratio and the AUC ratio of the oral administration group and the intravenous administration group.

Test Example 7

Clearance Evaluation Test

Test Materials and Methods (1) Animals used: rats were employed.

(2) Breeding conditions: the rats were allowed to freely ingest solid food and sterilised mains water.

(3) Settings for dosage and definition of groups: oral administration and intravenous administration were performed with prescribed dosages. The groups were set up as described below.

Intravenous administration 1 μmol/kg (n=2)

(4) Preparation of administration liquid: the administration liquid was prepared by solubilizing using dimethylsulfoxide/propylene glycol=1/1 solution.

(5) Method of administration: administration was affected from the tail vein, using a syringe fitted with an injection needle.

(6) Items evaluated: blood samples were collected over time, and the serum concentration of the compound according to the present invention was measured using LC/MS/MS.

(7) Statistical analysis based on the changes in the serum concentration of the compounds according to the present invention, the total body clearance (CLtot) and the half-life (t½) were calculated, using the method of moment analysis.

(Results)

The results for the example compounds relating to formula (I) of (A) are shown below.

Compound I-032: 0.111 mL/min/kg, 12.3 hr

Compound II-023: 0.102 mL/min/kg, 26.7 hr

Compound II-104: 0.0226 mL/min/kg, 35.4 hr

Compound II-110: 0.0364 mL/min/kg, 23.6 hr

From the above results, the clearance of the compounds according to the present invention is small and the half-life is long, so these compounds are useful as persistent integrase inhibiters.

Test Example 8

Metabolic Stability Test

The extent of metabolization of the compound according to the present invention in the liver was evaluated by reacting commercially available pooled human liver microsomes with the compound according to the present invention for a fixed time and calculating the remaining percentage by comparing the reaction sample with an unreacted sample.

The reaction (oxidative reaction) was conducted for 0 min or 30 min at 37° C. in the presence of 1 mmol/L of NADPH, in a 0.2 mL buffer solution containing 0.5 mg of human liver microsome protein/mL (50 mmol/L Tris-HCl pH 7.4, 150 mmol/L potassium chloride, 10 mmol/L magnesium chloride). After the reaction, 50 μL of reaction liquid were added to 100 μL of methanol/acetonitrile=1/1 (v/v) solution, mixed, and centrifuged for 15 minutes at 3000 rpm. The compound according to the present invention in the centrifuged supernatant was quantified using LC/MS/MS or solid phase extraction (SPE)/MS; the residual amount of the compound according to the present invention after the reaction was calculated, taking the amount of the compound at the 0 min reaction point as 100%.

(Results) The remaining percentages for a compound concentration of 0.5 μmol/L are shown in the following Table.

The results of the example compounds relating to formula (I) of (A) are shown below.

TABLE 17

| No. | Remaining percentage % |
|---|---|
| I-007 | 97.7 |
| I-011 | 93 |
| I-016 | 88 |
| I-022 | 72.2 |
| I-023 | 103 |
| I-024 | 92.5 |
| I-032 | 103 |
| II-001 | 81.6 |
| II-002 | 80.2 |
| II-005 | 80.8 |
| II-009 | 87 |
| II-013 | 77.6 |
| II-014 | 74.3 |
| II-016 | 89.1 |
| II-019 | 84.1 |
| II-021 | 87.5 |
| II-023 | 74.2 |
| II-026 | 86 |
| II-034 | 88.3 |
| II-036 | 97.4 |
| II-038 | 77.2 |
| II-039 | 84.3 |
| II-041 | 88.4 |
| II-043 | 83.2 |
| II-045 | 96 |
| II-052 | 61.6 |
| II-056 | 94.3 |
| II-058 | 97.7 |
| II-063 | 95.7 |
| II-064 | 104 |
| II-068 | 82.9 |
| II-070 | 100 |
| II-084 | 97.5 |
| II-088 | 101 |
| II-089 | 105 |
| II-091 | 96.9 |
| II-092 | 101 |
| II-093 | 96.1 |
| II-094 | 97.2 |
| II-096 | 90.7 |
| II-098 | 109 |
| II-102 | 106 |
| II-106 | 95.3 |
| II-109 | 98.3 |
| II-110 | 96.5 |
| II-112 | 90.5 |
| II-113 | 85.3 |
| II-117 | 93.4 |
| II-118 | 92.4 |
| II-120 | 95.5 |
| II-122 | 102 |
| II-124 | 103 |
| II-125 | 88.5 |
| II-126 | 97.2 |
| II-127 | 100 |
| II-128 | 103 |
| II-129 | 88.6 |
| II-130 | 92.9 |
| II-131 | 83.4 |
| II-132 | 101 |
| II-133 | 73.3 |
| II-136 | 98.8 |
| II-138 | 93.9 |
| II-139 | 75.4 |
| II-142 | 102 |
| II-143 | 82.5 |
| II-144 | 94.2 |
| II-147 | 91.5 |
| II-148 | 71.7 |
| II-149 | 96.5 |
| II-150 | 98.6 |
| II-I51 | 94.6 |
| II-152 | 105 |
| II-I55 | 93 |
| II-156 | 91.3 |
| II-157 | 90 |
| II-158 | 81.3 |

Test Example 9

Fluctuation Ames Test

The mutagenicity of the compounds according to the present invention was evaluated. 20 μL of rat typhus bacteria stored by freezing (*Salmonella typhimurium* TA98 strain, TA100 strain) were inoculated into 10 mL liquid nutrient medium (2.5% Oxoid nutrient broth No. 2) and precultured for 10 h at 37° C., while shaking. In the case of the TA98 strain, the culture medium was removed by centrifuging 7.70 to 8.00 mL of the bacterial liquid (2000×g, 10 min). The bacteria were suspended in Micro F buffer solution ($K_2HPO_4$: 3.5 g/L, $K_2PO_4$: 1 g/L, $(NH_4)_2$ $SO_4$: 1 g/L, trisodium citrate dihydrate: 0.25 g/L, $MgSO_4.7H_2O$: 0.1 g/L) of the same volume as the bacterial liquid used in centrifugation and added to 120 mL of exposure medium (Micro F buffer solution containing biotin: 8 μg/mL, histidine: 0.2 μg/mL, glucose: 8 mg/mL). In the case of the TA100 strain, a test bacterial solution was prepared by adding 3.10 mL to 3.42 mL of the bacterial liquid to 120 to 130 mL of exposure medium. DMSO solutions of the compounds according to the present invention (diluted in several stages, with a common ratio of two to three times, from a maximum amount of 50 mg/mL): DMSO as a negative control; in respect of the TA98 strain under non-metabolic activation conditions, a DMSO solution of 50 μg/mL of 4-nitroquinoline-1-oxide as a positive control; in respect of the TA100 strain, a DMSO solution of 0.25 μg/mL of 2-(2-furyl)-3-(5-nitro-2-furyl) acrylamide; in respect of the TA98 strain under metabolic activation conditions, a DMSO solution of 40 μg/mL of 2-aminoanthracene; and, in respect of the TA100 strain, a DMSO solution of 20 μg/mL of 2-aminoanthracene were respectively mixed with 12 μL and 588 μL (in the case of metabolic activation conditions, a mixed solution of 498 μL of the test bacterial liquid and 90 μL of S9 mix), and cultured while shaking for 90 min at 37° C. 460 μL of bacterial liquid which had been exposed to the compound according to the present invention were mixed with 2300 μL of indicator medium (Micro F buffer solution containing biotin: 8 μg/mL, histidine: 0.2 μg/mL, glucose: 8 mg/mL, bromocresol purple: 37.5 μg/mL) and dispensed to microplates with 48 wells per plate, each of capacity 50 μL, and cultured by leaving to stand for three days at 37° C. Wells containing bacteria that have acquired the ability to proliferate by mutation of the amino acid (histidine) synthase gene show a change in color from purple to yellow because of the pH change; evaluation is conducted by totaling, per dose, the number of bacteria proliferation cells in the 48 wells that succeeded in changing color to yellow and comparing with the negative control group. Negative mutagenicity is indicated by (−) and positive mutagenicity is indicated by (+).

Test Example 10 hERG Test

With the object of evaluating the electrocardiograph QT interval elongation risk of the compounds according to the present invention, the action of compounds according to the present invention on the delayed-rectifier K+ current ($I_{Kr}$), which performs an important role in the ventricular repolarization process, was studied; CHO cells, which express a human ether-a-go-go related gene (hERG) channel, were used.

Using a fully automatic patch clamp system (QPatch: Sophion Bioscience A/S), by the whole cell patch clamp method, the cells were maintained at a membrane potential of −80 mV and a leakage potential of −50 mV was then applied; after this, a depolarization stimulus of +20 mV was applied for 2 seconds and furthermore a repolarization stimulus of −50 mV, for two seconds; the induced $I_{Kr}$ when this was done was recorded. Extracellular fluid (NaCl: 145 mmol/L, KCl: 4 mmol/L, $CaCl_2$: 2 mmol/L, $MgCl_2$: 1 mmol/L, glucose: 10 mmol/L, HEPES (4-(2-hydroxyethyl)-1-piperazineethanesulfonic acid, 4-(2-hydroxyethyl)-1-1-piperazineethanesulfonic acid): 10 mmol/L, pH=7.4) was used as medium, prepared with 0.1% dimethyl sulfoxide; extracellular fluids in which the medium and the compound according to the present invention were dissolved in the target concentrations were applied to the cells for 7 min or more, respectively under room temperature conditions. From the $I_{Kr}$ obtained, using analysis software (QPatch: Sophion Bioscience A/S), the absolute value of the maximum tail current was measured, with reference to the current value at the maintained membrane potential. Furthermore, the ratio of the maximum tail current after application of the compound according to the present invention with respect to the maximum tail current after application of the medium was calculated as the percentage inhibition, and used to evaluate the effect of the compound according to the present invention on the $I_{Kr}$.

Test Example 11

Solubility Test

The solubility of the compounds according to the present invention was determined under 1% DMSO addition conditions. A 10 mmol/L compound solution was prepared using DMSO. 2 μL of the compound according to the present invention were respectively added to 198 μL of a JP-1 solution and a JP-2 solution. The mixture was subjected to suction filtration after shaking for 1 h at room temperature. The filtrate was diluted to 10 or 100 times, using methanol/water=1/1 (V/V) or acetone/acetonitrile/methanol/water=1/1/2 (V/V/V), and the concentration in the filtrate was measured using LC/MS or solid extraction (SPE)/MS, by the absolute calibration method.

The composition of the JP-1 solution was as follows.

2.0 g of sodium chloride and 7.0 mL of hydrochloric acid, made up to 1000 mL by adding water.

The composition of the JP-2 solution was as follows.

3.40 g of potassium dihydrogen phosphate and 3.55 g of anhydrous disodium hydrogen phosphate were dissolved in water and made up to 1000 mL, and the same volume of water was then added thereto.

Test Example 12

Test of Powder Solubility

A suitable amount of the compound according to the present invention was added to suitable containers, JP-1 solution (2.0 g of sodium chloride and 7.0 mL of hydrochloric acid, made up to 1000 mL by adding water), JP-2 solution (3.40 g of potassium dihydrogen phosphate and 3.55 g of anhydrous disodium hydrogen phosphate were dissolved in water and made up to 1000 mL, with the same volume of water then added thereto) were added to each container, and 20 mmol of sodium taurocorate (TCA)/JP-2 solution (made up to 100 μL by addition of JP-2 solution to 1.08 g of TCA) were added, 200 μL in each case. After adding all the reagents, when all had been dissolved, the compound according to the present invention was added as appropriate. The container was hermetically sealed and the contents filtered after shaking for 1 h at 37° C., and the filtrate then diluted by a factor of 2 by addition of 100 μL of methanol to each 100 μL of filtrate. The dilution factor was altered in accordance with requirements. After checking for absence of bubbles and precipitates, hermetic sealing and shaking were performed. The compound according to the present invention was quantified using HPLC, by the absolute calibration method.

Test Example 13

Ames Test

The mutagenicity of the compound according to the present invention was evaluated by an Ames test, using as test bacterial strains: *Salmonella* bacteria (*Salmonella typhimurium*) TA98 strain, TA100 strain, TA1535 strain, TA1537 strain and *Escherichia coli* bacteria (*Escherichia coli*) WP2uvrA strain. With 0.1 mL of a DMSO solution of the compound according to the present invention, in the case of metabolic activation conditions, 0.5 mL of S9 mix was admixed; in the case of non-metabolic activation conditions, 0.5 mL of phosphate buffer solution and 0.1 mL of the test bacterial liquid were admixed therewith. 2 mL of multilayer soft agar containing histidine and biotin or tryptophan, together with a minimal glucose agar plate were used to prepare a multilayer preparation. At the same time, the same process was conducted using a negative control substance (DMSO) and a positive control substance (2-(2-furyl)-3-(5-nitro-2-furyl)acrylamide, sodium azide, and 9-aminoacridine, or 2-aminoanthracene). After culturing for 48 hours at 37° C., the number of revertant colonies appearing was totaled, and the evaluation conducted by comparing with the negative control group. The number of revertant colonies increases in concentration-dependent manner and if the number of revertant colonies is twice or more that of the negative control group, this is considered to be a positive (+) evaluation.

Test Example 14

Nav Test

With the object of evaluating the arrythmia-induction risk of compounds according to the present invention, the action of compounds according to the present invention on the $Na^+$ current ($I_{Na}$) was investigated: this plays an important role in the depolarization process of the myocardium; for this purpose, HEK cells were employed, in which a voltage-gated sodium channel (Nav 1.5 channel) encoded by the SCN5A gene is expressed.

Using a fully automatic patch clamp system (QPatch: Sophion Bioscience A/S), by the whole cell patch clamp method, the cells were maintained at a membrane potential of −100 mV and the induced $I_{Na}$ when a −10 mV depolarization stimulus was applied for 20 msec was recorded. Extracellular fluid (NaCl: 145 mmol/L, KCl: 4 mmol/L, $CaCl_2$: 2 mmol/L, $MgCl_2$: 1 mmol/L, glucose: 10 mmol/L, HEPES (4-(2-hydroxyethyl)-1-piperazineethanesulfonic acid, 4-(2-hydroxyethyl)-1-1-piperazineethanesulfonic acid): 10 mmol/L, TEA (Tetraethylammonium hydroxide): 10 mmol/L, pH=7.4) prepared with 0.3% dimethyl sulfoxide was used as medium; extracellular fluids in which the medium and the compound according to the present invention were dissolved in the target concentrations were applied to the cells for 7 min or more, respectively under room temperature conditions. From the $I_{Na}$ obtained, using analysis software (QPatch: Sophion Bioscience A/S), the absolute value of the maximum peak current was measured, with reference to the current value at the maintained membrane potential. Furthermore, the ratio of the maximum peak current on application of the compound according to the present invention with respect to the maximum peak current on application of the medium was calculated and used to evaluate the effect of the compound according to the present invention on the $I_{Na}$.

(Results)

The results for the example compounds relating to formula (I) of (A) are shown below.

Compound I-007 103%
Compound I-011 102%
Compound I-022 97.1%
Compound I-023 101%
Compound I-032 92.1%
Compound II-026 79%
Compound II-098 96.7%
Compound II-106 109%
Compound II-109 93.3%
Compound II-110 89.3%
Compound II-117 88.8%
Compound II-118 86.2%
Compound II-12.0 78.8%
Compound I-158 90.7%

From the above results, no clear increase in current was found, so there is little risk that the compounds according to the present invention might produce pulse irregularity due to increased Na current.

Test Example 15

Anti-HIV Activity Evaluation Test Using Peripheral Blood Mononuclear Cells (PBMC)

A stage dilution series of the test samples was created on a 96-well microplate (50 μL/well).

Aliquots of HIV virus liquid and PBMC, stimulated with Phytohemagglutinin (PHA), corresponding to the required number of wells, in the amount of $1.0\times10^5$/well, were mixed and reacted for 1 h at 37° C. After the reaction, the cell suspension was centrifuged and the supernatant discarded; aliquots of infected cells were distributed to culture medium in the amount of 150 μL/well and were dispensed in the amount of 150 μL/well in each case into the wells of a 96-well microplate containing test samples. Mixing was performed using a plate mixer and culturing was performed for four days with a $CO_2$ incubator. The 90% HIV inhibition concentration (EC90) was determined from the concentration dependence curve, using the 4-parameter logistic curve fitting model shown below.

$$y=A+((B-A)/(1+(C/x)^D))$$

A=minimum inhibition rate (negative control, 0%)
B=maximum inhibition rate (positive control, 100%)
C=concentration of compound at point of inflexion
D=slope coefficient
x=compound concentration
y=inhibition rate (%)

(Results)

The results for the example compounds relating to formula (I) of (A) are shown below.

Compound I-007 1.0 nm
Compound II-026 0.73 nm
Compound II-045 3.3 nm
Compound II-109 1.7 nm Test Example 16

Test for Evaluation of Anti-HIV Activity in the Presence of Human Serum Protein

A stage dilution series of the test samples was created on a 96-well microplate (50 μL/well).

Aliquots of human serum protein solution (human serum protein concentration 50%) were dispensed in the amount of 100 μL/well to a 96-well microplate containing the test sample. This was then left to stand for 1 h at room temperature. Culture medium in the amount of 100 μL/well in each case was dispensed to a serum-free plate for control purposes. Aliquots of MT-4 cells in the amount of $3.0\times10^5$/well and HIV virus liquid in the amount of 3 μL/well were mixed for the necessary number of wells and reacted for 1 h at 37° C. After the reaction, the cell suspension was centrifuged and the supernatant discarded; aliquots of infected cells were distributed to culture medium in the amount of 50 μL/well and were dispensed in the amount of 50 μL/well in each case into the wells of a 96-well microplate containing test samples and human serum protein (human serum protein concentration: 25%). Mixing was performed using a plate mixer and culturing was performed for four days with a $CO_2$ incubator. The 90% HIV inhibition concentration (EC90) was determined from the concentration dependence curve, using the 4-parameter logistic curve fitting model shown below. MTT(3-(4, 5-dimethylthiazol-2-yl)-2, 5-diphenyltetrazolium bromide) liquid in the amount of 30 μL was dispensed to each of the wells. The reaction was performed for 1 h in a $CO_2$ incubator. 150 μL supernatant was removed to avoid aspirating cells from the wells. 150 μL of cell solution was added and thorough mixing was performed, using a plate mixer, until all the cells were dissolved. The optical absorbance on the mixed plate was measured at two wavelengths, namely, 560 nm/690 nm, using a microplate reader. The 50% HIV inhibition concentration (EC50) was determined from the concentration dependence curve, using a 4-parameter logistic curve fitting model as indicated below.

$$y=A+((B-A)/(1+(C/x)^D))$$

A=minimum inhibition rate (negative control, 0%)
B=maximum inhibition rate (positive control, 100%)
C=concentration of compound at point of inflexion
D=slope coefficient
x=compound concentration
y=inhibition rate (%)

Next, the potency shift (PS) was calculated, using the following formula. The PS is the value of the human serum protein concentration, extrapolated to 100%.

PS 4×(*EC*50 in the presence of 25% human serum protein/*EC*50 with no human serum protein present)

(Results)

The PS in the presence of human serum protein are shown in the Table below (100% extrapolation values).

The results for the example compounds relating to formula (I) of (A) are shown below.

Compound I-007 116
Compound II-026 364
Compound II-045 236
Compound II-109 56

From these test results, it can be seen that the pharmaceutical agent according to the present invention can be employed for treatment and/or prophylaxis of symptoms and/or diseases induced by REV infection.

Preparation Examples

The following examples of preparations are illustrative only and are not intended to limit the scope of the invention in any way.

The compounds according to the present invention may be administered by any conventional route, in particular enterically, such as for example orally, for example in the form of tablets or capsules, or non-orally, for example in the form of an injectant or suspension, or locally, for example in the form of a lotion, gel, ointment or cream, or nasally, or in the form of a suppository, as a pharmaceutical agent composition. A pharmaceutical agent composition containing a compound according to the present invention in free form or in the form of a pharmaceutically acceptable salt together with at least one pharmaceutically acceptable carrier or diluent may be manufactured by conventional methods, by mixture, granulation or coating. For example, as an enteric composition, tablets, granules, or capsules may be employed containing an excipient, disintegrant, binding agent, lubricating agent or the like as well as the active constituent. Also, as an injection composition, a solution or suspension may be employed, which may be sterilised and may contain preservatives, stabilisers, or buffering agents.

INDUSTRIAL AVAILABILITY

The pharmaceutical agent according to the present invention can be employed for treatment and/or prophylaxis of symptoms and/or diseases induced by HIV infection.

The invention claimed is:

1. A pharmaceutical composition comprising (A) a compound selected from the group of compounds:

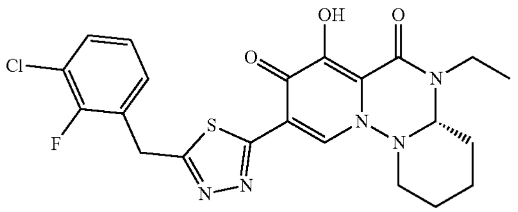
,

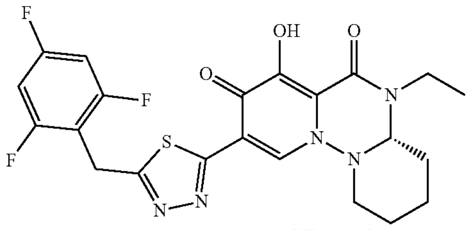
,

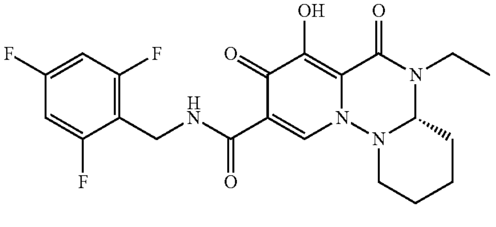
,

-continued
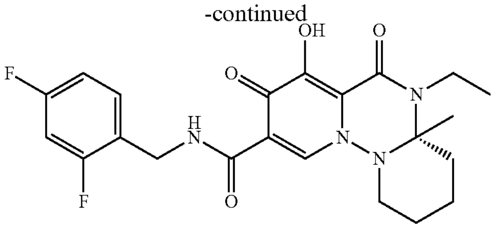
,
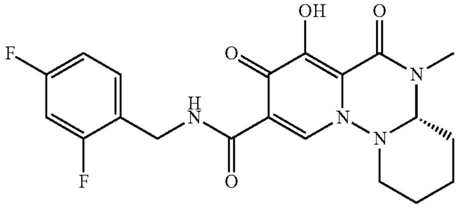
,
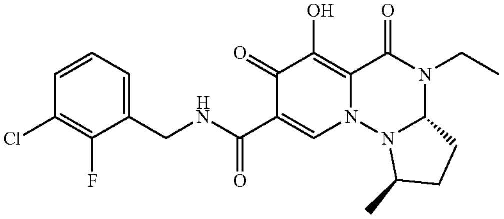
,
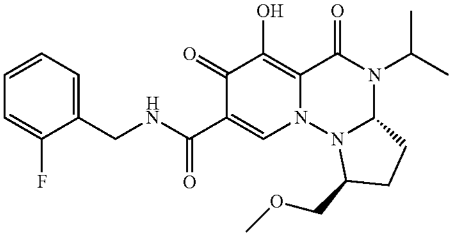
,
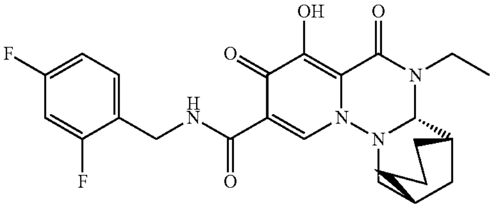
,
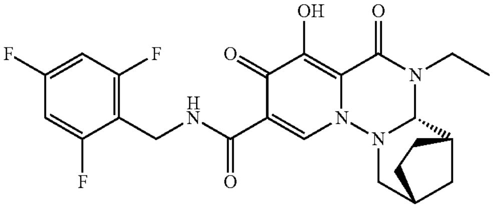
,
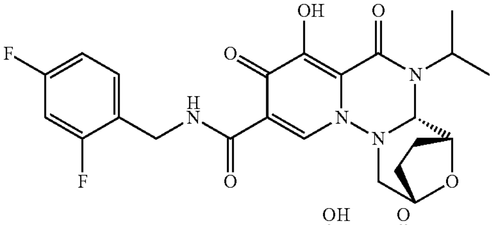
,
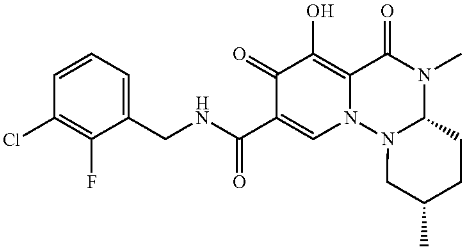
,
-continued
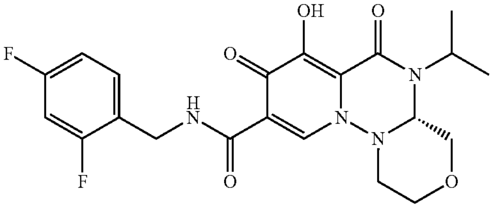
,
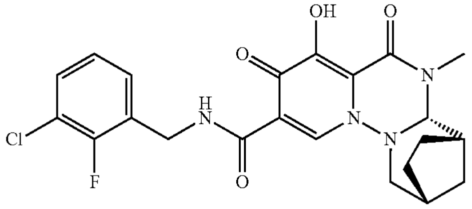
,
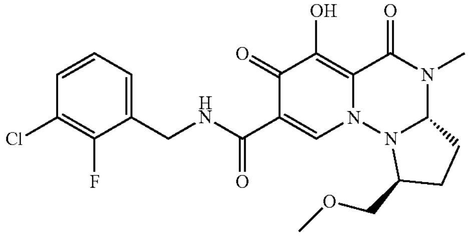
,
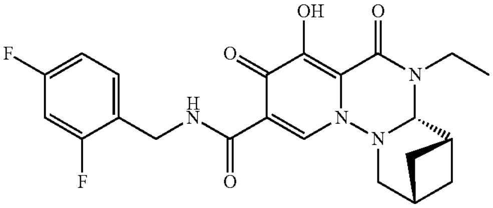
,
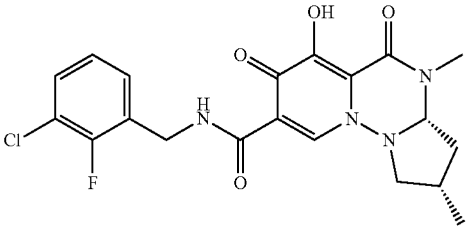
,
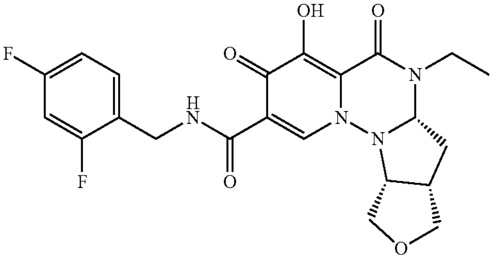
,
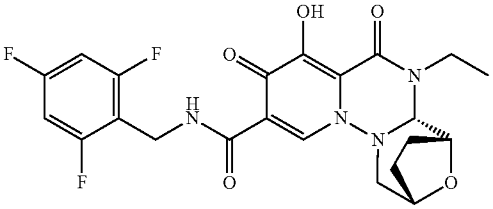
, -continued
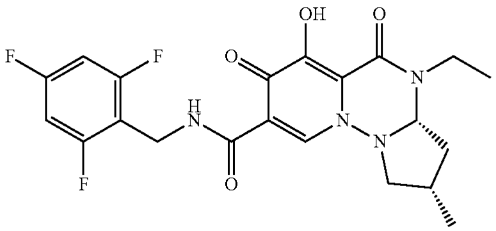,
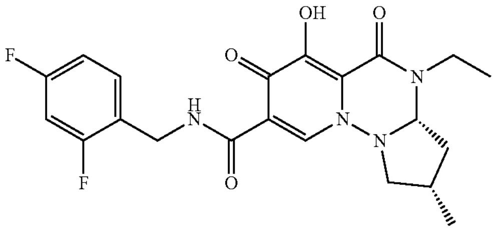,
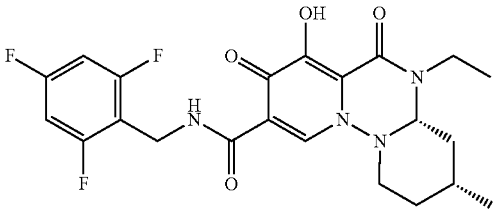,
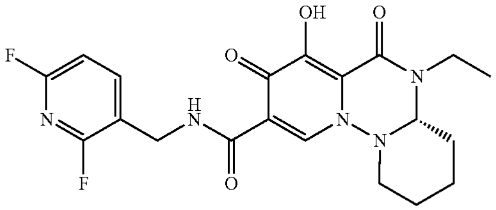,
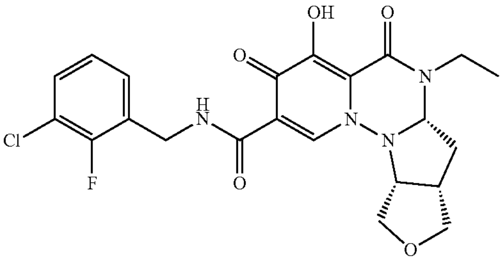,
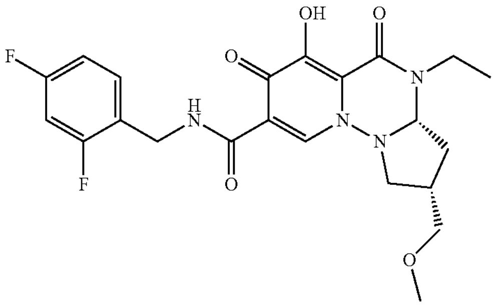,
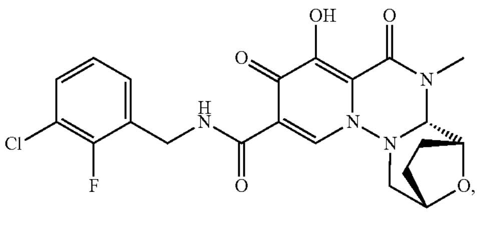,
-continued
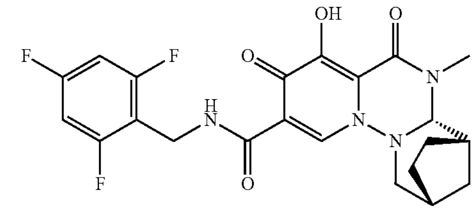,
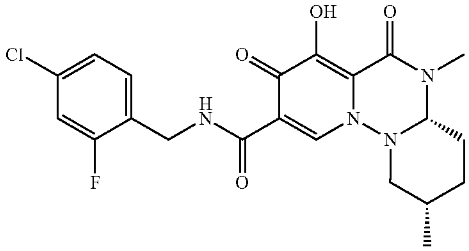,
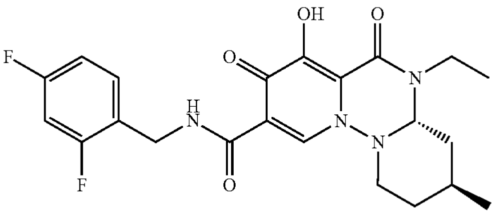,
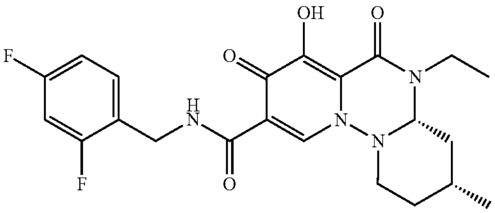,
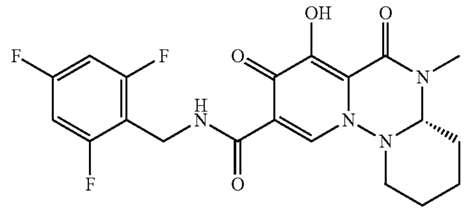,
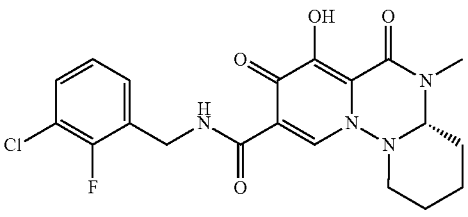,
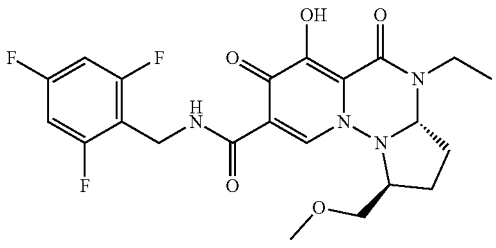, -continued
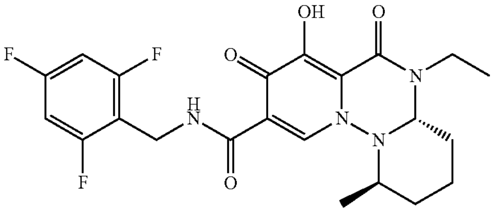,
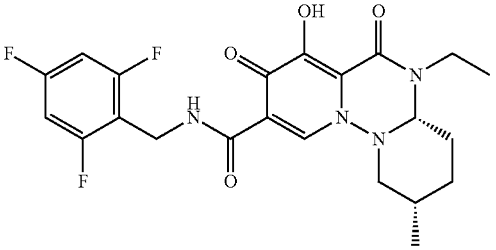,
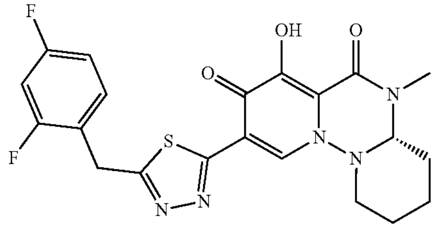,
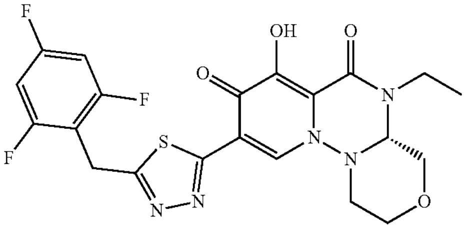,
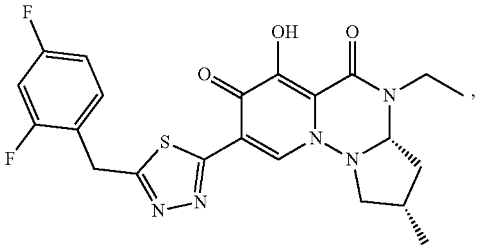,
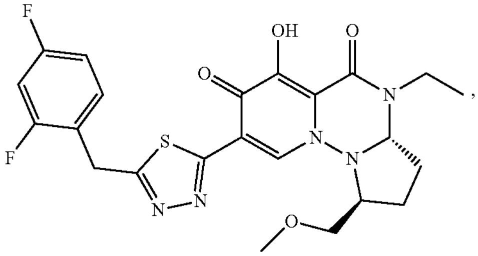,
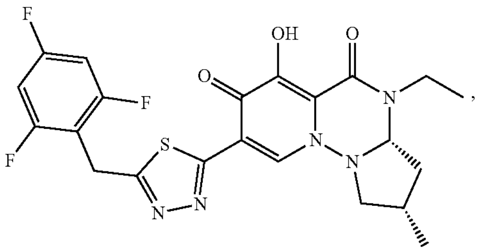,
-continued
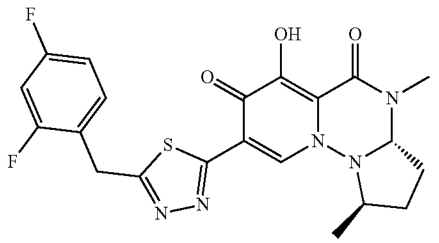,
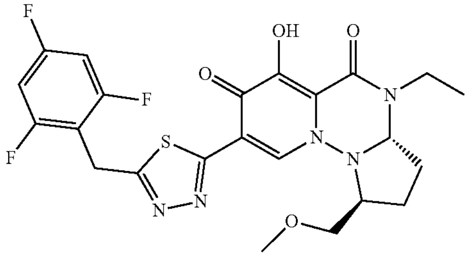,
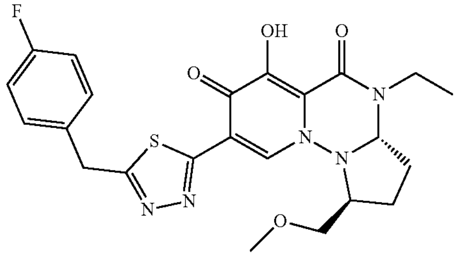,
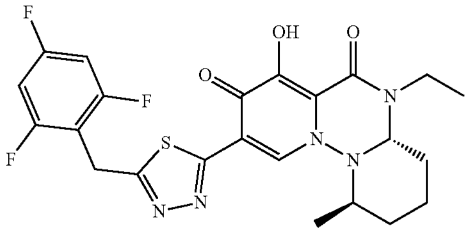,
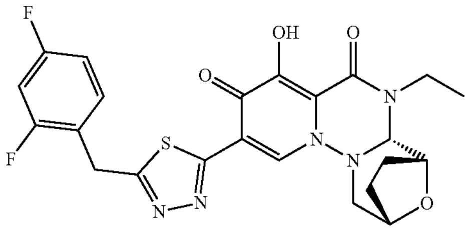,
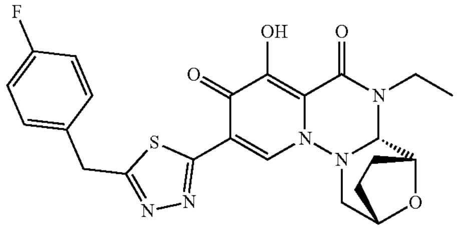,
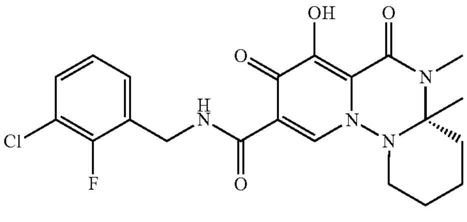, -continued
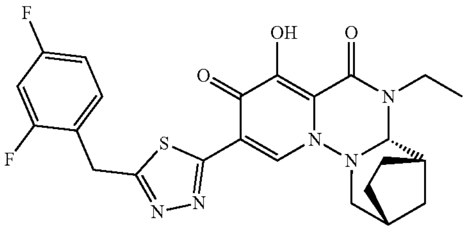
,
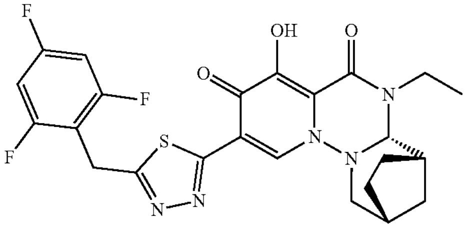
,
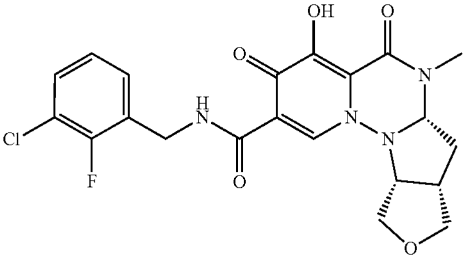
,
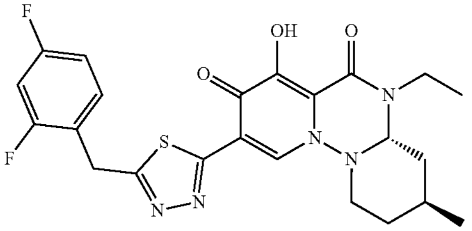
,
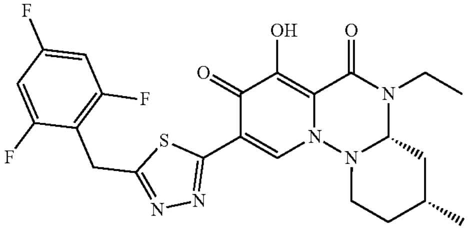
,
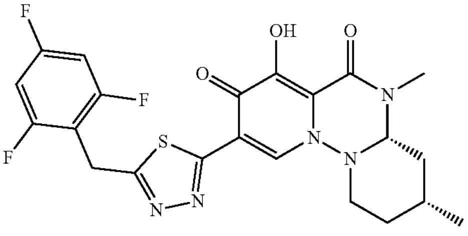
,
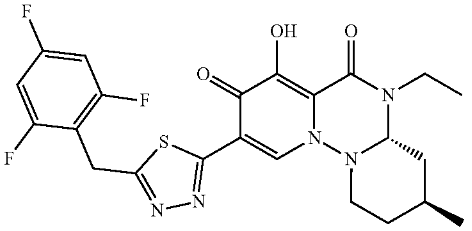
,
-continued
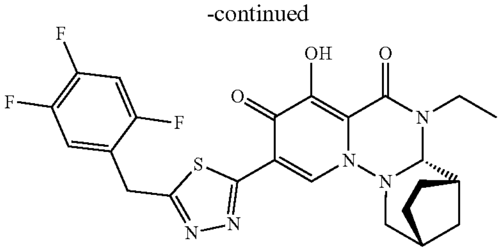
,
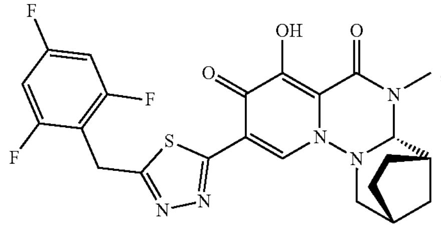
,
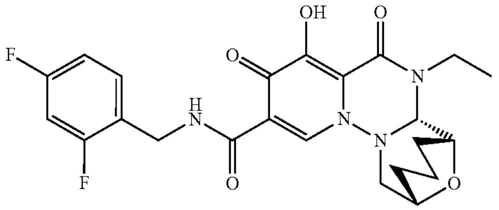
,
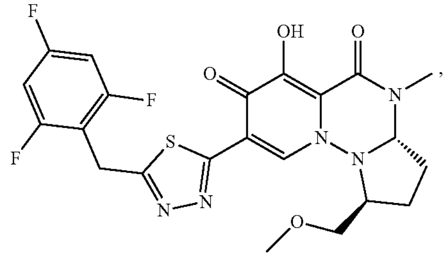
,
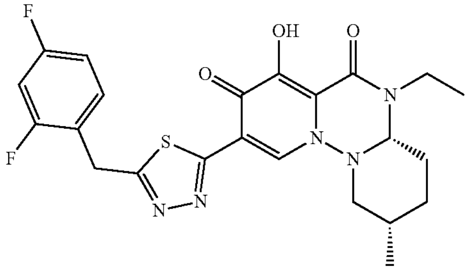
,
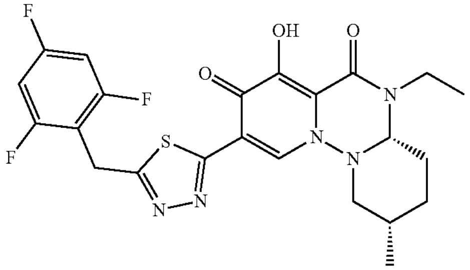
,
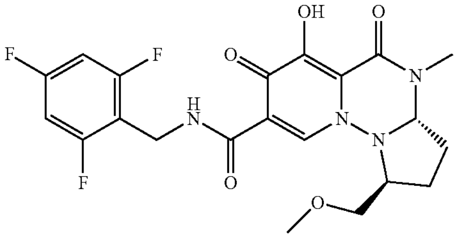
, and pharmaceutically acceptable salts thereof; and (B) at least one compound having anti-HIV activity, or a pharmaceutically acceptable salt thereof.

2. The pharmaceutical composition according to claim 1, wherein (B) is at least one selected from: compounds with a polymerase inhibitory activity; compounds with a ribonuclease H inhibitory activity; compounds with an HIV-1 integrase (IN)-lens epithelium-derived growth factor (LEDGF) complex allosteric inhibitory activity; compounds with a protease inhibitory activity; compounds with an adsorption and invasion inhibitory activity; compounds with a budding inhibitory activity; compounds with a maturation inhibitory activity; and compounds with a capsid inhibitory activity; and pharmaceutically acceptable salts thereof.

3. The pharmaceutical composition according to claim 2, wherein (B) is at least one selected from: AZT, 3TC, didanosine, zalcitabine, sanilvudine, abacavir, tenofovir, tenofovir disoproxil, tenofovir alafenamide, emtricitabine, nevirapine, efavirenz, capravirine, etravirine, delavirdine, rilpivirine, VM-1500A, VM-1500, doravirine, MK-8507, MK-8504, MK-8583, a following compound:

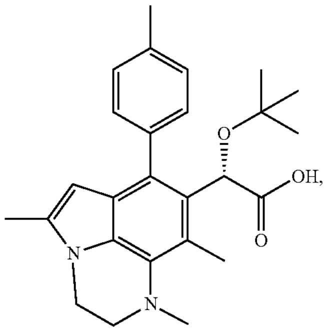

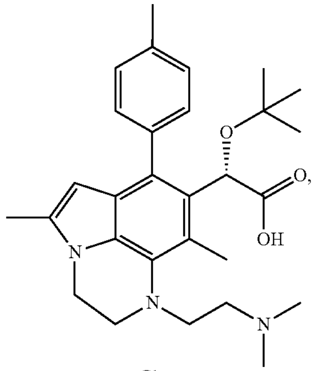

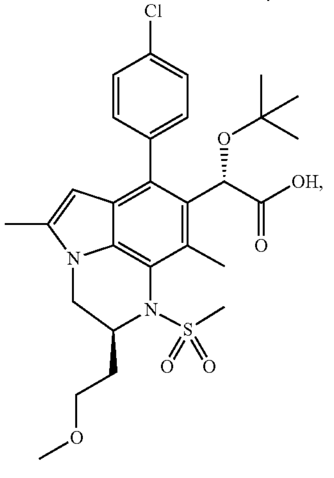

-continued

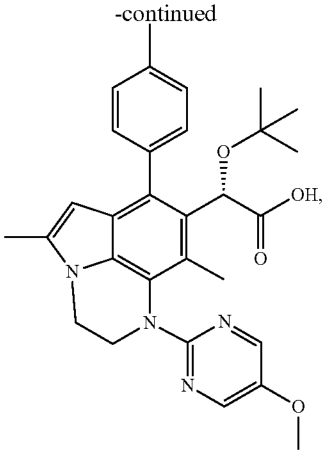

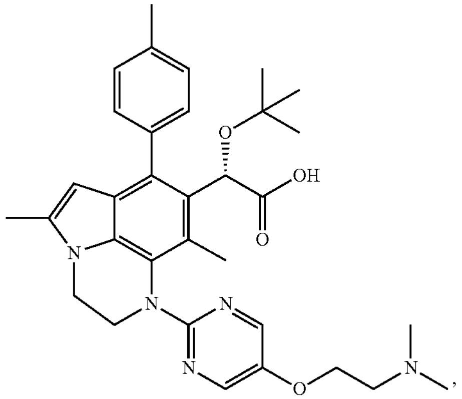

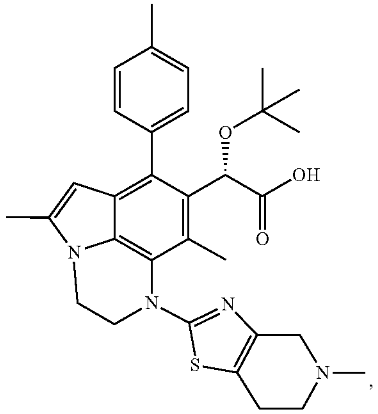

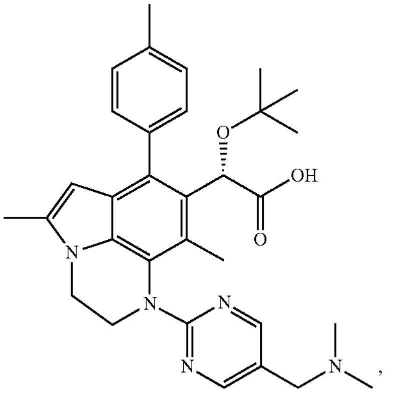

indinavir, ritonavir, saquinavir, nelfinavir, amprenavir, atazanavir, lopinavir, fosamprenavir, darunavir, maraviroc, enfuvirtide, ibalizumab, PRO-140, temsavir, fostemsavir tromethamine, combinectin, BDM-2, GSK-2838232, GSK-3640254, GS-6207, MK-8527 and MK-8558, and pharmaceutically acceptable salts thereof.
4. A kit comprising (A) a compound selected from the group of compounds:
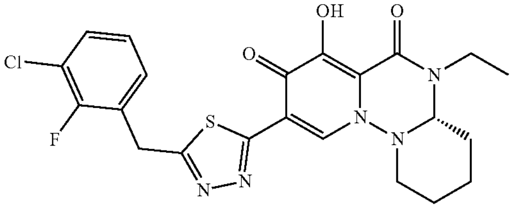
,
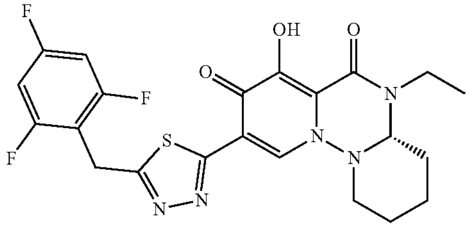
,
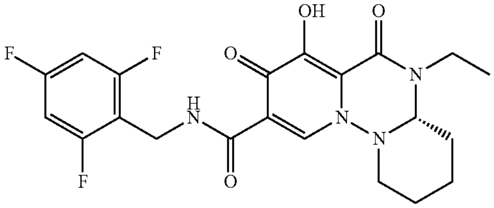
,
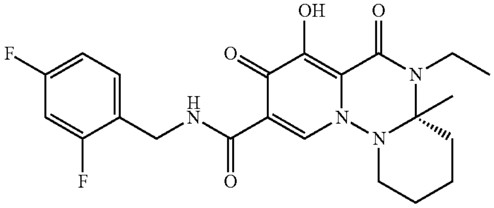
,
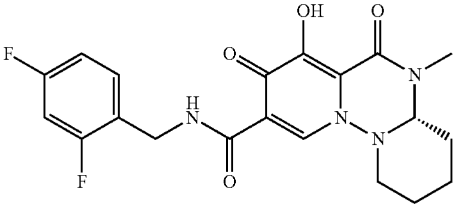
,
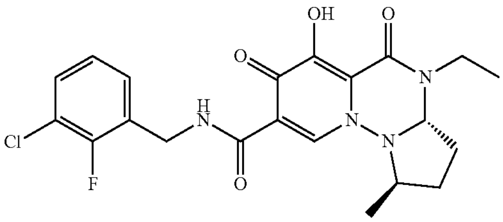
,
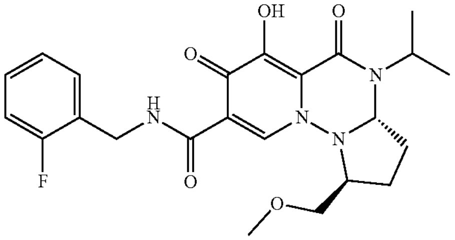
,
-continued
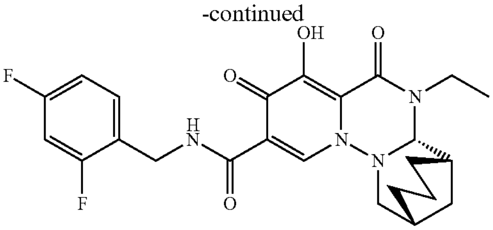
,
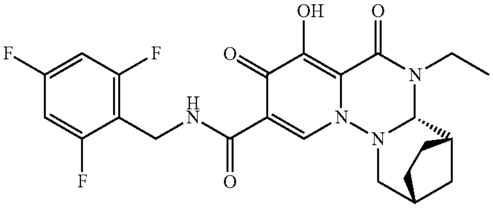
,
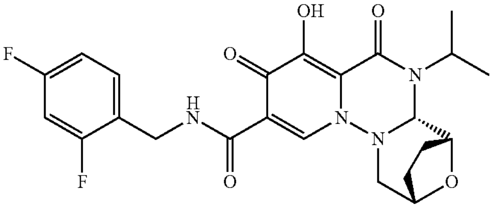
,
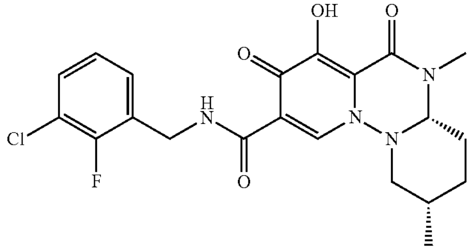
,
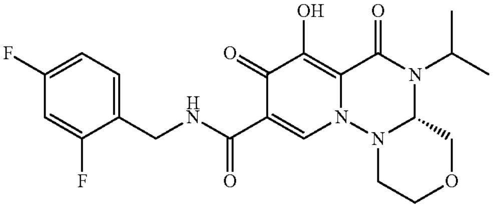
,
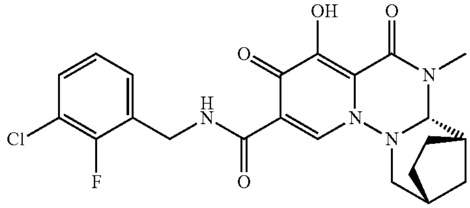
,
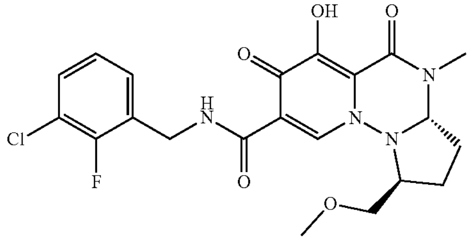
,
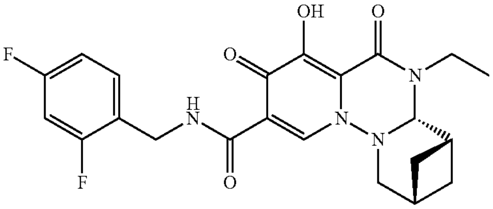
, -continued
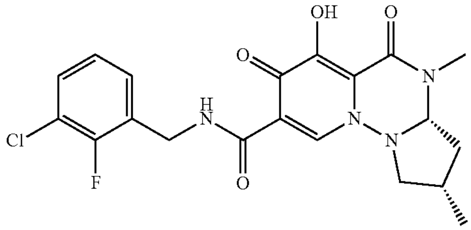,
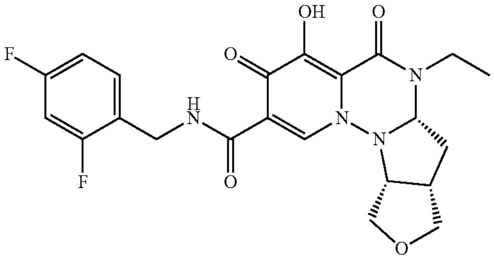,
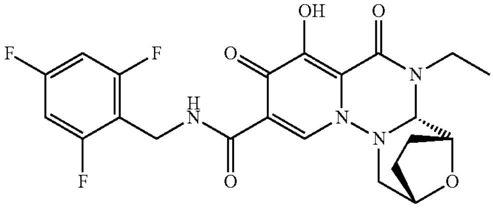,
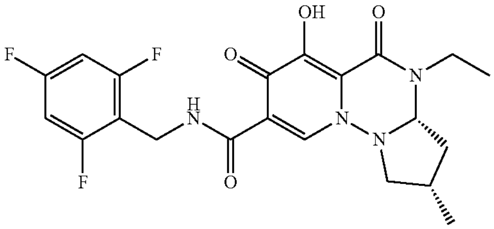,
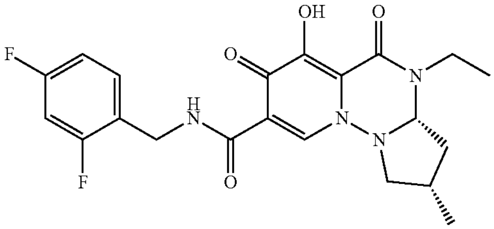,
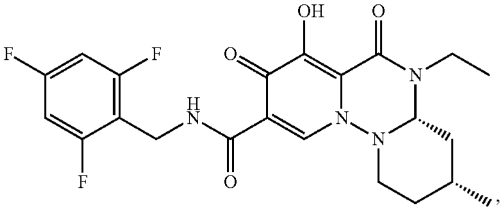,
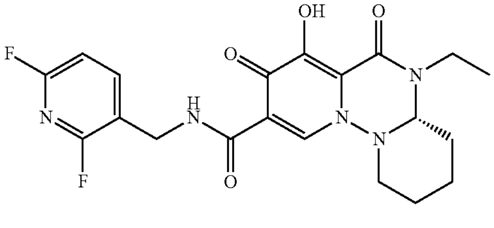,
-continued
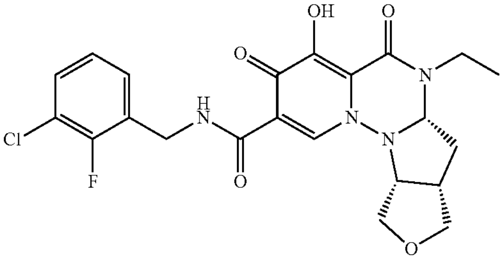,
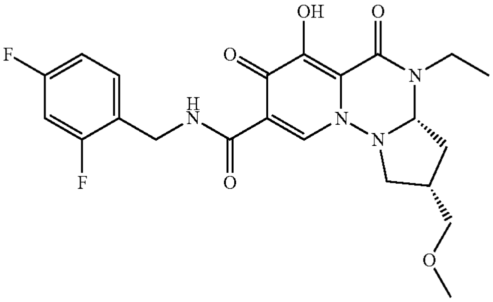,
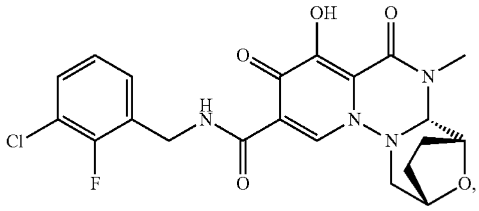,
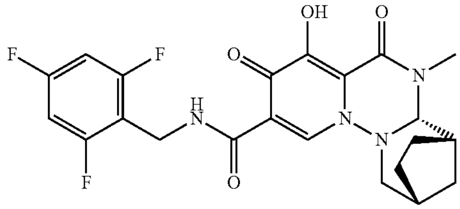,
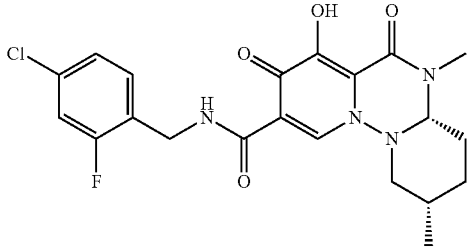,
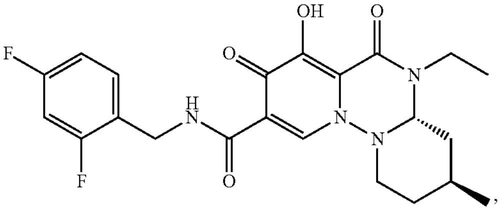,
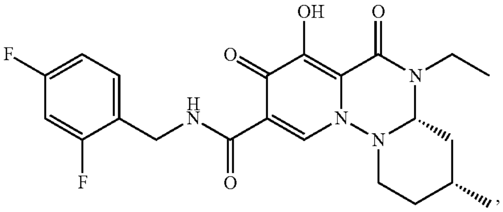, -continued
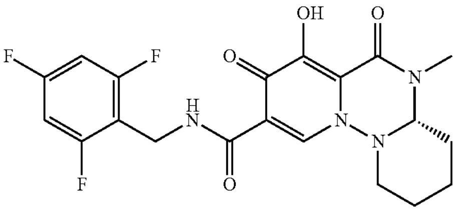
,
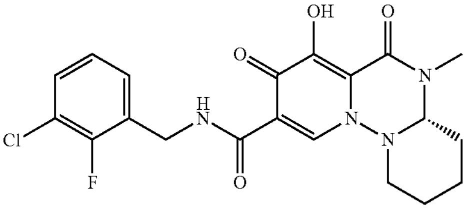
,
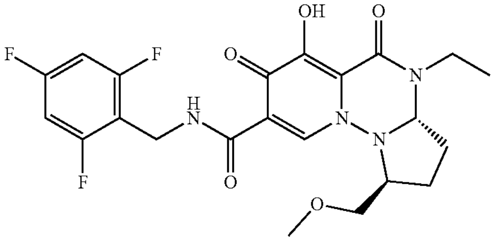
,
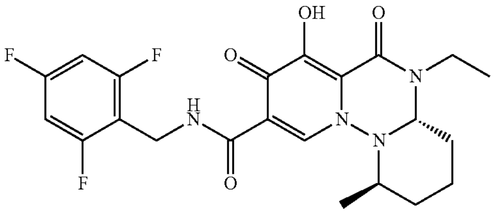
,
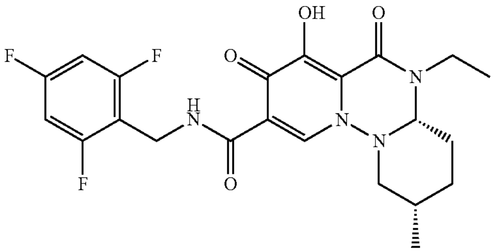
,
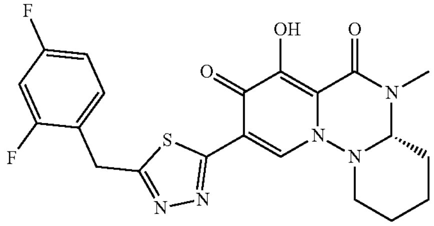
,
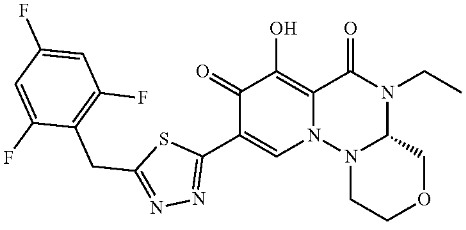
,
-continued
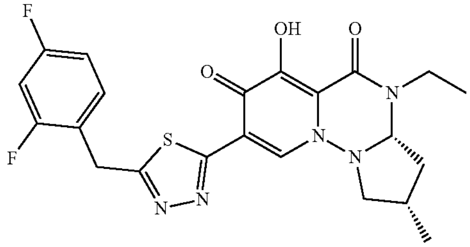
,
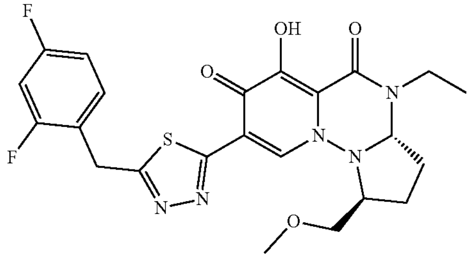
,
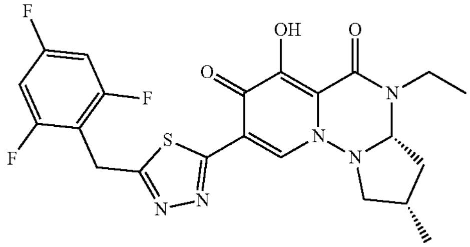
,
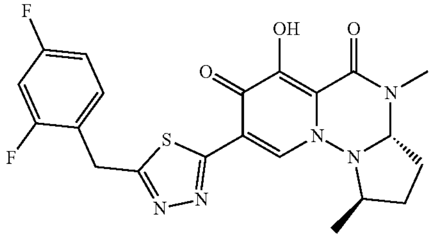
,
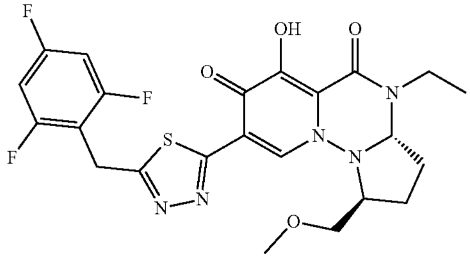
,
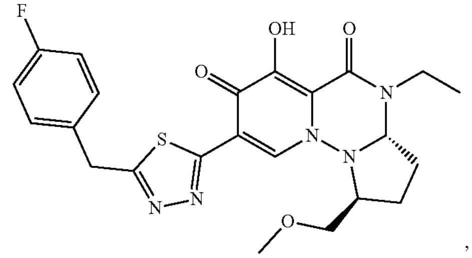
,
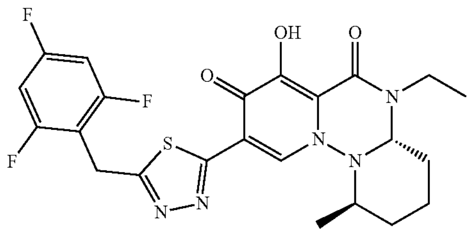
, -continued
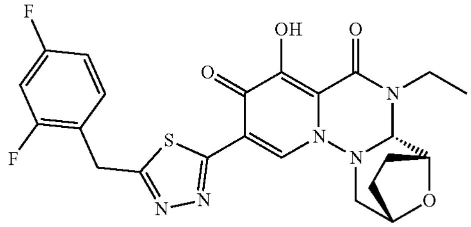
,
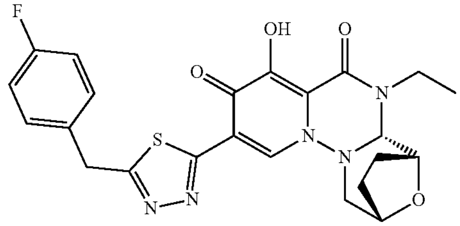
,
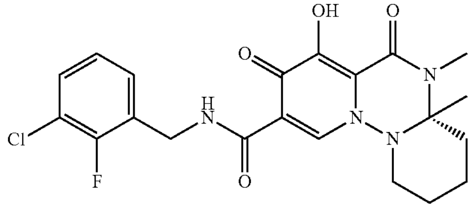
,
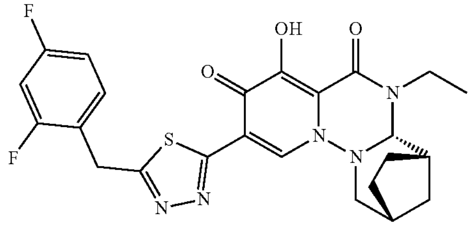
,
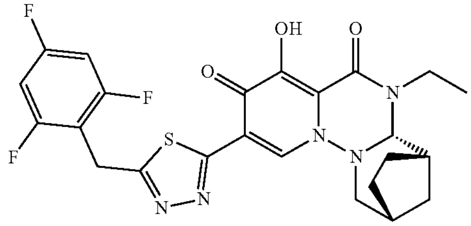
,
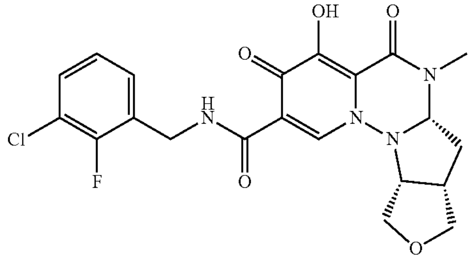
,
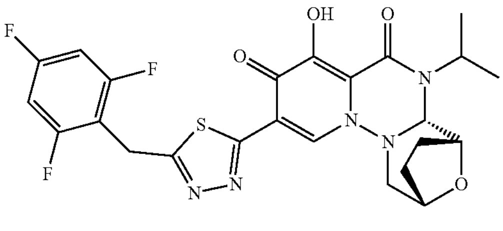
,
-continued
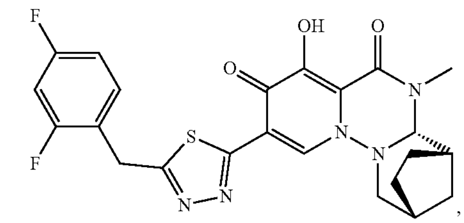
,
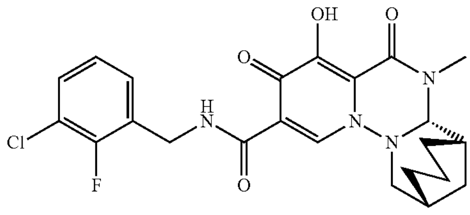
,
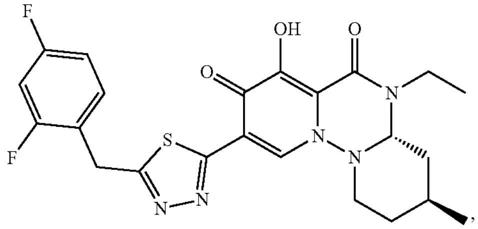
,
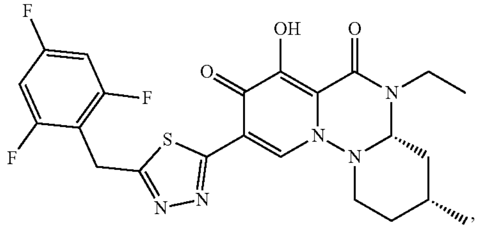
,
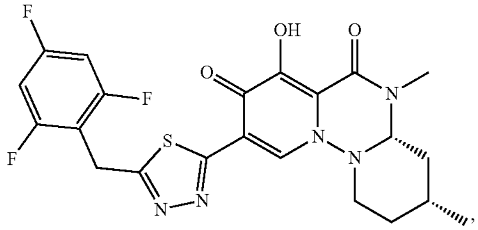
,
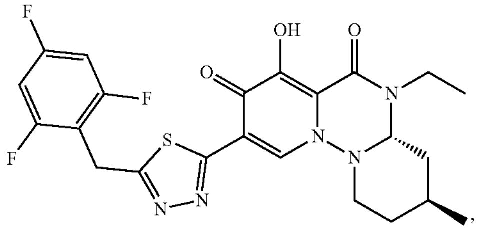
,
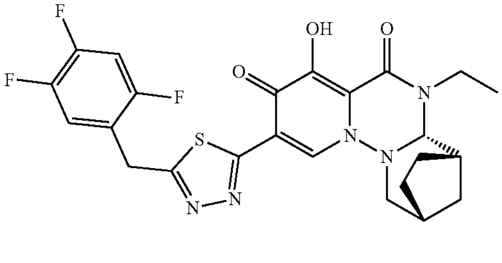
, -continued

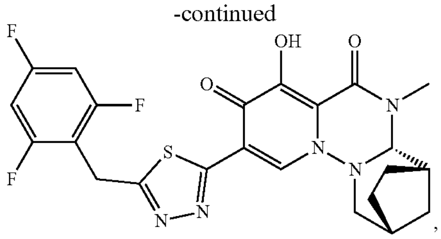
,
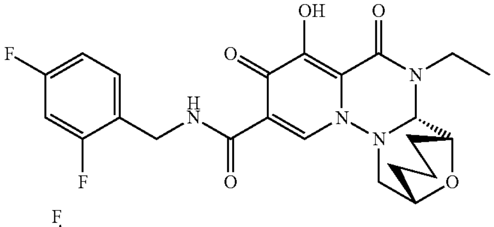
,
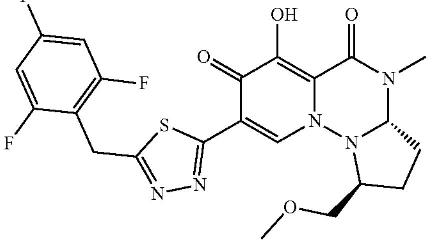
,
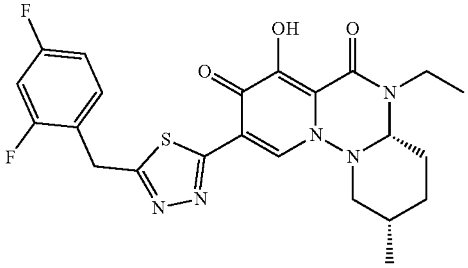
,
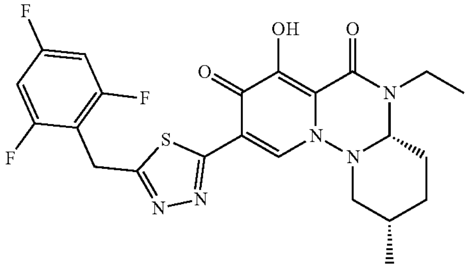
,
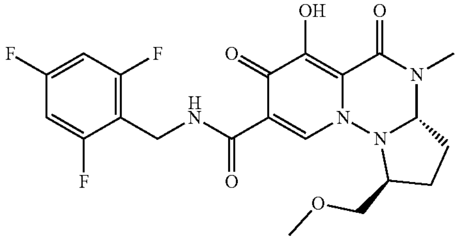
, and pharmaceutically acceptable salts thereof; and (B) at least one compound having anti-HIV activity, or a pharmaceutically acceptable salt thereof.

5. The kit according to claim 4, wherein (B) is at least one selected from: AZT, 3TC, didanosine, zalcitabine, sanilvudine, abacavir, tenofovir, tenofovir disoproxil, tenofovir alafenamide, emtricitabine, nevirapine, efavirenz, capravirine, etravirine, delavirdine, rilpivirine, VM-1500A, VM-1500, doravirine, MK-8507, MK-8504, MK-8583, a following compound:

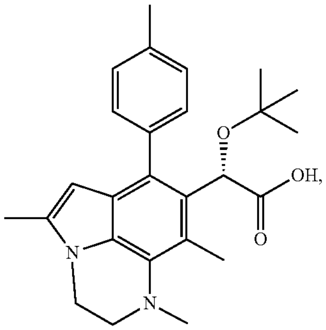

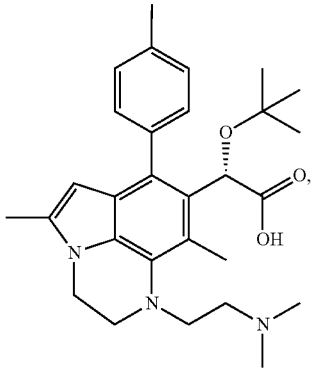

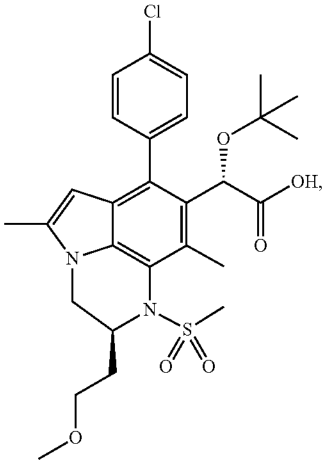

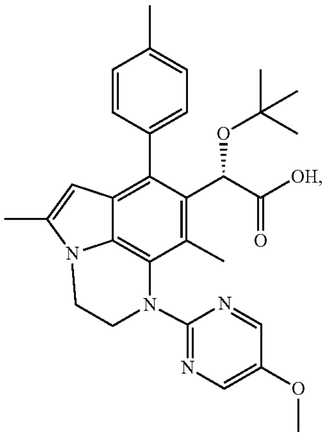

-continued

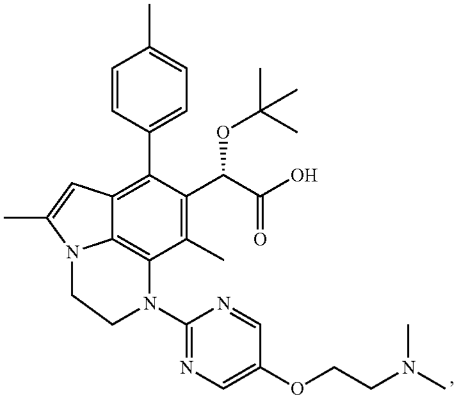
,

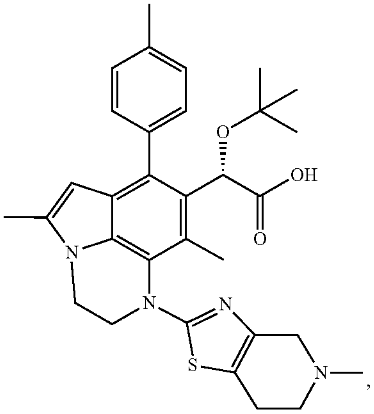
,

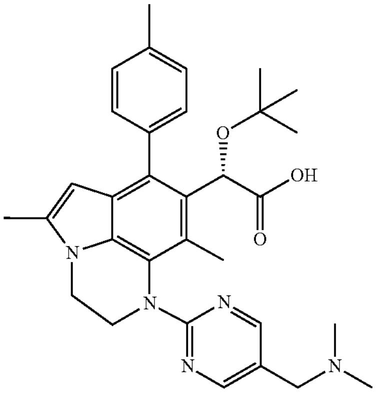
,

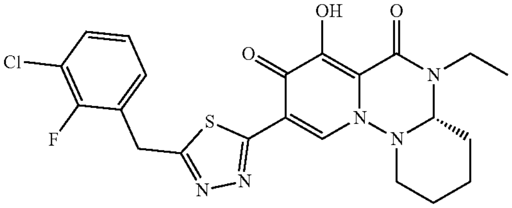
,

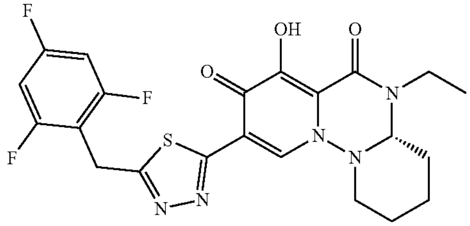
,

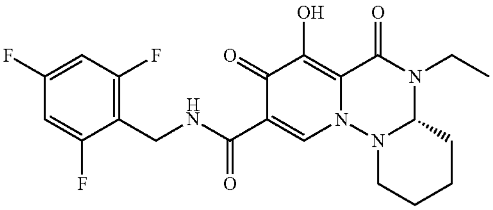
,

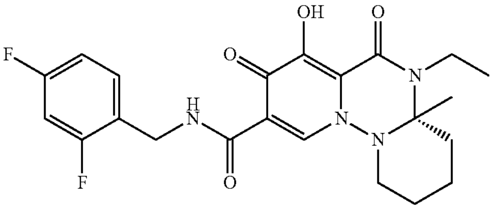
,

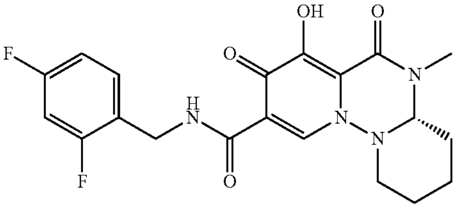
,

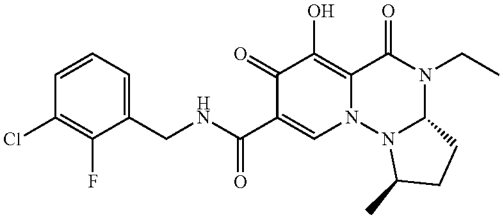
,

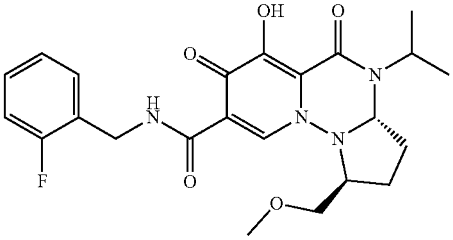
,

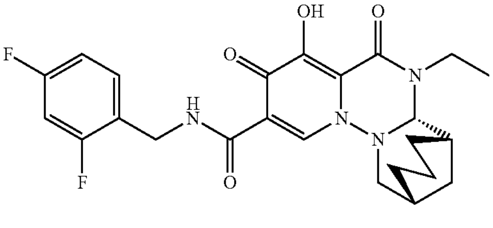
, indinavir, ritonavir, saquinavir, nelfinavir, amprenavir, atazanavir, lopinavir, fosamprenavir, darunavir, maraviroc, enfuvirtide, ibalizumab, PRO-140, temsavir, fostemsavir tromethamine, combinectin, BDM-2, GSK-2838232, GSK-3640254, GS-6207, MK-8527 and MK-8558, and pharmaceutically acceptable salts thereof.

6. The kit according to claim 5, wherein (A) and (B) are separate formulations.

7. A method for preventing symptoms, diseases, or symptoms and diseases induced by HIV infection comprising administering to a patient in need thereof (A) a compound selected from the group of compounds:

-continued
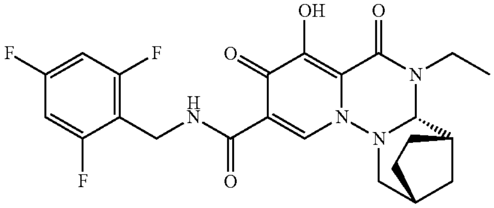
,
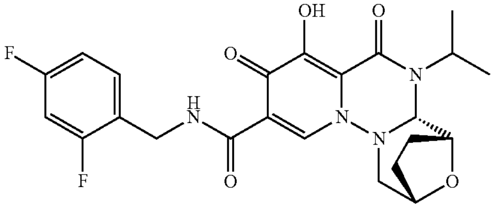
,
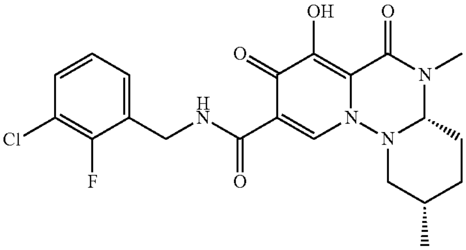
,
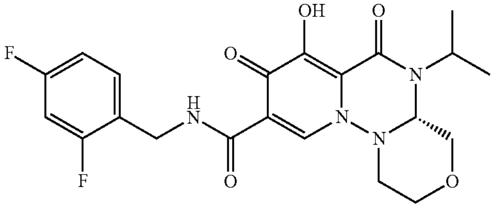
,
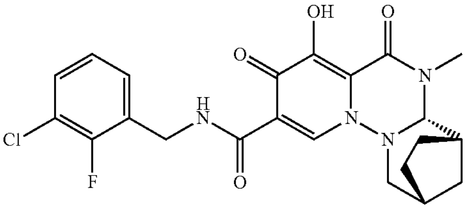
,
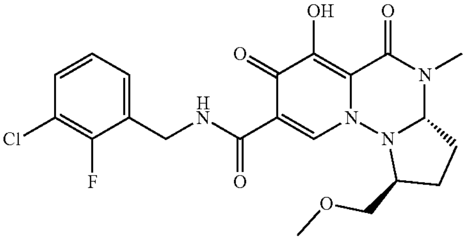
,
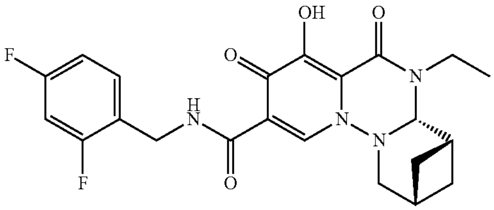
,
-continued
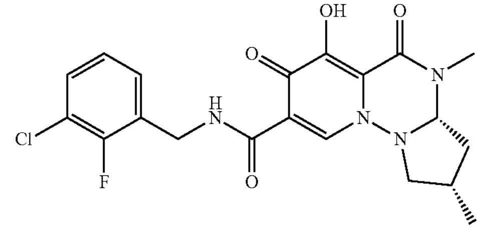
,
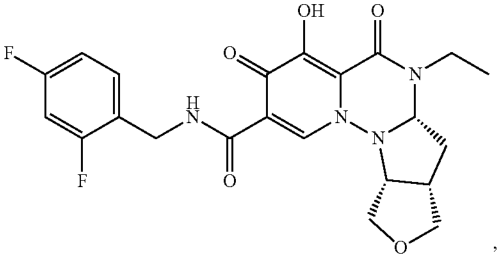
,
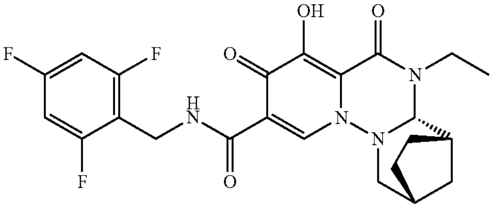
,
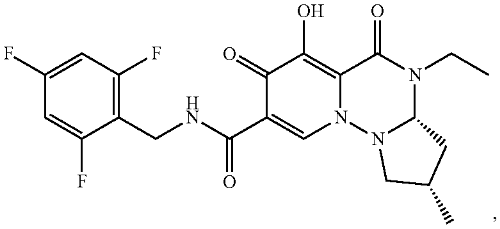
,
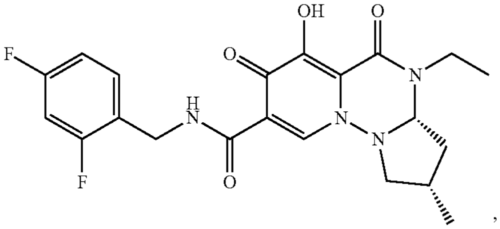
,
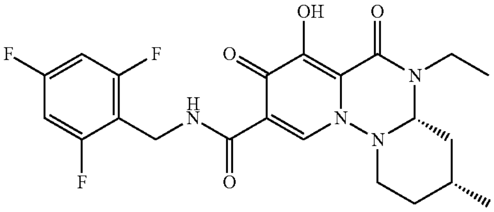
,
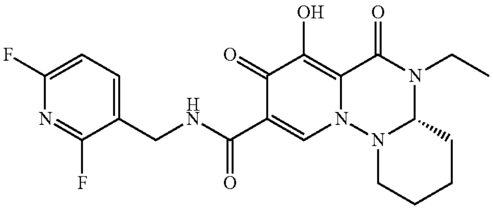
, -continued
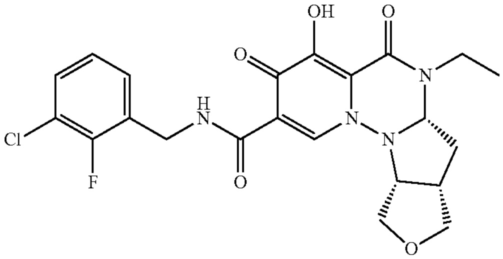
,
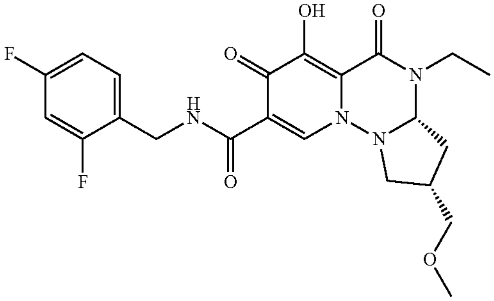
,
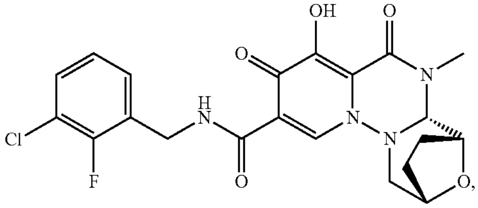
,
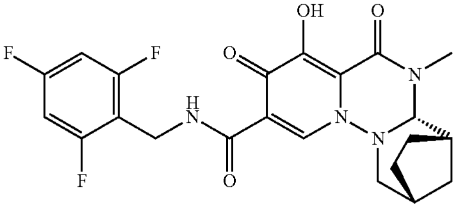
,
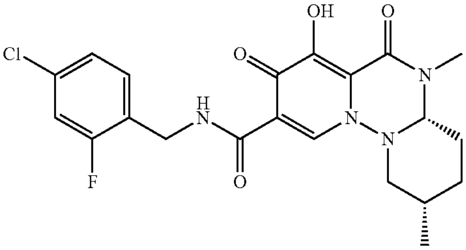
,
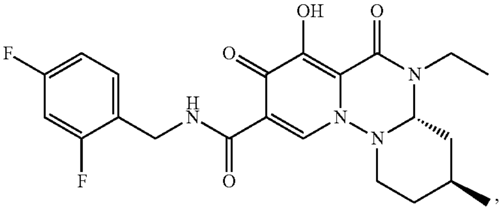
,
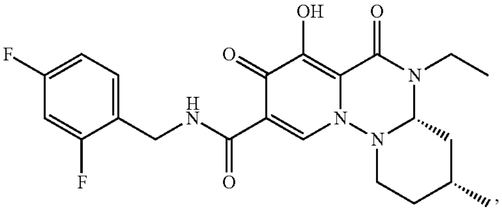
,
-continued
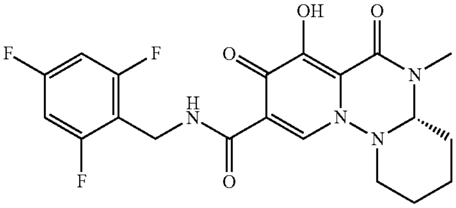
,
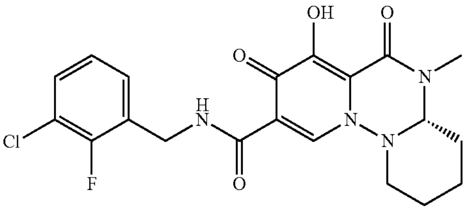
,
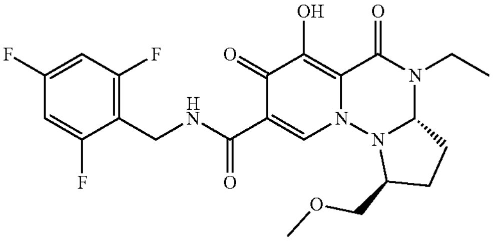
,
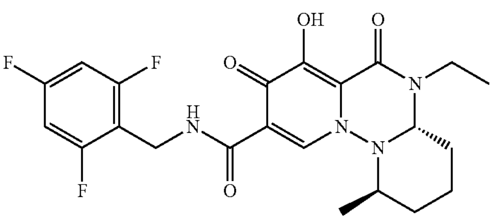
,
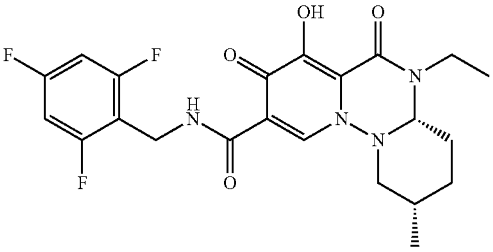
,
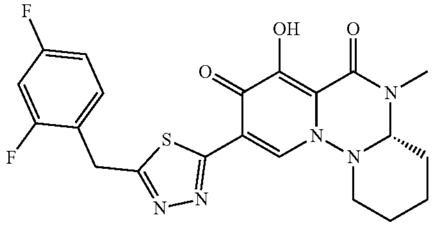
,
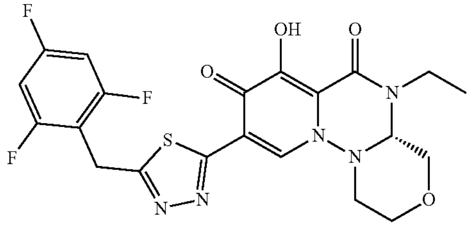
, -continued
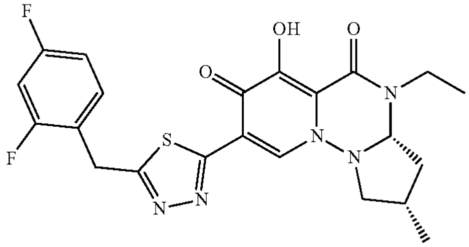
,
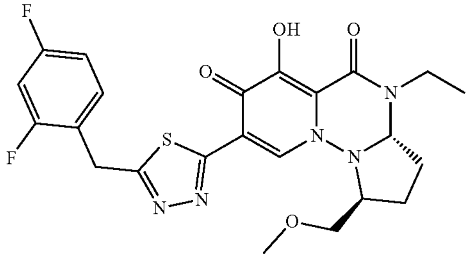
,
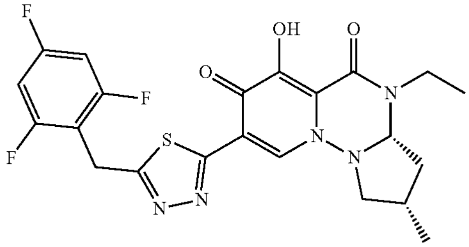
,
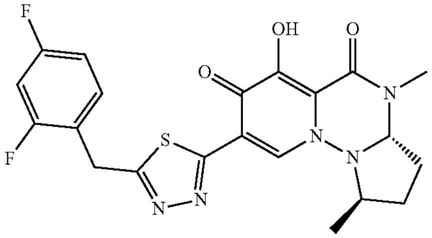
,
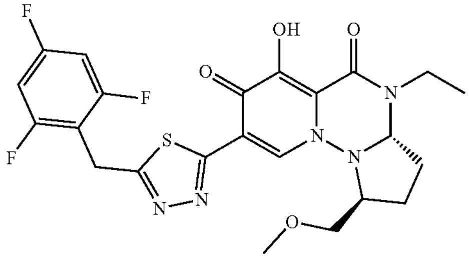
,
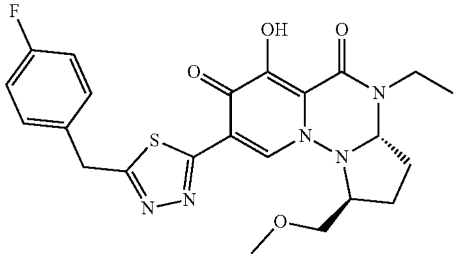
,
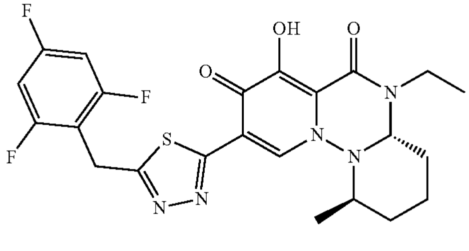
,
-continued
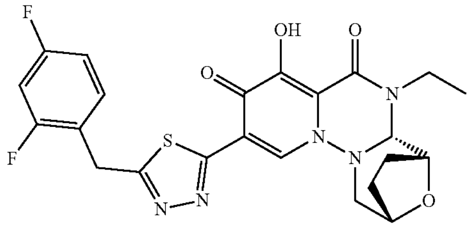
,
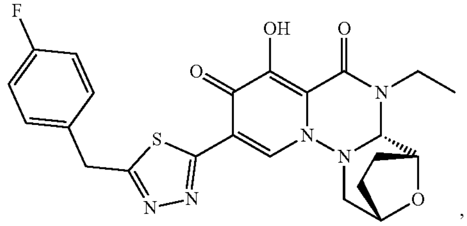
,
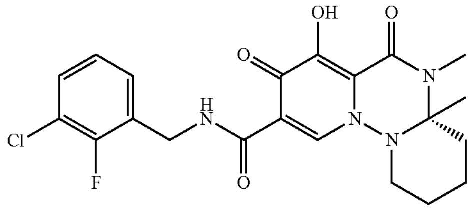
,
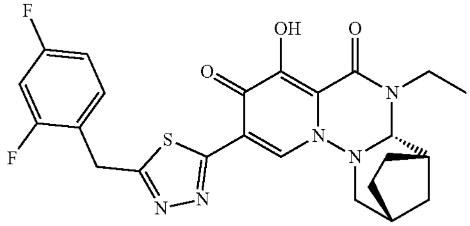
,
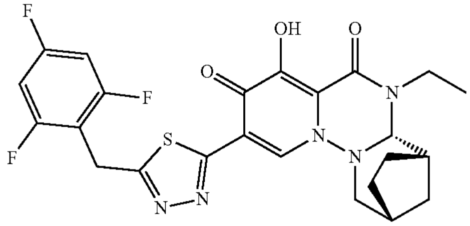
,
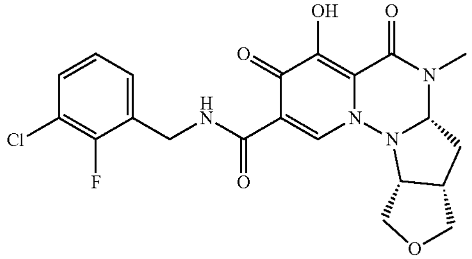
,
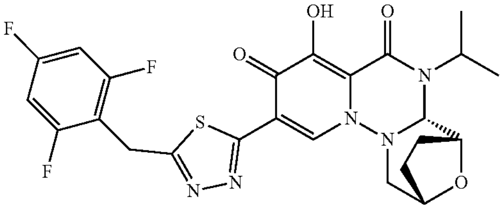
, -continued

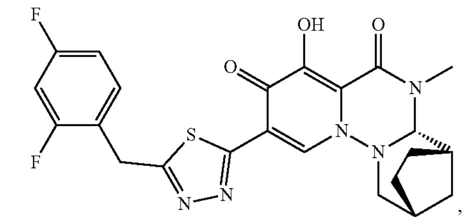

,

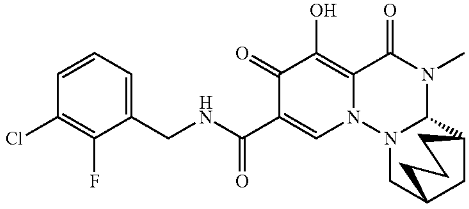

,

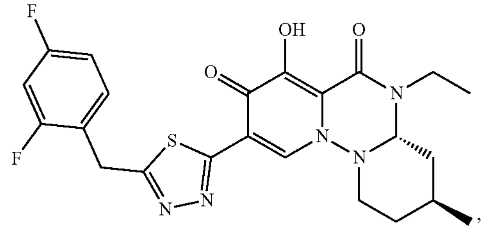

,

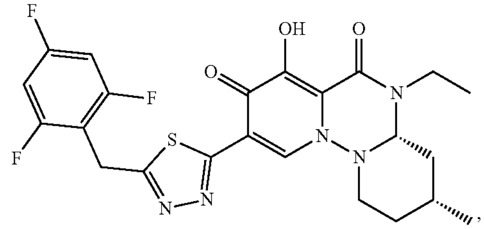

,

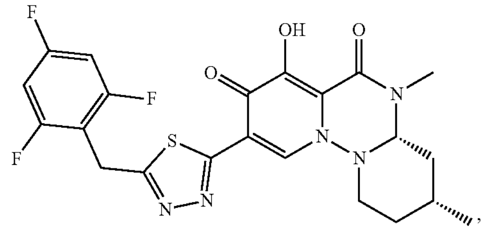

,

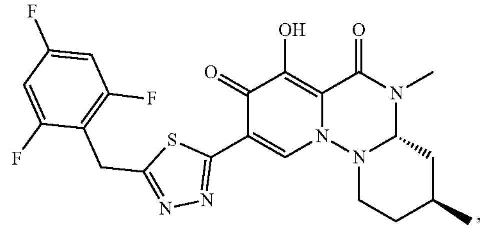

,

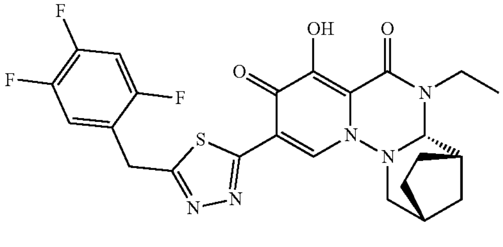

,

-continued

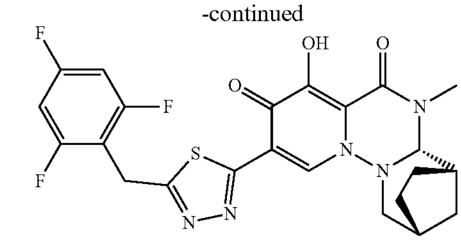

,

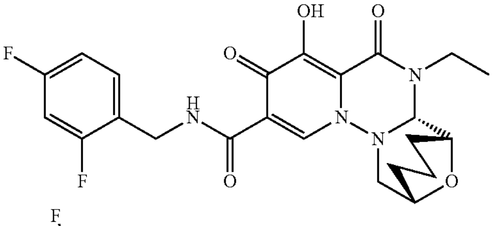

,

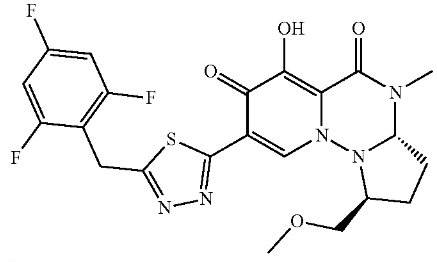

,

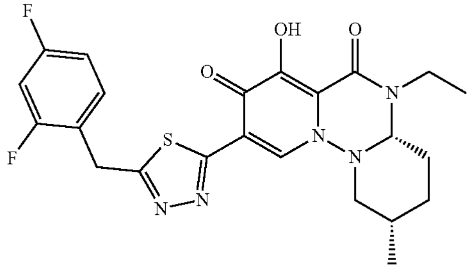

,

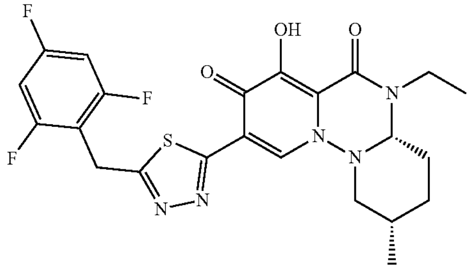

,

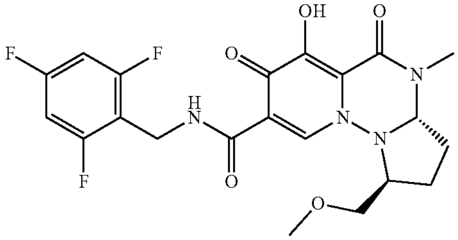

, and pharmaceutically acceptable salts thereof; and (B) at least one compound having anti-HIV activity, or a pharmaceutically acceptable salt thereof.

8. The method of claim 7, wherein (B) is at least one selected from: AZT, 3TC, didanosine, zalcitabine, sanilvudine, abacavir, tenofovir, tenofovir disoproxil, tenofovir alafenamide, emtricitabine, nevirapine, efavirenz, capravirine, etravirine, delavirdine, rilpivirine, VM-1500A, VM-1500, doravirine, MK-8507, MK-8504, MK-8583, a following compound:

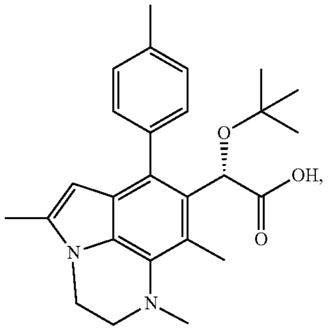

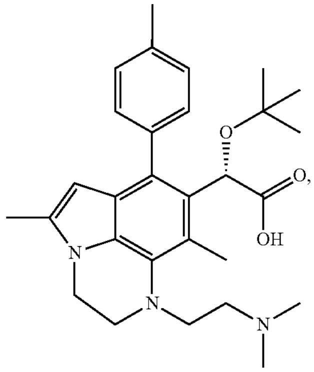

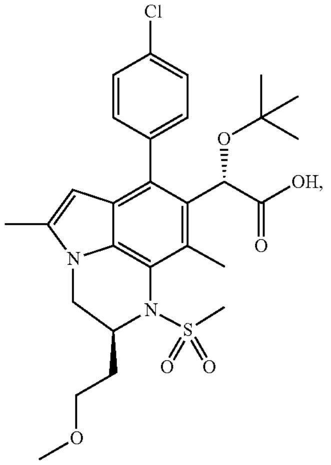

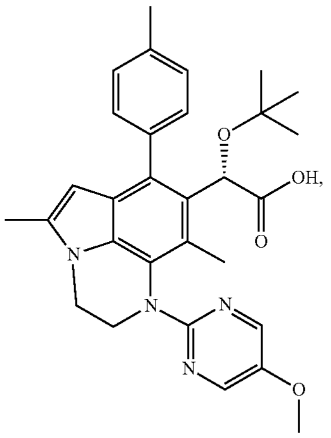

-continued

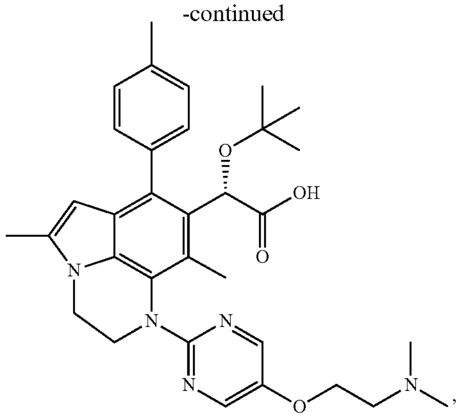

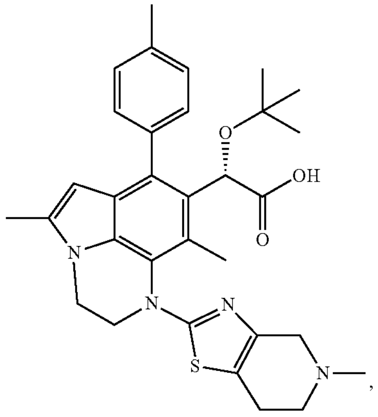

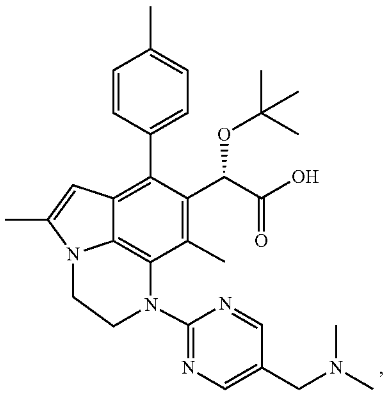

indinavir, ritonavir, saquinavir, nelfinavir, amprenavir, atazanavir, lopinavir, fosamprenavir, darunavir, maraviroc, enfuvirtide, ibalizumab, PRO-140, temsavir, fostemsavir tromethamine, combinectin, BDM-2, GSK-2838232, GSK-3640254, GS-6207, MK-8527 and MK-8558, and pharmaceutically acceptable salts thereof.

9. The method according to claim 8, wherein (A) and (B) are separate formulations.

10. A method of treating symptoms, diseases, or symptoms and diseases induced by HIV infection comprising administering to a patient in need thereof (A) a compound selected from the group of compounds:

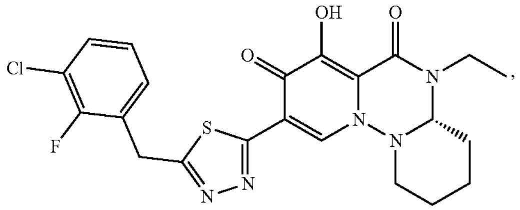
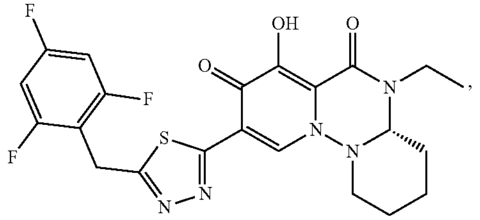
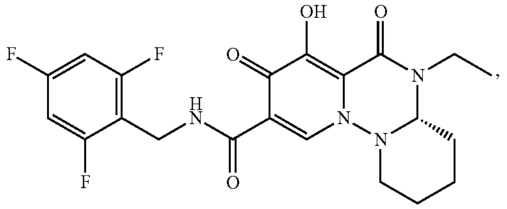
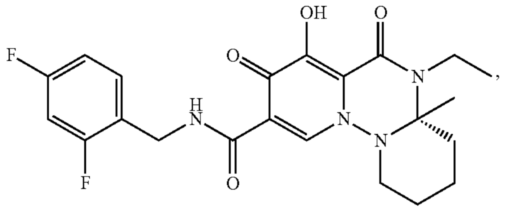
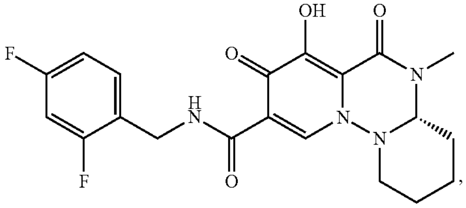
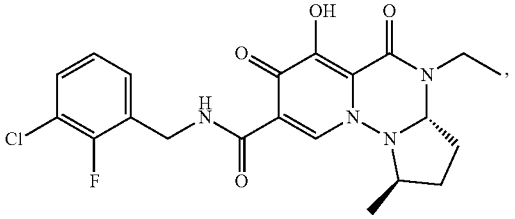
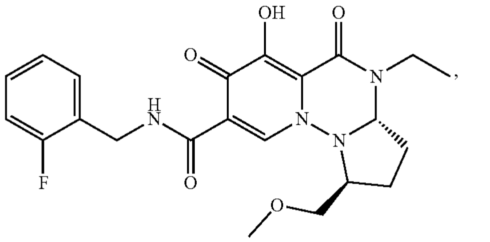
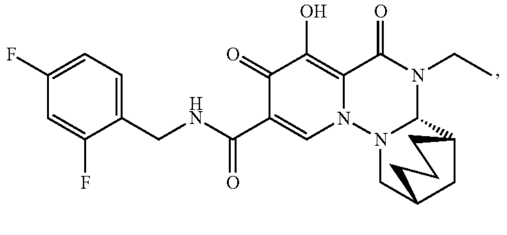
-continued
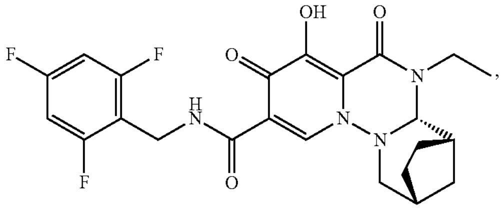
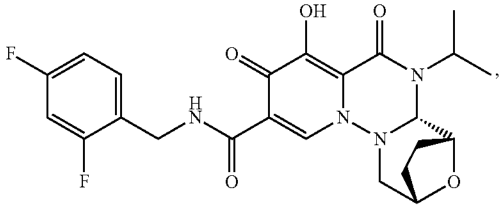
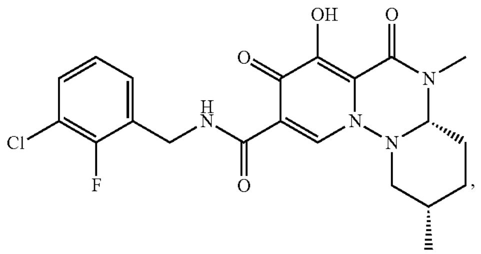
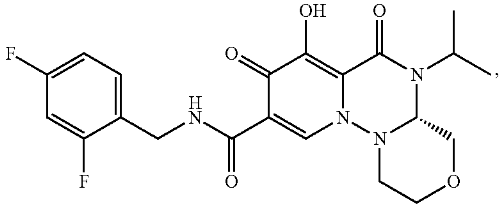
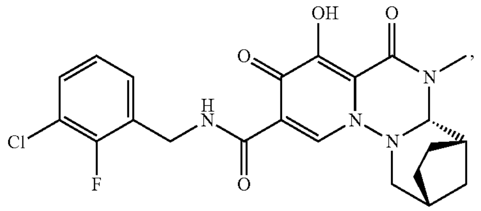
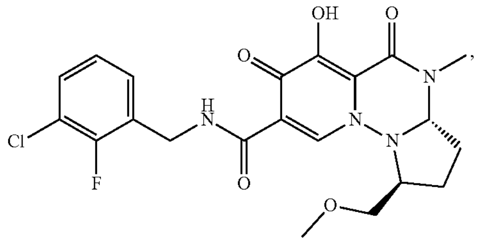
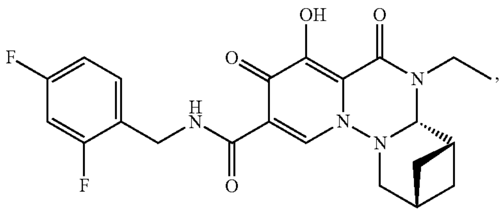

-continued
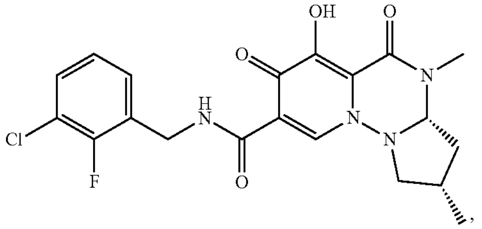
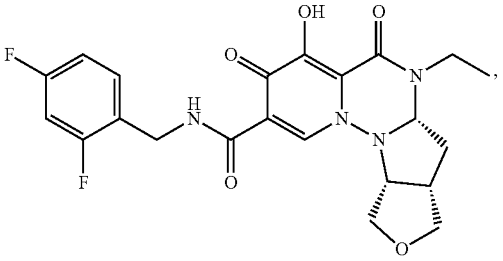
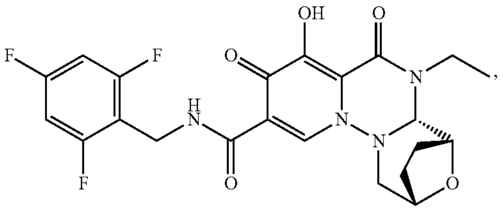
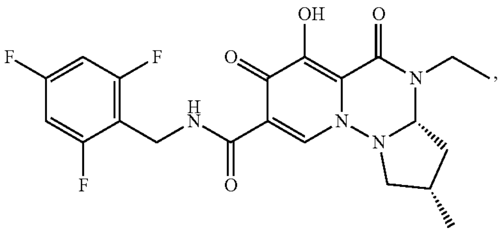
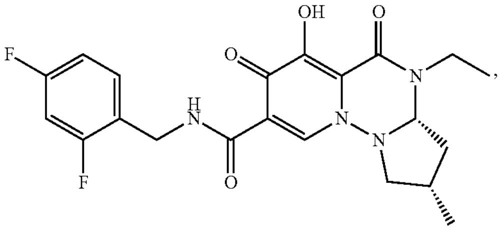
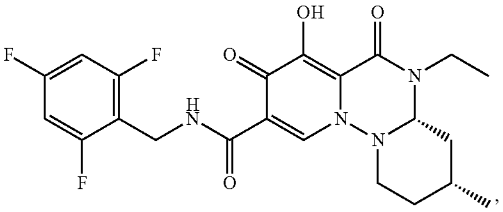
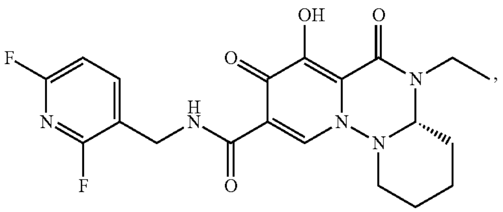
-continued
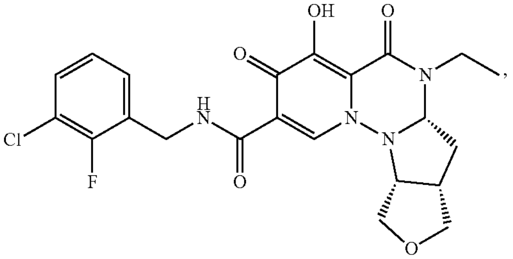
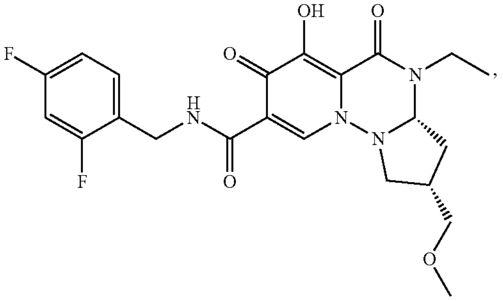
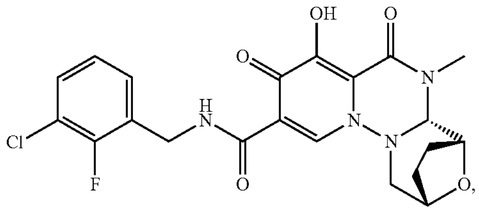
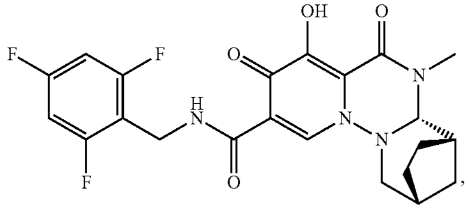
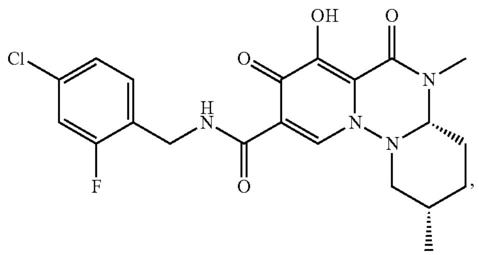
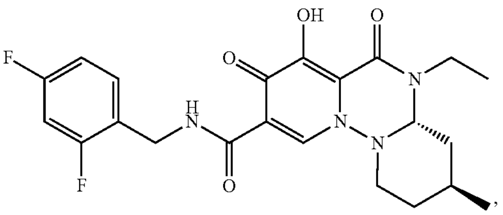
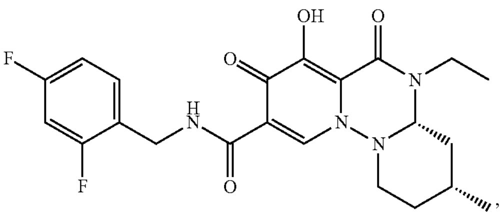

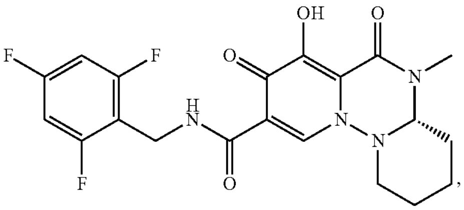
,
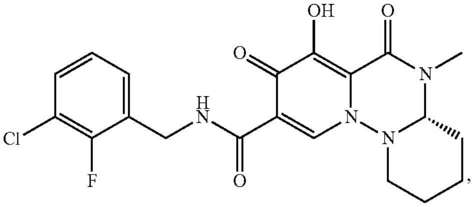
,
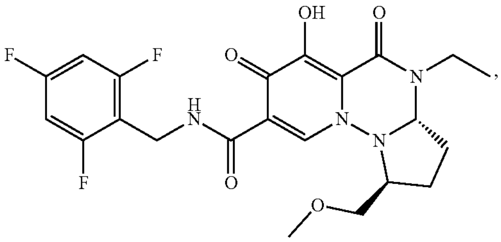
,
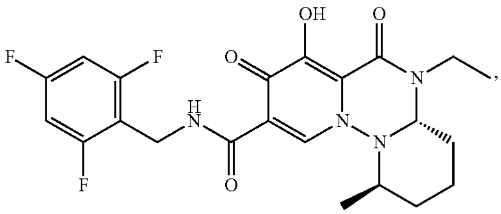
,
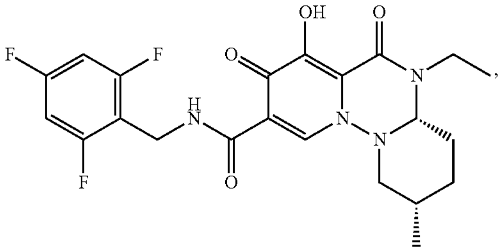
,
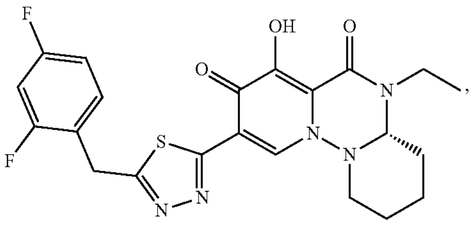
,
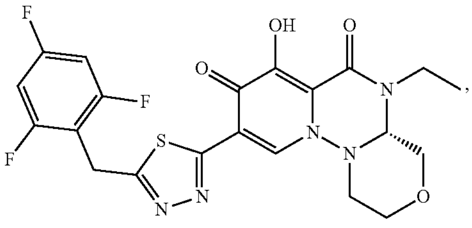
,
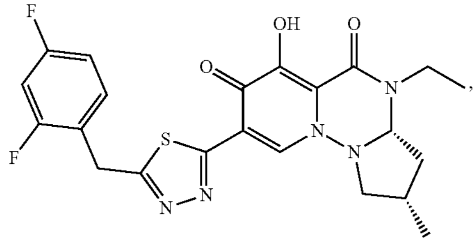
,
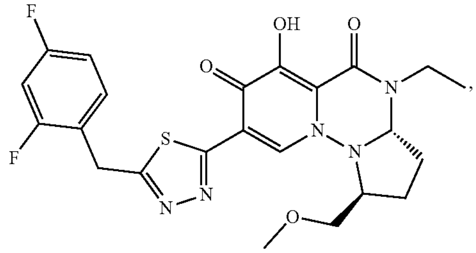
,
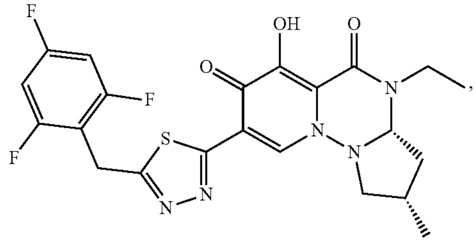
,
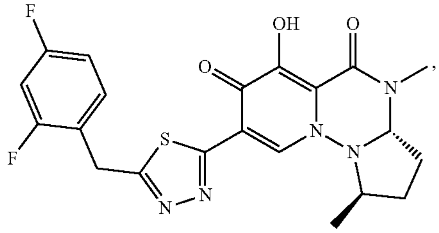
,
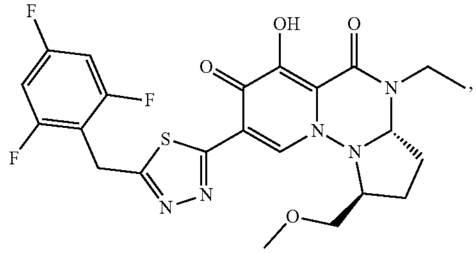
,
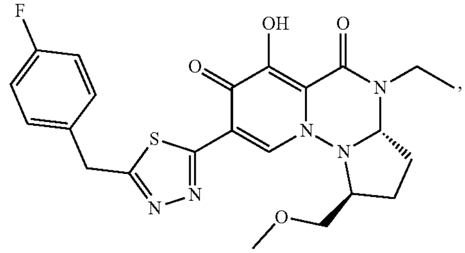
,
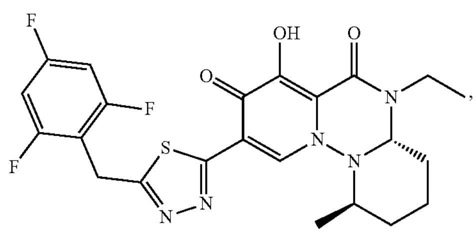
,

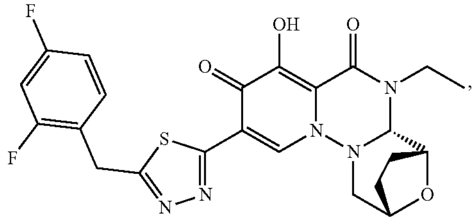
,
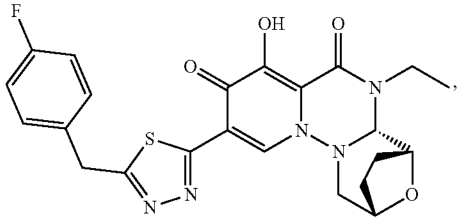
,
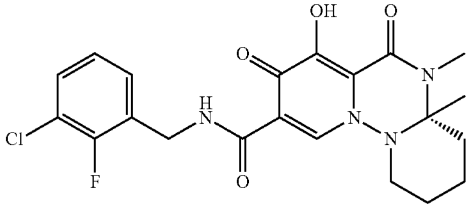
,
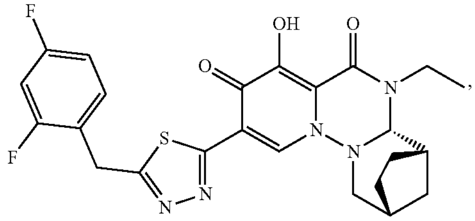
,
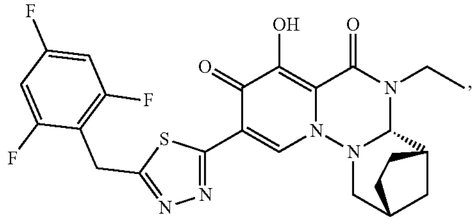
,
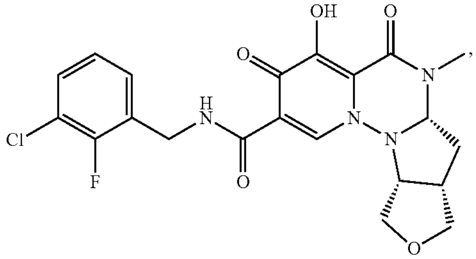
,
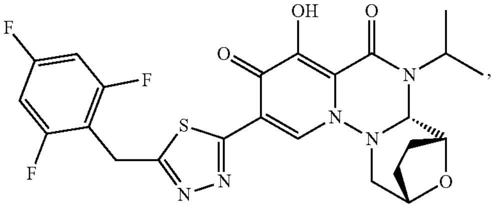
,
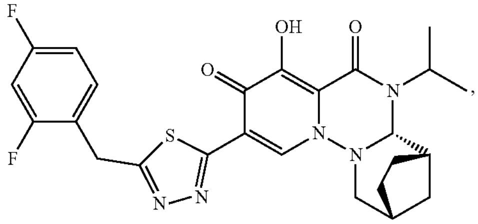
,
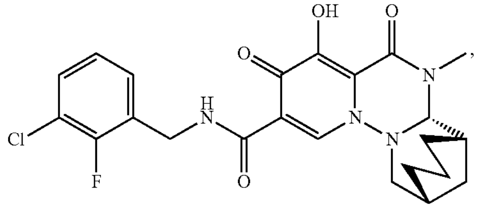
,
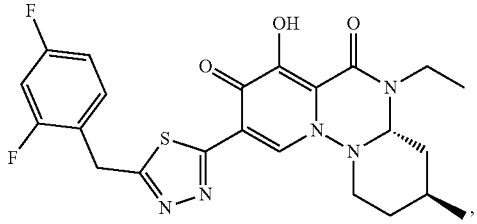
,
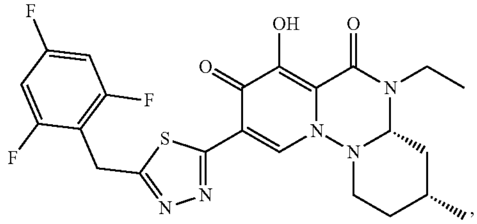
,
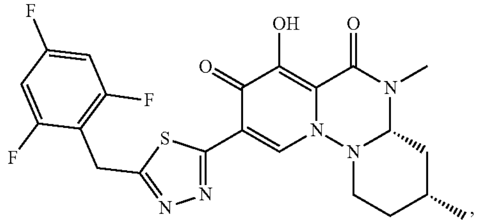
,
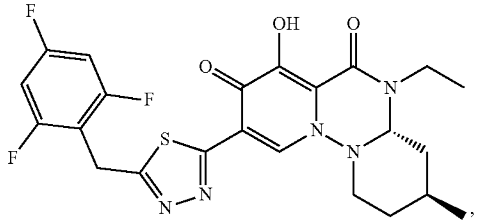
,
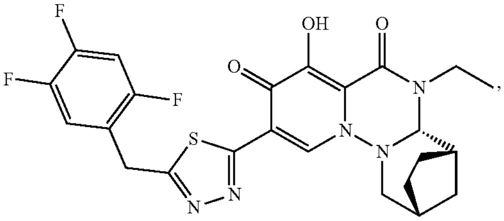
, -continued

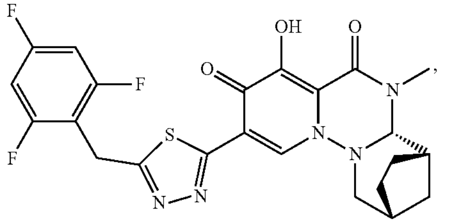

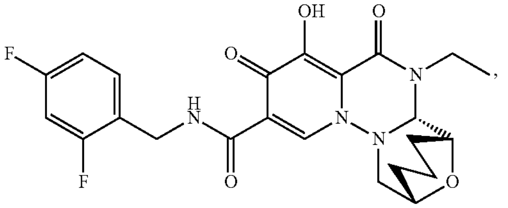

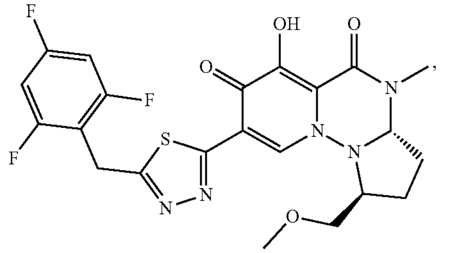

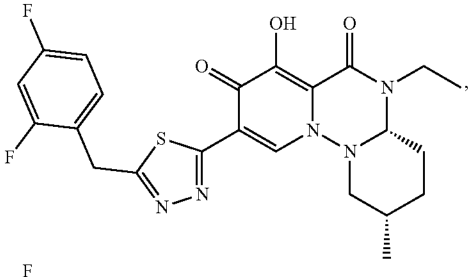

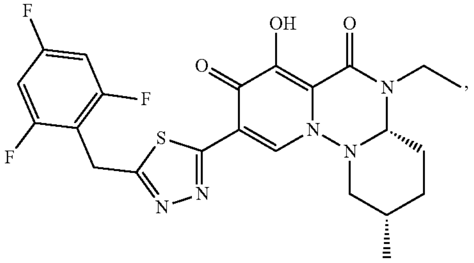

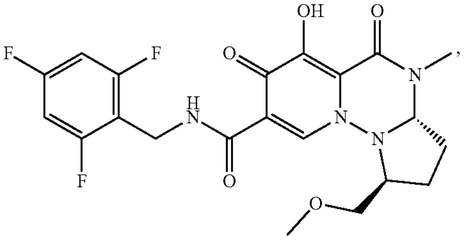

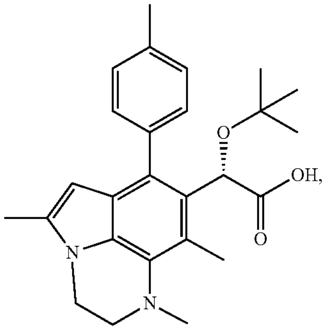

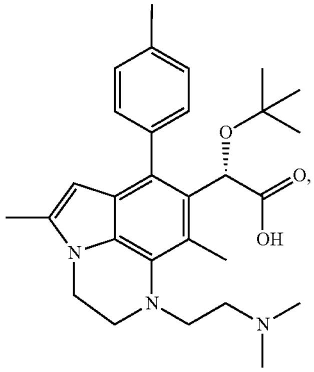

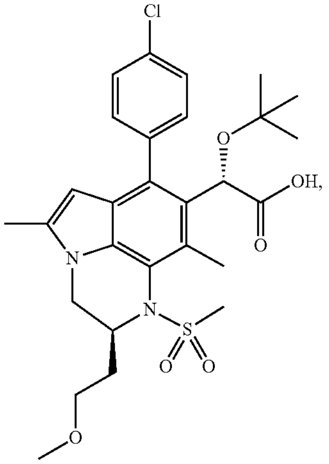

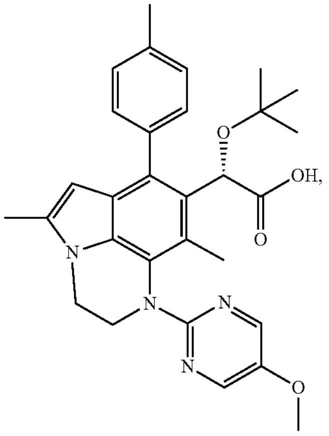

and pharmaceutically acceptable salts thereof; and (B) at least one compound having anti-HIV activity, or a pharmaceutically acceptable salt thereof.

11. The method of claim 10, wherein (B) is at least one selected from: AZT, 3TC, didanosine, zalcitabine, sanilvudine, abacavir, tenofovir, tenofovir disoproxil, tenofovir alafenamide, emtricitabine, nevirapine, efavirenz, capravirine, etravirine, delavirdine, rilpivirine, VM-1500A, VM-1500, doravirine, MK-8507, MK-8504, MK-8583, a following compound:

-continued

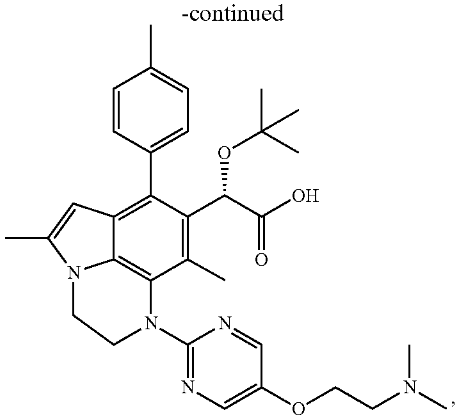

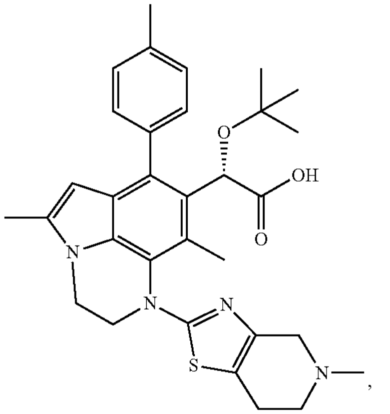

-continued

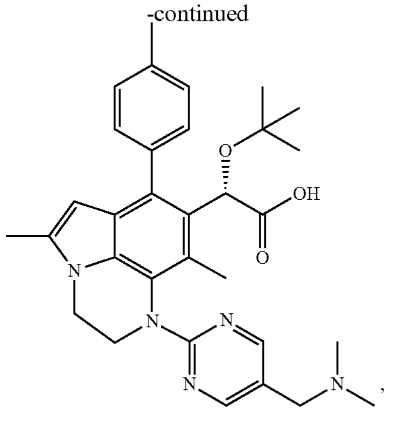

indinavir, ritonavir, saquinavir, nelfinavir, amprenavir, atazanavir, lopinavir, fosamprenavir, darunavir, maraviroc, enfuvirtide, ibalizumab, PRO-140, temsavir, fostemsavir tromethamine, combinectin, BDM-2, GSK-2838232, GSK-3640254, GS-6207, MK-8527 and MK-8558, and pharmaceutically acceptable salts thereof.

12. The method according to claim 11, wherein (A) and (B) are separate formulations.

* * * * *